US012766199B2

(12) United States Patent
Lombardi

(10) Patent No.: US 12,766,199 B2
(45) Date of Patent: Oct. 20, 2026

(54) GENE THERAPY VECTORS FOR TREATING HEART DISEASE

(71) Applicant: Tenaya Therapeutics, Inc., South San Francisco, CA (US)

(72) Inventor: Laura Lombardi, Redwood City, CA (US)

(73) Assignee: Tenaya Therapeutics, Inc., South San Francisco, CA (US)

(*) Notice: Subject to any disclaimer, the term of this patent is extended or adjusted under 35 U.S.C. 154(b) by 0 days.

(21) Appl. No.: 18/361,571

(22) Filed: Jul. 28, 2023

(65) Prior Publication Data

US 2023/0372541 A1 Nov. 23, 2023

Related U.S. Application Data

(60) Continuation of application No. 17/581,576, filed on Jan. 21, 2022, now Pat. No. 11,759,531, which is a continuation of application No. 17/383,138, filed on Jul. 22, 2021, now Pat. No. 12,478,691, which is a division of application No. 17/210,882, filed on Mar. 24, 2021, now Pat. No. 11,129,908, which is a continuation of application No. PCT/US2021/017699, filed on Feb. 11, 2021.

(60) Provisional application No. 63/047,633, filed on Jul. 2, 2020, provisional application No. 62/976,160, filed on Feb. 13, 2020.

(51) Int. Cl.

| | |
|---|---|
| ***A61K 48/00*** | (2006.01) |
| ***A61P 9/10*** | (2006.01) |
| ***C12N 15/86*** | (2006.01) |
| *C07H 21/04* | (2006.01) |
| *C12N 15/864* | (2006.01) |

(52) U.S. Cl.

CPC ............ *A61K 48/0058* (2013.01); *A61P 9/10* (2018.01); *C12N 15/86* (2013.01); *C07H 21/04* (2013.01); *C12N 15/8645* (2013.01)

(58) Field of Classification Search

CPC . A61K 48/0058; C12N 15/86; C12N 15/8645
USPC ........................................................... 514/44
See application file for complete search history.

(56) References Cited

U.S. PATENT DOCUMENTS

| | | | |
|---|---|---|---|
| 5,266,488 | A | 11/1993 | Ordahl et al. |
| 7,892,809 | B2 | 2/2011 | Bowles et al. |
| 8,617,534 | B2 | 12/2013 | Sussman et al. |
| 8,632,764 | B2 | 1/2014 | Xiao et al. |
| 8,734,809 | B2 | 5/2014 | Gao et al. |
| 8,889,641 | B2 | 11/2014 | Asokan et al. |
| 8,933,048 | B2 | 1/2015 | Stelzer |
| 9,018,440 | B2 | 4/2015 | Yu et al. |
| 9,051,387 | B2 | 6/2015 | Moss et al. |
| 9,114,148 | B2 | 8/2015 | Hajjar et al. |
| 9,395,354 | B2 | 7/2016 | Sun et al. |
| 9,441,244 | B2 | 9/2016 | Schaffer et al. |
| 9,475,845 | B2 | 10/2016 | Asokan et al. |
| 9,611,304 | B2 | 4/2017 | Simpson et al. |
| 9,732,345 | B2 | 8/2017 | Martin et al. |
| 9,868,937 | B2 | 1/2018 | Regnier et al. |
| 9,975,961 | B2 | 5/2018 | Weber et al. |
| 10,011,640 | B2 | 7/2018 | Srivastava et al. |
| 10,072,251 | B2 | 9/2018 | Gao et al. |
| 10,300,146 | B2 | 5/2019 | Gao et al. |
| 10,479,821 | B2 | 11/2019 | Chamberlain et al. |
| 10,480,011 | B2 | 11/2019 | Gao et al. |
| 10,501,756 | B2 | 12/2019 | Carrier et al. |
| 10,894,949 | B2 | 1/2021 | Gao et al. |
| 10,934,560 | B2 | 3/2021 | Li et al. |
| 11,118,192 | B2 | 9/2021 | Kirn et al. |
| 11,129,908 | B2 | 9/2021 | Lombardi |
| 11,242,368 | B2 | 2/2022 | Harris |
| 11,446,397 | B2 | 9/2022 | Lombardi |
| 11,759,531 | B2 | 9/2023 | Lombardi |
| 2003/0221207 | A1 | 11/2003 | McMahon et al. |
| 2004/0097454 | A1 | 5/2004 | Reusch et al. |
| 2009/0133138 | A1 | 5/2009 | Tsai |
| 2011/0158947 | A1 | 6/2011 | Jovanovic |
| 2011/0165680 | A1 | 7/2011 | Blattner et al. |
| 2013/0072549 | A1 | 3/2013 | Stelzer |
| 2013/0136729 | A1 | 5/2013 | French et al. |

(Continued)

FOREIGN PATENT DOCUMENTS

| | | |
|---|---|---|
| CN | 101988071 A | 3/2011 |
| CN | 105378089 A | 3/2016 |

(Continued)

OTHER PUBLICATIONS

Chamberlain et al., 2016 (Geneseq Accession No. BDC71261, computer printout, pp. 1-2).*
Strausberg et al., 2008 (GenEMBL Accession No. BC136543, computer printout, pp. 1-5).*
Katz et al., 2009 (Geneseq Accession No. AXS14079, computer printout, pp. 1-4).*
Keaveney et al., 2018 (GenEMBL Accession No. MH458079, computer printout, pp. 1-2) (5'ITR).*
Keaveney et al., 2018 (GenEMBL Accession No. MH458079, computer printout, pp. 1-2) (3'ITR).*

(Continued)

*Primary Examiner* — Valarie E Bertoglio
(74) *Attorney, Agent, or Firm* — Goodwin Procter LLP

(57) ABSTRACT

The present disclosure provides methods and compositions useful for the treatment or prevention of heart disease. In particular, the present disclosure provides a vector comprising a modified troponin T promoter operatively linked to a therapeutic gene product for the treatment or prevention of heart disease, e.g., cardiomyopathy. The gene product may be MYBPC3. The disclosure also provides recombinant adeno-associated virus (rAAV) virions, rAAV viral genomes, and expression cassettes and pharmaceutical compositions thereof. The disclosure further provides methods for treating a disease or disorder, such as heart disease.

24 Claims, 20 Drawing Sheets

Specification includes a Sequence Listing.

(56) References Cited

U.S. PATENT DOCUMENTS

| | | | |
|---|---|---|---|
| 2016/0108430 | A1 | 4/2016 | Carrier et al. |
| 2016/0237430 | A1 | 8/2016 | Seidman et al. |
| 2016/0340393 | A1 | 11/2016 | Schaffer et al. |
| 2017/0326256 | A1 | 11/2017 | Doering et al. |
| 2018/0066285 | A1 | 3/2018 | Ojala et al. |
| 2018/0148488 | A1 | 5/2018 | Chamberlain et al. |
| 2018/0265571 | A1 | 9/2018 | Esteves et al. |
| 2019/0010493 | A1 | 1/2019 | Kapiloff |
| 2019/0275035 | A1 | 9/2019 | Meyer et al. |
| 2019/0282709 | A1 | 9/2019 | Gao et al. |
| 2020/0095609 | A1 | 3/2020 | Carrier et al. |
| 2020/0405824 | A1 | 12/2020 | Odom et al. |
| 2021/0252165 | A1 | 8/2021 | Lombardi |
| 2021/0346521 | A1 | 11/2021 | Lombardi |
| 2021/0380643 | A1 | 12/2021 | Kirn et al. |
| 2022/0023384 | A1 | 1/2022 | Pu et al. |
| 2022/0031866 | A1 | 2/2022 | Lombardi |
| 2022/0160896 | A1 | 5/2022 | Lombardi |
| 2022/0273854 | A1 | 9/2022 | Holzmeister et al. |
| 2022/0389452 | A1 | 12/2022 | Voit et al. |
| 2023/0047424 | A1 | 2/2023 | Voit et al. |
| 2023/0220014 | A1 | 7/2023 | Cheng et al. |

FOREIGN PATENT DOCUMENTS

| | | | |
|---|---|---|---|
| CN | 107250364 | A | 10/2017 |
| CN | 108384806 | A | 8/2018 |
| CN | 109810981 | A | 5/2019 |
| DE | 102011018586 | A1 | 10/2012 |
| EP | 2792742 | A1 | 10/2014 |
| EP | 2986712 | B1 | 2/2019 |
| JP | 2014504871 | A | 2/2014 |
| JP | 2019500034 | A | 1/2019 |
| JP | 2020503869 | A | 2/2020 |
| WO | WO-02081632 | A2 | 10/2002 |
| WO | WO-2008093323 | A2 | 8/2008 |
| WO | WO-2008124724 | A1 | 10/2008 |
| WO | WO-2012094560 | A2 | 7/2012 |
| WO | WO-2012162705 | A2 | 11/2012 |
| WO | WO-2013009825 | A1 | 1/2013 |
| WO | WO 2014/028762 | A1 * | 2/2014 |
| WO | WO-2014170470 | A1 | 10/2014 |
| WO | WO-2015124546 | A1 | 8/2015 |
| WO | WO-2015153357 | A1 | 10/2015 |
| WO | WO-2016054554 | A1 | 4/2016 |
| WO | WO-2016115543 | A2 | 7/2016 |
| WO | WO-2017091807 | A1 | 6/2017 |
| WO | WO-2017100671 | A1 | 6/2017 |
| WO | WO-2017106236 | A1 | 6/2017 |
| WO | WO-2017106313 | A1 | 6/2017 |
| WO | WO-2017192750 | A1 | 11/2017 |
| WO | WO-2017212019 | A1 | 12/2017 |
| WO | WO-2018050783 | A1 | 3/2018 |
| WO | WO-2018067701 | A2 | 4/2018 |
| WO | WO-2018129296 | A1 | 7/2018 |
| WO | WO-2018152333 | A1 | 8/2018 |
| WO | WO-2018222503 | A1 | 12/2018 |
| WO | WO-2019010301 | A1 | 1/2019 |
| WO | WO-2019028306 | A2 | 2/2019 |
| WO | WO-2019060619 | A1 | 3/2019 |
| WO | WO 2019/143300 | A1 * | 7/2019 |
| WO | WO-2019162356 | A1 | 8/2019 |
| WO | WO-2019183630 | A2 | 9/2019 |
| WO | WO-2020014471 | A1 | 1/2020 |
| WO | WO-2020117898 | A1 | 6/2020 |
| WO | WO-2020191300 | A1 | 9/2020 |
| WO | WO-2020198737 | A1 | 10/2020 |
| WO | WO-2021038291 | A1 | 3/2021 |
| WO | WO-2021130503 | A1 | 7/2021 |
| WO | WO-2021163357 | A2 | 8/2021 |
| WO | WO-2022011151 | A1 | 1/2022 |
| WO | WO-2022031756 | A1 | 2/2022 |
| WO | WO-2022032226 | A1 | 2/2022 |
| WO | WO-2022136655 | A1 | 6/2022 |
| WO | WO-2022175545 | A1 | 8/2022 |
| WO | WO-2022175546 | A1 | 8/2022 |
| WO | WO-2022175547 | A1 | 8/2022 |

OTHER PUBLICATIONS

Butler, 2002, Genes and Development, 16:2583-2592.*

Al, J. et al., "Characterization of Recombinant Adeno-Associated Viral Transduction and Safety Profiles in Cardiomyocytes, Cell Physiol Biochem., 48(5):1894-1900 (2018) Epub Aug. 9, 2018.

Altschul, S. F., et al., "Gapped BLAST and PSI-BLAST: a new generation of protein database search programs", Nucleic Acids Research (Sep. 1, 1997); 25(17):3389-3402.

Altschul, S.F., et al., "Basic local alignment search tool," J. Mol. Biol. 215:403-410 (Oct. 5, 1990).

Asokan, A & Samulski, R. J., "An Emerging Adeno-Associated Viral Vector Pipeline for Cardiac Gene Therapy," Human Gene Therapy, 24:906-913 (2013).

Balaji, S. et al., "Pseudotyped adeno-associated viral vectors for gene transfer in dermal fibroblasts: implications for wound-healing applications," Journal of Surgical Research, 184:691-698 (2013).

Bardswell, S. C. et al., "Distinct Sarcomeric Substrates Are Responsible for Protein Kinase D-mediated Regulation of Cardiac Myofilament Ca2 Sensitivity and Cross-bridge Cycling," The Journal of Biological Chemistry, 285(8):5674-5682 (2010).

Barefield, D. et al., "Haploinsufficiency of MYBPC3 Exacerbates the Development of Hypertrophic Cardiomyopathy in Heterozygous Mice," J Mol Cell Cardiol., 79:234-243 (2015). doi:10.1016/j.yjmcc.2014.11.018.

Barefield, D. Y. et al., "Experimental modeling supports a role for MyBP-HL as a novel myofilament component in arrhythmia and dilated cardiomyopathy," Circulation, 136(16):1477-1491 (2017). doi:10.1161/CIRCULATIONAHA.117.028585.

Behrens-Gawlik, V. et al., "MYBPC3 in hypertrophic cardiomyopathy: from mutation identification to RNA-based correction," Pflugers Arch—Eur J Physiol, 466:215-223 (2014).

Bonne, G. et al., "Cardiac myosin binding protein-C gene splice acceptor site mutation is associated with familial hypertrophic cardiomyopathy," Nature Genetics, vol. 11, pp. 438-440 (Dec. 1995).

Borgeat, K. et al., "Association of the myosin binding protein C3 mutation (MYBPC3 R820W) with cardiac death in a survey of 236 Ragdoll cats," Journal of Veterinary Cardiology, 16:73-80 (2014).

Borgeat, K. et al., "The influence of clinical and genetic factors on left ventricular wall thickness in Ragdoll cats," Journal of Veterinary Cardiology, 17:S258-S267 (2015).

Buning, H. and Srivastava, A., "Capsid Modifications for Targeting and Improving the Efficacy of AAV Vectors," Molecular Therapy Methods & Clinical Development, vol. 12, 248-265 (Mar. 2019).

Burridge, P. W. et al., "Chemically Defined Culture and Cardiomyocyte Differentiation of Human Pluripotent Stem Cells," Curr Protoc Hum Genet., 87:21.3.1-21.3.15, Oct. 2015, doi:10.1002/0471142905.hg2103s87 (19 total pages).

Carrier, L. et al., "Asymmetric septal hypertrophy in heterozygous cMyBP-C null mice," Cardiovascular Research, 63:293-304 (2004).

Carrier, L. et al., "Cardiac myosin-binding protein C (MYBPC3) in cardiac pathophysiology," Gene, 573:188-197 (2015).

Carrier, L., et al., "Organization and Sequence of Human Cardiac Myosin Binding Protein C Gene (MYBPC3) and Identification of Mutations Predicted to Produce Truncated Proteins in Familial Hypertrophic Cardiomyopathy," Circulation Research, vol. 80, No. 3, pp. 427-434, Mar. 1997.

Carrier, L. et al., "The ubiquitin-proteasome system and nonsense-mediated mRNA decay in hypertrophic cardiomyopathy," Cardiovascular Research, 85:330-338 (2010).

Chamberlain, K., et al., "Cardiac gene therapy with adeno-associated virus-based vectors," Current Opinion in Cardiology 2017, vol. 32, pp. 275-282, DOI:10.1097/HCO.0000000000000386.

Chen, X. et al., "Human Cardiac Troponin T Regulatory Cassettes Facilitate High-Level Transient Expression in Differentiating Skeletal Muscle and Continuous Expression in Cardiac Muscle," Molecular Therapy, 19(1), 36:S14 (May 2011).

(56) References Cited

OTHER PUBLICATIONS

Choi, al., "AAV Hybrid Serotypes: Improved Vectors for Gene Delivery."; Current Gene Therapy; vol. 5, No. 3, pp. 299-310 (Jun. 2005).
Chu, G. and Sharp, P.A. "SV40 DNA transfection of cells in suspension: analysis of efficiency of transcription and translation of T-antigen." Gene. Mar. 1981;13(2):197-202. doi: 10.1016/0378-1119(81)90008-1.
Chute, J. P., "Stem cell homing," Current Opinion in Hematology 2006, vol. 13, pp. 399-406.
Clark, K. R. et al., "Cell Lines for the Production of Recombinant Adena-Associated Virus," Human Gene Therapy, 6:1329-1341 (1995).
Cohn, R. et al., "A Contraction Stress Model of Hypertrophic Cardiomyopathy due to Sarcomere Mutations," Stem Cell Reports, 12:71-83 (2019).
Colson, B. A et al., "Site-directed spectroscopy of cardiac myosin-binding protein C reveals effects of phosphorylation on protein structural dynamics," PNAS, 113(12):3233-3238 (2016).
Cooper, T. A. and Ordahl, C. P., "A Single Cardiac Troponin T Gene Generates Embryonic and Adult Isoforms via Developmentally Regulated Alternate Splicing," The Journal of Biological Chemistry, 1985, vol. 260, No. 20, Issue of Sep. 15, pp. 11140-11148.
Damdindorj, L. et al., "A Comparative Analysis of Constitutive Promoters Located in Adeno-Associated Viral Vectors," PLoS ONE, 9(8):e106472 (2014), 10 pages. doi:10.1371/journal.pone.0106472.
Dhandapany, P. S. et al., "A common MYBPC3 (cardiac myosin binding protein C) variant associated with cardiomyopathies in South Asia," Nature Genetics, 41(2):187-191 (2009).
Dong, B., et al., "Characterization of Genome Integrity for Oversized Recombinant AAV Vector," Molecular Therapy, Jan. 2010, vol. 18, No. 1, pp. 87-92, published online Nov. 10, 2009, DOI: 10.1038/mt.2009.258.
Dong, J. Y., et al., "Quantitative analysis of the packaging capacity of recombinant adeno-associated virus," Human Gene Therapy, 7:2101-2112 (Nov. 10, 1996), 31 pages.
Durymanov, Mikhail, et al., "Non-Viral Delivery of Nucleic Acids: Insight into Mechanisms of Overcoming Intracellular Barriers," Frontiers in Pharmacology, vol. 9, Article 971, pp. 1-15., Aug. 2018.
Final Office Action, mailed Mar. 21, 2022, for U.S. Appl. No. 17/507,362 (12 pages).
Final Rejection Office Action for U.S. Appl. No. 17/581,576, mailed on Nov. 4, 2022, 10 pages.
Foust, K. D., et al., "Rescue of the spinal muscular atrophy phenotype in a mouse model by early postnatal delivery of SMN," Nature Biotechnology, vol. 28, No. 3, Mar. 2010, pp. 271-274, including Online Methods, 2 pages, doi: 10.1038.nbt.1610 (Retracted).
Freeman, L. M. et al., "Feline Hypertrophic Cardiomyopathy: A Spontaneous Large Animal Model of Human HCM," Cardiol. Res., 8(4):139-142 (2017).
Galinska-Rakoczy, A. et al., "Structural Basis for the Regulation of Muscle Contraction by Troponin and Tropomyosin," J. Mol. Biol. 2008, vol. 379, pp. 929-935, doi:10.1016/j.jmb.2008.04.062.
Gallo, P. et al., "A lentiviral vector with a short troponin-I promoter for tracking cardiomyocyte differentiation of human embryonic stem cells," Gene Therapy, 15(3):161-70 (2008).
Geneseq Accession No. AXR77954, 2009, 2 pages, Bennett Seq ID 96; cited in an Office Action mailed on Dec. 3, 2021, in connection with U.S. Appl. No. 17/507,362.
Geneseq Accession No. AXR77954, 2009, 2 pages, Bennett Seq ID 97; cited in an Office Action mailed on Dec. 3, 2021, in connection with U.S. Appl. No. 17/507,362.
Geneseq Accession No. AXS14079, 2009, 4 pages, Katz Seq ID 102, cited in an Office Action mailed on Dec. 3, 2021, in connection with U.S. Appl. No. 17/507,362.
Geneseq Accession No. AXS14079, 2009, 4 pages. Katz Seq ID 86; cited in an Office Action mailed on Dec. 3, 2021, in connection with U.S. Appl. No. 17/507,362.
Geneseq Accession No. AXS14079, 2009, 4 pages, Katz Seq ID 95; cited in an Office Action mailed on Dec. 3, 2021, in connection with U.S. Appl. No. 17/507,362.
Geneseq Accession No. AXS14079, 2009, 5 pages. Katz Seq ID 103; cited in an Office Action mailed on Dec. 3, 2021, in connection with U.S. Appl. No. 17/507,362.
Geneseq Accession No. BDC71261, 2016, 2 pages, Chamberlain, et al.; cited in Office Action mailed Dec. 3, 2021 for U.S. Appl. No. 17/507,362 and in Office Action mailed Sep. 20, 2023 for U.S. Appl. No. 17/383,138.
Giles, J. et al., "Recovery of left ventricular function following in vivo reexpression of cardiac myosin binding protein C," J. Gen. Physiol., 151(1):77-89 (2018).
Glazier, A A et al., "Allelic imbalance and haploinsufficiency in MYBPC3-linked hypertrophic cardiomyopathy," Pflugers Archiv—European Journal of Physiology, published online: Nov. 20, 2018, 13 pages. https://doi.org/10.1007/s00424-018-2226-9.
Glazier, A A et al., "HSC70 is a chaperone for wild-type and mutant cardiac myosin binding protein C," JCI Insight. 2018; 3(11):e99319, 16 pages. https://doi.org/10.1172/jci.insight.99319.
Graham, F.L. and Van Der Eb, A.J. "A new technique for the assay of infectivity of human adenovirus 5 DNA." Virology. Apr. 1973;52(2):456-67. doi: 10.1016/0042-6822(73)90341-3.
Granstrom, S. et al., "Genotype-phenotype correlation between the cardiac myosin binding protein C mutation A31P and hypertrophic cardiomyopathy in a cohort of Maine Coon cats: a longitudinal study," Journal of Veterinary Cardiology, 17:S268-S281 (2015).
Grieger, J. C. et al., "Packaging Capacity of Adeno-Associated Virus Serotypes: Impact of Larger Genomes on Infectivity and Postentry Steps," Journal of Virology, Aug. 2005, vol. 79, No. 15, pp. 9933-9944, doi:10.1128/JVI.79.15.9933-9944.2005.
Grunhaus, A et al., "Association of Vaccinia Virus-Expressed Adenovirus E3-19K Glycoprotein with Class I MHC and Its Effects on Virulence in a Murine Pneumonia Model," Virology, 200:535-546 (1994).
Gu, X. et al., "Cardiac functional improvement in rats with myocardial infarction by up-regulating cardiac myosin light chain kinase with neuregulin," Cardiovascular Research (2010), vol. 88, pp. 334-343, doi:10.1093/cvr/cvq223.
Hannah-Shmouni, F., et al., "The Genetic Challenges and Opportunities in Advanced Heart Failure," Canadian Journal of Cardiology 2015, vol. 31, pp. 1338-1350, http://dx.doi.org/10.1016/j.cjca.2015.07.735.
Harlan, S. M., et al., "Requirement of TCTG (G/C) Direct Repeats and Overlapping GATA Site for Maintaining the Cardiac-Specific Expression of Cardiac troponin T in Developing and Adult Mice," The Anatomical Record 2008, 291:1574-1586, DOI 10.1002/ar.20772.
Harris, S. P. et al., "Hypertrophic Cardiomyopathy in Cardiac Myosin Binding Protein-C Knockout Mice," Circ Res., 90:594-601 (2002).
Harris, S. P. et al., "In the Thick of It HCM-Causing Mutations in Myosin Binding Proteins of the Thick Filament," Circ Res., 108:751-764 (2011).
Helms, A S. et al., "Sarcomere Mutation-Specific Expression Patterns in Human Hypertrophic Cardiomyopathy," Circ Cardiovasc Genet., 7:434-443 (2014).
Helms, A S. et al., "Effects of MYBPC3 loss of function mutations preceding hypertrophic cardiomyopathy," JCI Insight, Published Dec. 26, 2019, 42 pages. https://doi.orQ/10.1172/jci.insiQht.133782.
Helms, A S. et al., "Effects of MYBPC3 loss-of-function mutations preceding hypertrophic cardiomyopathy," JCI Insight, 5(2):e133782 (2020), 20 pages. https://doi.org/10.1172/jci.insight.133782.
Iannello, R. C., et al., "Characterization of a Promoter Element Required for Transcription in Myocardial Cells," The Journal of Biological Chemistry 1991,, vol. 266, No. 5, Issue of Feb. 15, pp. 3309-3316.
International Preliminary Report on Patentability for International Application No. PCT/US2021/017699, mailed on Aug. 25, 2022, 10 pages.
International Search Report and Written Opinion, mailed Nov. 3, 2021, for International Application No. PCT/US2021/017699 (14 total pages).

(56) References Cited

OTHER PUBLICATIONS

Irion et al., "Identification and targeting of the ROSA26 locus in human embryonic stem cells", Nat Biotechnol. Dec. 2007; 25(12): 1477-82. Epub Nov. 25, 2007.
Jaski, B. E. et al., "Calcium Upregulation by Percutaneous Administration of Gene Therapy in Cardiac Disease (CUPID Trial), a First-in-Human Phase ½ Clinical Trial," J Card Fail., 15(3):171-181 (2009). doi:10.1016/j.cardfail.2009.01.013.
John Hopkins Medicine, Heath, "Cardiomyopathy," https://www.hopkinsmedicine.org/heath/conditions-and-diseases/cardiomyopathy, retrieved from the internet Mar. 30, 2022 (4 pages).
Katz, M. G. et al., "Gene delivery technologies for cardiac applications," Gene Ther., 19(6):659-669 (2012). doi:10.1038/gt.2012.11.
Keaveney et al., GenEMBL Accession No. MH458079, 2018, 2 pages.
Khajetoorians, D., et al., "Replacement of Mybpc3 Mutation by 5'-trans-splicing in a Knock-in Mouse Model: A Step Towards Casual Therapy of Hypertrophic Cardiomyopathy," Circulation Research, vol. 111, No. 12, Dec. 7, 2012, p. e380.
Kittleson, M. D. et al., "Familial Hypertrophic Cardiomyopathy in Maine Coon Cats," Circulation, Jun. 22, 1999, 99:3172-3180.
Kittleson, M. D. et al., "The genetic basis of hypertrophic cardiomyopathy in cats and humans," Journal of Veterinary Cardiology, 17:S53-S73 (2015).
Knöll, R., "Myosin binding protein C: implications for signal-transduction," Journal of Muscle Research and Cell Motility 2012, vol. 33, pp. 31-42, published online Dec. 16, 2011, DOI: 10.1007/S10974-011-9281-6.
Konkalmatt, P.R. et al., "Cardiac-Selective Expression of EcSOD After Systemic Injection of AAV9 Protects the Heart Against Post-MI LV Remodeling," Circ Cardiovasc Imaging, 6(3):478-486 (2013). doi:10.1161/CIRCIMAGING.112.000320.
Kotterman, M.A. & Schaffer, D.V., Engineering adeno-associated viruses for clinical gene therapy, Nature Review: Genetics, vol. 15, pp. 445-451, Jul. 2014.
Lekanne Deprez, R. H. et al., "Two cases of severe neonatal hypertrophic cardiomyopathy caused by compound heterozygous mutations in the MYBPC3 gene," J Med Genet, 43:829-832 (2006). doi: 10.1136/jmg.2005.040329.
Lenzi et al., 2014, NCBI Bookshelf, a Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16.
Li, J. et al., "AAV9 gene transfer of cMyBPC N-terminal domains ameliorates cardiomyopathy in cMyBPC-deficient mice," JCI Insight, 5(17):e130182 (2020), 19 pages. https://doi.org/10.1172/jci.insight.130182.
Li, L. et al., "Effects of administration route on migration and distribution of neural progenitor cells transplanted into rats with focal cerebral ischemia, an MRI study," Journal of Cerebral Blood Flow and Metabolism 2010, vol. 30, pp. 653-662, published online Nov. 4, 2009.
Lian, X. et al., "Robust cardiomyocyte differentiation from human pluripotent stem cells via temporal modulation of canonical Wnt signaling," PNAS, Published online May 29, 2012, 109(27):E1848-E1857. https://doi.org/10.1073/pnas.1200250109.
Liu, X. et al., "Screening Mutations of MYBPC3 in 114 Unrelated Patients with Hypertrophic Cardiomyopathy by Targeted Capture and Next generation Sequencing," Scientific Reports, 5:11411 (2015), 8 pages. doi: 10.1038/srep11411.
Liu, Y. et al., "Generation of Targeted Adeno-Associated Virus (AAV) Vectors for Human Gene Therapy," Current Pharmaceutical Design, 21:3248-3256 (2015).
Lombardi, L., et al., Reversal of Cardiac Hypertrophy with an Optimized MYBPC3 Gene Therapy, 2021 American Society of Gene & Cell Therapy 24th Annual Meeting, Apr. 27, 2021, 1 page.
Lombardi, L. M., et al., Prevention of Premature Lethality and Reversal of Cardiac Hypertrophy with an Optimized MYBPC3 Gene Therapy, 2021 Congress of the European Society of Gene and Cell Therapy, Oct. 20, 2021, 1 page.
Longeri, M. et al., "Myosin-Binding Protein C DNA Variants in Domestic Cats (A31P, A74T, R820W) and their Association with Hypertrophic Cardiomyopathy," J Vet Intern Med, 27:275-285 (2013).
Lopez-Gordo, E., et al., "AAV Vectors for Efficient Gene Delivery to Rodent Hearts," Chapter 19, Adeno-Associated Virus Vectors: Design and Delivery, Methods in Molecular Biology, vol. 1950, pp. 311-332, https://doi.org/10.1007/978-1-4939-9139-6_19 (2019).
Lyon, A. R., et al., "Gene therapy: targeting the myocardium," Heart 2008, 94:89-99; doi:10.1136/hrt.2007.116483.
Ma, H. et al., "Cell-specific expression of SERCA, the exogenous Ca2+ transport ATPase, in cardiac myocytes," Am J Physiol Cell Physiol, 286:C556-C564 (2004). First published Oct. 30, 2003. 10.1152/aipcell.00328.2003.
Ma, Z. et al., "Contractile deficits in engineered cardiac microtissues as a result of MYBPC3 deficiency and mechanical overload," Nat Biomed Eng, 2:955-967 (2018). https://doi.org/10.1038/s41551-018-0280-4, and Supplementary Information, 16 pages.
Mamidi, R. et al., "Cardiac myosin binding protein-C: a novel sarcomeric target for gene therapy," Pflugers Arch—Eur J Physiol, 466:225-230 (2014).
Mar, J. H., et al., "A conserved CATTCCT motif is required for skeletal muscle-specific activity of the cardiac troponin T gene promoter," Proc. Natl. Acad. Sci., vol. 85, pp. 6404-6408, Sep. 1988.
Mar, J. H., et al., "Analysis of the Upstream Regions Governing Expression of the Chicken Cardiac Troponin T Gene in Embryonic Cardiac Skeletal Muscle Cells," The Journal of Cell Biology, vol. 107, Aug. 1988, pp. 573-585.
Marian, A J. & Braunwald, E., "Hypertrophic Cardiomyopathy Genetics, Pathogenesis, Clinical Manifestations, Diagnosis, and Therapy," Circ Res., 121:749-770 (2017). doi: 10.1161/CIRCRESAHA.117.311059.
Marian, A. J., "Hypertrophic cardiomyopathy: from genetics to treatment," European Journal of Clinical Investigation, vol. 40, pp. 360-369, Mar. 17, 2010, DOI: 10.1111/j.1365-2362.2010.02268.x.
Maron, B. J., "Clinical Course and Management of Hypertrophic Cardiomyopathy," N Engl J Med, 379:655-668 (2018).
Marston, S. et al., "Evidence From Human Myectomy Samples That MYBPC3 Mutations Cause Hypertrophic Cardiomyopathy Through Haploinsufficiency," Circ Res., 105:219-222 (2009).
Marziliano, N. et al., "A Case of Compound Mutations in the MYBPC3 Gene Associated with Biventricular Hypertrophy and Neonatal Death," Neonatology, 102:254-258 (2012).
McConnell, B. K. et al., "Dilated cardiomyopathy in homozygous myosin-binding protein-C mutant mice," J Clin Invest., 104(9):1235-1244 (1999).
McNamara, J. W. et al., "Ablation of cardiac myosin binding protein-C disrupts the super-relaxed state of myosin in murine cardiomyocytes," J Mol Cell Cardiol., 94:65-71 (2016). doi:10.1016/i.vimcc.2016.03.009.
McNamara, J. W. et al., "MYBPC3 mutations are associated with a reduced super-relaxed state in patients with hypertrophic cardiomyopathy," PLoS One, 12(6):e0180064 (2017), 22 pages. https://doi.org/10.1371/journal.pone.0180064.
Mearini, G. et al., "Mybpc3 gene therapy for neonatal cardiomyopathy enables long-term disease prevention in mice," Nature Communications, 5:5155 (2014), doi: 10.1038/ncomms6515, 10 pages. http://www.nature.com/naturecommunications.
Mearini, G. et al., "Repair of Mybpc3 mRNA by 5'-trans-splicing in a Mouse Model of Hypertrophic Cardiomyopathy," Molecular Therapy Nucleic Acids, Jul. 2, 2013;2(7):e102. doi: 10.1038/mtna.2013.31, 9 pages.
Merentie, M. et al., "Efficacy and safety of myocardial gene transfer of adenovirus, adeno-associated virus and lentivirus vectors in the mouse heart," Gene Therapy, 23, pp. 296-305, doi:10.1038/gt.2015.114 (2016).

(56) References Cited

OTHER PUBLICATIONS

Merkulov, S. et al., "In Vivo Cardiac Myosin Binding Protein C Gene Transfer Rescues Myofilament Contractile Dysfunction in Cardiac Myosin Binding Protein C Null Mice," Circ Heart Fail., 5(5):635-644 (2012).
Meurs, K. M. et al., "A cardiac myosin binding protein C mutation in the Maine Coon cat with familial hypertrophic cardiomyopathy," Human Molecular Genetics, 14(23):0 3587-3593 (2005).
Meurs, K. M. et al., "A substitution mutation in the myosin binding protein C gene in ragdoll hypertrophic cardiomyopathy," Genomics, 90:261-264 (2007).
Miller, "Human gene therapy comes of age," Nature. Jun. 11, 1992;357(6378):455-60.
Mohamed, T. M. A. et al., "Regulation of Cell Cycle to Stimulate Adult Cardiomyocyte Proliferation and Cardiac Regeneration," Cell, vol. 173, pp. 104-116 (Mar. 2018), https://doi.org/10.1016/j.cell.2018.02.014, 26 pages.
Moolman, J. A. et al., "A Newly Created Splice Donor Site in Exon 25 of the MyBP-C Gene Is Responsible for Inherited Hypertrophic Cardiomyopathy With Incomplete Disease Penetrance," Circulation, 101:1396-1402 (2000).
Mosqueira, D. et al., "CRISPR/Cas9 editing in human pluripotent stem cell-cardiomyocytes highlights arrhythmias, hypocontractility, and energy depletion as potential therapeutic targets for hypertrophic cardiomyopathy," European Heart Journal (2018), doi: 10.1093/eurheartj/ehy249, 16 pages.
Moss, R. L., "Cardiac myosin-binding protein C: A protein once at loose ends finds its regulatory groove," PNAS, 113(12):3133-3135 (2016).
Najafi, A et al., "Sexual dimorphic response to exercise in hypertrophic cardiomyopathy-associated MYBPC3-targeted knock-in mice," Pflugers Arch—Eur J Physiol, 467:1303-1317 (2015).
Naso, M. F. et al., "Adeno-Associated Virus (AAV) as a Vector for Gene Therapy", Biodrugs, vol. 31, No. 4, Jul. 1, 2017 (Jul. 1, 2017), NZ, pp. 317-334, XP055547503, ISSN: 1173-8804, Retrieved from the Internet DOI: 10.1007/s40259-017-0234-5.
Needleman, S.B. & Wunsch, C.D. "A general method applicable to the search for similarities in the amino acid sequences of two proteins." J. Mol. Biol. 48.3 (1970), pp. 443-453.
Non-Final Office Action, mailed Apr. 26, 2022, for U.S. Appl. No. 17/581,576 (24 pages).
Non-Final Office Action mailed Dec. 3, 2021 for U.S. Appl. No. 17/507,362, 27 pages.
Non-Final Office Action mailed May 25, 2021 for U.S. Appl. No. 17/210,882, 21 pages.
Non-Final Office Action, mailed Sep. 20, 2023, for U.S. Appl. No. 17/383,138 (14 total pages).
O'Leary, T. S. et al., "MYBPC3 truncation mutations enhance actomyosin contractile mechanics in human hypertrophic cardiomyopathy," J Mol Cell Cardiol., 127:165-173 (2019). doi:10.1016/j.yjmcc.2018.12.003.
Parr et al., "Bone marrow-derived mesenchymal stromal cells for the repair of central nervous system injury," Bone Marrow Transplantation 2007, vol. 40, pp. 609-619, doi:10.1038/sj.bmt.1705757; published online Jul. 2, 2007.
Pearson, WR., et al. "Improved tools for biological sequence comparison." Proceedings of the National Academy of Sciences 85.8 (1988): 2444-2448.
Pellegrino, A et al., "Assessment of regional left ventricular systolic function by strain imaging echocardiography in phenotypically normal and abnormal Maine coon cats tested for the A31P mutation in the MYBPC3 qene," The Canadian Journal of Veterinary Research, 81:137-146 (2017).
Phillips, M. I. et al., "Vigilant Vector: Heart-Specific Promoter in an Adena-Associated Virus Vector for Cardioprotection," Hypertension, 39[part2]:651-655 (2002).
Piras, B. A. et al., "Systemic injection of AAV9 carrying a periostin promoter targets gene expression to a myofibroblast-like lineage in mouse hearts after reperfused myocardial infarction," Gene Therapy, 23:469-478 (2016).
Pozsgai, E. R. et al., "Systemic AAV-Mediated b-Sarcoglycan Delivery Targeting Cardiac and Skeletal Muscle Ameliorates Histological and Functional Deficits in LGMD2E Mice," Molecular Therapy, 25(4): 855-869 (Apr. 2017).
Prasad, K.-M. et al., "Robust Cardiomyocyte-Specific Gene Expression Following Systemic Injection of AAV: In Vivo Gene Delivery Follows a Poisson Distribution," Gene Ther., 18(1):43-52, Jan. 2011, 22 pages, doi:10.1038/gt.2010.105.
Prasad, K.-M., et al., "A single direct injection into the left ventricular wall of an adeno-associated virus 9 (AAV9) vector expressing extracelluar superoxide dismutase from the cardiac troponin-T promoter protects mice against myocardial infarction," The Journal of Gene Medicine 2011, 13:333-341, DOI: 10.1002/jgm.1576.
Previs, M. J. et al., "Molecular Mechanics of Cardiac Myosin Binding Protein-C in Native Thick Filaments," Science, 337(6099): 1215-1218 (2012). doi:10.1126/science.1223602.
Prondzynski, M. et al., "Evaluation of MYBPC3 trans-Splicing and Gene Replacement as Therapeutic Options in Human iPSC-Derived Cardiomyocytes," Molecular Therapy: Nucleic Acids, 7:475-486 (2017).
Prondzynski, M. et al., "Gene therapy strategies in the treatment of hypertrophic cardiomyopathy," Pflugers Archiv—European Journal of Physiology, 471(6244), 9 pages (2018). doi:10.1007/s00424-018-2173-5.
Restriction Requirement, dated Jun. 13, 2023, for U.S. Appl. No. 17/383,138 (6 total pages).
Rosas, P. C. et al., "Phosphorylation of Cardiac Myosin Binding Protein-C is a Critical Mediator of Diastolic Function," Circ Heart Fail., 8(3):582-594 (2015).
Rottbauer, W. et al., "Novel splice donor site mutation in the cardiac myosin-binding protein-C gene in familial hypertrophic cardiomyopathy. Characterization of cardiac transcript and protein," J Clin Invest., 100(2):475-482 (1997). https://doi.org/10.1172/JCI119555.
Sadayappan, S. & De Tombe, P. P., "Cardiac myosin binding protein-C: redefining its structure and function," Biophys Rev, 4:93-106 (2012).
Schlegel, P., et al., "Locally Targeted Cardiac Gene Delivery by AAV Microbubble Destruction in a Large Animal Mode," Human Gene Therapy Methods (2016), vol. 27, No. 2, pp. 71-78, DOI: 10.1089/hgtb.2015.120, 9 pages.
Schlossarek, S. et al., "Defective proteolytic systems in Mybpc3-targeted mice with cardiac hypertrophy," Basic Res Cardiol, 107:235 (2012), 13 pages. doi: 10.1007/s00395-011-0235-3.
Seidman, C. E., et al., "Identifying Sarcomere Gene Mutations in Hypertrophic Cardiomyopathy," Circulation Research, Mar. 18, 2011, pp. 743-750, DOI: 10.1161/CIRCRESAHA.110.223834.
Shim, Gayong, et al., "Nonviral Delivery Systems for Cancer Gene Therapy: Strategies and Challenges," Current Gene Therapy, vol. 17, No. 5, pp. 1-18 (2017).
Stern, J. A et al., "A Small Molecule Inhibitor of Sarcomere Contractility Acutely Relieves Left Ventricular Outflow Tract Obstruction in Feline Hypertrophic Cardiomyopathy," PLoS ONE, 11(12): e0168407, Dec. 2016, 13 pages, doi:10.1371/iournal.pone.0168407.
Strausberg et al., 2008, GenEMBL Accession No. BC136543, computer printout, pp. 1-7.
Tidyman, W. E. et al., "In vivo regulation of the chicken cardiac troponin T gene promoter in zebrafish embryos," Developmental Dynamics, 227:484-496 (2003).
Toepfer, C. N. et al., "Hypertrophic cardiomyopathy mutations in MYBPC3 dysregulate myosin," Sci. Transl. Med., 11:eaat1199 (2019), 10 pages. doi: 10.1126/scitranslmed.aat1199.
Tohyama, S. et al., "Distinct Metabolic Flow Enables Large-Scale Purification of Mouse and Human Pluripotent Stem Cell-Derived Cardiomyocytes," Cell Stem Cell, 12(1):127-37 (2013).
Truong Dong-Jiunn, J., et al., "Development from an intein-mediated split-Cas9 system for gene therapy," Nucleic Acids Research, vol. 43, No. 13, pp. 6450-6458, doi: 10.1093/nar/gkv601 (Jun. 2015).
Tsui, J. H., et al., "Modeling Hypertrophic Cardiomyopathy Due to MYBPC3 Haploinsufficiency with Engineered Heart Tissues," Heart Development and Disease: From Genes to Cures—2023 Keystone Symposia Event, Feb. 12, 2023, 1 page.

(56) References Cited

OTHER PUBLICATIONS

Van Dijk, S. J. et al., "Cardiac Myosin-Binding Protein C Mutations and Hypertrophic Cardiomyopathy," Circulation, 119:1473-1483 (2009).
Van Dijk, S. J. et al., "Contractile Dysfunction Irrespective of the Mutant Protein in Human Hypertrophic Cardiomyopathy With Normal Systolic Function," Circ Heart Fail., 5:36-46 (Jan. 2012).
Van Dijk, S. J. et al., "Point mutations in the tri-helix bundle of the M-domain of cardiac myosin binding protein-C influence systolic duration and delay cardiac relaxation," J Mol Cell Cardiol., 119:116-124 (2018). doi:10.1016/i.vimcc.2018.05.001.
Van Dijk, S. J. et al., "The A31P missense mutation in cardiac myosin binding protein C alters protein structure but does not cause haploinsufficiency," Arch Biochem Biophys., 601:133-140 (2016). doi:10.1016/j.abb.2016.01.006.
Vera, T. R. et al., "The R820W mutation in the MYBPC3 gene, associated with hypertrophic cardiomyopathy in cats, causes hypertrophic cardiomyopathy and left ventricular non-compaction in humans," Int J Cardiol, 145(2):405-407 (2010). doi: 10.1016/j.ijcard.2010.04.032. Epub Jun. 14, 2010.
Vignier, N. et al., "Nonsense-Mediated mRNA Decay and Ubiquitin-Proteasome System Regulate Cardiac Myosin-Binding Protein C Mutant Levels in Cardiomyopathie Mice," Circ Res., 105:239-248 (2009).
Walsh, R. et al., "Reassessment of Mendelian gene pathogenicity using 7,855 cardiomyopathy cases and 60,706 reference samples," Genetics in Medicine, 19(2):192-203 (2017).
Watkins, H., et al., "Mutations in the cardiac myosin binding protein-C gene on chromosome 11 cause familial hypertrophic cardiomyopathy," Nature Genetics, vol. 11, pp. 434-437 (Dec. 1995).
Werfel, S. et al., "Rapid and highly efficient inducible cardiac gene knockout in adult mice using AAV-mediated expression of Cre recombinase," Cardiovascular Research, 104(1):15-23 ( 2014).
Wess, G. et al., "Association of A31P and A74T Polymorphisms in the Myosin Binding Protein C3 Gene and Hypertrophic Cardiomyopathy in Maine Coon and Other Breed Cats," J Vet Intern Med, 24:527-532 (2010).
Wessels, M. W. et al., "Compound heterozygous or homozygous truncating MYBPC3 mutations cause lethal cardiomyopathy with features of noncompaction and septal defects," European Journal of Human Genetics, 23:922-928 (2015).
Wijnker, P. J. M. et al., "Comparison of the effects of a truncating and a missense MYBPC3 mutation on contractile parameters of engineered heart tissue," Journal of Molecular and Cellular Cardiology, 97:82-92 (2016).
Wu, Z. et al., "Effect of Genome Size on AAV Vector Packaging," Molecular Therapy, vol. 18, No. 1, pp. 80-86 (Jan. 2010).
Wu, Z., et al., "Optimization of Self-complementary AAV Vectors for Liver-directed Expression Results in Sustained Correction of Hemophilia B at Low Vector Dose," Mol. Therapy, Feb. 2008, vol. 16, No. 2, pp. 280-289, published online Dec. 4, 2007, doi:10.1038/sj.mt.6300355.
Xin, B. et al., "Homozygosity for a Novel Splice Site Mutation in the Cardiac Myosin-Binding Protein C Gene Causes Severe Neonatal Hypertrophic Cardiomyopathy," American Journal of Medical Genetics Part A, 143A:2662-2667 (2007).
Yang, Q. et al., "A mouse model of myosin binding protein C human familial hypertrophic cardiomyopathy," J Clin Invest., 102(7):1292-1300 (1998). https://doi.org/10.1172/JCI3880.
Yardeni, T., et al., "Retro-orbital injections in mice," Lab Anim (NY), 40(5): 155-160, doi:10.1038/laban0511-155 (May 2011), 17 pages.
Zahka, K. et al., "Homozygous mutation of MYBPC3 associated with severe infantile hypertrophic cardiomyopathy at high frequency among the Amish," Heart, 94:1326-1330 (2008).
Zincarelli, C. et al., "Analysis of AAV Serotypes 1-9 Mediated Gene Expression and Tropism in Mice After Systemic Injection," Molecular Therapy, 16(6):1073-1080 (2008).
Final Office Action for U.S. Appl. No. 17/383,138 dated Mar. 1, 2024, 11 pages.
Fotin-Mleczek et al., 2017 (Geneseq Accession No. BFB95840, computer printout, pp. 1-5).
Grieger, J.C., et al., "Production and characterization of adeno-associated viral vectors," Nature Protocols, 2006, vol. 1(3), pp. 1412-1428.
Kaya, et al., "Comparison of IL-10 and MCP-1-7ND gene transfer with AAV9 vectors for protection from murine autoimmune myocarditis," Cardiovasc Res. Jul. 1, 2011; 91(1):116-23. Epub Feb. 25, 2011.
NCBI Reference Sequence: NG_007556.1: "*Homo sapiens* troponin T2, cardiac type (TNNT2), RefSeqGene (LRG_431) on chromosome 1," Oct. 6, 2024, 10 pages retrieved on Nov. 15, 2024 at https://www.ncbi.nlm.nih.gov/nuccore/NG_007556.1.
NCBI Reference Sequence: NM_000256.2: "*Homo sapiens* myosin binding protein C, cardiac (MYBPC3), mRNA," Jun. 3, 2007, 4 pages retrieved on Nov. 15, 2024 at https://www.ncbi.nlm.nih.gov/nuccore/NM_000256.2.
NCBI Reference Sequence: NP_000247.2: "Myosin-binding protein C, cardiac-type [*Homo sapiens*]," Oct. 7, 2024, 8 pages retrieved on Nov. 15, 2024 at https://www.ncbi.nlm.nih.gov/protein/NP_000247.2.
Non-Final Office Action for U.S. Appl. No. 17/383,138 mailed Aug. 23, 2024, 16 pages.
Fong, et al., "Modeling the Evolutionary Architectures of Transcribed Human Enhancer Sequences Reveals Distinct Origins, Functions, and Associations with Human Trait Variation," Mol Biol Evol. Aug. 23, 2021; 38(9):3681-3696.
Panigrahi, et al., "Mechanisms of enhancer action: the known and the unknown," Genome Biol. Apr. 15, 2021; 22(1):108, 30 pages.
Levitt, et al., "Definition of an efficient synthetic poly(A) site," Genes Dev. Jul. 1989; 3(7):1019-25.
Author Unknown, "Sequence 2 from U.S. Appl. No. 10/479,821," version 1, created and last updated Feb. 14, 2020, Database Accession No. M0519550, 1 page retrieved on Jun. 24, 2025 from https://www.ebi.ac.uk/ena/browser/api/embl/M0519950.1?lineLimit=1000.
Non-Final Office Action for U.S. Appl. No. 17/383,138 mailed Apr. 25, 2025, 10 pages.
Notice of Allowance for U.S. Appl. No. 17/383,138 mailed Jul. 29, 2025, 9 pages.
Pedersen, et al., "The biology of eukaryotic promoter prediction—a review," Comput Chem. Jun. 15, 1999; 23(3-4):191-207.

* cited by examiner

*MYBPC3-/-* iPSC-CMs were harvested 5 days post-infection with AAV6 at MOI 60k.

*MYBPC3*-/- iPSC-CMs were harvested 7 days post-infection with AAV6 at MOI 60k.

*MYBPC3*-/- iPSC-CMs were harvested 7 days post-transfection.

SEQUENCE LISTING

```
Sequence total quantity: 201
SEQ ID NO: 1            moltype = DNA  length = 600
FEATURE                 Location/Qualifiers
source                  1..600
                        mol_type = genomic DNA
                        organism = Homo sapiens
SEQUENCE: 1
gtcatggaga agacccacct tgcagatgtc ctcactgggg ctggcagagc cggcaacctg  60
cctaaggctg ctcagtccat taggagccag tagcctggaa gatgtcttta cccccagcat  120
cagttcaagt ggagcagcac ataactcttg ccctctgcct tccaagattc tggtgctgag  180
acttatggag tgtcttggag gttgccttct gccccccaac cctgctccca gctggccctc  240
ccaggcctgg gttgctggcc tctgctttat caggattctc aagagggaca gctggtttat  300
gttgcatgac tgttccctgc atatctgctc tggttttaaa tagcttatct gagcagctgg  360
aggaccacat gggcttatat ggcgtggggt acatgttcct gtagccttgt ccctggcacc  420
tgccaaaata gcagccaaca ccccccaccc ccaccgccat ccccctgccc cacccgtccc  480
ctgtcgcaca ttcctccctc cgcagggctg gctcaccagg ccccagccca catgcctgct  540
taaagccctc tccatcctct gcctcaccca gtccccgctg agactgagca gacgcctcca  600

SEQ ID NO: 2            moltype = DNA  length = 500
FEATURE                 Location/Qualifiers
source                  1..500
                        mol_type = other DNA
                        organism = Homo sapiens
SEQUENCE: 2
gatgtcttta cccccagcat cagttcaagt ggagcagcac ataactcttg ccctctgcct  60
tccaagattc tggtgctgag acttatggag tgtcttggag gttgccttct gccccccaac  120
cctgctccca gctggccctc ccaggcctgg gttgctggcc tctgctttat caggattctc  180
aagagggaca gctggtttat gttgcatgac tgttccctgc atatctgctc tggttttaaa  240
```

```
tagcttatct gagcagctgg aggaccacat gggcttatat ggcgtggggt acatgttcct  300
gtagccttgt ccctggcacc tgccaaaata gcagccaaca ccccccaccc ccaccgccat  360
ccccctgccc cacccgtccc ctgtcgcaca ttcctccctc cgcagggctg gctcaccagg  420
ccccagccca catgcctgct taaagccctc tccatcctct gcctcaccca gtccccgctg  480
agactgagca gacgcctcca                                               500

SEQ ID NO: 3            moltype = DNA  length = 400
FEATURE                 Location/Qualifiers
source                  1..400
                        mol_type = other DNA
                        organism = Homo sapiens
SEQUENCE: 3
gttgccttct gccccccaac cctgctccca gctggccctc ccaggcctgg gttgctggcc  60
tctgctttat caggattctc aagagggaca gctggtttat gttgcatgac tgttccctgc  120
atatctgctc tggttttaaa tagcttatct gagcagctgg aggaccacat gggcttatat  180
ggcgtggggt acatgttcct gtagccttgt ccctggcacc tgccaaaata gcagccaaca  240
ccccccaccc ccaccgccat ccccctgccc cacccgtccc ctgtcgcaca ttcctccctc  300
cgcagggctg gctcaccagg ccccagccca catgcctgct taaagccctc tccatcctct  360
gcctcaccca gtccccgctg agactgagca gacgcctcca                        400

SEQ ID NO: 4            moltype = DNA  length = 300
FEATURE                 Location/Qualifiers
source                  1..300
                        mol_type = other DNA
                        organism = Homo sapiens
SEQUENCE: 4
gttgcatgac tgttccctgc atatctgctc tggttttaaa tagcttatct gagcagctgg  60
aggaccacat gggcttatat ggcgtggggt acatgttcct gtagccttgt ccctggcacc  120
tgccaaaata gcagccaaca ccccccaccc ccaccgccat ccccctgccc cacccgtccc  180
ctgtcgcaca ttcctccctc cgcagggctg gctcaccagg ccccagccca catgcctgct  240
taaagccctc tccatcctct gcctcaccca gtccccgctg agactgagca gacgcctcca  300

SEQ ID NO: 5            moltype = DNA  length = 590
FEATURE                 Location/Qualifiers
source                  1..590
                        mol_type = other DNA
                        organism = Homo sapiens
SEQUENCE: 5
agacccacct tgcagatgtc ctcactgggg ctggcagagc cggcaacctg cctaaggctg  60
ctcagtccat taggagccag tagcctggaa gatgtcttta cccccagcat cagttcaagt  120
ggagcagcac ataactcttg ccctctgcct tccaagattc tggtgctgag acttatggag  180
tgtcttggag gttgccttct gccccccaac cctgctccca gctggccctc ccaggcctgg  240
gttgctggcc tctgctttat caggattctc aagagggaca gctggtttat gttgcatgac  300
tgttccctgc atatctgctc tggttttaaa tagcttatct gagcagctgg aggaccacat  360
gggcttatat ggcgtggggt acatgttcct gtagccttgt ccctggcacc tgccaaaata  420
gcagccaaca ccccccaccc ccaccgccat ccccctgccc cacccgtccc ctgtcgcaca  480
ttcctccctc cgcagggctg gctcaccagg ccccagccca catgcctgct taaagccctc  540
tccatcctct gcctcaccca gtccccgctg agactgagca gacgcctcca              590

SEQ ID NO: 6            moltype = DNA  length = 580
FEATURE                 Location/Qualifiers
source                  1..580
                        mol_type = other DNA
                        organism = Homo sapiens
SEQUENCE: 6
tgcagatgtc ctcactgggg ctggcagagc cggcaacctg cctaaggctg ctcagtccat  60
taggagccag tagcctggaa gatgtcttta cccccagcat cagttcaagt ggagcagcac  120
ataactcttg ccctctgcct tccaagattc tggtgctgag acttatggag tgtcttggag  180
gttgccttct gccccccaac cctgctccca gctggccctc ccaggcctgg gttgctggcc  240
tctgctttat caggattctc aagagggaca gctggtttat gttgcatgac tgttccctgc  300
atatctgctc tggttttaaa tagcttatct gagcagctgg aggaccacat gggcttatat  360
ggcgtggggt acatgttcct gtagccttgt ccctggcacc tgccaaaata gcagccaaca  420
ccccccaccc ccaccgccat ccccctgccc cacccgtccc ctgtcgcaca ttcctccctc  480
cgcagggctg gctcaccagg ccccagccca catgcctgct taaagccctc tccatcctct  540
gcctcaccca gtccccgctg agactgagca gacgcctcca                        580

SEQ ID NO: 7            moltype = DNA  length = 570
FEATURE                 Location/Qualifiers
source                  1..570
                        mol_type = other DNA
                        organism = Homo sapiens
SEQUENCE: 7
ctcactgggg ctggcagagc cggcaacctg cctaaggctg ctcagtccat taggagccag  60
tagcctggaa gatgtcttta cccccagcat cagttcaagt ggagcagcac ataactcttg  120
ccctctgcct tccaagattc tggtgctgag acttatggag tgtcttggag gttgccttct  180
gccccccaac cctgctccca gctggccctc ccaggcctgg gttgctggcc tctgctttat  240
caggattctc aagagggaca gctggtttat gttgcatgac tgttccctgc atatctgctc  300
tggttttaaa tagcttatct gagcagctgg aggaccacat gggcttatat ggcgtggggt  360
acatgttcct gtagccttgt ccctggcacc tgccaaaata gcagccaaca ccccccaccc  420
```

-continued

```
ccaccgccat ccccctgccc cacccgtccc ctgtcgcaca ttcctccctc cgcagggctg  480
gctcaccagg ccccagccca catgcctgct taaagccctc tccatcctct gcctcaccca  540
gtccccgctg agactgagca gacgcctcca                                   570

SEQ ID NO: 8            moltype = DNA  length = 560
FEATURE                 Location/Qualifiers
source                  1..560
                        mol_type = other DNA
                        organism = Homo sapiens
SEQUENCE: 8
ctggcagagc cggcaacctg cctaaggctg ctcagtccat taggagccag tagcctggaa  60
gatgtcttta cccccagcat cagttcaagt ggagcagcac ataactcttg ccctctgcct  120
tccaagattc tggtgctgag acttatggag tgtcttggag gttgccttct gccccccaac  180
cctgctccca gctggccctc ccaggcctgg gttgctggcc tctgctttat caggattctc  240
aagagggaca gctggtttat gttgcatgac tgttccctgc atatctgctc tggttttaaa  300
tagcttatct gagcagctgg aggaccacat gggcttatat ggcgtggggt acatgttcct  360
gtagccttgt ccctggcacc tgccaaaata gcagccaaca ccccccaccc ccaccgccat  420
ccccctgccc cacccgtccc ctgtcgcaca ttcctccctc cgcagggctg gctcaccagg  480
ccccagccca catgcctgct taaagccctc tccatcctct gcctcaccca gtccccgctg  540
agactgagca gacgcctcca                                              560

SEQ ID NO: 9            moltype = DNA  length = 550
FEATURE                 Location/Qualifiers
source                  1..550
                        mol_type = other DNA
                        organism = Homo sapiens
SEQUENCE: 9
cggcaacctg cctaaggctg ctcagtccat taggagccag tagcctggaa gatgtcttta  60
cccccagcat cagttcaagt ggagcagcac ataactcttg ccctctgcct tccaagattc  120
tggtgctgag acttatggag tgtcttggag gttgccttct gccccccaac cctgctccca  180
gctggccctc ccaggcctgg gttgctggcc tctgctttat caggattctc aagagggaca  240
gctggtttat gttgcatgac tgttccctgc atatctgctc tggttttaaa tagcttatct  300
gagcagctgg aggaccacat gggcttatat ggcgtggggt acatgttcct gtagccttgt  360
ccctggcacc tgccaaaata gcagccaaca ccccccaccc ccaccgccat ccccctgccc  420
cacccgtccc ctgtcgcaca ttcctccctc cgcagggctg gctcaccagg ccccagccca  480
catgcctgct taaagccctc tccatcctct gcctcaccca gtccccgctg agactgagca  540
gacgcctcca                                                         550

SEQ ID NO: 10           moltype = DNA  length = 540
FEATURE                 Location/Qualifiers
source                  1..540
                        mol_type = other DNA
                        organism = Homo sapiens
SEQUENCE: 10
cctaaggctg ctcagtccat taggagccag tagcctggaa gatgtcttta cccccagcat  60
cagttcaagt ggagcagcac ataactcttg ccctctgcct tccaagattc tggtgctgag  120
acttatggag tgtcttggag gttgccttct gccccccaac cctgctccca gctggccctc  180
ccaggcctgg gttgctggcc tctgctttat caggattctc aagagggaca gctggtttat  240
gttgcatgac tgttccctgc atatctgctc tggttttaaa tagcttatct gagcagctgg  300
aggaccacat gggcttatat ggcgtggggt acatgttcct gtagccttgt ccctggcacc  360
tgccaaaata gcagccaaca ccccccaccc ccaccgccat ccccctgccc cacccgtccc  420
ctgtcgcaca ttcctccctc cgcagggctg gctcaccagg ccccagccca catgcctgct  480
taaagccctc tccatcctct gcctcaccca gtccccgctg agactgagca gacgcctcca  540

SEQ ID NO: 11           moltype = DNA  length = 530
FEATURE                 Location/Qualifiers
source                  1..530
                        mol_type = other DNA
                        organism = Homo sapiens
SEQUENCE: 11
ctcagtccat taggagccag tagcctggaa gatgtcttta cccccagcat cagttcaagt  60
ggagcagcac ataactcttg ccctctgcct tccaagattc tggtgctgag acttatggag  120
tgtcttggag gttgccttct gccccccaac cctgctccca gctggccctc ccaggcctgg  180
gttgctggcc tctgctttat caggattctc aagagggaca gctggtttat gttgcatgac  240
tgttccctgc atatctgctc tggttttaaa tagcttatct gagcagctgg aggaccacat  300
gggcttatat ggcgtggggt acatgttcct gtagccttgt ccctggcacc tgccaaaata  360
gcagccaaca ccccccaccc ccaccgccat ccccctgccc cacccgtccc ctgtcgcaca  420
ttcctccctc cgcagggctg gctcaccagg ccccagccca catgcctgct taaagccctc  480
tccatcctct gcctcaccca gtccccgctg agactgagca gacgcctcca             530

SEQ ID NO: 12           moltype = DNA  length = 520
FEATURE                 Location/Qualifiers
source                  1..520
                        mol_type = other DNA
                        organism = Homo sapiens
SEQUENCE: 12
taggagccag tagcctggaa gatgtcttta cccccagcat cagttcaagt ggagcagcac  60
ataactcttg ccctctgcct tccaagattc tggtgctgag acttatggag tgtcttggag  120
gttgccttct gccccccaac cctgctccca gctggccctc ccaggcctgg gttgctggcc  180
```

```
tctgctttat caggattctc aagagggaca gctggtttat gttgcatgac tgttccctgc  240
atatctgctc tggttttaaa tagcttatct gagcagctgg aggaccacat gggcttatat  300
ggcgtggggt acatgttcct gtagccttgt ccctggcacc tgccaaaata gcagccaaca  360
ccccccaccc ccaccgccat ccccctgccc cacccgtccc ctgtcgcaca ttcctccctc  420
cgcagggctg gctcaccagg ccccagccca catgcctgct taaagccctc tccatcctct  480
gcctcaccca gtccccgctg agactgagca gacgcctcca                        520

SEQ ID NO: 13          moltype = DNA  length = 510
FEATURE                Location/Qualifiers
source                 1..510
                       mol_type = other DNA
                       organism = Homo sapiens
SEQUENCE: 13
tagcctggaa gatgtcttta cccccagcat cagttcaagt ggagcagcac ataactcttg  60
ccctctgcct tccaagattc tggtgctgag acttatggag tgtcttggag gttgccttct  120
gccccccaac cctgctccca gctggccctc ccaggcctgg gttgctggcc tctgctttat  180
caggattctc aagagggaca gctggtttat gttgcatgac tgttccctgc atatctgctc  240
tggttttaaa tagcttatct gagcagctgg aggaccacat gggcttatat ggcgtggggt  300
acatgttcct gtagccttgt ccctggcacc tgccaaaata gcagccaaca ccccccaccc  360
ccaccgccat ccccctgccc cacccgtccc ctgtcgcaca ttcctccctc cgcagggctg  420
gctcaccagg ccccagccca catgcctgct taaagccctc tccatcctct gcctcaccca  480
gtccccgctg agactgagca gacgcctcca                                    510

SEQ ID NO: 14          moltype = DNA  length = 490
FEATURE                Location/Qualifiers
source                 1..490
                       mol_type = other DNA
                       organism = Homo sapiens
SEQUENCE: 14
cccccagcat cagttcaagt ggagcagcac ataactcttg ccctctgcct tccaagattc  60
tggtgctgag acttatggag tgtcttggag gttgccttct gccccccaac cctgctccca  120
gctggccctc ccaggcctgg gttgctggcc tctgctttat caggattctc aagagggaca  180
gctggtttat gttgcatgac tgttccctgc atatctgctc tggttttaaa tagcttatct  240
gagcagctgg aggaccacat gggcttatat ggcgtggggt acatgttcct gtagccttgt  300
ccctggcacc tgccaaaata gcagccaaca ccccccaccc ccaccgccat ccccctgccc  360
cacccgtccc ctgtcgcaca ttcctccctc cgcagggctg gctcaccagg ccccagccca  420
catgcctgct taaagccctc tccatcctct gcctcaccca gtccccgctg agactgagca  480
gacgcctcca                                                          490

SEQ ID NO: 15          moltype = DNA  length = 480
FEATURE                Location/Qualifiers
source                 1..480
                       mol_type = other DNA
                       organism = Homo sapiens
SEQUENCE: 15
cagttcaagt ggagcagcac ataactcttg ccctctgcct tccaagattc tggtgctgag  60
acttatggag tgtcttggag gttgccttct gccccccaac cctgctccca gctggccctc  120
ccaggcctgg gttgctggcc tctgctttat caggattctc aagagggaca gctggtttat  180
gttgcatgac tgttccctgc atatctgctc tggttttaaa tagcttatct gagcagctgg  240
aggaccacat gggcttatat ggcgtggggt acatgttcct gtagccttgt ccctggcacc  300
tgccaaaata gcagccaaca ccccccaccc ccaccgccat ccccctgccc cacccgtccc  360
ctgtcgcaca ttcctccctc cgcagggctg gctcaccagg ccccagccca catgcctgct  420
taaagccctc tccatcctct gcctcaccca gtccccgctg agactgagca gacgcctcca  480

SEQ ID NO: 16          moltype = DNA  length = 470
FEATURE                Location/Qualifiers
source                 1..470
                       mol_type = other DNA
                       organism = Homo sapiens
SEQUENCE: 16
ggagcagcac ataactcttg ccctctgcct tccaagattc tggtgctgag acttatggag  60
tgtcttggag gttgccttct gccccccaac cctgctccca gctggccctc ccaggcctgg  120
gttgctggcc tctgctttat caggattctc aagagggaca gctggtttat gttgcatgac  180
tgttccctgc atatctgctc tggttttaaa tagcttatct gagcagctgg aggaccacat  240
gggcttatat ggcgtggggt acatgttcct gtagccttgt ccctggcacc tgccaaaata  300
gcagccaaca ccccccaccc ccaccgccat ccccctgccc cacccgtccc ctgtcgcaca  360
ttcctccctc cgcagggctg gctcaccagg ccccagccca catgcctgct taaagccctc  420
tccatcctct gcctcaccca gtccccgctg agactgagca gacgcctcca             470

SEQ ID NO: 17          moltype = DNA  length = 460
FEATURE                Location/Qualifiers
source                 1..460
                       mol_type = other DNA
                       organism = Homo sapiens
SEQUENCE: 17
ataactcttg ccctctgcct tccaagattc tggtgctgag acttatggag tgtcttggag  60
gttgccttct gccccccaac cctgctccca gctggccctc ccaggcctgg gttgctggcc  120
tctgctttat caggattctc aagagggaca gctggtttat gttgcatgac tgttccctgc  180
atatctgctc tggttttaaa tagcttatct gagcagctgg aggaccacat gggcttatat  240
```

```
ggcgtggggt acatgttcct gtagccttgt ccctggcacc tgccaaaata gcagccaaca  300
ccccccaccc ccaccgccat ccccctgccc cacccgtccc ctgtcgcaca ttcctccctc  360
cgcagggctg gctcaccagg ccccagccca catgcctgct taaagccctc tccatcctct  420
gcctcaccca gtccccgctg agactgagca gacgcctcca                        460

SEQ ID NO: 18          moltype = DNA  length = 450
FEATURE                Location/Qualifiers
source                 1..450
                       mol_type = other DNA
                       organism = Homo sapiens
SEQUENCE: 18
ccctctgcct tccaagattc tggtgctgag acttatggag tgtcttggag gttgccttct  60
gccccccaac cctgctccca gctggccctc ccaggcctgg gttgctggcc tctgctttat  120
caggattctc aagagggaca gctggtttat gttgcatgac tgttccctgc atatctgctc  180
tggttttaaa tagcttatct gagcagctgg aggaccacat gggcttatat ggcgtggggt  240
acatgttcct gtagccttgt ccctggcacc tgccaaaata gcagccaaca ccccccaccc  300
ccaccgccat ccccctgccc cacccgtccc ctgtcgcaca ttcctccctc cgcagggctg  360
gctcaccagg ccccagccca catgcctgct taaagccctc tccatcctct gcctcaccca  420
gtccccgctg agactgagca gacgcctcca                                   450

SEQ ID NO: 19          moltype = DNA  length = 440
FEATURE                Location/Qualifiers
source                 1..440
                       mol_type = other DNA
                       organism = Homo sapiens
SEQUENCE: 19
tccaagattc tggtgctgag acttatggag tgtcttggag gttgccttct gccccccaac  60
cctgctccca gctggccctc ccaggcctgg gttgctggcc tctgctttat caggattctc  120
aagagggaca gctggtttat gttgcatgac tgttccctgc atatctgctc tggttttaaa  180
tagcttatct gagcagctgg aggaccacat gggcttatat ggcgtggggt acatgttcct  240
gtagccttgt ccctggcacc tgccaaaata gcagccaaca ccccccaccc ccaccgccat  300
ccccctgccc cacccgtccc ctgtcgcaca ttcctccctc cgcagggctg gctcaccagg  360
ccccagccca catgcctgct taaagccctc tccatcctct gcctcaccca gtccccgctg  420
agactgagca gacgcctcca                                              440

SEQ ID NO: 20          moltype = DNA  length = 430
FEATURE                Location/Qualifiers
source                 1..430
                       mol_type = other DNA
                       organism = Homo sapiens
SEQUENCE: 20
tggtgctgag acttatggag tgtcttggag gttgccttct gccccccaac cctgctccca  60
gctggccctc ccaggcctgg gttgctggcc tctgctttat caggattctc aagagggaca  120
gctggtttat gttgcatgac tgttccctgc atatctgctc tggttttaaa tagcttatct  180
gagcagctgg aggaccacat gggcttatat ggcgtggggt acatgttcct gtagccttgt  240
ccctggcacc tgccaaaata gcagccaaca ccccccaccc ccaccgccat ccccctgccc  300
cacccgtccc ctgtcgcaca ttcctccctc cgcagggctg gctcaccagg ccccagccca  360
catgcctgct taaagccctc tccatcctct gcctcaccca gtccccgctg agactgagca  420
gacgcctcca                                                         430

SEQ ID NO: 21          moltype = DNA  length = 420
FEATURE                Location/Qualifiers
source                 1..420
                       mol_type = other DNA
                       organism = Homo sapiens
SEQUENCE: 21
acttatggag tgtcttggag gttgccttct gccccccaac cctgctccca gctggccctc  60
ccaggcctgg gttgctggcc tctgctttat caggattctc aagagggaca gctggtttat  120
gttgcatgac tgttccctgc atatctgctc tggttttaaa tagcttatct gagcagctgg  180
aggaccacat gggcttatat ggcgtggggt acatgttcct gtagccttgt ccctggcacc  240
tgccaaaata gcagccaaca ccccccaccc ccaccgccat ccccctgccc cacccgtccc  300
ctgtcgcaca ttcctccctc cgcagggctg gctcaccagg ccccagccca catgcctgct  360
taaagccctc tccatcctct gcctcaccca gtccccgctg agactgagca gacgcctcca  420

SEQ ID NO: 22          moltype = DNA  length = 410
FEATURE                Location/Qualifiers
source                 1..410
                       mol_type = other DNA
                       organism = Homo sapiens
SEQUENCE: 22
tgtcttggag gttgccttct gccccccaac cctgctccca gctggccctc ccaggcctgg  60
gttgctggcc tctgctttat caggattctc aagagggaca gctggtttat gttgcatgac  120
tgttccctgc atatctgctc tggttttaaa tagcttatct gagcagctgg aggaccacat  180
gggcttatat ggcgtggggt acatgttcct gtagccttgt ccctggcacc tgccaaaata  240
gcagccaaca ccccccaccc ccaccgccat ccccctgccc cacccgtccc ctgtcgcaca  300
ttcctccctc cgcagggctg gctcaccagg ccccagccca catgcctgct taaagccctc  360
tccatcctct gcctcaccca gtccccgctg agactgagca gacgcctcca             410

SEQ ID NO: 23          moltype = DNA  length = 390
```

```
FEATURE                Location/Qualifiers
source                 1..390
                       mol_type = other DNA
                       organism = Homo sapiens
SEQUENCE: 23
gccccccaac cctgctccca gctggccctc ccaggcctgg gttgctggcc tctgctttat  60
caggattctc aagagggaca gctggtttat gttgcatgac tgttccctgc atatctgctc  120
tggttttaaa tagcttatct gagcagctgg aggaccacat gggcttatat ggcgtggggt  180
acatgttcct gtagccttgt ccctggcacc tgccaaaata gcagccaaca ccccccaccc  240
ccaccgccat cccccctgccc cacccgtccc ctgtcgcaca ttcctccctc cgcagggctg  300
gctcaccagg ccccagccca catgcctgct taaagccctc tccatcctct gcctcaccca  360
gtccccgctg agactgagca gacgcctcca                                  390

SEQ ID NO: 24          moltype = DNA  length = 380
FEATURE                Location/Qualifiers
source                 1..380
                       mol_type = other DNA
                       organism = Homo sapiens
SEQUENCE: 24
cctgctccca gctggccctc ccaggcctgg gttgctggcc tctgctttat caggattctc  60
aagagggaca gctggtttat gttgcatgac tgttccctgc atatctgctc tggttttaaa  120
tagcttatct gagcagctgg aggaccacat gggcttatat ggcgtggggt acatgttcct  180
gtagccttgt ccctggcacc tgccaaaata gcagccaaca ccccccaccc ccaccgccat  240
cccccctgccc cacccgtccc ctgtcgcaca ttcctccctc cgcagggctg gctcaccagg  300
ccccagccca catgcctgct taaagccctc tccatcctct gcctcaccca gtccccgctg  360
agactgagca gacgcctcca                                             380

SEQ ID NO: 25          moltype = DNA  length = 370
FEATURE                Location/Qualifiers
source                 1..370
                       mol_type = other DNA
                       organism = Homo sapiens
SEQUENCE: 25
gctggccctc ccaggcctgg gttgctggcc tctgctttat caggattctc aagagggaca  60
gctggtttat gttgcatgac tgttccctgc atatctgctc tggttttaaa tagcttatct  120
gagcagctgg aggaccacat gggcttatat ggcgtggggt acatgttcct gtagccttgt  180
ccctggcacc tgccaaaata gcagccaaca ccccccaccc ccaccgccat cccccctgccc  240
cacccgtccc ctgtcgcaca ttcctccctc cgcagggctg gctcaccagg ccccagccca  300
catgcctgct taaagccctc tccatcctct gcctcaccca gtccccgctg agactgagca  360
gacgcctcca                                                        370

SEQ ID NO: 26          moltype = DNA  length = 360
FEATURE                Location/Qualifiers
source                 1..360
                       mol_type = other DNA
                       organism = Homo sapiens
SEQUENCE: 26
ccaggcctgg gttgctggcc tctgctttat caggattctc aagagggaca gctggtttat  60
gttgcatgac tgttccctgc atatctgctc tggttttaaa tagcttatct gagcagctgg  120
aggaccacat gggcttatat ggcgtggggt acatgttcct gtagccttgt ccctggcacc  180
tgccaaaata gcagccaaca ccccccaccc ccaccgccat cccccctgccc cacccgtccc  240
ctgtcgcaca ttcctccctc cgcagggctg gctcaccagg ccccagccca catgcctgct  300
taaagccctc tccatcctct gcctcaccca gtccccgctg agactgagca gacgcctcca  360

SEQ ID NO: 27          moltype = DNA  length = 350
FEATURE                Location/Qualifiers
source                 1..350
                       mol_type = other DNA
                       organism = Homo sapiens
SEQUENCE: 27
gttgctggcc tctgctttat caggattctc aagagggaca gctggtttat gttgcatgac  60
tgttccctgc atatctgctc tggttttaaa tagcttatct gagcagctgg aggaccacat  120
gggcttatat ggcgtggggt acatgttcct gtagccttgt ccctggcacc tgccaaaata  180
gcagccaaca ccccccaccc ccaccgccat cccccctgccc cacccgtccc ctgtcgcaca  240
ttcctccctc cgcagggctg gctcaccagg ccccagccca catgcctgct taaagccctc  300
tccatcctct gcctcaccca gtccccgctg agactgagca gacgcctcca             350

SEQ ID NO: 28          moltype = DNA  length = 340
FEATURE                Location/Qualifiers
source                 1..340
                       mol_type = other DNA
                       organism = Homo sapiens
SEQUENCE: 28
tctgctttat caggattctc aagagggaca gctggtttat gttgcatgac tgttccctgc  60
atatctgctc tggttttaaa tagcttatct gagcagctgg aggaccacat gggcttatat  120
ggcgtggggt acatgttcct gtagccttgt ccctggcacc tgccaaaata gcagccaaca  180
ccccccaccc ccaccgccat cccccctgccc cacccgtccc ctgtcgcaca ttcctccctc  240
cgcagggctg gctcaccagg ccccagccca catgcctgct taaagccctc tccatcctct  300
gcctcaccca gtccccgctg agactgagca gacgcctcca                        340
```

```
SEQ ID NO: 29          moltype = DNA  length = 330
FEATURE                Location/Qualifiers
source                 1..330
                       mol_type = other DNA
                       organism = Homo sapiens
SEQUENCE: 29
caggattctc aagagggaca gctggtttat gttgcatgac tgttccctgc atatctgctc  60
tggttttaaa tagcttatct gagcagctgg aggaccacat gggcttatat ggcgtggggt  120
acatgttcct gtagccttgt ccctggcacc tgccaaaata gcagccaaca ccccccaccc  180
ccaccgccat ccccctgccc cacccgtccc ctgtcgcaca ttcctccctc cgcagggctg  240
gctcaccagg ccccagccca catgcctgct taaagccctc tccatcctct gcctcaccca  300
gtccccgctg agactgagca gacgcctcca                                    330

SEQ ID NO: 30          moltype = DNA  length = 320
FEATURE                Location/Qualifiers
source                 1..320
                       mol_type = other DNA
                       organism = Homo sapiens
SEQUENCE: 30
aagagggaca gctggtttat gttgcatgac tgttccctgc atatctgctc tggttttaaa  60
tagcttatct gagcagctgg aggaccacat gggcttatat ggcgtggggt acatgttcct  120
gtagccttgt ccctggcacc tgccaaaata gcagccaaca ccccccaccc ccaccgccat  180
ccccctgccc cacccgtccc ctgtcgcaca ttcctccctc cgcagggctg gctcaccagg  240
ccccagccca catgcctgct taaagccctc tccatcctct gcctcaccca gtccccgctg  300
agactgagca gacgcctcca                                              320

SEQ ID NO: 31          moltype = DNA  length = 310
FEATURE                Location/Qualifiers
source                 1..310
                       mol_type = other DNA
                       organism = Homo sapiens
SEQUENCE: 31
gctggtttat gttgcatgac tgttccctgc atatctgctc tggttttaaa tagcttatct  60
gagcagctgg aggaccacat gggcttatat ggcgtggggt acatgttcct gtagccttgt  120
ccctggcacc tgccaaaata gcagccaaca ccccccaccc ccaccgccat ccccctgccc  180
cacccgtccc ctgtcgcaca ttcctccctc cgcagggctg gctcaccagg ccccagccca  240
catgcctgct taaagccctc tccatcctct gcctcaccca gtccccgctg agactgagca  300
gacgcctcca                                                         310

SEQ ID NO: 32          moltype = DNA  length = 290
FEATURE                Location/Qualifiers
source                 1..290
                       mol_type = other DNA
                       organism = Homo sapiens
SEQUENCE: 32
tgttccctgc atatctgctc tggttttaaa tagcttatct gagcagctgg aggaccacat  60
gggcttatat ggcgtggggt acatgttcct gtagccttgt ccctggcacc tgccaaaata  120
gcagccaaca ccccccaccc ccaccgccat ccccctgccc cacccgtccc ctgtcgcaca  180
ttcctccctc cgcagggctg gctcaccagg ccccagccca catgcctgct taaagccctc  240
tccatcctct gcctcaccca gtccccgctg agactgagca gacgcctcca             290

SEQ ID NO: 33          moltype = DNA  length = 280
FEATURE                Location/Qualifiers
source                 1..280
                       mol_type = other DNA
                       organism = Homo sapiens
SEQUENCE: 33
atatctgctc tggttttaaa tagcttatct gagcagctgg aggaccacat gggcttatat  60
ggcgtggggt acatgttcct gtagccttgt ccctggcacc tgccaaaata gcagccaaca  120
ccccccaccc ccaccgccat ccccctgccc cacccgtccc ctgtcgcaca ttcctccctc  180
cgcagggctg gctcaccagg ccccagccca catgcctgct taaagccctc tccatcctct  240
gcctcaccca gtccccgctg agactgagca gacgcctcca                        280

SEQ ID NO: 34          moltype = DNA  length = 270
FEATURE                Location/Qualifiers
source                 1..270
                       mol_type = other DNA
                       organism = Homo sapiens
SEQUENCE: 34
tggttttaaa tagcttatct gagcagctgg aggaccacat gggcttatat ggcgtggggt  60
acatgttcct gtagccttgt ccctggcacc tgccaaaata gcagccaaca ccccccaccc  120
ccaccgccat ccccctgccc cacccgtccc ctgtcgcaca ttcctccctc cgcagggctg  180
gctcaccagg ccccagccca catgcctgct taaagccctc tccatcctct gcctcaccca  240
gtccccgctg agactgagca gacgcctcca                                    270

SEQ ID NO: 35          moltype = DNA  length = 260
FEATURE                Location/Qualifiers
source                 1..260
```

```
                        mol_type = other DNA
                        organism = Homo sapiens
SEQUENCE: 35
tagcttatct gagcagctgg aggaccacat gggcttatat ggcgtggggt acatgttcct  60
gtagccttgt ccctggcacc tgccaaaata gcagccaaca ccccccaccc ccaccgccat  120
ccccctgccc cacccgtccc ctgtcgcaca ttcctccctc cgcagggctg gctcaccagg  180
ccccagccca catgcctgct taaagccctc tccatcctct gcctcaccca gtccccgctg  240
agactgagca gacgcctcca                                              260

SEQ ID NO: 36           moltype = DNA  length = 250
FEATURE                 Location/Qualifiers
source                  1..250
                        mol_type = other DNA
                        organism = Homo sapiens
SEQUENCE: 36
gagcagctgg aggaccacat gggcttatat ggcgtggggt acatgttcct gtagccttgt  60
ccctggcacc tgccaaaata gcagccaaca ccccccaccc ccaccgccat ccccctgccc  120
cacccgtccc ctgtcgcaca ttcctccctc cgcagggctg gctcaccagg ccccagccca  180
catgcctgct taaagccctc tccatcctct gcctcaccca gtccccgctg agactgagca  240
gacgcctcca                                                         250

SEQ ID NO: 37           moltype = DNA  length = 240
FEATURE                 Location/Qualifiers
source                  1..240
                        mol_type = other DNA
                        organism = Homo sapiens
SEQUENCE: 37
aggaccacat gggcttatat ggcgtggggt acatgttcct gtagccttgt ccctggcacc  60
tgccaaaata gcagccaaca ccccccaccc ccaccgccat ccccctgccc cacccgtccc  120
ctgtcgcaca ttcctccctc cgcagggctg gctcaccagg ccccagccca catgcctgct  180
taaagccctc tccatcctct gcctcaccca gtccccgctg agactgagca gacgcctcca  240

SEQ ID NO: 38           moltype = DNA  length = 230
FEATURE                 Location/Qualifiers
source                  1..230
                        mol_type = other DNA
                        organism = Homo sapiens
SEQUENCE: 38
gggcttatat ggcgtggggt acatgttcct gtagccttgt ccctggcacc tgccaaaata  60
gcagccaaca ccccccaccc ccaccgccat ccccctgccc cacccgtccc ctgtcgcaca  120
ttcctccctc cgcagggctg gctcaccagg ccccagccca catgcctgct taaagccctc  180
tccatcctct gcctcaccca gtccccgctg agactgagca gacgcctcca             230

SEQ ID NO: 39           moltype = DNA  length = 220
FEATURE                 Location/Qualifiers
source                  1..220
                        mol_type = other DNA
                        organism = Homo sapiens
SEQUENCE: 39
ggcgtggggt acatgttcct gtagccttgt ccctggcacc tgccaaaata gcagccaaca  60
ccccccaccc ccaccgccat ccccctgccc cacccgtccc ctgtcgcaca ttcctccctc  120
cgcagggctg gctcaccagg ccccagccca catgcctgct taaagccctc tccatcctct  180
gcctcaccca gtccccgctg agactgagca gacgcctcca                        220

SEQ ID NO: 40           moltype = DNA  length = 210
FEATURE                 Location/Qualifiers
source                  1..210
                        mol_type = other DNA
                        organism = Homo sapiens
SEQUENCE: 40
acatgttcct gtagccttgt ccctggcacc tgccaaaata gcagccaaca ccccccaccc  60
ccaccgccat ccccctgccc cacccgtccc ctgtcgcaca ttcctccctc cgcagggctg  120
gctcaccagg ccccagccca catgcctgct taaagccctc tccatcctct gcctcaccca  180
gtccccgctg agactgagca gacgcctcca                                   210

SEQ ID NO: 41           moltype = DNA  length = 200
FEATURE                 Location/Qualifiers
source                  1..200
                        mol_type = other DNA
                        organism = Homo sapiens
SEQUENCE: 41
gtagccttgt ccctggcacc tgccaaaata gcagccaaca ccccccaccc ccaccgccat  60
ccccctgccc cacccgtccc ctgtcgcaca ttcctccctc cgcagggctg gctcaccagg  120
ccccagccca catgcctgct taaagccctc tccatcctct gcctcaccca gtccccgctg  180
agactgagca gacgcctcca                                              200

SEQ ID NO: 42           moltype = DNA  length = 550
FEATURE                 Location/Qualifiers
source                  1..550
```

```
                        mol_type = other DNA
                        organism = Homo sapiens
SEQUENCE: 42
gtcatggaga agacccacct tgcagatgtc ctcactgggg ctggcagagc cggcaacctg  60
cctaaggctg ctcagtccat taggagccag tagcctggaa gatgtcttta cccccagcat  120
cagttcaagt ggagcagcac ataactcttg ccctctgcct tccaagattc tggtgctgag  180
acttatggag tgtcttggag gttgccttct gccccccaac cctgctccca gctggccctc  240
ccaggcctgg gttgctggcc tctgctttat caggattctc aagagggaca gctggtttat  300
gttgcatgac tgttccctgc atatctgctc tggttttaaa tagcttatct gagcagctgg  360
aggaccacat gggcttatat ggcgtggggt acatgttcct gtagccttgt ccctggcacc  420
tgccaaaata gcagccaaca ccccccaccc ccaccgccat ccccctgccc cacccgtccc  480
ctgtcgcaca ttcctccctc cgcagggctg gctcaccagg ccccagccca catgcctgct  540
taaagccctc                                                         550

SEQ ID NO: 43           moltype = DNA  length = 540
FEATURE                 Location/Qualifiers
source                  1..540
                        mol_type = other DNA
                        organism = Homo sapiens
SEQUENCE: 43
agacccacct tgcagatgtc ctcactgggg ctggcagagc cggcaacctg cctaaggctg  60
ctcagtccat taggagccag tagcctggaa gatgtcttta cccccagcat cagttcaagt  120
ggagcagcac ataactcttg ccctctgcct tccaagattc tggtgctgag acttatggag  180
tgtcttggag gttgccttct gccccccaac cctgctccca gctggccctc ccaggcctgg  240
gttgctggcc tctgctttat caggattctc aagagggaca gctggtttat gttgcatgac  300
tgttccctgc atatctgctc tggttttaaa tagcttatct gagcagctgg aggaccacat  360
gggcttatat ggcgtggggt acatgttcct gtagccttgt ccctggcacc tgccaaaata  420
gcagccaaca ccccccaccc ccaccgccat ccccctgccc cacccgtccc ctgtcgcaca  480
ttcctccctc cgcagggctg gctcaccagg ccccagccca catgcctgct taaagccctc  540

SEQ ID NO: 44           moltype = DNA  length = 530
FEATURE                 Location/Qualifiers
source                  1..530
                        mol_type = other DNA
                        organism = Homo sapiens
SEQUENCE: 44
tgcagatgtc ctcactgggg ctggcagagc cggcaacctg cctaaggctg ctcagtccat  60
taggagccag tagcctggaa gatgtcttta cccccagcat cagttcaagt ggagcagcac  120
ataactcttg ccctctgcct tccaagattc tggtgctgag acttatggag tgtcttggag  180
gttgccttct gccccccaac cctgctccca gctggccctc ccaggcctgg gttgctggcc  240
tctgctttat caggattctc aagagggaca gctggtttat gttgcatgac tgttccctgc  300
atatctgctc tggttttaaa tagcttatct gagcagctgg aggaccacat gggcttatat  360
ggcgtggggt acatgttcct gtagccttgt ccctggcacc tgccaaaata gcagccaaca  420
ccccccaccc ccaccgccat ccccctgccc cacccgtccc ctgtcgcaca ttcctccctc  480
cgcagggctg gctcaccagg ccccagccca catgcctgct taaagccctc             530

SEQ ID NO: 45           moltype = DNA  length = 520
FEATURE                 Location/Qualifiers
source                  1..520
                        mol_type = other DNA
                        organism = Homo sapiens
SEQUENCE: 45
ctcactgggg ctggcagagc cggcaacctg cctaaggctg ctcagtccat taggagccag  60
tagcctggaa gatgtcttta cccccagcat cagttcaagt ggagcagcac ataactcttg  120
ccctctgcct tccaagattc tggtgctgag acttatggag tgtcttggag gttgccttct  180
gccccccaac cctgctccca gctggccctc ccaggcctgg gttgctggcc tctgctttat  240
caggattctc aagagggaca gctggtttat gttgcatgac tgttccctgc atatctgctc  300
tggttttaaa tagcttatct gagcagctgg aggaccacat gggcttatat ggcgtggggt  360
acatgttcct gtagccttgt ccctggcacc tgccaaaata gcagccaaca ccccccaccc  420
ccaccgccat ccccctgccc cacccgtccc ctgtcgcaca ttcctccctc cgcagggctg  480
gctcaccagg ccccagccca catgcctgct taaagccctc                        520

SEQ ID NO: 46           moltype = DNA  length = 510
FEATURE                 Location/Qualifiers
source                  1..510
                        mol_type = other DNA
                        organism = Homo sapiens
SEQUENCE: 46
ctggcagagc cggcaacctg cctaaggctg ctcagtccat taggagccag tagcctggaa  60
gatgtcttta cccccagcat cagttcaagt ggagcagcac ataactcttg ccctctgcct  120
tccaagattc tggtgctgag acttatggag tgtcttggag gttgccttct gccccccaac  180
cctgctccca gctggccctc ccaggcctgg gttgctggcc tctgctttat caggattctc  240
aagagggaca gctggtttat gttgcatgac tgttccctgc atatctgctc tggttttaaa  300
tagcttatct gagcagctgg aggaccacat gggcttatat ggcgtggggt acatgttcct  360
gtagccttgt ccctggcacc tgccaaaata gcagccaaca ccccccaccc ccaccgccat  420
ccccctgccc cacccgtccc ctgtcgcaca ttcctccctc cgcagggctg gctcaccagg  480
ccccagccca catgcctgct taaagccctc                                   510

SEQ ID NO: 47           moltype = DNA  length = 500
```

```
FEATURE                 Location/Qualifiers
source                  1..500
                        mol_type = other DNA
                        organism = Homo sapiens
SEQUENCE: 47
cggcaacctg cctaaggctg ctcagtccat taggagccag tagcctggaa gatgtcttta  60
cccccagcat cagttcaagt ggagcagcac ataactcttg ccctctgcct tccaagattc  120
tggtgctgag acttatggag tgtcttggag gttgccttct gccccccaac cctgctccca  180
gctggccctc ccaggcctgg gttgctggcc tctgctttat caggattctc aagagggaca  240
gctggtttat gttgcatgac tgttccctgc atatctgctc tggttttaaa tagcttatct  300
gagcagctgg aggaccacat gggcttatat ggcgtggggt acatgttcct gtagccttgt  360
ccctggcacc tgccaaaata gcagccaaca ccccccaccc ccaccgccat ccccctgccc  420
cacccgtccc ctgtcgcaca ttcctccctc cgcagggctg gctcaccagg ccccagccca  480
catgcctgct taaagccctc                                              500

SEQ ID NO: 48           moltype = DNA  length = 490
FEATURE                 Location/Qualifiers
source                  1..490
                        mol_type = other DNA
                        organism = Homo sapiens
SEQUENCE: 48
cctaaggctg ctcagtccat taggagccag tagcctggaa gatgtcttta cccccagcat  60
cagttcaagt ggagcagcac ataactcttg ccctctgcct tccaagattc tggtgctgag  120
acttatggag tgtcttggag gttgccttct gccccccaac cctgctccca gctggccctc  180
ccaggcctgg gttgctggcc tctgctttat caggattctc aagagggaca gctggtttat  240
gttgcatgac tgttccctgc atatctgctc tggttttaaa tagcttatct gagcagctgg  300
aggaccacat gggcttatat ggcgtggggt acatgttcct gtagccttgt ccctggcacc  360
tgccaaaata gcagccaaca ccccccaccc ccaccgccat ccccctgccc cacccgtccc  420
ctgtcgcaca ttcctccctc cgcagggctg gctcaccagg ccccagccca catgcctgct  480
taaagccctc                                                         490

SEQ ID NO: 49           moltype = DNA  length = 480
FEATURE                 Location/Qualifiers
source                  1..480
                        mol_type = other DNA
                        organism = Homo sapiens
SEQUENCE: 49
ctcagtccat taggagccag tagcctggaa gatgtcttta cccccagcat cagttcaagt  60
ggagcagcac ataactcttg ccctctgcct tccaagattc tggtgctgag acttatggag  120
tgtcttggag gttgccttct gccccccaac cctgctccca gctggccctc ccaggcctgg  180
gttgctggcc tctgctttat caggattctc aagagggaca gctggtttat gttgcatgac  240
tgttccctgc atatctgctc tggttttaaa tagcttatct gagcagctgg aggaccacat  300
gggcttatat ggcgtggggt acatgttcct gtagccttgt ccctggcacc tgccaaaata  360
gcagccaaca ccccccaccc ccaccgccat ccccctgccc cacccgtccc ctgtcgcaca  420
ttcctccctc cgcagggctg gctcaccagg ccccagccca catgcctgct taaagccctc  480

SEQ ID NO: 50           moltype = DNA  length = 470
FEATURE                 Location/Qualifiers
source                  1..470
                        mol_type = other DNA
                        organism = Homo sapiens
SEQUENCE: 50
taggagccag tagcctggaa gatgtcttta cccccagcat cagttcaagt ggagcagcac  60
ataactcttg ccctctgcct tccaagattc tggtgctgag acttatggag tgtcttggag  120
gttgccttct gccccccaac cctgctccca gctggccctc ccaggcctgg gttgctggcc  180
tctgctttat caggattctc aagagggaca gctggtttat gttgcatgac tgttccctgc  240
atatctgctc tggttttaaa tagcttatct gagcagctgg aggaccacat gggcttatat  300
ggcgtggggt acatgttcct gtagccttgt ccctggcacc tgccaaaata gcagccaaca  360
ccccccaccc ccaccgccat ccccctgccc cacccgtccc ctgtcgcaca ttcctccctc  420
cgcagggctg gctcaccagg ccccagccca catgcctgct taaagccctc             470

SEQ ID NO: 51           moltype = DNA  length = 460
FEATURE                 Location/Qualifiers
source                  1..460
                        mol_type = other DNA
                        organism = Homo sapiens
SEQUENCE: 51
tagcctggaa gatgtcttta cccccagcat cagttcaagt ggagcagcac ataactcttg  60
ccctctgcct tccaagattc tggtgctgag acttatggag tgtcttggag gttgccttct  120
gccccccaac cctgctccca gctggccctc ccaggcctgg gttgctggcc tctgctttat  180
caggattctc aagagggaca gctggtttat gttgcatgac tgttccctgc atatctgctc  240
tggttttaaa tagcttatct gagcagctgg aggaccacat gggcttatat ggcgtggggt  300
acatgttcct gtagccttgt ccctggcacc tgccaaaata gcagccaaca ccccccaccc  360
ccaccgccat ccccctgccc cacccgtccc ctgtcgcaca ttcctccctc cgcagggctg  420
gctcaccagg ccccagccca catgcctgct taaagccctc                        460

SEQ ID NO: 52           moltype = DNA  length = 450
FEATURE                 Location/Qualifiers
source                  1..450
```

```
                         mol_type = other DNA
                         organism = Homo sapiens
SEQUENCE: 52
gatgtcttta cccccagcat cagttcaagt ggagcagcac ataactcttg ccctctgcct  60
tccaagattc tggtgctgag acttatggag tgtcttggag gttgccttct gccccccaac  120
cctgctccca gctggccctc ccaggcctgg gttgctggcc tctgctttat caggattctc  180
aagagggaca gctggtttat gttgcatgac tgttccctgc atatctgctc tggttttaaa  240
tagcttatct gagcagctgg aggaccacat gggcttatat ggcgtggggt acatgttcct  300
gtagccttgt ccctggcacc tgccaaaata gcagccaaca ccccccaccc ccaccgccat  360
ccccctgccc cacccgtccc ctgtcgcaca ttcctccctc cgcagggctg gctcaccagg  420
ccccagccca catgcctgct taaagccctc                                   450

SEQ ID NO: 53            moltype = DNA  length = 440
FEATURE                  Location/Qualifiers
source                   1..440
                         mol_type = other DNA
                         organism = Homo sapiens
SEQUENCE: 53
cccccagcat cagttcaagt ggagcagcac ataactcttg ccctctgcct tccaagattc  60
tggtgctgag acttatggag tgtcttggag gttgccttct gccccccaac cctgctccca  120
gctggccctc ccaggcctgg gttgctggcc tctgctttat caggattctc aagagggaca  180
gctggtttat gttgcatgac tgttccctgc atatctgctc tggttttaaa tagcttatct  240
gagcagctgg aggaccacat gggcttatat ggcgtggggt acatgttcct gtagccttgt  300
ccctggcacc tgccaaaata gcagccaaca ccccccaccc ccaccgccat ccccctgccc  360
cacccgtccc ctgtcgcaca ttcctccctc cgcagggctg gctcaccagg ccccagccca  420
catgcctgct taaagccctc                                              440

SEQ ID NO: 54            moltype = DNA  length = 430
FEATURE                  Location/Qualifiers
source                   1..430
                         mol_type = other DNA
                         organism = Homo sapiens
SEQUENCE: 54
cagttcaagt ggagcagcac ataactcttg ccctctgcct tccaagattc tggtgctgag  60
acttatggag tgtcttggag gttgccttct gccccccaac cctgctccca gctggccctc  120
ccaggcctgg gttgctggcc tctgctttat caggattctc aagagggaca gctggtttat  180
gttgcatgac tgttccctgc atatctgctc tggttttaaa tagcttatct gagcagctgg  240
aggaccacat gggcttatat ggcgtggggt acatgttcct gtagccttgt ccctggcacc  300
tgccaaaata gcagccaaca ccccccaccc ccaccgccat ccccctgccc cacccgtccc  360
ctgtcgcaca ttcctccctc cgcagggctg gctcaccagg ccccagccca catgcctgct  420
taaagccctc                                                         430

SEQ ID NO: 55            moltype = DNA  length = 420
FEATURE                  Location/Qualifiers
source                   1..420
                         mol_type = other DNA
                         organism = Homo sapiens
SEQUENCE: 55
ggagcagcac ataactcttg ccctctgcct tccaagattc tggtgctgag acttatggag  60
tgtcttggag gttgccttct gccccccaac cctgctccca gctggccctc ccaggcctgg  120
gttgctggcc tctgctttat caggattctc aagagggaca gctggtttat gttgcatgac  180
tgttccctgc atatctgctc tggttttaaa tagcttatct gagcagctgg aggaccacat  240
gggcttatat ggcgtggggt acatgttcct gtagccttgt ccctggcacc tgccaaaata  300
gcagccaaca ccccccaccc ccaccgccat ccccctgccc cacccgtccc ctgtcgcaca  360
ttcctccctc cgcagggctg gctcaccagg ccccagccca catgcctgct taaagccctc  420

SEQ ID NO: 56            moltype = DNA  length = 410
FEATURE                  Location/Qualifiers
source                   1..410
                         mol_type = other DNA
                         organism = Homo sapiens
SEQUENCE: 56
ataactcttg ccctctgcct tccaagattc tggtgctgag acttatggag tgtcttggag  60
gttgccttct gccccccaac cctgctccca gctggccctc ccaggcctgg gttgctggcc  120
tctgctttat caggattctc aagagggaca gctggtttat gttgcatgac tgttccctgc  180
atatctgctc tggttttaaa tagcttatct gagcagctgg aggaccacat gggcttatat  240
ggcgtggggt acatgttcct gtagccttgt ccctggcacc tgccaaaata gcagccaaca  300
ccccccaccc ccaccgccat ccccctgccc cacccgtccc ctgtcgcaca ttcctccctc  360
cgcagggctg gctcaccagg ccccagccca catgcctgct taaagccctc             410

SEQ ID NO: 57            moltype = DNA  length = 400
FEATURE                  Location/Qualifiers
source                   1..400
                         mol_type = other DNA
                         organism = Homo sapiens
SEQUENCE: 57
ccctctgcct tccaagattc tggtgctgag acttatggag tgtcttggag gttgccttct  60
gccccccaac cctgctccca gctggccctc ccaggcctgg gttgctggcc tctgctttat  120
caggattctc aagagggaca gctggtttat gttgcatgac tgttccctgc atatctgctc  180
```

```
tggttttaaa tagcttatct gagcagctgg aggaccacat gggcttatat ggcgtggggt  240
acatgttcct gtagccttgt ccctggcacc tgccaaaata gcagccaaca ccccccaccc  300
ccaccgccat ccccctgccc cacccgtccc ctgtcgcaca ttcctccctc cgcagggctg  360
gctcaccagg ccccagccca catgcctgct taaagccctc                         400

SEQ ID NO: 58          moltype = DNA  length = 390
FEATURE                Location/Qualifiers
source                 1..390
                       mol_type = other DNA
                       organism = Homo sapiens
SEQUENCE: 58
tccaagattc tggtgctgag acttatggag tgtcttggag gttgccttct gccccccaac  60
cctgctccca gctggccctc ccaggcctgg gttgctggcc tctgctttat caggattctc  120
aagagggaca gctggtttat gttgcatgac tgttccctgc atatctgctc tggttttaaa  180
tagcttatct gagcagctgg aggaccacat gggcttatat ggcgtggggt acatgttcct  240
gtagccttgt ccctggcacc tgccaaaata gcagccaaca ccccccaccc ccaccgccat  300
ccccctgccc cacccgtccc ctgtcgcaca ttcctccctc cgcagggctg gctcaccagg  360
ccccagccca catgcctgct taaagccctc                                    390

SEQ ID NO: 59          moltype = DNA  length = 380
FEATURE                Location/Qualifiers
source                 1..380
                       mol_type = other DNA
                       organism = Homo sapiens
SEQUENCE: 59
tggtgctgag acttatggag tgtcttggag gttgccttct gccccccaac cctgctccca  60
gctggccctc ccaggcctgg gttgctggcc tctgctttat caggattctc aagagggaca  120
gctggtttat gttgcatgac tgttccctgc atatctgctc tggttttaaa tagcttatct  180
gagcagctgg aggaccacat gggcttatat ggcgtggggt acatgttcct gtagccttgt  240
ccctggcacc tgccaaaata gcagccaaca ccccccaccc ccaccgccat ccccctgccc  300
cacccgtccc ctgtcgcaca ttcctccctc cgcagggctg gctcaccagg ccccagccca  360
catgcctgct taaagccctc                                               380

SEQ ID NO: 60          moltype = DNA  length = 370
FEATURE                Location/Qualifiers
source                 1..370
                       mol_type = other DNA
                       organism = Homo sapiens
SEQUENCE: 60
acttatggag tgtcttggag gttgccttct gccccccaac cctgctccca gctggccctc  60
ccaggcctgg gttgctggcc tctgctttat caggattctc aagagggaca gctggtttat  120
gttgcatgac tgttccctgc atatctgctc tggttttaaa tagcttatct gagcagctgg  180
aggaccacat gggcttatat ggcgtggggt acatgttcct gtagccttgt ccctggcacc  240
tgccaaaata gcagccaaca ccccccaccc ccaccgccat ccccctgccc cacccgtccc  300
ctgtcgcaca ttcctccctc cgcagggctg gctcaccagg ccccagccca catgcctgct  360
taaagccctc                                                          370

SEQ ID NO: 61          moltype = DNA  length = 360
FEATURE                Location/Qualifiers
source                 1..360
                       mol_type = other DNA
                       organism = Homo sapiens
SEQUENCE: 61
tgtcttggag gttgccttct gccccccaac cctgctccca gctggccctc ccaggcctgg  60
gttgctggcc tctgctttat caggattctc aagagggaca gctggtttat gttgcatgac  120
tgttccctgc atatctgctc tggttttaaa tagcttatct gagcagctgg aggaccacat  180
gggcttatat ggcgtggggt acatgttcct gtagccttgt ccctggcacc tgccaaaata  240
gcagccaaca ccccccaccc ccaccgccat ccccctgccc cacccgtccc ctgtcgcaca  300
ttcctccctc cgcagggctg gctcaccagg ccccagccca catgcctgct taaagccctc  360

SEQ ID NO: 62          moltype = DNA  length = 350
FEATURE                Location/Qualifiers
source                 1..350
                       mol_type = other DNA
                       organism = Homo sapiens
SEQUENCE: 62
gttgccttct gccccccaac cctgctccca gctggccctc ccaggcctgg gttgctggcc  60
tctgctttat caggattctc aagagggaca gctggtttat gttgcatgac tgttccctgc  120
atatctgctc tggttttaaa tagcttatct gagcagctgg aggaccacat gggcttatat  180
ggcgtggggt acatgttcct gtagccttgt ccctggcacc tgccaaaata gcagccaaca  240
ccccccaccc ccaccgccat ccccctgccc cacccgtccc ctgtcgcaca ttcctccctc  300
cgcagggctg gctcaccagg ccccagccca catgcctgct taaagccctc             350

SEQ ID NO: 63          moltype = DNA  length = 340
FEATURE                Location/Qualifiers
source                 1..340
                       mol_type = other DNA
                       organism = Homo sapiens
SEQUENCE: 63
```

```
gccccccaac cctgctccca gctggccctc ccaggcctgg gttgctggcc tctgctttat  60
caggattctc aagagggaca gctggtttat gttgcatgac tgttccctgc atatctgctc  120
tggttttaaa tagcttatct gagcagctgg aggaccacat gggcttatat ggcgtggggt  180
acatgttcct gtagccttgt ccctggcacc tgccaaaata gcagccaaca ccccccaccc  240
ccaccgccat ccccctgccc cacccgtccc ctgtcgcaca ttcctccctc cgcagggctg  300
gctcaccagg ccccagccca catgcctgct taaagccctc                        340

SEQ ID NO: 64          moltype = DNA  length = 330
FEATURE                Location/Qualifiers
source                 1..330
                       mol_type = other DNA
                       organism = Homo sapiens
SEQUENCE: 64
cctgctccca gctggccctc ccaggcctgg gttgctggcc tctgctttat caggattctc  60
aagagggaca gctggtttat gttgcatgac tgttccctgc atatctgctc tggttttaaa  120
tagcttatct gagcagctgg aggaccacat gggcttatat ggcgtggggt acatgttcct  180
gtagccttgt ccctggcacc tgccaaaata gcagccaaca ccccccaccc ccaccgccat  240
ccccctgccc cacccgtccc ctgtcgcaca ttcctccctc cgcagggctg gctcaccagg  300
ccccagccca catgcctgct taaagccctc                                   330

SEQ ID NO: 65          moltype = DNA  length = 320
FEATURE                Location/Qualifiers
source                 1..320
                       mol_type = other DNA
                       organism = Homo sapiens
SEQUENCE: 65
gctggccctc ccaggcctgg gttgctggcc tctgctttat caggattctc aagagggaca  60
gctggtttat gttgcatgac tgttccctgc atatctgctc tggttttaaa tagcttatct  120
gagcagctgg aggaccacat gggcttatat ggcgtggggt acatgttcct gtagccttgt  180
ccctggcacc tgccaaaata gcagccaaca ccccccaccc ccaccgccat ccccctgccc  240
cacccgtccc ctgtcgcaca ttcctccctc cgcagggctg gctcaccagg ccccagccca  300
catgcctgct taaagccctc                                              320

SEQ ID NO: 66          moltype = DNA  length = 310
FEATURE                Location/Qualifiers
source                 1..310
                       mol_type = other DNA
                       organism = Homo sapiens
SEQUENCE: 66
ccaggcctgg gttgctggcc tctgctttat caggattctc aagagggaca gctggtttat  60
gttgcatgac tgttccctgc atatctgctc tggttttaaa tagcttatct gagcagctgg  120
aggaccacat gggcttatat ggcgtggggt acatgttcct gtagccttgt ccctggcacc  180
tgccaaaata gcagccaaca ccccccaccc ccaccgccat ccccctgccc cacccgtccc  240
ctgtcgcaca ttcctccctc cgcagggctg gctcaccagg ccccagccca catgcctgct  300
taaagccctc                                                         310

SEQ ID NO: 67          moltype = DNA  length = 300
FEATURE                Location/Qualifiers
source                 1..300
                       mol_type = other DNA
                       organism = Homo sapiens
SEQUENCE: 67
gttgctggcc tctgctttat caggattctc aagagggaca gctggtttat gttgcatgac  60
tgttccctgc atatctgctc tggttttaaa tagcttatct gagcagctgg aggaccacat  120
gggcttatat ggcgtggggt acatgttcct gtagccttgt ccctggcacc tgccaaaata  180
gcagccaaca ccccccaccc ccaccgccat ccccctgccc cacccgtccc ctgtcgcaca  240
ttcctccctc cgcagggctg gctcaccagg ccccagccca catgcctgct taaagccctc  300

SEQ ID NO: 68          moltype = DNA  length = 290
FEATURE                Location/Qualifiers
source                 1..290
                       mol_type = other DNA
                       organism = Homo sapiens
SEQUENCE: 68
tctgctttat caggattctc aagagggaca gctggtttat gttgcatgac tgttccctgc  60
atatctgctc tggttttaaa tagcttatct gagcagctgg aggaccacat gggcttatat  120
ggcgtggggt acatgttcct gtagccttgt ccctggcacc tgccaaaata gcagccaaca  180
ccccccaccc ccaccgccat ccccctgccc cacccgtccc ctgtcgcaca ttcctccctc  240
cgcagggctg gctcaccagg ccccagccca catgcctgct taaagccctc             290

SEQ ID NO: 69          moltype = DNA  length = 280
FEATURE                Location/Qualifiers
source                 1..280
                       mol_type = other DNA
                       organism = Homo sapiens
SEQUENCE: 69
caggattctc aagagggaca gctggtttat gttgcatgac tgttccctgc atatctgctc  60
tggttttaaa tagcttatct gagcagctgg aggaccacat gggcttatat ggcgtggggt  120
acatgttcct gtagccttgt ccctggcacc tgccaaaata gcagccaaca ccccccaccc  180
```

-continued

```
ccaccgccat ccccctgccc cacccgtccc ctgtcgcaca ttcctccctc cgcagggctg  240
gctcaccagg ccccagccca catgcctgct taaagccctc                        280

SEQ ID NO: 70          moltype = DNA  length = 270
FEATURE                Location/Qualifiers
source                 1..270
                       mol_type = other DNA
                       organism = Homo sapiens
SEQUENCE: 70
aagagggaca gctggtttat gttgcatgac tgttccctgc atatctgctc tggttttaaa  60
tagcttatct gagcagctgg aggaccacat gggcttatat ggcgtggggt acatgttcct  120
gtagccttgt ccctggcacc tgccaaaata gcagccaaca ccccccaccc ccaccgccat  180
ccccctgccc cacccgtccc ctgtcgcaca ttcctccctc cgcagggctg gctcaccagg  240
ccccagccca catgcctgct taaagccctc                                   270

SEQ ID NO: 71          moltype = DNA  length = 260
FEATURE                Location/Qualifiers
source                 1..260
                       mol_type = other DNA
                       organism = Homo sapiens
SEQUENCE: 71
gctggtttat gttgcatgac tgttccctgc atatctgctc tggttttaaa tagcttatct  60
gagcagctgg aggaccacat gggcttatat ggcgtggggt acatgttcct gtagccttgt  120
ccctggcacc tgccaaaata gcagccaaca ccccccaccc ccaccgccat ccccctgccc  180
cacccgtccc ctgtcgcaca ttcctccctc cgcagggctg gctcaccagg ccccagccca  240
catgcctgct taaagccctc                                              260

SEQ ID NO: 72          moltype = DNA  length = 250
FEATURE                Location/Qualifiers
source                 1..250
                       mol_type = other DNA
                       organism = Homo sapiens
SEQUENCE: 72
gttgcatgac tgttccctgc atatctgctc tggttttaaa tagcttatct gagcagctgg  60
aggaccacat gggcttatat ggcgtggggt acatgttcct gtagccttgt ccctggcacc  120
tgccaaaata gcagccaaca ccccccaccc ccaccgccat ccccctgccc cacccgtccc  180
ctgtcgcaca ttcctccctc cgcagggctg gctcaccagg ccccagccca catgcctgct  240
taaagccctc                                                         250

SEQ ID NO: 73          moltype = DNA  length = 240
FEATURE                Location/Qualifiers
source                 1..240
                       mol_type = other DNA
                       organism = Homo sapiens
SEQUENCE: 73
tgttccctgc atatctgctc tggttttaaa tagcttatct gagcagctgg aggaccacat  60
gggcttatat ggcgtggggt acatgttcct gtagccttgt ccctggcacc tgccaaaata  120
gcagccaaca ccccccaccc ccaccgccat ccccctgccc cacccgtccc ctgtcgcaca  180
ttcctccctc cgcagggctg gctcaccagg ccccagccca catgcctgct taaagccctc  240

SEQ ID NO: 74          moltype = DNA  length = 230
FEATURE                Location/Qualifiers
source                 1..230
                       mol_type = other DNA
                       organism = Homo sapiens
SEQUENCE: 74
atatctgctc tggttttaaa tagcttatct gagcagctgg aggaccacat gggcttatat  60
ggcgtggggt acatgttcct gtagccttgt ccctggcacc tgccaaaata gcagccaaca  120
ccccccaccc ccaccgccat ccccctgccc cacccgtccc ctgtcgcaca ttcctccctc  180
cgcagggctg gctcaccagg ccccagccca catgcctgct taaagccctc             230

SEQ ID NO: 75          moltype = DNA  length = 220
FEATURE                Location/Qualifiers
source                 1..220
                       mol_type = other DNA
                       organism = Homo sapiens
SEQUENCE: 75
tggttttaaa tagcttatct gagcagctgg aggaccacat gggcttatat ggcgtggggt  60
acatgttcct gtagccttgt ccctggcacc tgccaaaata gcagccaaca ccccccaccc  120
ccaccgccat ccccctgccc cacccgtccc ctgtcgcaca ttcctccctc cgcagggctg  180
gctcaccagg ccccagccca catgcctgct taaagccctc                        220

SEQ ID NO: 76          moltype = DNA  length = 210
FEATURE                Location/Qualifiers
source                 1..210
                       mol_type = other DNA
                       organism = Homo sapiens
SEQUENCE: 76
tagcttatct gagcagctgg aggaccacat gggcttatat ggcgtggggt acatgttcct  60
```

```
gtagccttgt ccctggcacc tgccaaaata gcagccaaca ccccccaccc ccaccgccat  120
ccccctgccc cacccgtccc ctgtcgcaca ttcctccctc cgcagggctg gctcaccagg  180
ccccagccca catgcctgct taaagccctc                                   210

SEQ ID NO: 77          moltype = DNA  length = 200
FEATURE                Location/Qualifiers
source                 1..200
                       mol_type = other DNA
                       organism = Homo sapiens
SEQUENCE: 77
gagcagctgg aggaccacat gggcttatat ggcgtggggt acatgttcct gtagccttgt  60
ccctggcacc tgccaaaata gcagccaaca ccccccaccc ccaccgccat ccccctgccc  120
cacccgtccc ctgtcgcaca ttcctccctc cgcagggctg gctcaccagg ccccagccca  180
catgcctgct taaagccctc                                              200

SEQ ID NO: 78          moltype = DNA  length = 550
FEATURE                Location/Qualifiers
source                 1..550
                       mol_type = other DNA
                       organism = Homo sapiens
SEQUENCE: 78
gtcatggaga agacccacct tgcagatgtc ctcactgggg ctggcagagc cggcaacctg  60
cctaaggctg ctcagtccat taggagccag tagcctggaa gatgtcttta cccccagcat  120
cagttcaagt ggagcagcac ataactcttg ccctctgcct tccaagattc tggtgctgag  180
acttatggag tgtcttggag gttgccttct gccccccaac cctgctccca gctggccctc  240
ccaggcctgg gttgctggcc tctgctttat caggattctc aagagggaca gctggtttat  300
gttgcatgac tgttccctgc atatctgctc tggttttaaa tagcttatct gagcagctgg  360
aggaccacat gggcttatat ggcgtggggt acatgttcct gtagccttgt ccctggcacc  420
tgccaaaata gcagccaaca ccccccaccc ccaccgccat ccccctgccc cacccgtccc  480
ctgtcgcaca ttcctccctc cgcagggctg gctcaccagg ccccagccca catgcctgct  540
taaagccctc                                                         550

SEQ ID NO: 79          moltype = DNA  length = 500
FEATURE                Location/Qualifiers
source                 1..500
                       mol_type = other DNA
                       organism = Homo sapiens
SEQUENCE: 79
gtcatggaga agacccacct tgcagatgtc ctcactgggg ctggcagagc cggcaacctg  60
cctaaggctg ctcagtccat taggagccag tagcctggaa gatgtcttta cccccagcat  120
cagttcaagt ggagcagcac ataactcttg ccctctgcct tccaagattc tggtgctgag  180
acttatggag tgtcttggag gttgccttct gccccccaac cctgctccca gctggccctc  240
ccaggcctgg gttgctggcc tctgctttat caggattctc aagagggaca gctggtttat  300
gttgcatgac tgttccctgc atatctgctc tggttttaaa tagcttatct gagcagctgg  360
aggaccacat gggcttatat ggcgtggggt acatgttcct gtagccttgt ccctggcacc  420
tgccaaaata gcagccaaca ccccccaccc ccaccgccat ccccctgccc cacccgtccc  480
ctgtcgcaca ttcctccctc                                              500

SEQ ID NO: 80          moltype = DNA  length = 450
FEATURE                Location/Qualifiers
source                 1..450
                       mol_type = other DNA
                       organism = Homo sapiens
SEQUENCE: 80
gtcatggaga agacccacct tgcagatgtc ctcactgggg ctggcagagc cggcaacctg  60
cctaaggctg ctcagtccat taggagccag tagcctggaa gatgtcttta cccccagcat  120
cagttcaagt ggagcagcac ataactcttg ccctctgcct tccaagattc tggtgctgag  180
acttatggag tgtcttggag gttgccttct gccccccaac cctgctccca gctggccctc  240
ccaggcctgg gttgctggcc tctgctttat caggattctc aagagggaca gctggtttat  300
gttgcatgac tgttccctgc atatctgctc tggttttaaa tagcttatct gagcagctgg  360
aggaccacat gggcttatat ggcgtggggt acatgttcct gtagccttgt ccctggcacc  420
tgccaaaata gcagccaaca ccccccaccc                                   450

SEQ ID NO: 81          moltype = DNA  length = 400
FEATURE                Location/Qualifiers
source                 1..400
                       mol_type = other DNA
                       organism = Homo sapiens
SEQUENCE: 81
gtcatggaga agacccacct tgcagatgtc ctcactgggg ctggcagagc cggcaacctg  60
cctaaggctg ctcagtccat taggagccag tagcctggaa gatgtcttta cccccagcat  120
cagttcaagt ggagcagcac ataactcttg ccctctgcct tccaagattc tggtgctgag  180
acttatggag tgtcttggag gttgccttct gccccccaac cctgctccca gctggccctc  240
ccaggcctgg gttgctggcc tctgctttat caggattctc aagagggaca gctggtttat  300
gttgcatgac tgttccctgc atatctgctc tggttttaaa tagcttatct gagcagctgg  360
aggaccacat gggcttatat ggcgtggggt acatgttcct                        400

SEQ ID NO: 82          moltype = DNA  length = 350
FEATURE                Location/Qualifiers
```

```
source                  1..350
                        mol_type = other DNA
                        organism = Homo sapiens
SEQUENCE: 82
gtcatggaga agacccacct tgcagatgtc ctcactgggg ctggcagagc cggcaacctg  60
cctaaggctg ctcagtccat taggagccag tagcctggaa gatgtcttta cccccagcat  120
cagttcaagt ggagcagcac ataactcttg ccctctgcct tccaagattc tggtgctgag  180
acttatggag tgtcttggag gttgccttct gccccccaac cctgctccca gctggccctc  240
ccaggcctgg gttgctggcc tctgctttat caggattctc aagagggaca gctggtttat  300
gttgcatgac tgttccctgc atatctgctc tggttttaaa tagcttatct             350

SEQ ID NO: 83           moltype = DNA  length = 300
FEATURE                 Location/Qualifiers
source                  1..300
                        mol_type = other DNA
                        organism = Homo sapiens
SEQUENCE: 83
gtcatggaga agacccacct tgcagatgtc ctcactgggg ctggcagagc cggcaacctg  60
cctaaggctg ctcagtccat taggagccag tagcctggaa gatgtcttta cccccagcat  120
cagttcaagt ggagcagcac ataactcttg ccctctgcct tccaagattc tggtgctgag  180
acttatggag tgtcttggag gttgccttct gccccccaac cctgctccca gctggccctc  240
ccaggcctgg gttgctggcc tctgctttat caggattctc aagagggaca gctggtttat  300

SEQ ID NO: 84           moltype = DNA  length = 250
FEATURE                 Location/Qualifiers
source                  1..250
                        mol_type = other DNA
                        organism = Homo sapiens
SEQUENCE: 84
gtcatggaga agacccacct tgcagatgtc ctcactgggg ctggcagagc cggcaacctg  60
cctaaggctg ctcagtccat taggagccag tagcctggaa gatgtcttta cccccagcat  120
cagttcaagt ggagcagcac ataactcttg ccctctgcct tccaagattc tggtgctgag  180
acttatggag tgtcttggag gttgccttct gccccccaac cctgctccca gctggccctc  240
ccaggcctgg                                                         250

SEQ ID NO: 85           moltype = DNA  length = 200
FEATURE                 Location/Qualifiers
source                  1..200
                        mol_type = other DNA
                        organism = Homo sapiens
SEQUENCE: 85
gtcatggaga agacccacct tgcagatgtc ctcactgggg ctggcagagc cggcaacctg  60
cctaaggctg ctcagtccat taggagccag tagcctggaa gatgtcttta cccccagcat  120
cagttcaagt ggagcagcac ataactcttg ccctctgcct tccaagattc tggtgctgag  180
acttatggag tgtcttggag                                              200

SEQ ID NO: 86           moltype = DNA  length = 3825
FEATURE                 Location/Qualifiers
source                  1..3825
                        mol_type = genomic DNA
                        organism = Homo sapiens
SEQUENCE: 86
atgcctgagc cggggaagaa gccagtctca gcttttagca agaagccacg gtcagtggaa  60
gtggccgcag gcagccctgc cgtgttcgag gccgagacag agcgggcagg agtgaaggtg  120
cgctggcagc gcggaggcag tgacatcagc gccagcaaca agtacggcct ggccacagag  180
ggcacacggc atacgctgac agtgcgggaa gtgggccctg ccgaccaggg atcttacgca  240
gtcattgctg gctcctccaa ggtcaagttc gacctcaagg tcatagaggc agagaaggca  300
gagcccatgc tggcccctgc ccctgcccct gctgaggcca ctggagcccc tggagaagcc  360
ccggccccag ccgctgagct gggagaaagt gccccaagtc ccaaagggtc aagctcagca  420
gctctcaatg gtcctacccc tggagccccc gatgacccca ttggcctctt cgtgatgcgg  480
ccacaggatg gcgaggtgac cgtgggtggc agcatcacct tctcagcccg cgtggccggc  540
gccagcctcc tgaagccgcc tgtggtcaag tggttcaagg gcaaatgggt ggacctgagc  600
agcaaggtgg gccagcacct gcagctgcac gacagctacg accgcgccag caaggtctat  660
ctgttcgagc tgcacatcac cgatgcccag cctgccttca ctggcagcta ccgctgtgag  720
gtgtccacca aggacaaatt tgactgctcc aacttcaatc tcactgtcca cgaggccatg  780
ggcaccggag acctggacct cctatcagcc ttccgccgca cgagcctggc tggaggtggt  840
cggcggatca gtgatagcca tgaggacact gggattctgg acttcagctc actgctgaaa  900
aagagagaca gtttccggac cccgagggac tcgaagctgg aggcaccagc agaggaggac  960
gtgtgggaga tcctacggca ggcaccccca tctgagtacg agcgcatcgc cttccagtac  1020
ggcgtcactg acctgcgcgg catgctaaag aggctcaagg gcatgaggcg cgatgagaag  1080
aagagcacag cctttcagaa gaagctggag ccggcctacc aggtgagcaa aggccacaag  1140
atccggctga ccgtggaact ggctgaccat gacgctgagg tcaaatggct caagaatggc  1200
caggagatcc agatgagcgg cagcaagtac atctttgagt ccatcggtgc caagcgtacc  1260
ctgaccatca gccagtgctc attggcggac gacgcagcct accagtgcgt ggtgggtggc  1320
gagaagtgta gcacggagct ctttgtgaaa gagcccccctg tgctcatcac gcgcccccttg  1380
gaggaccagc tggtgatggt ggggcagcgg gtggagtttg agtgtgaagt atcggaggag  1440
ggggcgcaag tcaaatggct gaaggacggg gtggagctga cccgggagga gaccttcaaa  1500
taccggttca agaaggacgg gcagagacac cacctgatca tcaacgaggc catgctggag  1560
gacgcggggc actatgcact gtgcactagc gggggccagg cgctggctga gctcattgtg  1620
```

-continued

```
caggaaaaga agctggaggt gtaccagagc atcgcagacc tgatggtggg cgcaaaggac  1680
caggcggtgt tcaaatgtga ggtctcagat gagaatgttc ggggtgtgtg gctgaagaat  1740
gggaaggagc tggtgcccga cagccgcata aaggtgtccc acatcgggcg ggtccacaaa  1800
ctgaccattg acgacgtcac acctgccgac gaggctgact acagctttgt gcccgagggc  1860
ttcgcctgca acctgtcagc caagctccac ttcatggagg tcaagattga cttcgtaccc  1920
aggcaggaac ctcccaagat ccacctggac tgcccaggcc gcataccaga caccattgtg  1980
gttgtagctg gaaataagct acgtctggac gtccctatct ctggggaccc cgctcccact  2040
gtgatctggc agaaggctat cacgcagggg aataaggccc cagccaggcc agccccagat  2100
gccccagagg acacaggtga cagcgatgag tgggtgtttg acaagaagct gctgtgtgag  2160
accgagggcc gggtccgcgt ggagaccacc aaggaccgca gcatcttcac ggtcgagggg  2220
gcagagaagg aagatgaggg cgtctacacg gtcacagtga agaaccctgt gggcgaggac  2280
caggtcaacc tcacagtcaa ggtcatcgac gtgccagacg cacctgcggc ccccaagatc  2340
agcaacgtgg gagaggactc ctgcacagta cagtgggagc cgcctgccta cgatggcggg  2400
cagcccatcc tgggctacat cctggagcgc aagaagaaga agagctaccg gtggatgcgg  2460
ctgaacttcg acctgattca ggagctgagt catgaagcgc ggcgcatgat cgagggcgtg  2520
gtgtacgaga tgcgcgtcta cgcggtcaac gccatcggca tgtccaggcc cagccctgcc  2580
tcccagccct tcatgcctat cggtcccccc agcgaaccca cccacctggc agtagaggac  2640
gtctctgaca ccacggtctc cctcaagtgg cggcccccag agcgcgtggg agcaggaggc  2700
ctggatggct acagcgtgga gtactgccca gagggctgct cagagtgggt ggctgccctg  2760
caggggctga cagagcacac atcgatactg gtgaaggacc tgcccacggg ggcccggctg  2820
cttttccgag tgcgggcaca caatatggca gggcctggag cccctgttac caccacggag  2880
ccggtgacag tgcaggagat cctgcaacgg ccacggcttc agctgcccag gcacctgcgc  2940
cagaccattc agaagaaggt cggggagcct gtgaaccttc tcatcccttt ccagggcaag  3000
ccccggcctc aggtgacctg gaccaaagag gggcagcccc tggcaggcga ggaggtgagc  3060
atccgcaaca gccccacaga caccatcctg ttcatccggg ccgctcgccg cgtgcattca  3120
ggcacttacc aggtgacggt gcgcattgag aacatggagg acaaggccac gctggtgctg  3180
caggttgttg acaagccaag tcctctccag gatctccggg tgactgacgc ctggggtctt  3240
aatgtggctc tggagtggaa gccaccccag gatgtcggca acacggaact ctgggggtac  3300
acagtgcaga aagccgacaa gaagaccatg gagtggttca ccgtcttgga gcattaccgc  3360
cgcacccact gcgtggtgcc agagctcatc attggcaatg gctactactt ccgcgtcttc  3420
agccagaata tggttggctt tagtgacaga gcggccacca ccaaggagcc cgtctttatc  3480
cccagaccag gcatcaccta tgagccaccc aactataagg ccctggactt ctccgaggcc  3540
ccaagcttca cccagcccct ggtgaaccgc tcggtcatcg cgggctacac tgctatgctc  3600
tgctgtgctg tccggggtag ccccaagccc aagatttcct ggttcaagaa tggcctggac  3660
ctgggagaag acgcccgctt ccgcatgttc agcaagcagg gagtgttgac tctggagatt  3720
agaaagccct gccccttga cgggggcatc tatgtctgca gggccaccaa cttacagggc  3780
gaggcacggt gtgagtgccg cctggaggtg cgagtgcctc agtaa                3825
```

```
SEQ ID NO: 87           moltype = DNA  length = 3546
FEATURE                 Location/Qualifiers
source                  1..3546
                        mol_type = other DNA
                        organism = Homo sapiens
SEQUENCE: 87
atgcctgagc cggggaagaa gccagtctca gcttttagca agaagccacg gtcagtggaa  60
gtggccgcag gcagccctgc cgtgttcgag gccgagacag agcgggcagg agtgaaggtg  120
cgctggcagc gcggaggcag tgacatcagc gccagcaaca agtacggcct ggccacagag  180
ggcacacggc atacgctgac agtgcgggaa gtgggccctg ccgaccaggg atcttacgca  240
gtcattgctg gctcctccaa ggtcaagttc gacctcaagg tcatagaggc agagaaggca  300
gagcccatgc tggcccctgc ccctgcccct gctgaggcca ctggagcccc tggagaagcc  360
ccggccccag ccgctgagct gggagaaagt gccccaagtc ccaaagggtc aagctcagca  420
gctctcaatg gtcctacccc tggagccccc gatgacccca ttggcctctt cgtgatgcgg  480
ccacaggatg gcgaggtgac cgtgggtggc agcatcacct tctcagcccg cgtggccggc  540
gccagcctcc tgaagccgcc tgtggtcaag tggttcaagg gcaaatgggt ggacctgagc  600
agcaaggtgg gccagcacct gcagctgcac gacagctacg accgcgccag caaggtctat  660
ctgttcgagc tgcacatcac cgatgcccag cctgccttca ctggcagcta ccgctgtgag  720
gtgtccacca aggacaaatt tgactgctcc aacttcaatc tcactgtcca cgaggccatg  780
ggcaccggag acctggacct cctatcagcc ttccgccgca cgagcctggc tggaggtggt  840
cggcggatca gtgatagcca tgaggacact gggattctgg acttcagctc actgctgaaa  900
aagagagaca gtttccggac cccgagggac tcgaagctgg aggcaccagc agaggaggac  960
gtgtgggaga tcctacggca ggcaccccca tctgagtacg agcgcatcgc cttccagtac  1020
ggcgtcactg acctgcgcgg catgctaaag aggctcaagg gcatgaggcg cgatgagaag  1080
aagagcacag cctttcagaa gaagctggag ccggcctacc aggtgagcaa aggccacaag  1140
atccggctga ccgtggaact ggctgaccat gacgctgagg tcaaatggct caagaatggc  1200
caggagatcc agatgagcgg cagcaagtac atctttgagt ccatcggtgc caagcgtacc  1260
ctgaccatca gccagtgctc attggcggac gacgcagcct accagtgcgt ggtgggtggc  1320
gagaagtgta gcacggagct ctttgtgaaa gagccccctg tgtaccagag catcgcagac  1380
ctgatggtgg gcgcaaagga ccaggcggtg ttcaaatgtg aggtctcaga tgagaatgtt  1440
cggggtgtgt ggctgaagaa tgggaaggag ctggtgcccg acagccgcat aaaggtgtcc  1500
cacatcgggc gggtccacaa actgaccatt gacgacgtca cacctgccga cgaggctgac  1560
tacagctttg tgcccgaggg cttcgcctgc aacctgtcag ccaagctcca cttcatggag  1620
gtcaagattg acttcgtacc caggcaggaa cctcccaaga tccacctgga ctgcccaggc  1680
cgcataccag acaccattgt ggttgtagct ggaaataagc tacgtctgga cgtccctatc  1740
tctggggacc ccgctcccac tgtgatctgg cagaaggcta tcacgcaggg gaataaggcc  1800
ccagccaggc cagccccaga tgccccagag gacacaggtg acagcgatga gtgggtgttt  1860
gacaagaagc tgctgtgtga gaccgagggc cgggtccgcg tggagaccac caaggaccgc  1920
agcatcttca cggtcgaggg ggcagagaag gaagatgagg gcgtctacac ggtcacagtg  1980
aagaaccctg tgggcgagga ccaggtcaac ctcacagtca aggtcatcga cgtgccagac  2040
gcacctgcgg cccccaagat cagcaacgtg ggagaggact cctgcacagt acagtgggag  2100
```

```
ccgcctgcct acgatggcgg gcagcccatc ctgggctaca tcctggagcg caagaagaag  2160
aagagctacc ggtggatgcg gctgaacttc gacctgattc aggagctgag tcatgaagcg  2220
cggcgcatga tcgagggcgt ggtgtacgag atgcgcgtct acgcggtcaa cgccatcggc  2280
atgtccaggc ccagccctgc ctcccagccc ttcatgccta tcggtccccc cagcgaaccc  2340
acccacctgg cagtagagga cgtctctgac accacggtct ccctcaagtg gcggccccca  2400
gagcgcgtgg gagcaggagg cctggatggc tacagcgtgg agtactgccc agagggctgc  2460
tcagagtggg tggctgccct gcaggggctg acagagcaca catcgatact ggtgaaggac  2520
ctgcccacgg gggcccggct gcttttccga gtgcgggcac acaatatggc agggcctgga  2580
gcccctgtta ccaccacgga gccggtgaca gtgcaggaga tcctgcaacg gccacggctt  2640
cagctgccca ggcacctgcg ccagaccatt cagaagaagg tcggggagcc tgtgaacctt  2700
ctcatccctt tccagggcaa gccccggcct caggtgacct ggaccaaaga ggggcagccc  2760
ctggcaggcg aggaggtgag catccgcaac agccccacag acaccatcct gttcatccgg  2820
gccgctcgcc gcgtgcattc aggcacttac caggtgacgg tgcgcattga gaacatggag  2880
gacaaggcca cgctggtgct gcaggttgtt gacaagccaa gtcctcccca ggatctccgg  2940
gtgactgacg cctggggtct taatgtggct ctggagtgga agccacccca ggatgtcggc  3000
aacacggaac tctgggggta cacagtgcag aaagccgaca agaagaccat ggagtggttc  3060
accgtcttgg agcattaccg ccgcacccac tgcgtggtgc cagagctcat cattggcaat  3120
ggctactact tccgcgtctt cagccagaat atggttggct ttagtgacag agcggccacc  3180
accaaggagc ccgtctttat ccccagacca ggcatcacct atgagccacc caactataag  3240
gccctggact tctccgaggc ccccaagctt c acccagcccc tggtgaaccg ctcggtcatc  3300
gcgggctaca ctgctatgct ctgctgtgct gtccggggta gccccaagcc caagatttcc  3360
tggttcaaga atggcctgga cctgggagaa gacgcccgct tccgcatgtt cagcaagcag  3420
ggagtgttga ctctggagat tagaaagccc tgcccctttg acgggggcat ctatgtctgc  3480
agggccacca acttacaggg cgaggcacgg tgtgagtgcc gcctggaggt gcgagtgcct  3540
cagtaa                                                             3546
```

```
SEQ ID NO: 88          moltype = DNA  length = 3534
FEATURE                Location/Qualifiers
source                 1..3534
                       mol_type = other DNA
                       organism = Homo sapiens
SEQUENCE: 88
atgcctgagc cggggaagaa gccagtctca gcttttagca agaagccacg gtcagtggaa  60
gtggccgcag gcagccctgc cgtgttcgag gccgagacag agcgggcagg agtgaaggtg  120
cgctggcagc gcggaggcag tgacatcagc gccagcaaca agtacggcct ggccacagag  180
ggcacacggc atacgctgac agtgcgggaa gtgggccctg ccgaccaggg atcttacgca  240
gtcattgctg gctcctccaa ggtcaagttc gacctcaagg tcatagaggc agagaaggca  300
gagcccatgc tggcccctgc ccctgcccct gctgaggcca ctggagcccc tggagaagcc  360
ccggccccag ccgctgagct gggagaaagt gccccaagtc ccaaagggtc aagctcagca  420
gctctcaatg gtcctacccc tggagcccc gatgacccca ttggcctctt cgtgatgcgg  480
ccacaggatg gcgaggtgac cgtgggtggc agcatcacct tctcagcccg cgtggccggc  540
gccagcctcc tgaagccgcc tgtggtcaag tggttcaagg gcaaatgggt ggacctgagc  600
agcaaggtgg gccagcacct gcagctgcac gacagctacg accgcgccag caaggtctat  660
ctgttcgagc tgcacatcac cgatgcccag cctgccttca ctggcagcta ccgctgtgag  720
gtgtccacca aggacaaatt tgactgctcc aacttcaatc tcactgtcca cgaggccatg  780
ggcaccggag acctggacct cctatcagcc ttccgccgca cgagcctggc tggaggtggt  840
cggcggatca gtgatagcca tgaggacact gggattctgg acttcagctc actgctgaaa  900
aagagagaca gtttccggac cccgagggac tcgaagctgg aggcaccagc agaggaggac  960
gtgtgggaga tcctacggca ggcacccca tctgagtacg agcgcatcgc cttccagtac  1020
ggcgtcactg acctgcgcgg catgctaaag aggctcaagg gcatgaggcg cgatgagaag  1080
aagagcacag cctttcagaa gaagctggag ccggcctacc aggtgagcaa aggccacaag  1140
atccggctga ccgtggaact ggctgaccat gacgctgagg tcaaatggct caagaatggc  1200
caggagatcc agatgagcgg cagcaagtac atctttgagt ccatcggtgc caagcgtacc  1260
ctgaccatca gccagtgctc attggcggac gacgcagcct accagtgcgt ggtgggtggc  1320
gagaagtgta gcacggagct ctttgtgaaa gagccccctg tgctcatcac gcgccccttg  1380
gaggaccagc tggtgatggt ggggcagcgg gtggagtttg agtgtgaagt atcggaggag  1440
ggggcgcaag tcaaatggct gaaggacggg gtggagctga cccgggagga gaccttcaaa  1500
taccggttca agaaggacgg gcagagacac cacctgatca tcaacgaggc catgctggag  1560
gacgcggggc actatgcact gtgcactagc gggggccagg cgctggctga gctcattgtg  1620
caggaaaaga agctggagcc tcccaagatc cacctggact gcccaggccg cataccagac  1680
accattgtgg ttgtagctgg aaataagcta cgtctggacg tccctatctc tggggacccc  1740
gctcccactg tgatctggca gaaggctatc acgcaggga ataaggcccc agccaggcca  1800
gccccagatg ccccagagga cacaggtgac agcgatgagt gggtgtttga caagaagctg  1860
ctgtgtgaga ccgagggccg ggtccgcgtg gagaccacca aggaccgcag catcttcacg  1920
gtcgaggggg cagagaagga agatgagggc gtctacacgg tcacagtgaa gaaccctgtg  1980
ggcgaggacc aggtcaacct cacagtcaag gtcatcgacg tgccagacgc acctgcggcc  2040
cccaagatca gcaacgtggg agaggactcc tgcacagtac agtgggagcc gcctgcctac  2100
gatggcgggc agcccatcct gggctacatc ctggagcgca agaagaagaa gagctaccgg  2160
tggatgcggc tgaacttcga cctgattcag gagctgagtc atgaagcgcg gcgcatgatc  2220
gagggcgtgg tgtacgagat gcgcgtctac gcggtcaacg ccatcggcat gtccaggccc  2280
agccctgcct cccagccctt catgcctatc ggtcccccca gcgaacccac ccacctggca  2340
gtagaggacg tctctgacac cacggtctcc ctcaagtggc ggcccccaga gcgcgtggga  2400
gcaggaggcc tggatggcta cagcgtggag tactgcccag agggctgctc agagtgggtg  2460
gctgccctgc aggggctgac agagcacaca tcgatactgg tgaaggacct gcccacgggg  2520
gcccggctgc ttttccgagt gcgggcacac aatatggcag ggcctggagc ccctgttacc  2580
accacggagc cggtgacagt gcaggagatc ctgcaacggc cacggcttca gctgcccagg  2640
cacctgcgcc agaccattca gaagaaggtc ggggagcctg tgaaccttct catccctttc  2700
cagggcaagc cccggcctca ggtgacctgg accaaagagg ggcagcccct ggcaggcgag  2760
gaggtgagca tccgcaacag ccccacagac accatcctgt tcatccgggc cgctcgccgc  2820
```

```
gtgcattcag gcacttacca ggtgacggtg cgcattgaga acatggagga caaggccacg  2880
ctggtgctgc aggttgttga caagccaagt cctccccagg atctccgggt gactgacgcc  2940
tggggtctta atgtggctct ggagtggaag ccaccccagg atgtcggcaa cacggaactc  3000
tgggggtaca cagtgcagaa agccgacaag aagaccatgg agtggttcac cgtcttggag  3060
cattaccgcc gcacccactg cgtggtgcca gagctcatca ttggcaatgg ctactacttc  3120
cgcgtcttca gccagaatat ggttggcttt agtgacagag cggccaccac caaggagccc  3180
gtctttatcc ccagaccagg catcacctat gagccaccca actataaggc cctggacttc  3240
tccgaggccc caagcttcac ccagcccctg gtgaaccgct cggtcatcgc gggctacact  3300
gctatgctct gctgtgctgt ccggggtagc cccaagccca agatttcctg gttcaagaat  3360
ggcctggacc tgggagaaga cgcccgcttc cgcatgttca gcaagcaggg agtgttgact  3420
ctggagatta gaaagccctg cccctttgac gggggcatct atgtctgcag ggccaccaac  3480
ttacagggcg aggcacggtg tgagtgccgc ctggaggtgc gagtgcctca gtaa        3534

SEQ ID NO: 89          moltype = DNA  length = 3546
FEATURE                Location/Qualifiers
source                 1..3546
                       mol_type = other DNA
                       organism = Homo sapiens
SEQUENCE: 89
atgcctgagc cggggaagaa gccagtctca gcttttagca agaagccacg gtcagtggaa  60
gtggccgcag gcagccctgc cgtgttcgag gccgagacag agcgggcagg agtgaaggtg  120
cgctggcagc gcggaggcag tgacatcagc gccagcaaca agtacggcct ggccacagag  180
ggcacacggc atacgctgac agtgcgggaa gtgggccctg ccgaccaggg atcttacgca  240
gtcattgctg gctcctccaa ggtcaagttc gacctcaagg tcatagaggc agagaaggca  300
gagcccatgc tggcccctgc ccctgcccct gctgaggcca ctggagcccc tggagaagcc  360
ccggccccag ccgctgagct gggagaaagt gccccaagtc ccaaagggtc aagctcagca  420
gctctcaatg gtcctacccc tggagccccc gatgacccca ttggcctctt cgtgatgcgg  480
ccacaggatg gcgaggtgac cgtgggtggc agcatcacct tctcagcccg cgtggccggc  540
gccagcctcc tgaagccgcc tgtggtcaag tggttcaagg gcaaatgggt ggacctgagc  600
agcaaggtgg gccagcacct gcagctgcac gacagctacg accgcgccag caaggtctat  660
ctgttcgagc tgcacatcac cgatgcccag cctgccttca ctggcagcta ccgctgtgag  720
gtgtccacca aggacaaatt tgactgctcc aacttcaatc tcactgtcca cgaggccatg  780
ggcaccggag acctggacct cctatcagcc ttccgccgca cgagcctggc tggaggtggt  840
cggcggatca gtgatagcca tgaggacact gggattctgg acttcagctc actgctgaaa  900
aagagagaca gtttccggac cccgagggac tcgaagctgg aggcaccagc agaggaggac  960
gtgtgggaga tcctacggca ggcacccccca tctgagtacg agcgcatcgc cttccagtac  1020
ggcgtcactg acctgcgcgg catgctaaag aggctcaagg gcatgaggcg cgatgagaag  1080
aagagcacag cctttcagaa gaagctggag ccggcctacc aggtgagcaa aggccacaag  1140
atccggctga ccgtggaact ggctgaccat gacgctgagg tcaaatggct caagaatggc  1200
caggagatcc agatgagcgg cagcaagtac atctttgagt ccatcggtgc caagcgtacc  1260
ctgaccatca gccagtgctc attggcggac gacgcagcct accagtgcgt ggtgggtggc  1320
gagaagtgta gcacggagct ctttgtgaaa gagccccctg tgctcatcac gcgccccttg  1380
gaggaccagc tggtgatggt ggggcagcgg gtggagtttg agtgtgaagt atcggaggag  1440
ggggcgcaag tcaaatggct gaaggacggg gtggagctga cccgggagga gaccttcaaa  1500
taccggttca agaaggacgg gcagagacac cacctgatca tcaacgaggc catgctggag  1560
gacgcggggc actatgcact gtgcactagc gggggccagg cgctggctga gctcattgtg  1620
caggaaaaga agctggagcc caggcaggaa cctcccaaga tccacctgga ctgcccaggc  1680
cgcataccag acaccattgt ggttgtagct ggaaataagc tacgtctgga cgtccctatc  1740
tctggggacc ccgctcccac tgtgatctgg cagaaggcta tcacgcaggg gaataaggcc  1800
ccagccaggc cagccccaga tgccccagag gacacaggtg acagcgatga gtgggtgttt  1860
gacaagaagc tgctgtgtga gaccgagggc cgggtccgcg tggagaccac caaggaccgc  1920
agcatcttca cggtcgaggg ggcagagaag gaagatgagg gcgtctacac ggtcacagtg  1980
aagaaccctg tgggcgagga ccaggtcaac ctcacagtca aggtcatcga cgtgccagac  2040
gcacctgcgg cccccaagat cagcaacgtg ggagaggact cctgcacagt acagtgggag  2100
ccgcctgcct acgatggcgg gcagcccatc ctgggctaca tcctggagcg caagaagaag  2160
aagagctacc ggtggatgcg gctgaacttc gacctgattc aggagctgag tcatgaagcg  2220
cggcgcatga tcgagggcgt ggtgtacgag atgcgcgtct acgcggtcaa cgccatcggc  2280
atgtccaggc ccagccctgc ctcccagccc ttcatgccta tcggtccccc cagcgaaccc  2340
acccacctgg cagtagagga cgtctctgac accacggtct ccctcaagtg gcggccccca  2400
gagcgcgtgg gagcaggagg cctggatggc tacagcgtgg agtactgccc agagggctgc  2460
tcagagtggg tggctgccct gcaggggctg acagagcaca catcgatact ggtgaaggac  2520
ctgcccacgg gggcccggct gcttttccga gtgcgggcac acaatatggc agggcctgga  2580
gcccctgtta ccaccacgga gccggtgaca gtgcaggaga tcctgcaacg gccacggctt  2640
cagctgccca ggcacctgcg ccagaccatt cagaagaagg tcggggagcc tgtgaacctt  2700
ctcatccctt tccagggcaa gccccggcct caggtgacct ggaccaaaga ggggcagccc  2760
ctggcaggcg aggaggtgag catccgcaac agccccacag acaccatcct gttcatccgg  2820
gccgctcgcc gcgtgcattc aggcacttac caggtgacgg tgcgcattga gaacatggag  2880
gacaaggcca cgctggtgct gcaggttgtt gacaagccaa gtcctcccca ggatctccgg  2940
gtgactgacg cctggggtct taatgtggct ctggagtgga agccaccccca ggatgtcggc  3000
aacacggaac tctgggggta cacagtgcag aaagccgaca agaagaccat ggagtggttc  3060
accgtcttgg agcattaccg ccgcacccac tgcgtggtgc cagagctcat cattggcaat  3120
ggctactact tccgcgtctt cagccagaat atggttggct ttagtgacag agcggccacc  3180
accaaggagc ccgtctttat ccccagacca ggcatcacct atgagccacc caactataag  3240
gccctggact tctccgaggc cccaagcttc acccagcccc tggtgaaccg ctcggtcatc  3300
gcgggctaca ctgctatgct ctgctgtgct gtccggggta gccccaagcc caagatttcc  3360
tggttcaaga atggcctgga cctgggagaa gacgcccgct tccgcatgtt cagcaagcag  3420
ggagtgttga ctctggagat tagaaagccc tgcccctttg acgggggcat ctatgtctgc  3480
agggccacca acttacaggg cgaggcacgg tgtgagtgcc gcctggaggt gcgagtgcct  3540
cagtaa                                                            3546
```

```
SEQ ID NO: 90          moltype = DNA  length = 1156
FEATURE                Location/Qualifiers
source                 1..1156
                       mol_type = genomic DNA
                       organism = Homo sapiens
SEQUENCE: 90
agtccccgct gagactgagc agacgcctcc aggatctgtc ggcagctgct gttctgaggg  60
agagcagaga ccatgtctga catagaagag gtggtggaag agtacgagga ggaggagcag  120
gaagaagcag ctgttgaaga agaggaggac tggagagagg acgaagacga gcaggaggag  180
gcagcggaag aggatgctga agcagaggct gagaccgagg agaccagggc agaagaagat  240
gaagaagaag aggaagcaaa ggaggctgaa gatggcccaa tggaggagtc caaaccaaag  300
cccaggtcgt tcatgcccaa cttggtgcct cccaagatcc ccgatggaga gagagtggac  360
tttgatgaca tccaccggaa gcgcatggag aaggacctga atgagttgca ggcgctgatc  420
gaggctcact ttgagaacag gaagaaagag gaggaggagc tcgtttctct caaagacagg  480
atcgagagac gtcgggcaga gcgggccgag cagcagcgca tccggaatga gcgggagaag  540
gagcggcaga accgcctggc tgaagagagg gctcgacgag aggaggagga gaacaggagg  600
aaggctgagg atgaggcccg gaagaagaag gctttgtcca acatgatgca ttttgggggt  660
tacatccaga agacagagcg gaaaagtggg aagaggcaga ctgagcggga aaagaagaag  720
aagattctgg ctgagaggag gaaggtgctg gccattgacc acctgaatga agatcagctg  780
agggagaagg ccaaggagct gtggcagagc atctataact tggaggcaga gaagttcgac  840
ctgcaggaga agttcaagca gcagaaatat gagatcaatg ttctccgaaa caggatcaac  900
gataaccaga aagtctccaa gacccgcggg aaggctaaag tcaccgggcg ctggaaatag  960
agcctggcct ccttcaccaa agatctgctc ctcgctcgca cctgcctccg gcctgcactc  1020
ccccagttcc cgggccctcc tgggcacccc aggcagctcc tgtttggaaa tggggagctg  1080
gcctaggtgg gagccaccac tcctgcctgc ccccacaccc actccacacc agtaataaaa  1140
agccaccaca cactga                                                  1156

SEQ ID NO: 91          moltype =   length =
SEQUENCE: 91
000

SEQ ID NO: 92          moltype = DNA  length = 49
FEATURE                Location/Qualifiers
misc_feature           1..49
                       note = pCard1 polyA signal
source                 1..49
                       mol_type = other DNA
                       organism = synthetic construct
SEQUENCE: 92
aataaaagat ctttattttc attagatctg tgtgttggtt ttttgtgtg             49

SEQ ID NO: 93          moltype = DNA  length = 480
FEATURE                Location/Qualifiers
misc_feature           1..480
                       note = pCard1 5' segment
source                 1..480
                       mol_type = other DNA
                       organism = synthetic construct
SEQUENCE: 93
tgtagttaat gattaacccg ccatgctact tatctacgta gccatgctct aggaagatcg  60
gaattcgccc ttaagttgcc ttctgccccc caaccctgct cccagctggc cctcccaggc  120
ctgggttgct ggcctctgct ttatcaggat tctcaagagg gacagctggt ttatgttgca  180
tgactgttcc ctgcatatct gctctggttt taaatagctt atctgagcag ctggaggacc  240
acatgggctt atatggcgtg gggtacatgt tcctgtagcc ttgtccctgg cacctgccaa  300
aatagcagcc aacacccccc acccccaccg ccatcccccct gccccacccg tcccctgtcg  360
cacattcctc cctccgcagg gctggctcac caggccccag cccacatgcc tgcttaaagc  420
cctctccatc ctctgcctca cccagtcccc gctgagactg agcagacgcc tccagccacc  480

SEQ ID NO: 94          moltype = DNA  length = 148
FEATURE                Location/Qualifiers
misc_feature           1..148
                       note = pCard1 3' segment
source                 1..148
                       mol_type = other DNA
                       organism = synthetic construct
SEQUENCE: 94
agcttaataa aagatcttta ttttcattag atctgtgtgt tggttttttg tgtgctgggg  60
actcgagtta agggcgaatt cccgataagg atcttcctag agcatggcta cgtagataag  120
tagcatggcg ggttaatcat taactaca                                    148

SEQ ID NO: 95          moltype = DNA  length = 4453
FEATURE                Location/Qualifiers
misc_feature           1..4453
                       note = pCard1 with MYBPC3 no ITR
source                 1..4453
                       mol_type = other DNA
                       organism = synthetic construct
SEQUENCE: 95
```

```
tgtagttaat gattaacccg ccatgctact tatctacgta gccatgctct aggaagatcg  60
gaattcgccc ttaagttgcc ttctgccccc caaccctgct cccagctggc cctcccaggc  120
ctgggttgct ggcctctgct ttatcaggat tctcaagagg gacagctggt ttatgttgca  180
tgactgttcc ctgcatatct gctctggttt taaatagctt atctgagcag ctggaggacc  240
acatgggctt atatggcgtg ggtacatgt tcctgtagcc ttgtccctgg cacctgccaa  300
aatagcagcc aacacccccc acccccaccg ccatcccct gccccacccg tcccctgtcg  360
cacattcctc cctccgcagg gctggctcac caggccccag cccacatgcc tgcttaaagc  420
cctctccatc ctctgcctca cccagtcccc gctgagactg agcagacgcc tccagccacc  480
atgcctgagc cggggaagaa gccagtctca gcttttagca agaagccacg gtcagtggaa  540
gtggccgcag gcagccctgc cgtgttcgag gccgagacag agcgggcagg agtgaaggtg  600
cgctggcagc gcggaggcag tgacatcagc gccagcaaca agtacggcct ggccacagag  660
ggcacacggc atacgctgac agtgcgggaa gtgggccctg ccgaccaggg atcttacgca  720
gtcattgctg gctcctccaa ggtcaagttc gacctcaagg tcatagaggc agagaaggca  780
gagcccatgc tggcccctgc ccctgcccct gctgaggcca ctggagcccc tggagaagcc  840
ccggccccag ccgctgagct gggagaaagt gccccaagtc ccaaagggtc aagctcagca  900
gctctcaatg gtcctacccc tggagccccc gatgacccca ttggcctctt cgtgatgcgg  960
ccacaggatg gcgaggtgac cgtgggtggc agcatcacct tctcagcccg cgtggccggc  1020
gccagcctcc tgaagccgcc tgtggtcaag tggttcaagg gcaaatgggt ggacctgagc  1080
agcaaggtgg gccagcacct gcagctgcac gacagctacg accgcgccag caaggtctat  1140
ctgttcgagc tgcacatcac cgatgcccag cctgccttca ctggcagcta ccgctgtgag  1200
gtgtccacca aggacaaatt tgactgctcc aacttcaatc tcactgtcca cgaggccatg  1260
ggcaccggag acctggacct cctatcagcc ttccgccgca cgagcctggc tggaggtggt  1320
cggcggatca gtgatagcca tgaggacact gggattctgg acttcagctc actgctgaaa  1380
aagagagaca gtttccggac cccgagggac tcgaagctgg aggcaccagc agaggaggac  1440
gtgtgggaga tcctacggca ggcacccca tctgagtacg agcgcatcgc cttccagtac  1500
ggcgtcactg acctgcgcgg catgctaaag aggctcaagg gcatgaggcg cgatgagaag  1560
aagagcacag cctttcagaa gaagctggag ccggcctacc aggtgagcaa aggccacaag  1620
atccggctga ccgtggaact ggctgaccat gacgctgagg tcaaatggct caagaatggc  1680
caggagatcc agatgagcgg cagcaagtac atctttgagt ccatcggtgc caagcgtacc  1740
ctgaccatca gccagtgctc attggcggac gacgcagcct accagtgcgt ggtgggtggc  1800
gagaagtgta gcacggagct ctttgtgaaa gagcccctg tgctcatcac gcgcccttg  1860
gaggaccagc tggtgatggt ggggcagcgg gtggagtttg agtgtgaagt atcggaggag  1920
ggggcgcaag tcaaatggct gaaggacggg gtggagctga cccgggagga gaccttcaaa  1980
taccggttca agaaggacgg gcagagacac cacctgatca tcaacgaggc catgctggag  2040
gacgcggggc actatgcact gtgcactagc gggggccagg cgctggctga gctcattgtg  2100
caggaaaaga agctggaggt gtaccagagc atcgcagacc tgatggtggg cgcaaaggac  2160
caggcggtgt tcaaatgtga ggtctcagat gagaatgttc ggggtgtgtg gctgaagaat  2220
gggaaggagc tggtgcccga cagccgcata aaggtgtccc acatcgggcg ggtccacaaa  2280
ctgaccattg acgacgtcac acctgccgac gaggctgact acagctttgt gcccgagggc  2340
ttcgcctgca acctgtcagc caagctccac ttcatggagg tcaagattga cttcgtaccc  2400
aggcaggaac ctcccaagat ccacctggac tgcccaggcc gcataccaga caccattgtg  2460
gttgtagctg gaaataagct acgtctggac gtccctatct ctggggaccc cgctcccact  2520
gtgatctggc agaaggctat cacgcagggg aataaggccc cagccaggcc agccccagat  2580
gccccagagg acacaggtga cagcgatgag tgggtgtttg acaagaagct gctgtgtgag  2640
accgagggcc gggtccgcgt ggagaccacc aaggaccgca gcatcttcac ggtcgagggg  2700
gcagagaagg aagatgaggg cgtctacacg gtcacagtga agaaccctgt gggcgaggac  2760
caggtcaacc tcacagtcaa ggtcatcgac gtgccagacg cacctgcggc ccccaagatc  2820
agcaacgtgg gagaggactc ctgcacagta cagtgggagc cgcctgccta cgatggcggg  2880
cagcccatcc tgggctacat cctggagcgc aagaagaaga agagctaccg gtggatgcgg  2940
ctgaacttcg acctgattca ggagctgagt catgaagcgc ggcgcatgat cgagggcgtg  3000
gtgtacgaga tgcgcgtcta cgcggtcaac gccatcggca tgtccaggcc cagccctgcc  3060
tcccagccct tcatgcctat cggtcccccc agcgaaccca cccacctggc agtagaggac  3120
gtctctgaca ccacggtctc cctcaagtgg cggcccccag agcgcgtggg agcaggaggc  3180
ctggatggct acagcgtgga gtactgccca gagggctgct cagagtgggt ggctgccctg  3240
caggggctga cagagcacac atcgatactg gtgaaggacc tgcccacggg ggcccggctg  3300
cttttccgag tgcgggcaca caatatggca gggcctggag cccctgttac caccacggag  3360
ccggtgacag tgcaggagat cctgcaacgg ccacggcttc agctgcccag gcacctgcgc  3420
cagaccattc agaagaaggt cggggagcct gtgaaccttc tcatcccttt ccagggcaag  3480
ccccggcctc aggtgacctg gaccaaagag gggcagcccc tggcaggcga ggaggtgagc  3540
atccgcaaca gccccacaga caccatcctg ttcatccggg ccgctcgccg cgtgcattca  3600
ggcacttacc aggtgacggt gcgcattgag aacatggagg acaaggccac gctggtgctg  3660
caggttgttg acaagccaag tcctccccag gatctccggg tgactgacgc ctggggtctt  3720
aatgtggctc tggagtggaa gccaccccag gatgtcggca acacggaact ctgggggtac  3780
acagtgcaga aagccgacaa gaagaccatg gagtggttca ccgtcttgga gcattaccgc  3840
cgcacccact gcgtggtgcc agagctcatc attggcaatg gctactactt ccgcgtcttc  3900
agccagaata tggttggctt tagtgacaga gcggccacca ccaaggagcc cgtctttatc  3960
cccagaccag gcatcaccta tgagccaccc aactataagg ccctggactt ctccgaggcc  4020
ccaagcttca cccagcccct ggtgaaccgc tcggtcatcg cgggctacac tgctatgctc  4080
tgctgtgctg tccggggtag ccccaagccc aagatttcct ggttcaagaa tggcctggac  4140
ctgggagaag acgcccgctt ccgcatgttc agcaagcagg gagtgttgac tctggagatt  4200
agaaagccct gccccttga cggggcatc tatgtctgca gggccaccaa cttacagggc  4260
gaggcacggt gtgagtgccg cctggaggtg cgagtgcctc agtaaagctt aataaaagat  4320
ctttatttc attagatctg tgtgttggtt ttttgtgtgc tggggactcg agttaagggc  4380
gaattcccga taaggatctt cctagagcat ggctacgtag ataagtagca tggcgggtta  4440
atcattaact aca                                                     4453
```

```
SEQ ID NO: 96          moltype = DNA  length = 130
FEATURE                Location/Qualifiers
misc_feature           1..130
```

```
                        note = 5' ITR
source                  1..130
                        mol_type = other DNA
                        organism = synthetic construct
SEQUENCE: 96
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct                                                         130

SEQ ID NO: 97           moltype = DNA  length = 130
FEATURE                 Location/Qualifiers
misc_feature            1..130
                        note = 3' ITR
source                  1..130
                        mol_type = other DNA
                        organism = synthetic construct
SEQUENCE: 97
aggaacccct agtgatggag ttggccactc cctctctgcg cgctcgctcg ctcactgagg  60
ccgggcgacc aaaggtcgcc cgacgcccgg gctttgcccg ggcggcctca gtgagcgagc  120
gagcgcgcag                                                         130

SEQ ID NO: 98           moltype = DNA  length = 1089
FEATURE                 Location/Qualifiers
misc_feature            1..1089
                        note = pCard0 viral genome
source                  1..1089
                        mol_type = other DNA
                        organism = synthetic construct
SEQUENCE: 98
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctacgta gccatgctct  180
aggaagatcg gaattcgccc ttaagtcatg gagaagaccc accttgcaga tgtcctcact  240
ggggctggca gagccggcaa cctgcccaag gctgctcagt ccattaggag ccagtagcct  300
ggaagatgtc tttaccccca gcatcagttc aagtggagca gcacataact cttgccctct  360
gccttccaag attctggtgc tgagacttat ggagtgtctt ggaggttgcc ttctgccccc  420
caaccctgct cccagctggc cctcccaggc ctgggttgct ggcctctgct ttatcaggat  480
tctcaagagg gacagctggt ttatgttgca tgactgttcc ctgcatatct gctctggttt  540
taaatagctt atctgagcag ctggaggacc acatgggctt atatggcgtg gggtacatgt  600
tcctgtagcc ttgtccctgg cacctgccaa aatagcagcc aacacccccc acccccaccg  660
ccatccccct gccccacccg tcccctgtcg cacattcctc cctccgcagg gctggctcac  720
caggccccag cccacatgcc tgcttaaagc cctctccatc ctctgcctca cccagtcccc  780
gctgagactg agcagacgcc tccagccacc aagcttaata aaagatcttt attttcatta  840
gatctgtgtg ttggtttttt gtgtgctggg gactcgagtt aagggcgaat tcccgataag  900
gatcttccta gagcatggct acgtagataa gtagcatggc gggttaatca ttaactacaa  960
ggaaccccta gtgatggagt tggccactcc ctctctgcgc gctcgctcgc tcactgaggc  1020
cgggcgacca aaggtcgccc gacgcccggg ctttgcccgg gcggcctcag tgagcgagcg  1080
agcgcgcag                                                          1089

SEQ ID NO: 99           moltype = DNA  length = 830
FEATURE                 Location/Qualifiers
misc_feature            1..830
                        note = pCard0 expression cassette
source                  1..830
                        mol_type = other DNA
                        organism = synthetic construct
SEQUENCE: 99
tgtagttaat gattaacccg ccatgctact tatctacgta gccatgctct aggaagatcg  60
gaattcgccc ttaagtcatg gagaagaccc accttgcaga tgtcctcact ggggctggca  120
gagccggcaa cctgcccaag gctgctcagt ccattaggag ccagtagcct ggaagatgtc  180
tttaccccca gcatcagttc aagtggagca gcacataact cttgccctct gccttccaag  240
attctggtgc tgagacttat ggagtgtctt ggaggttgcc ttctgccccc caaccctgct  300
cccagctggc cctcccaggc ctgggttgct ggcctctgct ttatcaggat tctcaagagg  360
gacagctggt ttatgttgca tgactgttcc ctgcatatct gctctggttt taaatagctt  420
atctgagcag ctggaggacc acatgggctt atatggcgtg gggtacatgt tcctgtagcc  480
ttgtccctgg cacctgccaa aatagcagcc aacacccccc acccccaccg ccatccccct  540
gccccacccg tcccctgtcg cacattcctc cctccgcagg gctggctcac caggccccag  600
cccacatgcc tgcttaaagc cctctccatc ctctgcctca cccagtcccc gctgagactg  660
agcagacgcc tccagccacc aagcttaata aaagatcttt attttcatta gatctgtgtg  720
ttggtttttt gtgtgctggg gactcgagtt aagggcgaat tcccgataag gatcttccta  780
gagcatggct acgtagataa gtagcatggc gggttaatca ttaactacaa             830

SEQ ID NO: 100          moltype = DNA  length = 889
FEATURE                 Location/Qualifiers
misc_feature            1..889
                        note = pCard1 viral genome
source                  1..889
                        mol_type = other DNA
                        organism = synthetic construct
```

```
SEQUENCE: 100
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctacgta gccatgctct  180
aggaagatcg gaattcgccc ttaagttgcc ttctgccccc caaccctgct cccagctggc  240
cctcccaggc ctgggttgct ggcctctgct ttatcaggat tctcaagagg gacagctggt  300
ttatgttgca tgactgttcc ctgcatatct gctctggttt taaatagctt atctgagcag  360
ctggaggacc acatgggctt atatggcgtg ggtacatgt tcctgtagcc ttgtccctgg  420
cacctgccaa aatagcagcc aacacccccc acccccaccg ccatccccct gccccacccg  480
tcccctgtcg cacattcctc cctccgcagg gctggctcac caggccccag cccacatgcc  540
tgcttaaagc cctctccatc ctctgcctca cccagtcccc gctgagactg agcagacgcc  600
tccagccacc aagcttaata aaagatcttt attttcatta gatctgtgtg ttggtttttt  660
gtgtgctggg gactcgagtt aagggcgaat tcccgataag gatcttccta gagcatggct  720
acgtagataa gtagcatggc gggttaatca ttaactacaa ggaaccccta gtgatggagt  780
tggccactcc ctctctgcgc gctcgctcgc tcactgaggc cgggcgacca aaggtcgccc  840
gacgcccggg ctttgcccgg gcggcctcag tgagcgagcg agcgcgcag             889

SEQ ID NO: 101          moltype = DNA  length = 629
FEATURE                 Location/Qualifiers
misc_feature            1..629
                        note = pCard1 expression cassette
source                  1..629
                        mol_type = other DNA
                        organism = synthetic construct
SEQUENCE: 101
tgtagttaat gattaacccg ccatgctact tatctacgta gccatgctct aggaagatcg  60
gaattcgccc ttaagttgcc ttctgccccc caaccctgct cccagctggc cctcccaggc  120
ctgggttgct ggcctctgct ttatcaggat tctcaagagg gacagctggt ttatgttgca  180
tgactgttcc ctgcatatct gctctggttt taaatagctt atctgagcag ctggaggacc  240
acatgggctt atatggcgtg ggtacatgt tcctgtagcc ttgtccctgg cacctgccaa  300
aatagcagcc aacacccccc acccccaccg ccatccccct gccccacccg tcccctgtcg  360
cacattcctc cctccgcagg gctggctcac caggccccag cccacatgcc tgcttaaagc  420
cctctccatc ctctgcctca cccagtcccc gctgagactg agcagacgcc tccagccacc  480
aagcttaata aaagatcttt attttcatta gatctgtgtg ttggtttttt gtgtgctggg  540
gactcgagtt aagggcgaat tcccgataag gatcttccta gagcatggct acgtagataa  600
gtagcatggc gggttaatca ttaactaca                                     629

SEQ ID NO: 102          moltype = DNA  length = 4713
FEATURE                 Location/Qualifiers
misc_feature            1..4713
                        note = pCard1 viral genome with MYBPC3
source                  1..4713
                        mol_type = other DNA
                        organism = synthetic construct
SEQUENCE: 102
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctacgta gccatgctct  180
aggaagatcg gaattcgccc ttaagttgcc ttctgccccc caaccctgct cccagctggc  240
cctcccaggc ctgggttgct ggcctctgct ttatcaggat tctcaagagg gacagctggt  300
ttatgttgca tgactgttcc ctgcatatct gctctggttt taaatagctt atctgagcag  360
ctggaggacc acatgggctt atatggcgtg ggtacatgt tcctgtagcc ttgtccctgg  420
cacctgccaa aatagcagcc aacacccccc acccccaccg ccatccccct gccccacccg  480
tcccctgtcg cacattcctc cctccgcagg gctggctcac caggccccag cccacatgcc  540
tgcttaaagc cctctccatc ctctgcctca cccagtcccc gctgagactg agcagacgcc  600
tccagccacc atgcctgagc cggggaagaa gccagtctca gcttttagca agaagccacg  660
gtcagtggaa gtggccgcag gcagccctgc cgtgttcgag gccgagacag agcgggcagg  720
agtgaaggtg cgctggcagc gcggaggcag tgacatcagc gccagcaaca agtacggcct  780
ggccacagag ggcacacggc atacgctgac agtgcgggaa gtgggccctg ccgaccaggg  840
atcttacgca gtcattgctg gctcctccaa ggtcaagttc gacctcaagg tcatagaggc  900
agagaaggca gagcccatgc tggcccctgc ccctgcccct gctgaggcca ctggagcccc  960
tggagaagcc ccggccccag ccgctgagct gggagaaagt gccccaagtc ccaaagggtc  1020
aagctcagca gctctcaatg gtcctacccc tggagccccc gatgacccca ttggcctctt  1080
cgtgatgcgg ccacaggatg gcgaggtgac cgtgggtggc agcatcacct tctcagcccg  1140
cgtggccggc gccagcctcc tgaagccgcc tgtggtcaag tggttcaagg gcaaatgggt  1200
ggacctgagc agcaaggtgg gccagcacct gcagctgcac gacagctacg accgcgccag  1260
caaggtctat ctgttcgagc tgcacatcac cgatgcccag cctgccttca ctggcagcta  1320
ccgctgtgag gtgtccacca aggacaaatt tgactgctcc aacttcaatc tcactgtcca  1380
cgaggccatg ggcaccggag acctggacct cctatcagcc ttccgccgca cgagcctggc  1440
tggaggtggt cggcggatca gtgatagcca tgaggacact gggattctgg acttcagctc  1500
actgctgaaa aagagagaca gtttccggac cccgagggac tcgaagctgg aggcaccagc  1560
agaggaggac gtgtgggaga tcctacggca ggcaccccca tctgagtacg agcgcatcgc  1620
cttccagtac ggcgtcactg acctgcgcgg catgctaaag aggctcaagg gcatgaggcg  1680
cgatgagaag aagagcacag cctttcagaa gaagctggag ccggcctacc aggtgagcaa  1740
aggccacaag atccggctga ccgtggaact ggctgaccat gacgctgagg tcaaatggct  1800
caagaatggc caggagatcc agatgagcgg cagcaagtac atctttgagt ccatcggtgc  1860
caagcgtacc ctgaccatca gccagtgctc attggcggac gacgcagcct accagtgcgt  1920
ggtgggtggc gagaagtgta gcacggagct ctttgtgaaa gagcccccctg tgctcatcac  1980
gcgcccccttg gaggaccagc tggtgatggt ggggcagcgg gtggagtttg agtgtgaagt  2040
```

```
atcggaggag ggggcgcaag tcaaatggct gaaggacggg gtggagctga cccgggagga  2100
gaccttcaaa taccggttca agaaggacgg gcagagacac cacctgatca tcaacgaggc  2160
catgctggag gacgcggggc actatgcact gtgcactagc gggggccagg cgctggctga  2220
gctcattgtg caggaaaaga agctggaggt gtaccagagc atcgcagacc tgatggtggg  2280
cgcaaaggac caggcggtgt tcaaatgtga ggtctcagat gagaatgttc ggggtgtgtg  2340
gctgaagaat gggaaggagc tggtgcccga cagccgcata aaggtgtccc acatcgggcg  2400
ggtccacaaa ctgaccattg acgacgtcac acctgccgac gaggctgact acagctttgt  2460
gcccgagggc ttcgcctgca acctgtcagc caagctccac ttcatggagg tcaagattga  2520
cttcgtaccc aggcaggaac ctcccaagat ccacctggac tgcccaggcc gcataccaga  2580
caccattgtg gttgtagctg gaaataagct acgtctggac gtccctatct ctggggaccc  2640
cgctcccact gtgatctggc agaaggctat cacgcagggg aataaggccc cagccaggcc  2700
agccccagat gccccagagg acacaggtga cagcgatgag tgggtgtttg acaagaagct  2760
gctgtgtgag accgagggcc gggtccgcgt ggagaccacc aaggaccgca gcatcttcac  2820
ggtcgagggg gcagagaagg aagatgaggg cgtctacacg gtcacagtga agaaccctgt  2880
gggcgaggac caggtcaacc tcacagtcaa ggtcatcgac gtgccagacg cacctgcggc  2940
ccccaagatc agcaacgtgg gagaggactc ctgcacagta cagtgggagc cgcctgccta  3000
cgatggcggg cagcccatcc tgggctacat cctggagcgc aagaagaaga agagctaccg  3060
gtggatgcgg ctgaacttcg acctgattca ggagctgagt catgaagcgc ggcgcatgat  3120
cgagggcgtg gtgtacgaga tgcgcgtcta cgcggtcaac gccatcggca tgtccaggcc  3180
cagccctgcc tcccagccct tcatgcctat cggtcccccc agcgaaccca cccacctggc  3240
agtagaggac gtctctgaca ccacggtctc cctcaagtgg cggcccccag agcgcgtggg  3300
agcaggaggc ctggatggct acagcgtgga gtactgccca gagggctgct cagagtgggt  3360
ggctgccctg caggggctga cagagcacac atcgatactg gtgaaggacc tgcccacggg  3420
ggcccggctg cttttccgag tgcgggcaca caatatggca gggcctggag cccctgttac  3480
caccacggag ccggtgacag tgcaggagat cctgcaacgg ccacggcttc agctgcccag  3540
gcacctgcgc cagaccattc agaagaaggt cggggagcct gtgaaccttc tcatcccttt  3600
ccagggcaag ccccggcctc aggtgacctg gaccaaagag gggcagcccc tggcaggcga  3660
ggaggtgagc atccgcaaca gccccacaga caccatcctg ttcatccggg ccgctcgccg  3720
cgtgcattca ggcacttacc aggtgacggt gcgcattgag aacatggagg acaaggccac  3780
gctggtgctg caggttgttg acaagccaag tcctccccag gatctccggg tgactgacgc  3840
ctggggtctt aatgtggctc tggagtggaa gccaccccag gatgtcggca acacggaact  3900
ctgggggtac acagtgcaga aagccgacaa gaagaccatg gagtggttca ccgtcttgga  3960
gcattaccgc cgcacccact gcgtggtgcc agagctcatc attggcaatg gctactactt  4020
ccgcgtcttc agccagaata tggttggctt tagtgacaga gcggccacca ccaaggagcc  4080
cgtctttatc cccagaccag gcatcaccta tgagccaccc aactataagg ccctggactt  4140
ctccgaggcc ccaagcttca cccagcccct ggtgaaccgc tcggtcatcg cgggctacac  4200
tgctatgctc tgctgtgctg tccggggtag ccccaagccc aagatttcct ggttcaagaa  4260
tggcctggac ctgggagaag acgcccgctt ccgcatgttc agcaagcagg gagtgttgac  4320
tctggagatt agaaagccct gcccctttga cgggggcatc tatgtctgca gggccaccaa  4380
cttacagggc gaggcacggt gtgagtgccg cctggaggtg cgagtgcctc agtaaagctt  4440
aataaaagat ctttattttc attagatctg tgtgttggtt ttttgtgtgc tggggactcg  4500
agttaagggc gaattcccga taaggatctt cctagagcat ggctacgtag ataagtagca  4560
tggcgggtta atcattaact acaaggaacc cctagtgatg gagttggcca ctccctctct  4620
gcgcgctcgc tcgctcactg aggccgggcg accaaaggtc gcccgacgcc cgggctttgc  4680
ccgggcggcc tcagtgagcg agcgagcgcg cag                              4713
```

```
SEQ ID NO: 103          moltype = AA  length = 1274
FEATURE                 Location/Qualifiers
source                  1..1274
                        mol_type = protein
                        organism = Homo sapiens
SEQUENCE: 103
MPEPGKKPVS AFSKKPRSVE VAAGSPAVFE AETERAGVKV RWQRGGSDIS ASNKYGLATE  60
GTRHTLTVRE VGPADQGSYA VIAGSSKVKF DLKVIEAEKA EPMLAPAPAP AEATGAPGEA  120
PAPAAELGES APSPKGSSSA ALNGPTPGAP DDPIGLFVMR PQDGEVTVGG SITFSARVAG  180
ASLLKPPVVK WFKGKWVDLS SKVGQHLQLH DSYDRASKVY LFELHITDAQ PAFTGSYRCE  240
VSTKDKFDCS NFNLTVHEAM GTGDLDLLSA FRRTSLAGGG RRISDSHEDT GILDFSSLLK  300
KRDSFRTPRD SKLEAPAEED VWEILRQAPP SEYERIAFQY GVTDLRGMLK RLKGMRRDEK  360
KSTAFQKKLE PAYQVSKGHK IRLTVELADH DAEVKWLKNG QEIQMSGSKY IFESIGAKRT  420
LTISQCSLAD DAAYQCVVGG EKCSTELFVK EPPVLITRPL EDQLVMVGQR VEFECEVSEE  480
GAQVKWLKDG VELTREETFK YRFKKDGQRH HLIINEAMLE DAGHYALCTS GGQALAELIV  540
QEKKLEVYQS IADLMVGAKD QAVFKCEVSD ENVRGVWLKN GKELVPDSRI KVSHIGRVHK  600
LTIDDVTPAD EADYSFVPEG FACNLSAKLH FMEVKIDFVP RQEPPKIHLD CPGRIPDTIV  660
VVAGNKLRLD VPISGDPAPT VIWQKAITQG NKAPARPAPD APEDTGDSDE WVFDKKLLCE  720
TEGRVRVETT KDRSIFTVEG AEKEDEGVYT VTVKNPVGED QVNLTVKVID VPDAPAAPKI  780
SNVGEDSCTV QWEPPAYDGG QPILGYILER KKKKSYRWMR LNFDLIQELS HEARRMIEGV  840
VYEMRVYAVN AIGMSRPSPA SQPFMPIGPP SEPTHLAVED VSDTTVSLKW RPPERVGAGG  900
LDGYSVEYCP EGCSEWVAAL QGLTEHTSIL VKDLPTGARL LFRVRAHNMA GPGAPVTTTE  960
PVTVQEILQR PRLQLPRHLR QTIQKKVGEP VNLLIPFQGK PRPQVTWTKE GQPLAGEEVS  1020
IRNSPTDTIL FIRAARRVHS GTYQVTVRIE NMEDKATLVL QVVDKPSPPQ DLRVTDAWGL  1080
NVALEWKPPQ DVGNTELWGY TVQKADKKTM EWFTVLEHYR RTHCVVPELI IGNGYYFRVF  1140
SQNMVGFSDR AATTKEPVFI PRPGITYEPP NYKALDFSEA PSFTQPLVNR SVIAGYTAML  1200
CCAVRGSPKP KISWFKNGLD LGEDARFRMF SKQGVLTLEI RKPCPFDGGI YVCRATNLQG  1260
EARCECRLEV RVPQ                                                    1274
```

```
SEQ ID NO: 104          moltype = AA  length = 1181
FEATURE                 Location/Qualifiers
source                  1..1181
                        mol_type = protein
```

```
                         organism = Homo sapiens
SEQUENCE: 104
MPEPGKKPVS AFSKKPRSVE VAAGSPAVFE AETERAGVKV RWQRGGSDIS ASNKYGLATE  60
GTRHTLTVRE VGPADQGSYA VIAGSSKVKF DLKVIEAEKA EPMLAPAPAP AEATGAPGEA  120
PAPAAELGES APSPKGSSSA ALNGPTPGAP DDPIGLFVMR PQDGEVTVGG SITFSARVAG  180
ASLLKPPVVK WFKGKWVDLS SKVGQHLQLH DSYDRASKVY LFELHITDAQ PAFTGSYRCE  240
VSTKDKFDCS NFNLTVHEAM GTGDLDLLSA FRRTSLAGGG RRISDSHEDT GILDFSSLLK  300
KRDSFRTPRD SKLEAPAEED VWEILRQAPP SEYERIAFQY GVTDLRGMLK RLKGMRRDEK  360
KSTAFQKKLE PAYQVSKGHK IRLTVELADH DAEVKWLKNG QEIQMSGSKY IFESIGAKRT  420
LTISQCSLAD DAAYQCVVGG EKCSTELFVK EPPVYQSIAD LMVGAKDQAV FKCEVSDENV  480
RGVWLKNGKE LVPDSRIKVS HIGRVHKLTI DDVTPADEAD YSFVPEGFAC NLSAKLHFME  540
VKIDFVPRQE PPKIHLDCPG RIPDTIVVVA GNKLRLDVPI SGDPAPTVIW QKAITQGNKA  600
PARPAPDAPE DTGDSDEWVF DKKLLCETEG RVRVETTKDR SIFTVEGAEK EDEGVYTVTV  660
KNPVGEDQVN LTVKVIDVPD APAAPKISNV GEDSCTVQWE PPAYDGGQPI LGYILERKKK  720
KSYRWMRLNF DLIQELSHEA RRMIEGVVYE MRVYAVNAIG MSRPSPASQP FMPIGPPSEP  780
THLAVEDVSD TTVSLKWRPP ERVGAGGLDG YSVEYCPEGC SEWVAALQGL TEHTSILVKD  840
LPTGARLLFR VRAHNMAGPG APVTTTEPVT VQEILQRPRL QLPRHLRQTI QKKVGEPVNL  900
LIPFQGKPRP QVTWTKEGQP LAGEEVSIRN SPTDTILFIR AARRVHSGTY QVTVRIENME  960
DKATLVLQVV DKPSPPQDLR VTDAWGLNVA LEWKPPQDVG NTELWGYTVQ KADKKTMEWF  1020
TVLEHYRRTH CVVPELIIGN GYYFRVFSQN MVGFSDRAAT TKEPVFIPRP GITYEPPNYK  1080
ALDFSEAPSF TQPLVNRSVI AGYTAMLCCA VRGSPKPKIS WFKNGLDLGE DARFRMFSKQ  1140
GVLTLEIRKP CPFDGGIYVC RATNLQGEAR CECRLEVRVP Q                    1181

SEQ ID NO: 105           moltype = AA  length = 1177
FEATURE                  Location/Qualifiers
source                   1..1177
                         mol_type = protein
                         organism = Homo sapiens
SEQUENCE: 105
MPEPGKKPVS AFSKKPRSVE VAAGSPAVFE AETERAGVKV RWQRGGSDIS ASNKYGLATE  60
GTRHTLTVRE VGPADQGSYA VIAGSSKVKF DLKVIEAEKA EPMLAPAPAP AEATGAPGEA  120
PAPAAELGES APSPKGSSSA ALNGPTPGAP DDPIGLFVMR PQDGEVTVGG SITFSARVAG  180
ASLLKPPVVK WFKGKWVDLS SKVGQHLQLH DSYDRASKVY LFELHITDAQ PAFTGSYRCE  240
VSTKDKFDCS NFNLTVHEAM GTGDLDLLSA FRRTSLAGGG RRISDSHEDT GILDFSSLLK  300
KRDSFRTPRD SKLEAPAEED VWEILRQAPP SEYERIAFQY GVTDLRGMLK RLKGMRRDEK  360
KSTAFQKKLE PAYQVSKGHK IRLTVELADH DAEVKWLKNG QEIQMSGSKY IFESIGAKRT  420
LTISQCSLAD DAAYQCVVGG EKCSTELFVK EPPVLITRPL EDQLVMVGQR VEFECEVSEE  480
GAQVKWLKDG VELTREETFK YRFKKDGQRH HLIINEAMLE DAGHYALCTS GGQALAELIV  540
QEKKLEPPKI HLDCPGRIPD TIVVVAGNKL RLDVPISGDP APTVIWQKAI TQGNKAPARP  600
APDAPEDTGD SDEWVFDKKL LCETEGRVRV ETTKDRSIFT VEGAEKEDEG VYTVTVKNPV  660
GEDQVNLTVK VIDVPDAPAA PKISNVGEDS CTVQWEPPAY DGGQPILGYI LERKKKKSYR  720
WMRLNFDLIQ ELSHEARRMI EGVVYEMRVY AVNAIGMSRP SPASQPFMPI GPPSEPTHLA  780
VEDVSDTTVS LKWRPPERVG AGGLDGYSVE YCPEGCSEWV AALQGLTEHT SILVKDLPTG  840
ARLLFRVRAH NMAGPGAPVT TTEPVTVQEI LQRPRLQLPR HLRQTIQKKV GEPVNLLIPF  900
QGKPRPQVTW TKEGQPLAGE EVSIRNSPTD TILFIRAARR VHSGTYQVTV RIENMEDKAT  960
LVLQVVDKPS PPQDLRVTDA WGLNVALEWK PPQDVGNTEL WGYTVQKADK KTMEWFTVLE  1020
HYRRTHCVVP ELIIGNGYYF RVFSQNMVGF SDRAATTKEP VFIPRPGITY EPPNYKALDF  1080
SEAPSFTQPL VNRSVIAGYT AMLCCAVRGS PKPKISWFKN GLDLGEDARF RMFSKQGVLT  1140
LEIRKPCPFD GGIYVCRATN LQGEARCECR LEVRVPQ                          1177

SEQ ID NO: 106           moltype = AA  length = 1181
FEATURE                  Location/Qualifiers
source                   1..1181
                         mol_type = protein
                         organism = Homo sapiens
SEQUENCE: 106
MPEPGKKPVS AFSKKPRSVE VAAGSPAVFE AETERAGVKV RWQRGGSDIS ASNKYGLATE  60
GTRHTLTVRE VGPADQGSYA VIAGSSKVKF DLKVIEAEKA EPMLAPAPAP AEATGAPGEA  120
PAPAAELGES APSPKGSSSA ALNGPTPGAP DDPIGLFVMR PQDGEVTVGG SITFSARVAG  180
ASLLKPPVVK WFKGKWVDLS SKVGQHLQLH DSYDRASKVY LFELHITDAQ PAFTGSYRCE  240
VSTKDKFDCS NFNLTVHEAM GTGDLDLLSA FRRTSLAGGG RRISDSHEDT GILDFSSLLK  300
KRDSFRTPRD SKLEAPAEED VWEILRQAPP SEYERIAFQY GVTDLRGMLK RLKGMRRDEK  360
KSTAFQKKLE PAYQVSKGHK IRLTVELADH DAEVKWLKNG QEIQMSGSKY IFESIGAKRT  420
LTISQCSLAD DAAYQCVVGG EKCSTELFVK EPPVLITRPL EDQLVMVGQR VEFECEVSEE  480
GAQVKWLKDG VELTREETFK YRFKKDGQRH HLIINEAMLE DAGHYALCTS GGQALAELIV  540
QEKKLEPRQE PPKIHLDCPG RIPDTIVVVA GNKLRLDVPI SGDPAPTVIW QKAITQGNKA  600
PARPAPDAPE DTGDSDEWVF DKKLLCETEG RVRVETTKDR SIFTVEGAEK EDEGVYTVTV  660
KNPVGEDQVN LTVKVIDVPD APAAPKISNV GEDSCTVQWE PPAYDGGQPI LGYILERKKK  720
KSYRWMRLNF DLIQELSHEA RRMIEGVVYE MRVYAVNAIG MSRPSPASQP FMPIGPPSEP  780
THLAVEDVSD TTVSLKWRPP ERVGAGGLDG YSVEYCPEGC SEWVAALQGL TEHTSILVKD  840
LPTGARLLFR VRAHNMAGPG APVTTTEPVT VQEILQRPRL QLPRHLRQTI QKKVGEPVNL  900
LIPFQGKPRP QVTWTKEGQP LAGEEVSIRN SPTDTILFIR AARRVHSGTY QVTVRIENME  960
DKATLVLQVV DKPSPPQDLR VTDAWGLNVA LEWKPPQDVG NTELWGYTVQ KADKKTMEWF  1020
TVLEHYRRTH CVVPELIIGN GYYFRVFSQN MVGFSDRAAT TKEPVFIPRP GITYEPPNYK  1080
ALDFSEAPSF TQPLVNRSVI AGYTAMLCCA VRGSPKPKIS WFKNGLDLGE DARFRMFSKQ  1140
GVLTLEIRKP CPFDGGIYVC RATNLQGEAR CECRLEVRVP Q                    1181

SEQ ID NO: 107           moltype = DNA  length = 3480
FEATURE                  Location/Qualifiers
```

```
source                  1..3480
                        mol_type = genomic DNA
                        organism = Homo sapiens
SEQUENCE: 107
atgccggtgc ggaggggcca cgtcgcgccg cagaacacct tcctggacac catcatccgc  60
aagtttgagg gccagagccg taagttcatc atcgccaacg ctcgggtgga gaactgcgcc  120
gtcatctact gcaacgacgg cttctgcgag ctgtgcggct actcgcgggc cgaggtgatg  180
cagcgaccct gcacctgcga cttcctgcac gggccgcgca cgcagcgccg cgctgccgcg  240
cagatcgcgc aggcactgct gggcgccgag gagcgcaaag tggaaatcgc cttctaccgg  300
aaagatggga gctgcttcct atgtctggtg gatgtggtgc ccgtgaagaa cgaggatggg  360
gctgtcatca tgttcatcct caatttcgag gtggtgatgg agaaggacat ggtggggtcc  420
ccggctcatg acaccaacca ccggggcccc cccaccagct ggctggcccc aggccgcgcc  480
aagaccttcc gcctgaagct gcccgcgctg ctggcgctga cggcccggga gtcgtcggtg  540
cggtcgggcg gcgcgggcgg cgcgggcgcc ccgggggccg tggtggtgga cgtggacctg  600
acgcccgcgg cacccagcag cgagtcgctg gccctggacg aagtgacagc catggacaac  660
cacgtggcag ggctcgggcc cgcggaggag cggcgtgcgc tggtgggtcc cggctctccg  720
ccccgcagcg cgcccggcca gctcccatcg ccccgggcgc acagcctcaa ccccgacgcc  780
tcgggctcca gctgcagcct ggcccggacg cgctcccgag aaagctgcgc cagcgtgcgc  840
cgcgcctcgt cggccgacga catcgaggcc atgcgcgccg gggtgctgcc cccgccaccg  900
cgccacgcca gcaccggggc catgcaccca ctgcgcagcg gcttgctcaa ctccacctcg  960
gactccgacc tcgtgcgcta ccgcaccatt agcaagattc cccaaatcac cctcaacttt  1020
gtggacctca agggcgaccc cttcttggct tcgcccacca gtgaccgtga gatcatagca  1080
cctaagataa aggagcgaac ccacaatgtc actgagaagg tcacccaggt cctgtccctg  1140
ggcgccgacg tgctgcctga gtacaagctg caggcaccgc gcatccaccg ctggaccatc  1200
ctgcattaca gccccttcaa ggccgtgtgg gactggctca tcctgctgct ggtcatctac  1260
acggctgtct tcacacccta ctcggctgcc ttcctgctga aggagacgga agaaggcccg  1320
cctgctaccg agtgtggcta cgcctgccag ccgctggctg tggtggacct catcgtggac  1380
atcatgttca ttgtggacat cctcatcaac ttccgcacca cctacgtcaa tgccaacgag  1440
gaggtggtca gccaccccgg ccgcatcgcc gtccactact tcaagggctg gttcctcatc  1500
gacatggtgg ccgccatccc cttcgacctg ctcatcttcg gctctggctc tgaggagctg  1560
atcgggctgc tgaagactgc gcggctgctg cggctggtgc gcgtggcgcg gaagctggat  1620
cgctactcag agtacggcgc ggccgtgctg ttcttgctca tgtgcacctt tgcgctcatc  1680
gcgcactggc tagcctgcat ctggtacgcc atcggcaaca tggagcagcc acacatggac  1740
tcacgcatcg gctggctgca caacctgggc gaccagatag gcaaacccta caacagcagc  1800
ggcctgggcg gcccctccat caaggacaag tatgtgacgg cgctctactt caccttcagc  1860
agcctcacca gtgtgggctt cggcaacgtc tctcccaaca ccaactcaga gaagatcttc  1920
tccatctgcg tcatgctcat tggctccctc atgtatgcta gcatcttcgg caacgtgtcg  1980
gccatcatcc agcggctgta ctcgggcaca gcccgctacc acacacagat gctgcgggtg  2040
cgggagttca tccgcttcca ccagatcccc aatcccctgc gccagcgcct cgaggagtac  2100
ttccagcacg cctggtccta caccaacggc atcgacatga acgcggtgct gaagggcttc  2160
cctgagtgcc tgcaggctga catctgcctg cacctgaacc gctcactgct gcagcactgc  2220
aaacccttcc gagggggccac caagggctgc cttcgggccc tggccatgaa gttcaagacc  2280
acacatgcac cgccagggga cacactggtg catgctgggg acctgctcac cgccctgtac  2340
ttcatctccc ggggctccat cgagatcctg cggggcgacg tcgtcgtggc catcctgggg  2400
aagaatgaca tctttgggga gcctctgaac ctgtatgcaa ggcctggcaa gtcgaacggg  2460
gatgtgcggg ccctcaccta ctgtgaccta cacaagatcc atcgggacga cctgctggag  2520
gtgctggaca tgtaccctga gttctccgac cacttctggt ccagcctgga gatcaccttc  2580
aacctgcgag ataccaacat gatcccgggc tcccccggca gtacggagtt agagggtggc  2640
ttcagtcggc aacgcaagcg caagttgtcc ttccgcaggc gcacggacaa ggacacggag  2700
cagccagggg aggtgtcggc cttggggccg ggccgggcgg gggcagggcc gagtagccgg  2760
ggccggccgg gggggccgtg gggggagagc ccgtccagtg gcccctccag ccctgagagc  2820
agtgaggatg agggcccagg ccgcagctcc agccccctcc gcctggtgcc cttctccagc  2880
cccaggcccc ccggagagcc gccgggtggg gagcccctga tggaggactg cgagaagagc  2940
agcgacactt gcaacccccct gtcaggcgcc ttctcaggag tgtccaacat tttcagcttc  3000
tggggggaca gtcggggccg ccagtaccag gagctccctc gatgccccgc ccccaccccc  3060
agcctcctca acatccccct ctccagcccg ggtcggcggc cccggggcga cgtggagagc  3120
aggctggatg ccctccagcg ccagctcaac aggctggaga cccggctgag tgcagacatg  3180
gccactgtcc tgcagctgct acagaggcag atgacgctgg tcccgcccgc ctacagtgct  3240
gtgaccaccc cggggcctgg ccccacttcc acatccccgc tgttgcccgt cagccccctc  3300
cccaccctca ccttggactc gctttctcag gtttcccagt tcatggcgtg tgaggagctg  3360
cccccggggg ccccagagct tccccaagaa ggccccacac gacgcctctc cctaccgggc  3420
cagctggggg ccctcacctc ccagcccctg cacagacacg gctcggaccc gggcagttag  3480

SEQ ID NO: 108          moltype = AA  length = 1159
FEATURE                 Location/Qualifiers
source                  1..1159
                        mol_type = protein
                        organism = Homo sapiens
SEQUENCE: 108
MPVRRGHVAP QNTFLDTIIR KFEGQSRKFI IANARVENCA VIYCNDGFCE LCGYSRAEVM  60
QRPCTCDFLH GPRTQRRAAA QIAQALLGAE ERKVEIAFYR KDGSCFLCLV DVVPVKNEDG  120
AVIMFILNFE VVMEKDMVGS PAHDTNHRGP PTSWLAPGRA KTFRLKLPAL LALTARESSV  180
RSGGAGGAGA PGAVVVDVDL TPAAPSSESL ALDEVTAMDN HVAGLGPAEE RRALVGPGSP  240
PRSAPGQLPS PRAHSLNPDA SGSSCSLART RSRESCASVR RASSADDIEA MRAGVLPPPP  300
RHASTGAMHP LRSGLLNSTS DSDLVRYRTI SKIPQITLNF VDLKGDPFLA SPTSDREIIA  360
PKIKERTHNV TEKVTQVLSL GADVLPEYKL QAPRIHRWTI LHYSPFKAVW DWLILLLVIY  420
TAVFTPYSAA FLLKETEEGP PATECGYACQ PLAVVDLIVD IMFIVDILIN FRTTYVNANE  480
EVVSHPGRIA VHYFKGWFLI DMVAAIPFDL LIFGSGSEEL IGLLKTARLL RLVRVARKLD  540
RYSEYGAAVL FLLMCTFALI AHWLACIWYA IGNMEQPHMD SRIGWLHNLG DQIGKPYNSS  600
```

-continued

```
GLGGPSIKDK YVTALYFTFS SLTSVGFGNV SPNTNSEKIF SICVMLIGSL MYASIFGNVS  660
AIIQRLYSGT ARYHTQMLRV REFIRFHQIP NPLRQRLEEY FQHAWSYTNG IDMNAVLKGF  720
PECLQADICL HLNRSLLQHC KPFRGATKGC LRALAMKFKT THAPPGDTLV HAGDLLTALY  780
FISRGSIEIL RGDVVVAILG KNDIFGEPLN LYARPGKSNG DVRALTYCDL HKIHRDDLLE  840
VLDMYPEFSD HFWSSLEITF NLRDTNMIPG SPGSTELEGG FSRQRKRKLS FRRRTDKDTE  900
QPGEVSALGP GRAGAGPSSR GRPGGPWGES PSSGPSSPES SEDEGPGRSS SPLRLVPFSS  960
PRPPGEPPGG EPLMEDCEKS SDTCNPLSGA FSGVSNIFSF WGDSRGRQYQ ELPRCPAPTP  1020
SLLNIPLSSP GRRPRGDVES RLDALQRQLN RLETRLSADM ATVLQLLQRQ MTLVPPAYSA  1080
VTTPGPGPTS TSPLLPVSPL PTLTLDSLSQ VSQFMACEEL PPGAPELPQE GPTRRLSLPG  1140
QLGALTSQPL HRHGSDPGS                                             1159

SEQ ID NO: 109         moltype = DNA  length = 3645
FEATURE                Location/Qualifiers
source                 1..3645
                       mol_type = genomic DNA
                       organism = Homo sapiens
SEQUENCE: 109
atggtggtgc cggagaagga gcagagctgg atccccaaga tcttcaagaa gaagacctgc  60
acgacgttca tagttgactc cacagatccg ggagggacct tgtgccagtg tgggcgcccc  120
cggaccgccc accccgcagt ggccatggag gatgccttcg gggcagccgt ggtgaccgtg  180
tgggacagcg atgcacacac cacggagaag cccaccgatg cctacggaga gctggacttc  240
acgggggccg gccgcaagca cagcaatttc ctccggctct ctgaccgaac ggatccagct  300
gcagtttata gtctggtcac acgcacatgg ggcttccgtg ccccgaacct ggtggtgtca  360
gtgctggggg gatcgggggg ccccgtcctc cagacctggc tgcaggacct gctgcgtcgt  420
gggctggtgc gggctgccca gagcacagga gcctggattg tcactggggg tctgcacacg  480
ggcatcggcc ggcatgttgg tgtggctgta cgggaccatc agatggccag cactgggggc  540
accaaggtgg tggccatggg tgtggccccc tggggtgtgg tccggaatag agacaccctc  600
atcaacccca agggctcgtt ccctgcgagg taccggtggc gcggtgaccc ggaggacggg  660
gtccagtttc ccctggacta caactactcg gccttcttcc tggtggacga cggcacacac  720
ggctgcctgg ggggcgagaa ccgcttccgc ttgcgcctgg agtcctacat ctcacagcag  780
aagacgggcg tgggagggac tggaattgac atccctgtcc tgctcctcct gattgatggt  840
gatgagaaga tgttgacgcg aatagagaac gccacccagg ctcagctccc atgtctcctc  900
gtggctggct caggggggagc tgcggactgc ctggcggaga ccctggaaga cactctggcc  960
ccagggagtg gggggagccag gcaaggcgaa gcccgagatc gaatcaggcg tttctttccc  1020
aaaggggacc ttgaggtcct gcaggcccag gtggagagga ttatgacccg gaaggagctc  1080
ctgacagtct attcttctga ggatgggtct gaggaattcg agaccatagt tttgaaggcc  1140
cttgtgaagg cctgtgggag ctcggaggcc tcagcctacc tggatgagct gcgtttggct  1200
gtggcttgga accgcgtgga cattgcccag agtgaactct ttcgggggga catccaatgg  1260
cggtccttcc atctcgaagc ttccctcatg gacgccctgc tgaatgaccg gcctgagttc  1320
gtgcgcttgc tcatttccca cggcctcagc ctgggccact tcctgacccc gatgcgcctg  1380
gcccaactct acagcgcggc gccctccaac tcgctcatcc gcaacctttt ggaccaggcg  1440
tcccacagcg caggcaccaa agccccagcc ctaaaagggg gagctgcgga gctccggccc  1500
cctgacgtgg ggcatgtgct gaggatgctg ctggggaaga tgtgcgcgcc gaggtacccc  1560
tccgggggcg cctgggaccc tcacccaggc cagggcttcg gggagagcat gtatctgctc  1620
tcggacaagg ccacctcgcc gctctcgctg gatgctggcc tcgggcaggc cccctggagc  1680
gacctgcttc tttgggcact gttgctgaac agggcacaga tggccatgta cttctgggag  1740
atgggttcca atgcagtttc ctcagctctt ggggcctgtt tgctgctccg ggtgatggca  1800
cgcctggagc ctgacgctga ggaggcagca cggaggaaag acctggcgtt caagtttgag  1860
gggatgggcg ttgacctctt tggcgagtgc tatcgcagca gtgaggtgag ggctgcccgc  1920
ctcctcctcc gtcgctgccc gctctggggg gatgccactt gcctccagct ggccatgcaa  1980
gctgacgccc gtgccttctt tgcccaggat ggggtacagt ctctgctgac acagaagtgg  2040
tggggagata tggccagcac tacacccatc tgggccctgg ttctcgcctt cttttgccct  2100
ccactcatct acacccgcct catcaccttc aggaaatcag aagaggagcc cacacgggag  2160
gagctagagt ttgacatgga tagtgtcatt aatggggaag ggcctgtcgg gacggcggac  2220
ccagccgaga agacgccgct gggggtcccg cgccagtcgg gccgtccggg ttgctgcggg  2280
ggccgctgcg gggggcgccg gtgcctacgc cgctggttcc acttctgggg cgcgccggtg  2340
accatcttca tgggcaacgt ggtcagctac ctgctgttcc tgctgctttt ctcgcgggtg  2400
ctgctcgtgg atttccagcc ggcgccgccc ggctccctgg agctgctgct ctatttctgg  2460
gctttcacgc tgctgtgcga ggaactgcgc cagggcctga gcggaggcgg gggcagcctc  2520
gccagcgggg gccccgggcc tggccatgcc tcactgagcc agcgcctgcg cctctacctc  2580
gccgacagct ggaaccagtg cgacctagtg gctctcacct gcttcctcct gggcgtgggc  2640
tgccggctga ccccgggttt gtaccacctg ggccgcactg tcctctgcat cgacttcatg  2700
gttttcacgg tgcggctgct tcacatcttc acggtcaaca aacagctggg gcccaagatc  2760
gtcatcgtga gcaagatgat gaaggacgtg ttcttcttcc tcttcttcct cggcgtgtgg  2820
ctggtagcct atggcgtggc cacggagggg ctcctgaggc cacgggacag tgacttccca  2880
agtatcctgc gccgcgtctt ctaccgtccc tacctgcaga tcttcgggca gattccccag  2940
gaggacatgg acgtggccct catggagcac agcaactgct cgtcggagcc cggcttctgg  3000
gcacaccctc ctggggccca ggcgggcacc tgcgtctccc agtatgccaa ctggctggtg  3060
gtgctgctcc tcgtcatctt cctgctcgtg gccaacatcc tgctggtcaa cttgctcatt  3120
gccatgttca gttacacatt cggcaaagta cagggcaaca gcgatctcta ctggaaggcg  3180
cagcgttacc gcctcatccg ggaattccac tctcggcccg cgctggcccc gccctttatc  3240
gtcatctccc acttgcgcct cctgctcagg caattgtgca ggcgaccccg gagcccccag  3300
ccgtcctccc cggccctcga gcatttccgg gtttaccttt ctaaggaagc cgagcggaag  3360
ctgctaacgt gggaatcggt gcataaggag aactttctgc tggcacgcgc tagggacaag  3420
cgggagagcg actccgagcg tctgaagcgc acgtcccaga aggtggactt ggcactgaaa  3480
cagctgggac acatccgcga gtacgaacag cgcctgaaag tgctggagcg ggaggtccag  3540
cagtgtagcc gcgtcctggg gtgggtggcc gaggccctga gccgctctgc cttgctgccc  3600
ccaggtgggc cgccaccccc tgacctgcct gggtccaaag actga                  3645
```

```
SEQ ID NO: 110         moltype = AA  length = 1214
FEATURE                Location/Qualifiers
source                 1..1214
                       mol_type = protein
                       organism = Homo sapiens
SEQUENCE: 110
MVVPEKEQSW IPKIFKKKTC TTFIVDSTDP GGTLCQCGRP RTAHPAVAME DAFGAAVVTV  60
WDSDAHTTEK PTDAYGELDF TGAGRKHSNF LRLSDRTDPA AVYSLVTRTW GFRAPNLVVS  120
VLGGSGGPVL QTWLQDLLRR GLVRAAQSTG AWIVTGGLHT GIGRHVGVAV RDHQMASTGG  180
TKVVAMGVAP WGVVRNRDTL INPKGSFPAR YRWRGDPEDG VQFPLDYNYS AFFLVDDGTH  240
GCLGGENRFR LRLESYISQQ KTGVGGTGID IPVLLLLIDG DEKMLTRIEN ATQAQLPCLL  300
VAGSGGAADC LAETLEDTLA PGSGGARQGE ARDRIRRFFP KGDLEVLQAQ VERIMTRKEL  360
LTVYSSEDGS EEFETIVLKA LVKACGSSEA SAYLDELRLA VAWNRVDIAQ SELFRGDIQW  420
RSFHLEASLM DALLNDRPEF VRLLISHGLS LGHFLTPMRL AQLYSAAPSN SLIRNLLDQA  480
SHSAGTKAPA LKGGAAELRP PDVGHVLRML LGKMCAPRYP SGGAWDPHPG QGFGESMYLL  540
SDKATSPLSL DAGLGQAPWS DLLLWALLLN RAQMAMYFWE MGSNAVSSAL GACLLLRVMA  600
RLEPDAEEAA RRKDLAFKFE GMGVDLFGEC YRSSEVRAAR LLLRRCPLWG DATCLQLAMQ  660
ADARAFFAQD GVQSLLTQKW WGDMASTTPI WALVLAFFCP PLIYTRLITF RKSEEEPTRE  720
ELEFDMDSVI NGEGPVGTAD PAEKTPLGVP RQSGRPGCCG GRCGGRRCLR RWFHFWGAPV  780
TIFMGNVVSY LLFLLLFSRV LLVDFQPAPP GSLELLLYFW AFTLLCEELR QGLSGGGGSL  840
ASGGPGPGHA SLSQRLRLYL ADSWNQCDLV ALTCFLLGVG CRLTPGLYHL GRTVLCIDFM  900
VFTVRLLHIF TVNKQLGPKI VIVSKMMKDV FFFLFFLGVW LVAYGVATEG LLRPRDSDFP  960
SILRRVFYRP YLQIFGQIPQ EDMDVALMEH SNCSSEPGFW AHPPGAQAGT CVSQYANWLV  1020
VLLLVIFLLV ANILLVNLLI AMFSYTFGKV QGNSDLYWKA QRYRLIREFH SRPALAPPFI  1080
VISHLRLLLR QLCRRPRSPQ PSSPALEHFR VYLSKEAERK LLTWESVHKE NFLLARARDK  1140
RESDSERLKR TSQKVDLALK QLGHIREYEQ RLKVLEREVQ QCSRVLGWVA EALSRSALLP  1200
PGGPPPPDLP GSKD                                                   1214

SEQ ID NO: 111         moltype = DNA  length = 3357
FEATURE                Location/Qualifiers
source                 1..3357
                       mol_type = genomic DNA
                       organism = Homo sapiens
SEQUENCE: 111
atggcgcgga gcccgggacg cgcgtacgcc ctgctgcttc tcctgatctg ctttaacgtt  60
ggaagtggac ttcacttaca ggtcttaagc acaagaaatg aaaataagct gcttcctaaa  120
catcctcatt tagtgcggca aaagcgcgcc tggatcaccg cccccgtggc tcttcgggag  180
ggagaggatc tgtccaagaa gaatccaatt gccaagatac attctgatct tgcagaagaa  240
agaggactca aaattactta caaatacact ggaaaaggga ttacagagcc accttttggt  300
atatttgtct ttaacaaaga tactggagaa ctgaatgtta ccagcattct tgatcgagaa  360
gaaacaccat tttttctgct aacaggttac gctttggatg caagaggaaa caatgtagag  420
aaacccttag agctacgcat taaggttctt gatatcaatg acaacgaacc agtgttcaca  480
caggatgtct ttgttgggtc tgttgaagag ttgagtgcag cacatactct tgtgatgaaa  540
atcaatgcaa cagatgcaga tgagcccaat accctgaatt cgaaaatttc ctatagaatc  600
gtatctctgg agcctgctta tcctccagtg ttctacctaa ataaagatac aggagagatt  660
tatacaacca gtgttacctt ggacagagag gaacacagca gctacacttt gacagtagaa  720
gcaagagatg gcaatggaga agttacagac aaacctgtaa aacaagctca agttcagatt  780
cgtattttgg atgtcaatga caatatacct gtagtagaaa ataaagtgct tgaagggatg  840
gttgaagaaa atcaagtcaa cgtagaagtt acgcgcataa aagtgttcga tgcagatgaa  900
ataggttctg ataattggct ggcaaatttt acatttgcat caggaaatga aggaggttat  960
ttccacatag aaacagatgc tcaaactaac gaaggaattg tgacccttat taaggaagta  1020
gattatgaag aaatgaagaa tcttgacttc agtgttattg tcgctaataa agcagctttt  1080
cacaagtcga ttaggagtaa atacaagcct acacccattc ccatcaaggt caaagtgaaa  1140
aatgtgaaag aaggcattca ttttaaaagc agcgtcatct caatttatgt tagcgagagc  1200
atggatagat caagcaaagg ccaaataatt ggaaattttc aagcttttga tgaggacact  1260
ggactaccag cccatgcaag atatgtaaaa ttagaagata gagataattg gatctctgtg  1320
gattctgtca catctgaaat taaacttgca aaacttcctg attttgaatc tagatatgtt  1380
caaaatggca catacactgt aaagattgtg gccatatcag aagattatcc tagaaaaacc  1440
atcactggca cagtccttat caatgttgaa gacatcaacg acaactgtcc cacactgata  1500
gagcctgtgc agacaatctg tcacgatgca gagtatgtga atgttactgc agaggacctg  1560
gatggacacc caaacagtgg ccctttcagt ttctccgtca ttgacaaacc acctggcatg  1620
gcagaaaaat ggaaaatagc acgccaagaa agtaccagtg tgctgctgca acaaagtgag  1680
aaaaagcttg ggagaagtga aattcagttc ctgatttcag acaatcaggg ttttagttgt  1740
cctgaaaagc aggtccttac actcacagtt tgtgagtgtc tgcatggcag cggctgcagg  1800
gaagcacagc atgactccta tgtgggcctg ggacccgcag caattgcgct catgattttg  1860
gcctttctgc tcctgctatt ggtaccactt ttactgctga tgtgccattg cggaaagggc  1920
gccaaaggct ttacccccat acctggcacc atagagatgc tgcatccttg gaataatgaa  1980
ggagcaccac ctgaagacaa ggtggtgcca tcatttctgc cagtggatca agggggcagt  2040
ctagtaggaa gaaatggagt aggaggtatg gccaaggaag ccacgatgaa aggaagtagc  2100
tctgcttcca ttgtcaaagg gcaacatgag atgtccgaga tggatggaag gtgggaagaa  2160
cacagaagcc tgctttctgg tagagctacc cagtttacag gggccacagg cgctatcatg  2220
accactgaaa ccacgaagac cgcaagggcc acaggggctt ccagagacat ggccggagct  2280
caggcagctg ctgttgcact gaacgaagaa ttcttaagaa attatttcac tgataaagcg  2340
gcctcttaca ctgaggaaga tgaaaatcac acagccaaag attgccttct ggtttattct  2400
caggaagaaa ctgaatcgct gaatgcttct attggttgtt gcagttttat tgaaggagag  2460
ctagatgacc gcttcttaga tgatttggga cttaaattca agacactagc tgaagtttgc  2520
ctgggtcaaa aaatagatat aaataaggaa attgagcaga gacaaaaacc tgccacagaa  2580
acaagtatga acacagcttc acattcactc tgtgagcaaa ctatggttaa ttcagagaat  2640
acctactcct ctggcagtag cttcccagtt ccaaaatctt tgcaagaagc caatgcagag  2700
```

```
aaagtaactc aggaaatagt cactgaaaga tctgtgtctt ctaggcaggc gcaaaaggta  2760
gctacacctc ttcctgaccc aatggcttct agaaatgtga tagcaacaga aacttcctat  2820
gtcacagggt ccactatgcc accaaccact gtgatcctgg gtcctagcca gccacagagc  2880
cttattgtga cagagagggt gtatgctcca gcttctacct tggtagatca gccttatgct  2940
aatgaaggta cagttgtggt cactgaaaga gtaatacagc ctcatggggg tggatcgaat  3000
cctctggaag gcactcagca tcttcaagat gtaccttacg tcatggtgag ggaaagagag  3060
agcttccttg cccccagctc aggtgtgcag cctactctgg ccatgcctaa tatagcagta  3120
ggacagaatg tgacagtgac agaaagagtt ctagcacctg cttccactct gcaatccagt  3180
taccagattc ccactgaaaa ttctatgacg gctaggaaca ccacggtgtc tggagctgga  3240
gtccctggcc ctctgccaga ttttggttta gaggaatctg gtcattctaa ttctaccata  3300
accacatctt ccaccagagt taccaagcat agcactgtac agcattctta ctcctaa     3357

SEQ ID NO: 112          moltype = AA  length = 1118
FEATURE                 Location/Qualifiers
source                  1..1118
                        mol_type = protein
                        organism = Homo sapiens
SEQUENCE: 112
MARSPGRAYA LLLLLICFNV GSGLHLQVLS TRNENKLLPK HPHLVRQKRA WITAPVALRE  60
GEDLSKKNPI AKIHSDLAEE RGLKITYKYT GKGITEPPFG IFVFNKDTGE LNVTSILDRE  120
ETPFFLLTGY ALDARGNNVE KPLELRIKVL DINDNEPVFT QDVFVGSVEE LSAAHTLVMK  180
INATDADEPN TLNSKISYRI VSLEPAYPPV FYLNKDTGEI YTTSVTLDRE EHSSYTLTVE  240
ARDGNGEVTD KPVKQAQVQI RILDVNDNIP VVENKVLEGM VEENQVNVEV TRIKVFDADE  300
IGSDNWLANF TFASGNEGGY FHIETDAQTN EGIVTLIKEV DYEEMKNLDF SVIVANKAAF  360
HKSIRSKYKP TPIPIKVKVK NVKEGIHFKS SVISIYVSES MDRSSKGQII GNFQAFDEDT  420
GLPAHARYVK LEDRDNWISV DSVTSEIKLA KLPDFESRYV QNGTYTVKIV AISEDYPRKT  480
ITGTVLINVE DINDNCPTLI EPVQTICHDA EYVNVTAEDL DGHPNSGPFS FSVIDKPPGM  540
AEKWKIARQE STSVLLQQSE KKLGRSEIQF LISDNQGFSC PEKQVLTLTV CECLHGSGCR  600
EAQHDSYVGL GPAAIALMIL AFLLLLLVPL LLLMCHCGKG AKGFTPIPGT IEMLHPWNNE  660
GAPPEDKVVP SFLPVDQGGS LVGRNGVGGM AKEATMKGSS SASIVKGQHE MSEMDGRWEE  720
HRSLLSGRAT QFTGATGAIM TTETTKTARA TGASRDMAGA QAAAVALNEE FLRNYFTDKA  780
ASYTEEDENH TAKDCLLVYS QEETESLNAS IGCCSFIEGE LDDRFLDDLG LKFKTLAEVC  840
LGQKIDINKE IEQRQKPATE TSMNTASHSL CEQTMVNSEN TYSSGSSFPV PKSLQEANAE  900
KVTQEIVTER SVSSRQAQKV ATPLPDPMAS RNVIATETSY VTGSTMPPTT VILGPSQPQS  960
LIVTERVYAP ASTLVDQPYA NEGTVVVTER VIQPHGGGSN PLEGTQHLQD VPYVMVRERE  1020
SFLAPSSGVQ PTLAMPNIAV GQNVTVTERV LAPASTLQSS YQIPTENSMT ARNTTVSGAG  1080
VPGPLPDFGL EESGHSNSTI TTSSTRVTKH STVQHSYS                          1118

SEQ ID NO: 113          moltype = DNA  length = 2994
FEATURE                 Location/Qualifiers
source                  1..2994
                        mol_type = genomic DNA
                        organism = Homo sapiens
SEQUENCE: 113
atggagaacg cgcacaccaa gacggtggag gaggtgctgg gccacttcgg cgtcaacgag  60
agtacggggc tgagcctgga acaggtcaag aagcttaagg agagatgggg ctccaacgag  120
ttaccggctg aagaaggaaa aaccttgctg gaacttgtga ttgagcagtt tgaagacttg  180
ctagttagga ttttattact ggcagcatgt atatcttttg ttttggcttg gtttgaagaa  240
ggtgaagaaa caattacagc ctttgtagaa ccttttgtaa ttttactcat attagtagcc  300
aatgcaattg tgggtgtatg gcaggaaaga aatgctgaaa atgccatcga agcccttaag  360
gaatatgagc ctgaaatggg caaagtgtat cgacaggaca gaaagagtgt gcagcggatt  420
aaagctaaag acatagttcc tggtgatatt gtagaaattg ctgttggtga caaagttcct  480
gctgatataa ggttaacttc catcaaatct accacactaa gagttgacca gtcaattctc  540
acaggtgaat ctgtctctgt catcaagcac actgatcccg tccctgaccc acgagctgtc  600
aaccaagata aaaagaacat gctgttttct ggtacaaaca ttgctgctgg gaaagctatg  660
ggagtggtgg tagcaactgg agttaacacc gaaattggca agatccggga tgaaatggtg  720
gcaacagaac aggagagaac acccccttcag caaaaactag atgaatttgg ggaacagctt  780
tccaaagtca tctcccttat ttgcattgca gtctggatca taaatattgg gcacttcaat  840
gacccggttc atggagggtc ctggatcaga ggtgctattt actactttaa aattgcagtg  900
gccctggctg tagcagccat tcctgaaggt ctgcctgcag tcatcaccac ctgcctggct  960
cttggaactc gcagaatggc aaagaaaaat gccattgttc gaagcctccc gtctgtggaa  1020
acccttggtt gtacttctgt tatctgctca gacaagactg gtacacttac aacaaaccag  1080
atgtcagtct gcaggatgtt cattctggac agagtggaag gtgatacttg ttcccttaat  1140
gagtttacca taactggatc aacttatgca cctattggag aagtgcataa agatgataaa  1200
ccagtgaatt gtcaccagta tgatggtctg gtagaattag caacaatttg tgctctttgt  1260
aatgactctg ctttggatta caatgaggca aagggtgtgt atgaaaaagt tggagaagct  1320
acagagactg ctctcacttg cctagtagag aagatgaatg tatttgatac cgaattgaag  1380
ggtctttcta aaatagaacg tgcaaatgcc tgcaactcag tcattaaaca gctgatgaaa  1440
aaggaattca ctctagagtt ttcacgtgac agaaagtcaa tgtcggttta ctgtacacca  1500
aataaaccaa gcaggacatc aatgagcaag atgtttgtga agggtgctcc tgaaggtgtc  1560
attgacaggt gcacccacat tcgagttgga agtactaagg ttcctatgac ctctggagtc  1620
aaacagaaga tcatgtctgt cattcgagag tggggtagtg gcagcgacac actgcgatgc  1680
ctggccctgg ccactcatga caacccactg agaagagaag aaatgcacct tgaggactct  1740
gccaacttta ttaaatatga gaccaatctg accttcgttg gctgcgtggg catgctggat  1800
cctccgagaa tcgaggtggc ctcctccgtg aagctgtgcc ggcaagcagg catccgggtc  1860
atcatgatca ctggggacaa caagggcact gctgtggcca tctgtcgccg catcggcatc  1920
ttcgggcagg atgaggacgt gacgtcaaaa gctttcacag gccgggagtt tgatgaactc  1980
aacccctccg cccagcgaga cgcctgcctg aacgcccgct gtttgctcg agttgaaccc  2040
tcccacaagt ctaaaatcgt agaatttctt cagtcttttg atgagattac agctatgact  2100
```

```
ggcgatggcg tgaacgatgc tcctgctctg aagaaagccg agattggcat tgctatgggc  2160
tctggcactg cggtggctaa aaccgcctct gagatggtcc tggcggatga caacttctcc  2220
accattgtgg ctgccgttga ggaggggcgg gcaatctaca acaacatgaa acagttcatc  2280
cgctacctca tctcgtccaa cgtcggggaa gttgtctgta ttttcctgac agcagccctt  2340
ggatttcccg aggctttgat tcctgttcag ctgctctggg tcaatctggt gacagatggc  2400
ctgcctgcca ctgcactggg gttcaaccct cctgatctgg acatcatgaa taaacctccc  2460
cggaacccaa aggaaccatt gatcagcggg tggctctttt tccgttactt ggctattggc  2520
tgttacgtcg gcgctgctac cgtgggtgct gctgcatggt ggttcattgc tgctgacggt  2580
ggtccaagag tgtccttcta ccagctgagt catttcctac agtgtaaaga ggacaacccg  2640
gactttgaag gcgtggattg tgcaatcttt gaatccccat acccgatgac aatggcgctc  2700
tctgttctag taactataga aatgtgtaac gccctcaaca gcttgtccga aaaccagtcc  2760
ttgctgagga tgccccctg ggagaacatc tggctcgtgg gctccatctg cctgtccatg  2820
tcactccact tcctgatcct ctatgtcgaa cccttgccac tcatcttcca gatcacaccg  2880
ctgaacgtga cccagtggct gatggtgctg aaaatctcct tgcccgtgat tctcatggat  2940
gagacgctca agtttgtggc ccgcaactac ctggaacctg caatactgga gtaa        2994
```

```
SEQ ID NO: 114          moltype = AA  length = 997
FEATURE                 Location/Qualifiers
source                  1..997
                        mol_type = protein
                        organism = Homo sapiens
SEQUENCE: 114
MENAHTKTVE EVLGHFGVNE STGLSLEQVK KLKERWGSNE LPAEEGKTLL ELVIEQFEDL  60
LVRILLLAAC ISFVLAWFEE GEETITAFVE PFVILLILVA NAIVGVWQER NAENAIEALK  120
EYEPEMGKVY RQDRKSVQRI KAKDIVPGDI VEIAVGDKVP ADIRLTSIKS TTLRVDQSIL  180
TGESVSVIKH TDPVPDPRAV NQDKKNMLFS GTNIAAGKAM GVVVATGVNT EIGKIRDEMV  240
ATEQERTPLQ QKLDEFGEQL SKVISLICIA VWIINIGHFN DPVHGGSWIR GAIYYFKIAV  300
ALAVAAIPEG LPAVITTCLA LGTRRMAKKN AIVRSLPSVE TLGCTSVICS DKTGTLTTNQ  360
MSVCRMFILD RVEGDTCSLN EFTITGSTYA PIGEVHKDDK PVNCHQYDGL VELATICALC  420
NDSALDYNEA KGVYEKVGEA TETALTCLVE KMNVFDTELK GLSKIERANA CNSVIKQLMK  480
KEFTLEFSRD RKSMSVYCTP NKPSRTSMSK MFVKGAPEGV IDRCTHIRVG STKVPMTSGV  540
KQKIMSVIRE WGSGSDTLRC LALATHDNPL RREEMHLEDS ANFIKYETNL TFVGCVGMLD  600
PPRIEVASSV KLCRQAGIRV IMITGDNKGT AVAICRRIGI FGQDEDVTSK AFTGREFDEL  660
NPSAQRDACL NARCFARVEP SHKSKIVEFL QSFDEITAMT GDGVNDAPAL KKAEIGIAMG  720
SGTAVAKTAS EMVLADDNFS TIVAAVEEGR AIYNNMKQFI RYLISSNVGE VVCIFLTAAL  780
GFPEALIPVQ LLWVNLVTDG LPATALGFNP PDLDIMNKPP RNPKEPLISG WLFFRYLAIG  840
CYVGAATVGA AAWWFIAADG GPRVSFYQLS HFLQCKEDNP DFEGVDCAIF ESPYPMTMAL  900
SVLVTIEMCN ALNSLSENQS LLRMPPWENI WLVGSICLSM SLHFLILYVE PLPLIFQITP  960
LNVTQWLMVL KISLPVILMD ETLKFVARNY LEPAILE                          997
```

```
SEQ ID NO: 115          moltype = DNA  length = 6666
FEATURE                 Location/Qualifiers
source                  1..6666
                        mol_type = genomic DNA
                        organism = Homo sapiens
SEQUENCE: 115
atggtcaatg agaatacgag gatgtacatt ccagaggaaa accaccaagg ttccaactat  60
gggagcccac gccccgccca tgccaacatg aatgccaatg cggcagcggg gctggcccct  120
gagcacatcc ccacccccggg ggctgccctg tcgtggcagg cggccatcga cgcagcccgg  180
caggctaagc tgatgggcag cgctggcaat gcgaccatct ccacagtcag ctccacgcag  240
cggaagcggc agcaatatgg gaaacccaag aagcagggca gcaccacggc cacacgcccg  300
ccccgagccc tgctctgcct gaccctgaag aaccccatcc ggagggcctg catcagcatt  360
gtcgaatgga aaccatttga aataattatt ttactgacta tttttgccaa ttgtgtggcc  420
ttagcgatct atattccctt tccagaagat gattccaacg ccaccaattc caacctggaa  480
cgagtggaat atctctttct cataattttt acggtggaag cgtttttaaa agtaatcgcc  540
tatggactcc tctttcaccc caatgcctac ctccgcaacg gctggaacct actagatttt  600
ataattgtgg ttgtggggct ttttagtgca attttagaac aagcaaccaa agcagatggg  660
gcaaacgctc tcggagggaa aggggccgga tttgatgtga aggcgctgag ggccttccgc  720
gtgctgcgcc ccctgcggct ggtgtccgga gtcccaagtc tccaggtggt cctgaattcc  780
atcatcaagg ccatggtccc cctgctgcac atcgccctgc ttgtgctgtt tgtcatcatc  840
atctacgcca tcatcggctt ggagctcttc atggggaaga tgcacaagac ctgctacaac  900
caggagggca tagcagatgt tccagcagaa gatgacccctt cccttgtgc gctggaaacg  960
ggccacgggc ggcagtgcca gaacggcacg gtgtgcaagc ccggctggga tggtcccaag  1020
cacggcatca ccaactttga caactttgcc ttcgccatgc tcacggtgtt ccagtgcatc  1080
accatggagg gctggacgga cgtgctgtac tgggtcaatg atgccgtagg aagggactgg  1140
ccctggatct attttgttac actaatcatc atagggtcat tttttgtact taacttggtt  1200
ctcggtgtgc ttagcggaga gttttccaaa gagagggaga aggccaaggc ccggggagat  1260
ttccagaagc tgcgggagaa gcagcagcta gaagaggatc tcaaaggcta cctggattgg  1320
atcactcagg ccgaagacat cgatcctgag aatgaggacg aaggcatgga tgaggagaag  1380
ccccgaaaca tgagcatgcc caccagtgag accgagtccg tcaacaccga aaacgtggct  1440
ggaggtgaca tcgagggaga aaactgcggg gccaggctgg cccaccggat ctccaagtca  1500
aagttcagcc gctactggcg ccggtggaat cggttctgca gaaggaagtg ccgcgccgca  1560
gtcaagtcta atgtcttcta ctggctggtg attttcctgg tgttcctcaa cacgctcacc  1620
attgcctctg agcactacaa ccagcccaac tggctcacag aagtccaaga cacggcaaac  1680
aaggccctgc tggccctgtt cacggcagag atgctcctga agatgtacag cctgggcctg  1740
caggcctact tcgtgtccct cttcaaccgc tttgactgct tcgtcgtgtg tggcggcatc  1800
ctggagacca tcctggtgga gaccaagatc atgtccccac tgggcatctc cgtgctcaga  1860
tgcgtccggc tgctgaggat tttcaagatc acgaggtact ggaactcctt gagcaacctg  1920
gtggcatcct tgctgaactc tgtgcgctcc atcgcctccc tgctccttct cctcttcctc  1980
```

-continued

```
ttcatcatca tcttctccct cctggggatg cagctctttg gaggaaagtt caactttgat  2040
gagatgcaga cccggaggag cacattcgat aacttccccc agtccctcct cactgtgttt  2100
cagatcctga ccggggagga ctggaattcg gtgatgtatg atgggatcat ggcttatggc  2160
ggcccctctt ttccagggat gttagtctgt atttacttca tcatcctctt catctgtgga  2220
aactatatcc tactgaatgt gttcttggcc attgctgtgg acaacctggc tgatgctgag  2280
agcctcacat ctgcccaaaa ggaggaggaa gaggagaagg agagaaagaa gctggccagg  2340
actgccagcc cagagaagaa acaagagttg gtggagaagc cggcagtggg ggaatccaag  2400
gaggagaaga ttgagctgaa atccatcacg gctgacggag agtctccacc cgccaccaag  2460
atcaacatgg atgacctcca gcccaatgaa aatgaggata agagccccta ccccaaccca  2520
gaaactacag gagaagagga tgaggaggag ccagagatgc ctgtcggccc tcgcccacga  2580
ccactctctg agcttcacct taaggaaaag gcagtgccca tgccagaagc cagcgcgttt  2640
ttcatcttca gctctaacaa caggtttcgc ctccagtgcc accgcattgt caatgacacg  2700
atcttcacca acctgatcct cttcttcatt ctgctcagca gcatttccct ggctgctgag  2760
gacccggtcc agcacacctc cttcaggaac catattctgt tttattttga tattgttttt  2820
accaccattt tcaccattga aattgctctg aagatcctag gcaatgcaga ctatgtcttc  2880
actagtatct ttacattaga aattatcctt aagatgactg cttatggggc tttcttgcac  2940
aagggttctt tctgccggaa ctacttcaac atcctggacc tgctggtggt cagcgtgtcc  3000
ctcatctcct ttggcatcca gtccagtgca atcaatgtcg tgaagatctt gcgagtcctg  3060
cgagtactca ggcccctgag ggccatcaac agggccaagg ggctaaagca tgtggttcag  3120
tgtgtgtttg tcgccatccg gaccatcggg aacatcgtga ttgtcaccac cctgctgcag  3180
ttcatgtttg cctgcatcgg ggtccagctc ttcaagggaa agctgtacac ctgttcagac  3240
agttccaagc agacagaggc ggaatgcaag ggcaactaca tcacgtacaa agacgggggag  3300
gttgaccacc ccatcatcca accccgcagc tgggagaaca gcaagtttga ctttgacaat  3360
gttctggcag ccatgatggc cctcttcacc gtctccacct tcgaagggtg gccagagctg  3420
ctgtaccgct ccatcgactc ccacacggaa gacaagggcc ccatctacaa ctaccgtgtg  3480
gagatctcca tcttcttcat catctacatc atcatcatcg ccttcttcat gatgaacatc  3540
ttcgtgggct tcgtcatcgt caccttttcag gagcaggggg agcaggagta caagaactgt  3600
gagctggaca agaaccagcg acagtgcgtg gaatacgccc tcaaggcccg gcccctgcgg  3660
aggtacatcc ccaagaacca gcaccagtac aaagtgtggt acgtggtcaa ctccacctac  3720
ttcgagtacc tgatgttcgt cctcatcctg ctcaacacca tctgcctggc catgcagcac  3780
tacggccaga gctgcctgtt caaaatcgcc atgaacatcc tcaacatgct cttcactggc  3840
ctcttcaccg tggagatgat cctgaagctc attgccttca aacccaaggg ttactttagt  3900
gatccctgga atgtttttga cttcctcatc gtaattggca gcataattga cgtcattctc  3960
agtgagacta atcactattt ctgtgatgca tggaatacat ttgacgcctt gattgttgtg  4020
ggtagcattg ttgatatagc aatcaccgag gtaaacccag ctgaacatac ccaatgctct  4080
ccctctatga acgcagagga aaactcccgc atctccatca ccttcttccg cctgttccgg  4140
gtcatgcgtc tggtgaagct gctgagccgt ggggagggca tccggacgct gctgtggacc  4200
ttcatcaagt ccttccaggc cctgccctat gtggccctcc tgatcgtgat gctgttcttc  4260
atctacgcgg tgatcgggat gcaggtgttt gggaaaattg ccctgaatga taccacagag  4320
atcaaccgga acaacaactt tcagaccttc ccccaggccg tgctgctcct cttcaggtgt  4380
gccaccgggg aggcctggca ggacatcatg ctggcctgca tgccaggcaa gaagtgtgcc  4440
ccagagtccg agcccagcaa cagcacggag ggtgaaacac cctgtggtag cagctttgct  4500
gtcttctact tcatcagctt ctacatgctc tgtgccttcc tgatcatcaa cctctttgta  4560
gctgtcatca tggacaactt tgactacctg acaagggact ggtccatcct tggtccccac  4620
cacctggatg agtttaaaag aatctgggca gagtatgacc ctgaagccaa gggtcgtatc  4680
aaacacctgg atgtggtgac cctcctccgg cggattcagc cgccactagg ttttgggaag  4740
ctgtgccctc accgcgtggc ttgcaaacgc ctggtctcca tgaacatgcc tctgaacagc  4800
gacgggacag tcatgttcaa tgccaccctg tttgccctgg tcaggacggc cctgaggatc  4860
aaaacagaag ggaacctaga acaagccaat gaggagctgc gggcgatcat caagaagatc  4920
tggaagcgga ccagcatgaa gctgctggac caggtggtgc cccctgcagg tgatgatgag  4980
gtcaccgttg gcaagttcta cgccacgttc ctgatccagg agtacttccg gaagttcaag  5040
aagcgcaaag agcagggcct tgtgggcaag ccctcccaga ggaacgcgct gtctctgcag  5100
gctggcttgc gcacactgca tgacatcggg cctgagatcc gacgggccat ctctggagat  5160
ctcaccgctg aggaggagct ggacaaggcc atgaaggagg ctgtgtccgc tgcttctgaa  5220
gatgacatct tcaggagggc cggtggcctg ttcggcaacc acgtcagcta ctaccaaagc  5280
gacggccgga gcgccttccc ccagaccttc accactcagc gcccgctgca catcaacaag  5340
gcgggcagca gccagggcga cactgagtcg ccatcccacg agaagctggt ggactccacc  5400
ttcaccccga gcagctactc gtccaccggc tccaacgcca acatcaacaa cgccaacaac  5460
accgccctgg gtcgcctccc tcgccccgcc ggctacccca gcacggtcag cactgtggag  5520
ggccacgggc ccccccttgtc ccctgccatc cgggtgcagg aggtggcgtg gaagctcagc  5580
tccaacaggg aaaggcacgt tccgatgtgt gaggatctgg agctcaggag ggattcaggc  5640
tcagcaggga ctcaggctca ctgccttctg ctcaggagag caaacccctc taggtgccac  5700
tcccgggaga gccaggcagc catggcgggt caggaggaga cgtctcagga tgagacctat  5760
gaagtgaaga tgaaccatga cacggaggcc tgcagtgagc ccagcctgct ctccacagag  5820
atgctctcct accaggatga cgaaaatcgg caactgacgc tcccagagga ggacaagagg  5880
gacatccggc aatctccgaa gaggggtttc ctccgctctg cctcactagg tcgaagggcc  5940
tccttccacc tggaatgtct gaagcgacag aaggaccgag gggagagacat ctctcagaag  6000
acagtcctgc ccttgcatct ggttcatcat caggcattgg cagtggcagg cctgagcccc  6060
ctcctccaga gaagccattc ccctgcctca ttccctaggc cttttgccac cccaccagcc  6120
acacctggca gccgaggctg gcccccacag cccgtcccca ccctgcggct tgagggggtc  6180
gagtccagtg agaaaactcaa cagcagcttc ccatccatcc actgcggctc ctgggctgag  6240
accacccccg gtggcggggg cagcagcgcc gcccggagag tccggcccgt ctccctcatg  6300
gtgcccagcc aggctggggc cccagggagg cagttccacg gcagtgccag cagcctggtg  6360
gaagcggtct tgatttcaga aggactgggg cagtttgctc aagatcccaa gttcatcgag  6420
gtcaccaccc aggagctggc cgacgcctgc gacatgacca tagaggagat ggagagcgcg  6480
gccgacaaca tcctcagcgg gggcgcccca cagagcccca atggcgccct cttacccttt  6540
gtgaactgca gggacgcggg gcaggaccga gccgggggcg aagaggacgc gggctgtgtg  6600
cgcgcgcggg gtcgaccgag tgaggaggag ctccaggaca gcagggtcta cgtcagcagc  6660
ctgtag                                                              6666
```

```
SEQ ID NO: 116          moltype = AA  length = 2221
FEATURE                 Location/Qualifiers
source                  1..2221
                        mol_type = protein
                        organism = Homo sapiens
SEQUENCE: 116
MVNENTRMYI PEENHQGSNY GSPRPAHANM NANAAAGLAP EHIPTPGAAL SWQAAIDAAR  60
QAKLMGSAGN ATISTVSSTQ RKRQQYGKPK KQGSTTATRP PRALLCLTLK NPIRRACISI  120
VEWKPFEIII LLTIFANCVA LAIYIPFPED DSNATNSNLE RVEYLFLIIF TVEAFLKVIA  180
YGLLFHPNAY LRNGWNLLDF IIVVVGLFSA ILEQATKADG ANALGGKGAG FDVKALRAFR  240
VLRPLRLVSG VPSLQVVLNS IIKAMVPLLH IALLVLFVII IYAIIGLELF MGKMHKTCYN  300
QEGIADVPAE DDPSPCALET GHGRQCQNGT VCKPGWDGPK HGITNFDNFA FAMLTVFQCI  360
TMEGWTDVLY WVNDAVGRDW PWIYFVTLII IGSFFVLNLV LGVLSGEFSK EREKAKARGD  420
FQKLREKQQL EEDLKGYLDW ITQAEDIDPE NEDEGMDEEK PRNMSMPTSE TESVNTENVA  480
GGDIEGENCG ARLAHRISKS KFSRYWRRWN RFCRRKCRAA VKSNVFYWLV IFLVFLNTLT  540
IASEHYNQPN WLTEVQDTAN KALLALFTAE MLLKMYSLGL QAYFVSLFNR FDCFVVCGGI  600
LETILVETKI MSPLGISVLR CVRLLRIFKI TRYWNSLSNL VASLLNSVRS IASLLLLLFL  660
FIIIFSLLGM QLFGGKFNFD EMQTRRSTFD NFPQSLLTVF QILTGEDWNS VMYDGIMAYG  720
GPSFPGMLVC IYFIILFICG NYILLNVFLA IAVDNLADAE SLTSAQKEEE EEKERKKLAR  780
TASPEKKQEL VEKPAVGESK EEKIELKSIT ADGESPPATK INMDDLQPNE NEDKSPYPNP  840
ETTGEEDEEE PEMPVGPRPR PLSELHLKEK AVPMPEASAF FIFSSNNRFR LQCHRIVNDT  900
IFTNLILFFI LLSSISLAAE DPVQHTSFRN HILFYFDIVF TTIFTIEIAL KILGNADYVF  960
TSIFTLEIIL KMTAYGAFLH KGSFCRNYFN ILDLLVVSVS LISFGIQSSA INVVKILRVL  1020
RVLRPLRAIN RAKGLKHVVQ CVFVAIRTIG NIVIVTTLLQ FMFACIGVQL FKGKLYTCSD  1080
SSKQTEAECK GNYITYKDGE VDHPIIQPRS WENSKFDFDN VLAAMMALFT VSTFEGWPEL  1140
LYRSIDSHTE DKGPIYNYRV EISIFFIIYI IIIAFFMMNI FVGFVIVTFQ EQGEQEYKNC  1200
ELDKNQRQCV EYALKARPLR RYIPKNQHQY KVWYVVNSTY FEYLMFVLIL LNTICLAMQH  1260
YGQSCLFKIA MNILNMLFTG LFTVEMILKL IAFKPKGYFS DPWNVFDFLI VIGSIIDVIL  1320
SETNHYFCDA WNTFDALIVV GSIVDIAITE VNPAEHTQCS PSMNAEENSR ISITFFRLFR  1380
VMRLVKLLSR GEGIRTLLWT FIKSFQALPY VALLIVMLFF IYAVIGMQVF GKIALNDTTE  1440
INRNNNFQTF PQAVLLLFRC ATGEAWQDIM LACMPGKKCA PESEPSNSTE GETPCGSSFA  1500
VFYFISFYML CAFLIINLFV AVIMDNFDYL TRDWSILGPH HLDEFKRIWA EYDPEAKGRI  1560
KHLDVVTLLR RIQPPLGFGK LCPHRVACKR LVSMNMPLNS DGTVMFNATL FALVRTALRI  1620
KTEGNLEQAN EELRAIIKKI WKRTSMKLLD QVVPPAGDDE VTVGKFYATF LIQEYFRKFK  1680
KRKEQGLVGK PSQRNALSLQ AGLRTLHDIG PEIRRAISGD LTAEEELDKA MKEAVSAASE  1740
DDIFRRAGGL FGNHVSYYQS DGRSAFPQTF TTQRPLHINK AGSSQGDTES PSHEKLVDST  1800
FTPSSYSSTG SNANINNANN TALGRLPRPA GYPSTVSTVE GHGPPLSPAI RVQEVAWKLS  1860
SNRERHVPMC EDLELRRDSG SAGTQAHCLL LRRANPSRCH SRESQAAMAG QEETSQDETY  1920
EVKMNHDTEA CSEPSLLSTE MLSYQDDENR QLTLPEEDKR DIRQSPKRGF LRSASLGRRA  1980
SFHLECLKRQ KDRGGDISQK TVLPLHLVHH QALAVAGLSP LLQRSHSPAS FPRPFATPPA  2040
TPGSRGWPPQ PVPTLRLEGV ESSEKLNSSF PSIHCGSWAE TTPGGGGSSA ARRVRPVSLM  2100
VPSQAGAPGR QFHGSASSLV EAVLISEGLG QFAQDPKFIE VTTQELADAC DMTIEEMESA  2160
ADNILSGGAP QSPNGALLPF VNCRDAGQDR AGGEEDAGCV RARGRPSEEE LQDSRVYVSS  2220
L                                                                 2221

SEQ ID NO: 117          moltype = DNA  length = 1869
FEATURE                 Location/Qualifiers
source                  1..1869
                        mol_type = genomic DNA
                        organism = Homo sapiens
SEQUENCE: 117
atgagggaac agctcaaagg ccacgagact caaacaactt gctgggacca tcccaaaatg  60
acagagctct accagtcttt agctgacctg aataatgtca gattctcagc ttataggact  120
gccatgaaac tccgaagact gcagaaggcc ctttgcttgg atctcttgag cctgtcagct  180
gcatgtgatg ccttggacca gcacaacctc aagcaaaatg accagcccat ggatatcctg  240
cagattatta attgtttgac cactatttat gaccgcctgg agcaagagca caacaatttg  300
gtcaacgtcc ctctctgcgt ggatatgtgt ctgaactggc tgctgaatgt ttatgatacg  360
ggacgaacag ggaggatccg tgtcctgtct tttaaaactg gcatcatttc cctgtgtaaa  420
gcacatttgg aagacaagta cagatacctt ttcaagcaag tggcaagttc aacaggattt  480
tgtgaccagc gcaggctggg cctccttctg catgattcta tccaaattcc aagacagttg  540
ggtgaagttg catcctttgg gggcagtaac attgagccaa gtgtccggag ctgcttccaa  600
tttgctaata ataagccaga gatcgaagcg gccctcttcc tagactggat gagactggaa  660
ccccagtcca tggtgtggct gcccgtcctg cacagagtgg ctgctgcaga aactgccaag  720
catcaggcca aatgtaacat ctgcaaagag tgtccaatca ttggattcag gtacaggagt  780
ctaaagcact ttaattatga catctgccaa agctgctttt tttctggtcg agttgcaaaa  840
ggccataaaa tgcactatcc catggtggaa tattgcactc cgactacatc aggagaagat  900
gttcgagact ttgccaaggt actaaaaaac aaatttcgaa ccaaaaggta ttttgcgaag  960
catccccgaa tgggctacct gccagtgcag actgtcttag agggggacaa catggaaacg  1020
cctgcctcgt cccctcagct ttcacacgat gatactcatt cacgcattga acattatgct  1080
agcaggctag cagaaatgga aaacagcaat ggatcttatc taaatgatag catctctcct  1140
aatgagagca tagatgatga acatttgtta atccagcatt actgccaaag tttgaaccag  1200
gactcccccc tgagccagcc tcgtagtcct gcccagatct tgatttcctt agagagtgag  1260
gaaagagggg agctagagag aatcctagca gatcttgagg aagaaaacag gaatctgcaa  1320
gcagaatatg accgtctaaa gcagcagcac gaacataaag gcctgtcccc actgccgtcc  1380
cctcctgaaa tgatgcccac ctctccccag agtccccggg atgctgagct cattgctgag  1440
gccaagctac tgcgtcaaca caaaggccgc ctggaagcca ggatgcaaat cctggaagac  1500
cacaataaac agctggagtc acagttacac aggctaaggc agctgctgga gcaaccccag  1560
gcagaggcca aagtgaatgg cacaacggtg tcctctcctt ctacctctct acagaggtcc  1620
```

-continued

```
gacagcagtc agcctatgct gctccgagtg gttggcagtc aaacttcgga ctccatgggt  1680
gaggaagatc ttctcagtcc tccccaggac acaagcacag ggttagagga ggtgatggag  1740
caactcaaca actccttccc tagttcaaga ggacacaatg taggaagtct tttccacatg  1800
gcagatgatt tgggcagagc gatggagtcc ttagtatcag tcatgacaga tgaagaagga  1860
gcagaataa                                                          1869

SEQ ID NO: 118         moltype = AA  length = 622
FEATURE                Location/Qualifiers
source                 1..622
                       mol_type = protein
                       organism = Homo sapiens
SEQUENCE: 118
MREQLKGHET QTTCWDHPKM TELYQSLADL NNVRFSAYRT AMKLRRLQKA LCLDLLSLSA  60
ACDALDQHNL KQNDQPMDIL QIINCLTTIY DRLEQEHNNL VNVPLCVDMC LNWLLNVYDT  120
GRTGRIRVLS FKTGIISLCK AHLEDKYRYL FKQVASSTGF CDQRRLGLLL HDSIQIPRQL  180
GEVASFGGSN IEPSVRSCFQ FANNKPEIEA ALFLDWMRLE PQSMVWLPVL HRVAAAETAK  240
HQAKCNICKE CPIIGFRYRS LKHFNYDICQ SCFFSGRVAK GHKMHYPMVE YCTPTTSGED  300
VRDFAKVLKN KFRTKRYFAK HPRMGYLPVQ TVLEGDNMET PASSPQLSHD DTHSRIEHYA  360
SRLAEMENSN GSYLNDSISP NESIDDEHLL IQHYCQSLNQ DSPLSQPRSP AQILISLESE  420
ERGELERILA DLEEENRNLQ AEYDRLKQQH EHKGLSPLPS PPEMMPTSPQ SPRDAELIAE  480
AKLLRQHKGR LEARMQILED HNKQLESQLH RLRQLLEQPQ AEAKVNGTTV SSPSTSLQRS  540
DSSQPMLLRV VGSQTSDSMG EEDLLSPPQD TSTGLEEVME QLNNSFPSSR GHNVGSLFHM  600
ADDLGRAMES LVSVMTDEEG AE                                           622

SEQ ID NO: 119         moltype = DNA  length = 1920
FEATURE                Location/Qualifiers
source                 1..1920
                       mol_type = genomic DNA
                       organism = Homo sapiens
SEQUENCE: 119
atgggagggc atttttggcc cccagaacct tacacggtgt ttatgtgggg aagcccctgg  60
gaagcagaca gtcctagggt gaagctgaga ggcagagaga aggggagaca gacagagggt  120
ggggctttcc cccttgtctc cagtgccctt tctggtgacc ctcggttctt ttcccccacc  180
acccccccag cggagcccat cgtggtgagg cttaaggagg tccgactgca gagggacgac  240
ttcgagattc tgaaggtgat cggacgcggg gcgttcagcg aggtagcggt agtgaagatg  300
aagcagacgg gccaggtgta tgccatgaag atcatgaaca agtgggacat gctgaagagg  360
ggcgaggtgt cgtgcttccg tgaggagagg gacgtgttgg tgaatgggga ccggcggtgg  420
atcacgcagc tgcacttcgc cttccaggat gagaactacc tgtacctggt catggagtat  480
tacgtgggcg gggacctgct gacactgctg agcaagtttg gggagcggat tccggccgag  540
atggcgcgct tctacctggc ggagattgtc atggccatag actcggtgca ccggcttggc  600
tacgtgcaca gggacatcaa acccgacaac atcctgctgg accgctgtgg ccacatccgc  660
ctggccgact tcggctcttg cctcaagctg cgggcagatg gaacggtgcg gtcgctggtg  720
gctgtgggca ccccagacta cctgtccccc gagatcctgc aggctgtggg cggtgggcct  780
gggacaggca gctacgggcc cgagtgtgac tggtgggcgc tgggtgtatt cgcctatgaa  840
atgttctatg ggcagacgcc cttctacgcg gattccacgg cggagaccta tggcaagatc  900
gtccactaca aggagcacct ctctctgccg ctggtggacg aaggggtccc tgaggaggct  960
cgagacttca ttcagcggtt gctgtgtccc ccggagacac ggctgggccg gggtggagca  1020
ggcgacttcc ggacacatcc cttcttcttt ggcctcgact gggatggtct ccgggacagc  1080
gtgcccccct ttacaccgga tttcgaaggt gccaccgaca catgcaactt cgacttggtg  1140
gaggacgggc tcactgccat ggtgagcggg ggcggggaga cactgtcgga cattcgggaa  1200
ggtgcgccgc taggggtcca cctgcctttt gtgggctact cctactcctg catggccctc  1260
agggacagtg aggtcccagg ccccacaccc atggaactgg aggccgagca gctgcttgag  1320
ccacacgtgc aagcgcccag cctggagccc tcggtgtccc cacaggatga aacagctgaa  1380
gtggcagttc cagcggctgt ccctgcggca gaggctgagg ccgaggtgac gctgcgggag  1440
ctccaggaag ccctggagga ggaggtgctc acccggcaga gcctgagccg ggagatggag  1500
gccatccgca cggacaacca gaacttcgcc agtcaactac gcgaggcaga ggctcggaac  1560
cgggacctag aggcacacgt ccggcagttg caggagcgga tggagttgct gcaggcagag  1620
ggagccacag ctgtcacggg ggtccccagt ccccgggcca cggatccacc ttcccatcta  1680
gatggccccc cggccgtggc tgtgggccag tgcccgctgg tggggccagg ccccatgcac  1740
cgccgccacc tgctgctccc tgccagggtc cctaggcctg gcctatcgga ggcgctttcc  1800
ctgctcctgt tcgccgttgt tctgtctcgt gccgccgccc tgggctgcat tgggttggtg  1860
gcccacgccg gccaactcac cgcagtctgg cgccgcccag gagccgcccg cgctccctga  1920

SEQ ID NO: 120         moltype = AA  length = 639
FEATURE                Location/Qualifiers
source                 1..639
                       mol_type = protein
                       organism = Homo sapiens
SEQUENCE: 120
MGGHFWPPEP YTVFMWGSPW EADSPRVKLR GREKGRQTEG GAFPLVSSAL SGDPRFFSPT  60
TPPAEPIVVR LKEVRLQRDD FEILKVIGRG AFSEVAVVKM KQTGQVYAMK IMNKWDMLKR  120
GEVSCFREER DVLVNGDRRW ITQLHFAFQD ENYLYLVMEY YVGGDLLTLL SKFGERIPAE  180
MARFYLAEIV MAIDSVHRLG YVHRDIKPDN ILLDRCGHIR LADFGSCLKL RADGTVRSLV  240
AVGTPDYLSP EILQAVGGGP GTGSYGPECD WWALGVFAYE MFYGQTPFYA DSTAETYGKI  300
VHYKEHLSLP LVDEGVPEEA RDFIQRLLCP PETRLGRGGA GDFRTHPFFF GLDWDGLRDS  360
VPPFTPDFEG ATDTCNFDLV EDGLTAMVSG GGETLSDIRE GAPLGVHLPF VGYSYSCMAL  420
RDSEVPGPTP MELEAEQLLE PHVQAPSLEP SVSPQDETAE VAVPAAVPAA EAEAEVTLRE  480
LQEALEEEVL TRQSLSREME AIRTDNQNFA SQLREAEARN RDLEAHVRQL QERMELLQAE  540
GATAVTGVPS PRATDPPSHL DGPPAVAVGQ CPLVGPGPMH RRHLLLPARV PRPGLSEALS  600
```

```
LLLFAVVLSR AAALGCIGLV AHAGQLTAVW RRPGAARAP                    639

SEQ ID NO: 121          moltype = DNA  length = 7740
FEATURE                 Location/Qualifiers
source                  1..7740
                        mol_type = genomic DNA
                        organism = Homo sapiens
SEQUENCE: 121
atggccgagg cggtgaagcc ccagcgccgg gccaaggcca aggccagccg gactaaaaca  60
aaggaaaaga agaagtatga aactcctcag agggaagagt ccagtgaagt ctcccttcca  120
aaaacctcca gagagcagga aatcccttct ctagcctgtg aattcaaagg agaccatctg  180
aaggtggtaa ctgattccca gctccaggat gatgccagtg gacaaaatga gagtgaaatg  240
tttgatgtac cactcacctc cttaactata agcaatgaag agtccctgac gtgtaacaca  300
gagcccccaa aggaaggggg agaggccaga ccctgtgtgg gggacagtgc agtcactcca  360
aaggtccacc ctggagacaa tgttggaact aaagtagaaa cccccaagaa cttcacagag  420
gtagaggaaa atatgtcggt acaaggtgga ctttcagaaa gtgcacccca atctaatttt  480
tcttatactc agccagcaat ggaaaatata caagtcagag aaactcagaa tagtaaagaa  540
gacaaacaag gcctggtttg ttcttcagag gtgccacaga atgttggctt gcagagttct  600
tgcccagcca aacatggttt tcagacacct agagtgaaga aactgtatcc ccagttgcca  660
gctgaaattg ctggagaagc accagctttg gtggcagtga aacccttgct tcgcagtgag  720
cgactctacc cagaactccc gtctcaactg gaactagtac catttactaa agaacagcta  780
aaaatcttgg agcctggttc atggctggaa aatgttgagt catatttaga agaatttgac  840
agcatggctc atcaagacag gcatgaattt tatgagttgc ttttgaacta ctcacgatgt  900
aggaagcaac tgctgctggc tgaagctgag ctgcttactc tgacatctga ttgccaaaat  960
gctaaaagtc ggctgtggca gtttaaggag gaacaaatgt ctgtacaggg tatctgtgca  1020
gatcaagtga aagttttcag ctatcatcgc taccaaagag tagaaatgaa tgaaaatgca  1080
ctggtggagc taaagaagct attcgatgcc aaatctgagc acctccacca gaccctggcc  1140
cttcattctt atacttctgt gctctcaaga ttgcaagtgg agtcttacat ctatgcattg  1200
ctcagtagtt cagctgttct gagatcttca gcaattcacc agcaaggccg agcgtctaag  1260
cagacagaaa gcattccctc tgatctgtgt caactaaagg aatgcattag tgtcttattc  1320
atgttcacca ggagagttaa tgaagatact cagtttcatg atgatattct tctctggctg  1380
cagaaattgg tatccgtgct acaaagagtt ggctgtcctg gagatcacct cttccttcta  1440
aaccatattc ttcgatgccc cgctggtgtt agtaaatggg ctgttccttt tatccagatc  1500
aaagtgttgc ataacccatc aggggtcttt cattttatgc aatcccttgc cctgctgatg  1560
tctcctgtca aaaatcgagc tgagtttatg tgccacatga agcccagcga gcggaagcca  1620
tcctcctcag ggcctgggtc tgggacttgg acgctagtag acgaaggagg agaagaggat  1680
gaagaccctg agaccagttg gattctcctt aatgaagatg atttggttac cattttagca  1740
cagttcccct ttcatgaact ctttcagcat cttcttgggt ttaaagcaaa aggtgattat  1800
ttacctgaaa caacaagacc tcaagagatg atgaaaattt ttgcctttgc caactcacta  1860
gtggaacttc tggctgtggg gttagaaacc tttaatagag cacgctatag gcagtttgtg  1920
aagcgaattg gttatatgat caggatgact cttggttatg taagtgacca ttgggcacag  1980
tatgtgagcc ataaccaagg ctcaggattg gcccaacagc cctactctat ggagaaacta  2040
caggttgaat ttgatgaact gtttttgagg gctgtcctac atgtgctgaa ggccaaaaga  2100
cttggcattt ggctgtttat gtccgagatg ccctttggga ctctgtctgt gcaaatgctg  2160
tggaagctct tctacctcat gcaccaggtg gagagcgaga acctgcagca gctctcctcc  2220
tccctgcagc ccgcccagtg caagcagcag ctccaagacc cagaacattt taccaacttt  2280
gagaagtgtc tttcttctat gaatagctca gaagagattt gccttctgac tacctttgct  2340
cagatggctc aggccagaag aaccaatgtg gacgaagact tcataaaaat tattgttctg  2400
gagatatatg aggtatctta tgtcaccttg tctaccagag agactttttc aaaggttggt  2460
cgagagcttt tagggactat cacagctgtt caccctgaga taatttccgt ccttctggat  2520
agagttcaag agaccattga ccaggttgga atggtttctc tatacttgtt taaagaactg  2580
cctttgtatc tttggcaacc ttctgcatct gagatagcgg tgattcggga ttggttattg  2640
aattacaacc tgacagtggt gaagaataaa ctggcctgtg ttattcttga aggactgaat  2700
tggggatttg ctaaacaggc taccttcat ctggatcaag cagtccatgc tgaagtggct  2760
ttaatggttc ttgaagctta tcagaagtac cttgcacaga agccatatgc tgggattctc  2820
tctgaaagta tgaagcaggt ttcatatttg gccagtattg ttcgatatgg agagacaccc  2880
gagacctcat ttaaccaatg ggcctggaat ttaatcttga ggctaaaact gcacaaaaac  2940
gattatggaa tacagccgaa ttgtccagct gttcccttct ccgtcactgt gcctgacatg  3000
acagagtcac ccacgtttca tcctctcttg aaggctgtga aagcgggcat gcccattggc  3060
tgttatctag ccttatctat gacagctgtg ggccacagca ttgagaagtt ctgtgcagaa  3120
ggcatcccac tattgggaat tctggtccag tcaagacatt tgagaacagt ggttcatgtc  3180
ctggataaga ttctgccttt attttaccct tgccagtatt accttctgaa gaatgagcag  3240
tttttatcgc atctcctctt gttcctacac ttggacagcg gtgtccctca gggtgtcaca  3300
caacaggtca cccacaaggt ggcacagcac ctgacaggag ccagccatgg ggacaacgtg  3360
aagcttctca acagcatgat ccaggcacac atatctgtaa gcactcagcc caatgaagtg  3420
ggccccgttg ctgtgttgga gttctgggtt caggctctca taagccagca tctctggtac  3480
cgagaacaac ctatcctctt cctcatggac cacttgtgta aagcagcttt tcagctgatg  3540
caggaagact gcatacagaa attactctac caacaacata agaatgcctt gggttaccac  3600
tgtgaccgga gtctgctctc atctttggta agctggattg tggcaggcaa catcactcct  3660
tcctttgtgg agggcttggc cacgcccact caggtctggt ttgcctggac agtgctcaac  3720
atggaatcca tctttgaaga ggactcccag ctccggagag ttattgaagg ggaattggtg  3780
ataaactctg ctttcacccc tgaccaagct ctgaagaaag cccagaccca gctgaagctc  3840
cccatcgtgc catccctcca gaggctgctg atttatcgct gggcccacca ggctctggtc  3900
acaccttctg atcacccccct cctgccactc atttggcaga agttcttcct tctgtatctt  3960
caccgtccgg gaccacagta tgggttaccc atagatggtt gtattggaag aaggtttttt  4020
caaagtcctg ctcatatcaa tttgttgaaa gaaatgaaga gacgtttgac cgaggtggct  4080
gacttccacc atgctgcaag caaggccctc cgtgttccag cagagggcag tgaagggctg  4140
ccagagagcc actctggcac ccctggttac ctgacttcac cagaactgca caaggagctg  4200
gtgaggctct tcaatgtata tatattatgg ctagaagatg agaattttca aaaaggagat  4260
```

-continued

```
acctatatcc cttctctacc aaagcattat gatattcaca ggctagcaaa agtgatgcag  4320
aatcagcagg atctgtggat ggagtatttg aacatggagc gcatctatca tgagtttcag  4380
gagactgttg gtctgtggac acaggccaag cttgagtccc attccacacc ctgcagtttg  4440
tccgtgcagc tggacttcac tgatcctttg ctggctaaag aaagggtttt aagtaacttg  4500
cggaagcatg aggctcccca gcctcccctt gctctgcacc cgacgaagcc tcctgtgcca  4560
gttatttcct ctgctgtgct attgagtcag aaggacgcca cccagctggt gtgcacagac  4620
ctgaatctgt tgcaacagca ggccagaacc gcagctcttc gggaatctca gcaggttgct  4680
ctggatggtg agctgttaga cacaatgcca aagcagtatg tgaatcgtga agaacagacc  4740
acactacatt tggagtgcag aggcagcagc ggtaagaaat gccaaggagc cgcagttgtc  4800
acggttcagt ttgaaggcat gcataagaat gaagccataa gccaacagct tcatgtttta  4860
cggaaggaag tgaagcagtt gcaagcagaa gctgctaaac caccatcact taatattgtg  4920
gaagctgctg tacatgcaga aaacttgatc acggccttag tgaatgccta caagttgcag  4980
cctacacctg ggattcagaa agttggcatt agccttttct ttactattgt ggattacgtc  5040
agcgatgaga cgcagcgtca tcccccaaca aggcagttct ttacttcatg tattgagatc  5100
ttgggacagg tatttatcag tggcattaaa tcagagtgca gaaaagtact tgaaaccatt  5160
ctgaagaaca gcaggctctg ctccctgctg tctcctttct tcactcccaa tgctgcacct  5220
gcagagttca tacagctgta tgagcaagtg gtgaagtttc taagtgagga caacagtgat  5280
atgattttca tgctgctaac caagttcgat cttaaacaat ggttaagcgc cactaaacct  5340
cctctgtctg atcgtaccag gcttctggag tccattcact tggcacttac tgcctggggc  5400
cttgaaccag atgaggatat tttgatgcca tttaatcttt tctgtaagca ctggacttat  5460
cttcttctct accagtttcc tgaccagtac agtgacattc tcaggctgct tatgcaaagc  5520
tccgcggagc agcttctgag ccccgagtgt tggaaggcca ctctgagagc cctgggctgc  5580
tgcgcccccca gctgccagca gggggcagcg tccaccgagg gcgccgtgct tcccagctct  5640
tctgatgctc tcttgtcaga caagcaggta atggagacta tacagtggct ttcagacttt  5700
ttttataagc ttcggttatc caagatggac tttaaaagct ttggtttatt ctcaaaatgg  5760
agtccttata tggctgatgt gaagacattc ttgggctacc ttgtgaaaag gctgattgac  5820
ttagaaatga cctgtttggc ccaagaccca actgccagca ggaaaacagt gctgaaatcc  5880
ctacattcag taatcattca gctctttaag ccatggatcc tggttttaga ggacaacgaa  5940
agcagccaac agcggcatta cccctggcta gagagtgata ctgtggtggc ctcaagcatt  6000
gtgcagctgt tcactgactg tattgactca ctgcatgaga gttttaaaga taagctgttg  6060
ccaggtgatg caggagccct ttggttgcac ctgatgcatt attgtgaagc atgtacagca  6120
cccaaaatgc cagagttcat tctgtacgct ttccatagca cgtaccggaa actgccatgg  6180
aaggacctgc accctgacca gatgctcatg gaggccttct tcaaagtgga acgaggaagc  6240
cccaagagct gtttcttatt tttggggtct gtactctgtg aagtcaactg ggttagtgtg  6300
ctctctgatg cctggaattc cagtccccac ccagaaaccc gcagcatgat tgtctgcctc  6360
cttttcatga tgattttatt ggcaaaggaa gttcaactgg tagaccaaac agattcacct  6420
ttacttagtc tccttggaca gacaagctca ctttcatggc atcttgtgga tattgtgtcg  6480
taccagagtg tgctaagtta tttcagcagc cattacccgc cgtccatcat cctggcaaaa  6540
gaatcttatg ctgaattaat catgaagctc ctaaaagtgt ctgcgggcct ttctattcct  6600
actgacagcc agaagcatct tgatgcagtt ccaaaatgcc aagcttttac tcatcagatg  6660
gttcaattcc tcagcaccct ggaacaaaat ggaaaaatca ccttagcagt cctagaacag  6720
gaaatgtcta agctcttaga cgatatcatt gtctttaacc cgcccgacat ggacagccag  6780
acccgccaca tggccctcag cagcctcttt atggaagtcc tgatgatgat gaacaacgcg  6840
actattccaa cagcagagtt ccttcggggc agtatccgga cctggattgg ccaaaaaatg  6900
catgggctgg tggtgctgcc ccttttaaca gcagcctgcc agagcctggc gtccgtccgc  6960
cacatggctg agactacaga agcctgcatc actgcctact tcaaagaaag ccctctcaat  7020
cagaattcag gatggggacc cattctggta tcccttcagg ttcccgagct caccatggaa  7080
gagttcctgc aggagtgcct caccttgggc agttacttga ctctttacgt ctacttgctt  7140
cagtgtttaa acagcgaaca gactttaagg aatgaaatga aagtgctgct catcttaagc  7200
aagtggctgg aacaggtgta cccaagctcc gtggaggaag aggcaaagct gtttttgtgg  7260
tggcaccaag tccttcagct ctccctcatt cagacagagc agaatgactc cgtcctgaca  7320
gaatctgtca ttcgaattct gctcttggtt cagagcaggc agaacctcgt ggctgaggag  7380
agactcagct ctgggatcct gggggcaatt gggtttggcc ggaagtcgcc tttgtctaac  7440
aggttccgag tggttgcccg aagcatggct gccttccttt cagttcaggt tcctatggaa  7500
gatcagatcc gtttgaggcc tggctctgaa ttacatctga cccccaaagc tcagcaggct  7560
ctgaatgctc ttgaatccat ggcatcaagt aagcagtatg ttgaatacca ggatcaaata  7620
ttgcaagcca cccaatttat aaggcatcct ggccattgcc ttcaagatgg gaaaagcttc  7680
ttggctcttc tcgttaactg tctgtatcca gaagtgcatt atttggacca catacgatag  7740
```

```
SEQ ID NO: 122          moltype = AA  length = 2579
FEATURE                 Location/Qualifiers
source                  1..2579
                        mol_type = protein
                        organism = Homo sapiens
SEQUENCE: 122
MAEAVKPQRR AKAKASRTKT KEKKKYETPQ REESSEVSLP KTSREQEIPS LACEFKGDHL  60
KVVTDSQLQD DASGQNESEM FDVPLTSLTI SNEESLTCNT EPPKEGGEAR PCVGDSAVTP  120
KVHPGDNVGT KVETPKNFTE VEENMSVQGG LSESAPQSNF SYTQPAMENI QVRETQNSKE  180
DKQGLVCSSE VPQNVGLQSS CPAKHGFQTP RVKKLYPQLP AEIAGEAPAL VAVKPLLRSE  240
RLYPELPSQL ELVPFTKEQL KILEPGSWLE NVESYLEEFD SMAHQDRHEF YELLLNYSRC  300
RKQLLLAEAE LLTLTSDCQN AKSRLWQFKE EQMSVQGICA DQVKVFSYHR YQRVEMNENA  360
LVELKKLFDA KSEHLHQTLA LHSYTSVLSR LQVESYIYAL LSSSAVLRSS AIHQQGRASK  420
QTESIPSDLC QLKECISVLF MFTRRVNEDT QFHDDILLWL QKLVSVLQRV GCPGDHLFLL  480
NHILRCPAGV SKWAVPFIQI KVLHNPSGVF HFMQSLALLM SPVKNRAEFM CHMKPSERKP  540
SSSGPGSGTW TLVDEGGEED EDPETSWILL NEDDLVTILA QFPFHELFQH LLGFKAKGDY  600
LPETTRPQEM MKIFAFANSL VELLAVGLET FNRARYRQFV KRIGYMIRMT LGYVSDHWAQ  660
YVSHNQGSGL AQQPYSMEKL QVEFDELFLR AVLHVLKAKR LGIWLFMSEM PFGTLSVQML  720
WKLFYLMHQV ESENLQQLSS SLQPAQCKQQ LQDPEHFTNF EKCLSSMNSS EEICLLTTFA  780
QMAQARRTNV DEDFIKIIVL EIYEVSYVTL STRETFSKVG RELLGTITAV HPEIISVLLD  840
```

```
RVQETIDQVG MVSLYLFKEL PLYLWQPSAS EIAVIRDWLL NYNLTVVKNK LACVILEGLN  900
WGFAKQATLH LDQAVHAEVA LMVLEAYQKY LAQKPYAGIL SESMKQVSYL ASIVRYGETP  960
ETSFNQWAWN LILRLKLHKN DYGIQPNCPA VPFSVTVPDM TESPTFHPLL KAVKAGMPIG  1020
CYLALSMTAV GHSIEKFCAE GIPLLGILVQ SRHLRTVVHV LDKILPLFYP CQYYLLKNEQ  1080
FLSHLLLFLH LDSGVPQGVT QQVTHKVAQH LTGASHGDNV KLLNSMIQAH ISVSTQPNEV  1140
GPVAVLEFWV QALISQHLWY REQPILFLMD HLCKAAFQLM QEDCIQKLLY QQHKNALGYH  1200
CDRSLLSSLV SWIVAGNITP SFVEGLATPT QVWFAWTVLN MESIFEEDSQ LRRVIEGELV  1260
INSAFTPDQA LKKAQTQLKL PIVPSLQRLL IYRWAHQALV TPSDHPLLPL IWQKFFLLYL  1320
HRPGPQYGLP IDGCIGRRFF QSPAHINLLK EMKRRLTEVA DFHHAASKAL RVPAEGSEGL  1380
PESHSGTPGY LTSPELHKEL VRLFNVYILW LEDENFQKGD TYIPSLPKHY DIHRLAKVMQ  1440
NQQDLWMEYL NMERIYHEFQ ETVGLWTQAK LESHSTPCSL SVQLDFTDPL LAKERVLSNL  1500
RKHEAPQPPL ALHPTKPPVP VISSAVLLSQ KDATQLVCTD LNLLQQQART AALRESQQVA  1560
LDGELLDTMP KQYVNREEQT TLHLECRGSS GKKCQGAAVV TVQFEGMHKN EAISQQLHVL  1620
RKEVKQLQAE AAKPPSLNIV EAAVHAENLI TALVNAYKLQ PTPGIQKVGI SLFFTIVDYV  1680
SDETQRHPPT RQFFTSCIEI LGQVFISGIK SECRKVLETI LKNSRLCSLL SPFFTPNAAP  1740
AEFIQLYEQV VKFLSEDNSD MIFMLLTKFD LKQWLSATKP PLSDRTRLLE SIHLALTAWG  1800
LEPDEDILMP FNLFCKHWTY LLLYQFPDQY SDILRLLMQS SAEQLLSPEC WKATLRALGC  1860
CAPSCQQGAA STEGAVLPSS SDALLSDKQV METIQWLSDF FYKLRLSKMD FKSFGLFSKW  1920
SPYMADVKTF LGYLVKRLID LEMTCLAQDP TASRKTVLKS LHSVIIQLFK PWILVLEDNE  1980
SSQQRHYPWL ESDTVVASSI VQLFTDCIDS LHESFKDKLL PGDAGALWLH LMHYCEACTA  2040
PKMPEFILYA FHSTYRKLPW KDLHPDQMLM EAFFKVERGS PKSCFLFLGS VLCEVNWVSV  2100
LSDAWNSSPH PETRSMIVCL LFMMILLAKE VQLVDQTDSP LLSLLGQTSS LSWHLVDIVS  2160
YQSVLSYFSS HYPPSIILAK ESYAELIMKL LKVSAGLSIP TDSQKHLDAV PKCQAFTHQM  2220
VQFLSTLEQN GKITLAVLEQ EMSKLLDDII VFNPPDMDSQ TRHMALSSLF MEVLMMMNNA  2280
TIPTAEFLRG SIRTWIGQKM HGLVVLPLLT AACQSLASVR HMAETTEACI TAYFKESPLN  2340
QNSGWGPILV SLQVPELTME EFLQECLTLG SYLTLYVYLL QCLNSEQTLR NEMKVLLILS  2400
KWLEQVYPSS VEEEAKLFLW WHQVLQLSLI QTEQNDSVLT ESVIRILLLV QSRQNLVAEE  2460
RLSSGILGAI GFGRKSPLSN RFRVVARSMA AFLSVQVPME DQIRLRPGSE LHLTPKAQQA  2520
LNALESMASS KQYVEYQDQI LQATQFIRHP GHCLQDGKSF LALLVNCLYP EVHYLDHIR   2579

SEQ ID NO: 123          moltype = DNA  length = 2979
FEATURE                 Location/Qualifiers
source                  1..2979
                        mol_type = genomic DNA
                        organism = Homo sapiens
SEQUENCE: 123
atggcccgcg gcggggcggc ctgcaagagc gacgcgcggc tgctgctggg gcgggacgcg  60
ctgcggccgg cgcccgccct gctggccccc gccgtgctgc tgggcgccgc gctcggcctc  120
ggcctcggcc tttggcttgg ctgccgcgcg ggccgccagc gcacgcgaca ccagaaagac  180
gacactcaaa atctgctcaa gaatttggag tctaatgcgc agacccccctc ggaaactggc  240
tccccatcaa ggaggaggaa gagagaagtg cagatgtcga aggacaagga agctgttgat  300
gaatgtgagc cgccttccaa cagcaatatc acagcattcg ccctgaaggc caaagtcatc  360
taccccatca atcagaagtt ccggcctctg gccgatggct cctccaaccc gtctctgcat  420
gaaaacttaa agcaggctgt tttgccacac cagccggtag aggcctctcc ttccagcagt  480
ctggggagcc tgagccaggg tgagaaggac gactgcagct cctcatccag cgtccactcg  540
gccaccagcg atgacaggtt tctcagccgc accttcctcc gggtgaacgc cttccctgaa  600
gtgctggcct gcgagagtgt agacgttgac ctgtgtatct acagccttca cttaaaagac  660
ctgctgcatt tggacacggc actgaggcag gaaaagcata tgatgtttat tcagattttt  720
aaaatgtgcc tccttgacct tcttcctaaa aagaagtcag atgatgaact ataccagaag  780
atcctttcaa aacaagaaaa agatttggag gaactagaaa agggacttca ggtcaaactg  840
tcaaacacag aaatgtcggg ggctggtgac tctgagtaca tcaccctggc tgatgtggaa  900
aagaaggaga gagaatactc tgaacagcta atcgataata tggaagcttt ctggaaacag  960
atggcaaata tccagcactt tcttgtggac cagtttaagt gttccagctc caaagcccga  1020
cagctgatga tgactctgac ggaaagaatg attgcagccg aagggctatt gtgcgattct  1080
caggagctgc aggctctgga cgccctggag aggacgatgg ggcgggcgca catggcaaaa  1140
gtgattgagt ttctgaagct gcaagtccag gaggagacca ggtgccggct ggctgccatc  1200
tcccacggcc tggagctgct ggctggtgag gggaagctgt ccgggcggca gaaggaggag  1260
ctgctcacgc agcagcacaa ggccttctgg caggaggcag agcgcttcag ccgggagttt  1320
gtccagcgag gcaaagacct ggtcacggcg tctctggctc accaggtgga gggaacggca  1380
aaactcacgc tggcccaaga ggaggaacag agaagcttcc tggctgaggc ccagccgact  1440
gctgacccgg aaaagtttct cgaggctttt catgaggtcc tggagaggca gaggctgatg  1500
cagtgtgacc tggaggaaga ggagaatgtc agagccaccg aggctgtggt tgcactctgc  1560
caggagctgt acttcagcac cgtggacact ttccagaagt tcgtggatgc cctgttcctt  1620
cagacgctcc ctggcatgac tggcctcccc ccggaagagt gtgactactt gaggcaggaa  1680
gtccaggaga acgctgcctg gcagctgggg aagtcaaatc gcttccggag gcagcagtgg  1740
aaactcttcc aggagctcct agagcaagac cagcaggtgt ggatggagga gtgtgcgctg  1800
tccagcgtgc tgcagacaca cctgcgggag gaccacgagg gcaccatccg cggcgtcttg  1860
ggccgactgg gcggcctcac tgaagagtcc acgcggtgtg tcctgcaggg gcatgacctg  1920
ctgttgcgct cagccctccg gaggctggca ctccgcggca acgccctggc caccctgacg  1980
cagatgcggc tatcggggaa gaagcacctc ctgcaggagc tgcgggaaca gcgtgcactg  2040
gagcaggggt cctcccagtg cctggacgag catcagtggc agctgctcag ggccctggag  2100
gcgcgtgtgc tggaggaggc cagccggcta gaggaggaag cacagcagac acggctgcag  2160
ctccagcagc ggctcctggc cgaggcccag gaggtggggc agcttctgca gcagcacatg  2220
gagtgcgcca ttgggcaggc gctgctggtg catgcacgga atgcagccac caagagccgg  2280
gccaaggaca gggatgactt caagaggaca ctgatggagg cggcagtgga gagcgtctac  2340
gtgaccagcg ctggtgtcag ccgcctggtg caggcgtatt accagcaaat cggaaggatc  2400
atggaggacc acgaggagag aaaactgcag cacctgaaga ccctgcaggg tgagaggatg  2460
gaaaattaca aactgcggaa aaagcaagaa ctcagcaacc cttcgtcggg cagcaggacg  2520
gcaggtggcg ctcatgagac ctcccaggcg gtccaccaga ggatgctgtc ccagcagaag  2580
```

```
aggttcctgg cccagttccc agtgcaccag cagatgcgtc tgcacgccca gcagcagcag  2640
gcaggagtca tggaccttct ggaagcccag ctggagaccc agctacagga agctgaacag  2700
aacttcatct ccgagctggc agccttggcc cgagtgcccc ttgctgaaag caaactgttg  2760
cctgctaagc gtgggctgct agagaagccc ctaaggacta aaaggaagaa gcccctgccc  2820
caggaaagag gggacctggg ggtgcccaac aatgaggacc ttgcctccgg ggaccagacc  2880
tcaggctcac tcagcagcaa aaggctgagt cagcaagaaa gtgaagctgg ggacagtggg  2940
aactcaaaga agatgctaaa gagaagaagc aacttgtag                         2979

SEQ ID NO: 124          moltype = AA  length = 992
FEATURE                 Location/Qualifiers
source                  1..992
                        mol_type = protein
                        organism = Homo sapiens
SEQUENCE: 124
MARGGAACKS DARLLLGRDA LRPAPALLAP AVLLGAALGL GLGLWLGCRA GRQRTRHQKD  60
DTQNLLKNLE SNAQTPSETG SPSRRRKREV QMSKDKEAVD ECEPPSNSNI TAFALKAKVI  120
YPINQKFRPL ADGSSNPSLH ENLKQAVLPH QPVEASPSSS LGSLSQGEKD DCSSSSSVHS  180
ATSDDRFLSR TFLRVNAFPE VLACESVDVD LCIYSLHLKD LLHLDTALRQ EKHMMFIQIF  240
KMCLLDLLPK KKSDDELYQK ILSKQEKDLE ELEKGLQVKL SNTEMSGAGD SEYITLADVE  300
KKEREYSEQL IDNMEAFWKQ MANIQHFLVD QFKCSSSKAR QLMMTLTERM IAAEGLLCDS  360
QELQALDALE RTMGRAHMAK VIEFLKLQVQ EETRCRLAAI SHGLELLAGE GKLSGRQKEE  420
LLTQQHKAFW QEAERFSREF VQRGKDLVTA SLAHQVEGTA KLTLAQEEEQ RSFLAEAQPT  480
ADPEKFLEAF HEVLERQRLM QCDLEEEENV RATEAVVALC QELYFSTVDT FQKFVDALFL  540
QTLPGMTGLP PEECDYLRQE VQENAAWQLG KSNRFRRQQW KLFQELLEQD QQVWMEECAL  600
SSVLQTHLRE DHEGTIRGVL GRLGGLTEES TRCVLQGHDL LLRSALRRLA LRGNALATLT  660
QMRLSGKKHL LQELREQRAL EQGSSQCLDE HQWQLLRALE ARVLEEASRL EEEAQQTRLQ  720
LQQRLLAEAQ EVGQLLQQHM ECAIGQALLV HARNAATKSR AKDRDDFKRT LMEAAVESVY  780
VTSAGVSRLV QAYYQQIGRI MEDHEERKLQ HLKTLQGERM ENYKLRKKQE LSNPSSGSRT  840
AGGAHETSQA VHQRMLSQQK RFLAQFPVHQ QMRLHAQQQQ AGVMDLLEAQ LETQLQEAEQ  900
NFISELAALA RVPLAESKLL PAKRGLLEKP LRTKRKKPLP QERGDLGVPN NEDLASGDQT  960
SGSLSSKRLS QQESEAGDSG NSKKMLKRRS NL                                992

SEQ ID NO: 125          moltype = DNA  length = 3687
FEATURE                 Location/Qualifiers
source                  1..3687
                        mol_type = genomic DNA
                        organism = Homo sapiens
SEQUENCE: 125
atgatttggc ccaaagtgga atgctgtcac tttaagactg cagtggaagc accacttgga  60
atgaaattgg acaagaaaat ggaagtcttc atcccactct caacttctgc agcctctagt  120
gggccatggg ctcattcctt atttgctttt ataccctcct ggcctaagaa gaacttattt  180
aaaagagagt ctcctataac acaccgcctg tatggggaca tttcaagaga agttcaaggg  240
acttctgaaa atggagtaat ttttcagaaa tgtgcactgg tgtctgggtc gagtgaagca  300
cagacagccc gcatatggct gcttgttaac aacaccaaga caacctcgtc agccaacctc  360
tcggagctgc tcttgctgga cagcattgct ggtctcacca tttgggactc tgtgggaaac  420
aggacctcgg aaggattcca ggcttttagc aagaagtttc tgcaagtggg agatgccttt  480
gctgtcagct acgcagccac gctccaggct ggagacctcg ggaacgggga gagcctcaag  540
cttcctgccc aactcacctt tcagagctcg tcacggaaca gaacacagct gaaagtgctt  600
ttttccataa cagcagaaga aaacgtaacg gttctgccgc accacggcct ccacgcagca  660
gggttcttca ttgccttcct cctctccctt gtgctgacct gggctgccct cttcctcatg  720
gttcgctatc agtgtctgaa gggaaacatg ctcaccagac atcgggtttg gcagtatgag  780
agcaagctgg aacccttgcc gttcacctca gctgatggcg tgaatgagga cctttccctt  840
aacgaccaaa tgatagacat tctgtcttcc gaggaccctg ggagcatgct tcaagcctta  900
gaagagttgg agattgcaac cctgaatcgg gcagatgcag atctggaggc ttgtcgaaca  960
caaatcagca aggatatcat tgcccttctg ctgaaaaatc tcaccagcag tggccacctc  1020
tcaccccaag tagagagaaa aatgagtgct gttttcaaaa agcagtttct attgctggaa  1080
aatgaaatac aagaggagta cgatcggaag atggtggcat tgacagctga atgtgacctg  1140
gaaacaagaa agaagatgga aaaccagtac cagagagaga tgatggcaat ggaggaagca  1200
gaagagttgc tgaaacgtgc tggtgagagg tctgctgtag agtgcagcaa ccttctgcgg  1260
accctccatg gcctggaaca ggagcacttg aggaagtctc tcgctttgca acaagaagaa  1320
gactttgcca aagctcacag acagctggct gttttccaga gaaatgaact gcacagtatc  1380
ttttttaccc agataaaaag tgctattttc aaaggggaat tgaaaccaga ggcagctaaa  1440
atgctgctgc aaaattattc taaaatacag gagaatgtag aagagttaat ggactttttc  1500
caggctagta agaggtatca tctaagtaaa agatttggcc acagggaata tctggtccag  1560
aacctccagt catcagagac ccgtgtgcag ggccttctga gcaccgctgc agcccagctg  1620
actcacctca ttcagaagca cgagagagca gggtacctgg atgaagacca aatggaaatg  1680
ctattggagc gggctcagac agaagtcttt tcaatcaagc agaagttgga caatgactta  1740
aagcaggaaa agaaaaagct ccaccaaaaa ttaataacta agagaagacg agagttgcta  1800
caaaagcaca gggagcagcg tagggagcag gcgtccgtcg gcgaggcctt ccgaacggtt  1860
gaggatgccg gccagtacct gcaccagaag aggagcctga tggaggagca cggtgccacc  1920
ctggaggagc tgcaggagcg tctggaccag gccgccctgg acgatctcag gaccctgacc  1980
ctttcgctgt ttgaaaaggc caccgacgag ctgcggcgcc tgcagaactc agccatgacc  2040
caggagctgc tcaagcgtgg ggtgccctgg ctcttcctgc agcagatcct ggaggagcac  2100
ggcaaggaga tggctgcacg ggccgagcag ctggaggggg aggagaggga cagggaccag  2160
gagggtgtcc agagcgtgag gcagagactg aaggatgacg ctcctgaggc cgtgacagag  2220
gagcaggcag agctgcgacg ctgggagcac ctgatcttca tgaagctctg ctcctcagtc  2280
ttctccctgt ctgaagagga gctgctcagg atgaggcagg aggtccatgg ctgctttgct  2340
cagatggaca ggagcttggc cctcccccaag atccgggccc gagttctgct gcagcaattt  2400
cagactgcgt ggcgagaagc agagttcgtg aagctggacc aggccgtggc tgcccctgag  2460
```

```
ctgcagcaac agtccaaggt gagaaagtca cggtccaaga gtaaaagcaa gggagagctt  2520
ctgaagaagt gcatcgaaga caaaattcac ctctgtgagg aacaggcctc tgaagacctg  2580
gtggaaaagg ttcgaggtga attgctgcgg gagagagtgc agcggatgga ggcacaggag  2640
ggaggctttg cacagtcgct tgttgctctg cagttccaga aggcgtcccg ggtgaccgag  2700
actctgtcgg cctacaccgc cctcctcagc atccaggact tgctcctgga agagctgagt  2760
gcatctgaga tgctgaccaa gtcggcctgc acacagatcc tggagtcgca cagccgggag  2820
ctccaggagt tggagaggaa gctggaggac cagctggtgc agcaggaggc agcccagcag  2880
cagcaggccc tggcgagctg gcagcagtgg gtggccgatg ggcccgggat tctgaacgaa  2940
cctggggagg tggattctga aaggcaggtc tctactgtcc tgcaccaagc cctgagcaag  3000
agccagacat tactggagca acatcagcag tgtttgagag aggaacaaca gaacagtgtc  3060
gtgctagaag acttgttgga aaacatggag gcagacacct ttgcaaccct gtgcagccag  3120
gagctgagac tggcatcgta cctggcgagg atggccatgg tgcccggggc cacgcttcgc  3180
cggctcctga gtgtggtact gccccacagcc tcacagcctc agctgctggc cctgctggat  3240
tcggccaccg agagacatgt ggaccacgca gctgagagcg atggcggagc ggagcaggcc  3300
gacgtgggca ggcggaggaa acaccagagc tggtggcaag ccttagatgg caaactgcga  3360
ggagatctga taagcagagg attagaaaag atgctgtggg cccgcaagag aaagcagagc  3420
atattaaaga agacatgtct ccctctcaga gagaggatga tattctctgg aaaaggaagt  3480
tggccacacc tgtcactgga gcccattggc gaactggccc ctgtacccat tgtaggggca  3540
gaaaccattg atctattaaa cacaggagag aagctcttta tattcagaaa tccaaaggag  3600
ccagagatct cactgcacgt tcctcccagg aaaaagaaga actttttgaa tgccaaaaag  3660
gccatgaggg ccttgggcat ggactag                                      3687
```

```
SEQ ID NO: 126          moltype = AA  length = 1228
FEATURE                 Location/Qualifiers
source                  1..1228
                        mol_type = protein
                        organism = Homo sapiens
SEQUENCE: 126
MIWPKVECCH FKTAVEAPLG MKLDKKMEVF IPLSTSAASS GPWAHSLFAF IPSWPKKNLF  60
KRESPITHRL YGDISREVQG TSENGVIFQK CALVSGSSEA QTARIWLLVN NTKTTSSANL  120
SELLLLDSIA GLTIWDSVGN RTSEGFQAFS KKFLQVGDAF AVSYAATLQA GDLGNGESLK  180
LPAQLTFQSS SRNRTQLKVL FSITAEENVT VLPHHGLHAA GFFIAFLLSL VLTWAALFLM  240
VRYQCLKGNM LTRHRVWQYE SKLEPLPFTS ADGVNEDLSL NDQMIDILSS EDPGSMLQAL  300
EELEIATLNR ADADLEACRT QISKDIIALL LKNLTSSGHL SPQVERKMSA VFKKQFLLLE  360
NEIQEEYDRK MVALTAECDL ETRKKMENQY QREMMAMEEA EELLKRAGER SAVECSNLLR  420
TLHGLEQEHL RKSLALQQEE DFAKAHRQLA VFQRNELHSI FFTQIKSAIF KGELKPEAAK  480
MLLQNYSKIQ ENVEELMDFF QASKRYHLSK RFGHREYLVQ NLQSSETRVQ GLLSTAAAQL  540
THLIQKHERA GYLDEDQMEM LLERAQTEVF SIKQKLDNDL KQEKKKLHQK LITKRRRELL  600
QKHREQRREQ ASVGEAFRTV EDAGQYLHQK RSLMEEHGAT LEELQERLDQ AALDDLRTLT  660
LSLFEKATDE LRRLQNSAMT QELLKRGVPW LFLQQILEEH GKEMAARAEQ LEGEERDRDQ  720
EGVQSVRQRL KDDAPEAVTE EQAELRRWEH LIFMKLCSSV FSLSEEELLR MRQEVHGCFA  780
QMDRSLALPK IRARVLLQQF QTAWREAEFV KLDQAVAAPE LQQQSKVRKS RSKSKSKGEL  840
LKKCIEDKIH LCEEQASEDL VEKVRGELLR ERVQRMEAQE GGFAQSLVAL QFQKASRVTE  900
TLSAYTALLS IQDLLLEELS ASEMLTKSAC TQILESHSRE LQELERKLED QLVQQEAAQQ  960
QQALASWQQW VADGPGILNE PGEVDSERQV STVLHQALSK SQTLLEQHQQ CLREEQQNSV  1020
VLEDLLENME ADTFATLCSQ ELRLASYLAR MAMVPGATLR RLLSVVLPTA SQPQLLALLD  1080
SATERHVDHA AESDGGAEQA DVGRRRKHQS WWQALDGKLR GDLISRGLEK MLWARKRKQS  1140
ILKKTCLPLR ERMIFSGKGS WPHLSLEPIG ELAPVPIVGA ETIDLLNTGE KLFIFRNPKE  1200
PEISLHVPPR KKKNFLNAKK AMRALGMD                                     1228
```

```
SEQ ID NO: 127          moltype = DNA  length = 8616
FEATURE                 Location/Qualifiers
source                  1..8616
                        mol_type = genomic DNA
                        organism = Homo sapiens
SEQUENCE: 127
atgcgtcgag ggcgtctgct ggagatcgcc ctgggattta ccgtgctttt agcgtcctac  60
acgagccatg gggcggacgc caatttggag gctgggaacg tgaaggaaac cagagccagt  120
cgggccaaga gaagaggcgg tggaggacac gacgcgctta aaggacccaa tgtctgtgga  180
tcacgttata atgcttactg ttgccctgga tggaaaacct tacctggcgg aaatcagtgt  240
attgtcccca tttgccggca ttcctgtggg gatggatttt gttcgaggcc aaatatgtgc  300
acttgcccat ctggtcagat agctccttcc tgtggctcca gatccataca acactgcaat  360
attcgctgta tgaatggagg tagctgcagt gacgatcact gtctatgcca gaaaggatac  420
atagggactc actgtggaca acctgtttgt gaaagtggct gtctcaatgg aggaaggtgt  480
gtggccccaa atcgatgtgc atgcacttac ggatttactg gaccccagtg tgaaagagat  540
tacaggacag gcccatgttt tactgtgatc agcaaccaga tgtgccaggg acaactcagc  600
gggattgtct gcacaaaaac gctctgctgt gccacagtcg gccgagcctg gggccacccc  660
tgtgagatgt gtcctgccca gcctcacccc tgccgccgtg gcttcattcc aaatatccgc  720
acgggagctt gtcaagatgt ggatgaatgc caggccatcc ccgggctctg tcagggagga  780
aattgcatta atactgttgg gtcttttgag tgcaaatgcc ctgctggaca caaacttaat  840
gaagtgtcac aaaaatgtga agatattgat gaatgcagca ccattcctgg aatctgtgaa  900
gggggtgaat gtacaaacac agtcagcagt tacttttgca aatgtccccc tggtttttac  960
acctctccag atggtaccag atgcatagat gttcgcccag gatactgtta cacagctctg  1020
acaaacgggc gctgctctaa ccagctgcca cagtccataa ccaaaatgca gtgctgctgt  1080
gatgccggcc gatgctggtc tccaggggtc actgtcgccc ctgagatgtg tcccatcaga  1140
gcaaccgagg atttcaacaa gctgtgctct gttcctatgg taattcctgg gagaccagaa  1200
tatcctcccc cacccc ttgg ccccattcct ccagttctcc ctgttcctcc tggctttcct  1260
cctggacctc aaattccggt ccctcgacca ccagtggaat atctgtatcc atctcgggag  1320
ccaccaaggg tgctgccagt aaacgttact gattactgcc agttggtccg ctatctctgt  1380
```

-continued caaaatggac gctgcattcc aactcctggg agttaccggt gtgagtgcaa caaagggttc 1440
cagctggacc tccgtgggga gtgtattgat gttgatgaat gtgagaaaaa cccctgtgct 1500
ggtggtgagt gtattaacaa ccagggttcg tacacctgtc agtgccgagc tggatatcag 1560
agcacactca cgcggacaga atgccgagac attgatgagt gtttacagaa tggccggatc 1620
tgcaataatg gacgctgcat caacacagat ggcagttttc attgcgtgtg taatgcgggc 1680
tttcatgtta cacgagatgg gaagaactgt gaagatatgg atgaatgcag cataaggaac 1740
atgtgcctta atggaatgtg tatcaatgaa gatggcagtt ttaaatgtat ttgcaaacct 1800
ggattccagc tggcatcaga tggacgttat tgcaaagaca ttaacgagtg tgaaacccct 1860
gggatctgca tgaatgggcg ttgcgtcaac actgatggct cctacagatg tgaatgcttc 1920
cctggactgg ctgtgggtct ggatggccgt gtgtgtgttg acacacacat gcggagcaca 1980
tgctatggtg gatacaagag aggccagtgt atcaaacctt tgtttggtgc tgtcactaaa 2040
tctgaatgct gttgcgccag cactgagtat gcatttgggg aaccttgcca gccgtgtcct 2100
gcacagaatt cagcggaata tcaggcactc tgcagcagtg ggccaggaat gacgtcagca 2160
ggcagtgata taaatgaatg tgcactagat cctgatattt gcccaaatgg aatctgtgaa 2220
aaccttcgtg ggacctataa atgtatatgc aattcaggat atgaagtgga ttcaactggg 2280
aaaaactgcg ttgatattaa tgaatgtgta ctgaacagtc tcctttgtga caatggacaa 2340
tgtagaaata ctcctggaag ttttgtctgt acctgcccca agggatttat ctacaaacct 2400
gatctaaaaa catgtgaaga cattgatgaa tgcgaatcaa gtccttgcat taatggagtc 2460
tgcaagaaca gcccaggctc ttttatttgt gaatgttctt ctgaaagtac tttggatcca 2520
acaaaaacca tctgcataga aaccatcaag ggcacttgct ggcagactgt cattgatggg 2580
cgatgtgaga tcaacatcaa tggagccacc ttaaagtccc agtgctgctc ctccctcggt 2640
gctgcgtggg gaagcccgtg caccctatgc caagttgatc ccatatgtgg taaagggtac 2700
tcaagaatta aaggaacaca atgtgaagat atagatgaat gtgaagtgtt cccaggagtg 2760
tgtaaaaatg gcctgtgtgt taacactagg gggtcattca agtgtcagtg tcccagtgga 2820
atgactttgg atgccacagg aaggatctgt cttgatatcc gcctggaaac ctgcttcctg 2880
aggtacgagg acgaggagtg caccctgcct attgctggcc gccaccgcat ggacgcctgc 2940
tgctgctccg tcggggcagc ctggggtact gaggaatgcg aggagtgtcc catgagaaat 3000
actcctgagt acgaggagct gtgtccgaga ggacccggat ttgccacaaa agaaattaca 3060
aatggaaagc ctttcttcaa agatatcaat gagtgcaaga tgatacccag cctctgcacc 3120
cacggcaagt gcagaaacac cattggcagc tttaagtgca ggtgtgacag cggctttgct 3180
cttgattctg aagaaaggaa ctgcacagac attgacgaat gccgcatatc tcctgacctc 3240
tgtggcagag gccagtgtgt gaacacccct ggggactttg aatgcaagtg tgacgaaggc 3300
tatgaaagtg gattcatgat gatgaagaac tgcatggata ttgatgagtg tcagagagat 3360
cctctcctat gccgaggtgg tgtttgccat aacacagagg gaagttaccg ctgtgaatgc 3420
ccgcctggcc atcagctgtc ccccaacatc tccgcgtgta tcgacatcaa tgaatgtgag 3480
ctgagtgcac acctgtgccc caatggccgt tgcgtgaacc tcatagggaa gtatcagtgt 3540
gcctgcaacc ctggctacca ttcaactccc gataggctat tttgtgttga cattgatgaa 3600
tgcagcataa tgaatggtgg ttgtgaaacc ttctgcacaa actctgaagg cagctatgaa 3660
tgtagctgtc agccgggatt tgcactaatg cctgaccaga gatcatgcac cgacatcgat 3720
gagtgtgaag ataatcccaa tatctgtgat ggtggtcagt gcacaaatat ccctggagag 3780
tacaggtgct tgtgttatga tggattcatg gcatctgaag acatgaagac ttgtgtagat 3840
gtcaatgagt gtgacctgaa tccaaatatc tgcctaagtg ggacctgtga aaacacgaaa 3900
ggctcattta tctgccactg tgatatgggc tactccggca aaaaaggaaa aactggctgt 3960
acagacatca atgaatgtga aattggagca cacaactgtg gcaaacatgc tgtatgtacc 4020
aatacagcag gaagcttcaa atgtagctgc agtcccgggt ggattggaga tggcattaag 4080
tgcactgatc tggacgaatg ttccaatgga acccatatgt gcagccagca tgcagactgc 4140
aagaatacca tgggatctta ccgctgtctg tgcaaggaag gatacacagg tgatggcttc 4200
acttgtacag accttgatga gtgctctgag aacctgaatc tctgtggcaa tggccagtgc 4260
ctcaatgcac caggaggata ccgctgtgaa tgcgacatgg gcttcgtgcc cagtgctgac 4320
gggaaagcct gtgaagatat tgatgagtgc tcccttccga acatctgtgt ctttggaact 4380
tgccacaacc tccctggcct gttccgctgt gagtgtgaga taggctacga actggacaga 4440
agcggcggga actgcacaga tgtgaatgaa tgcctggatc caaccacgtg catcagtggg 4500
aactgtgtca acactccagg cagctatatc tgtgactgcc cacctgattt tgaactgaac 4560
ccaactcgag ttggctgtgt tgatacccgc tctggaaatt gctatttgga tattcgacct 4620
cgaggagaca atggagatac agcctgcagc aatgaaattg gagttggtgt ttccaaagct 4680
tcctgctgct gttctctggg taaagcctgg ggtactcctt gtgagatgtg tcctgctgtg 4740
aacacatccg agtacaaaat tctttgtcct ggaggggaag gtttccgacc aaatcctatc 4800
accgttatat tggaagatat tgatgagtgc caggagctac cagggctgtg ccaaggagga 4860
aaatgtatca acacctttgg gagtttccag tgccgctgtc caaccggcta ctacctgaat 4920
gaagatacac gagtgtgtga tgatgtgaat gaatgtgaga ctcctggaat ctgtggtcca 4980
gggacatgtt acaacaccgt tggcaactac acctgtatct gtcctccaga ctacatgcaa 5040
gtgaatgggg gaaataattg catggatatg agaagaagtt tgtgctacag aaactactat 5100
gctgacaacc agacctgtga tggagaattg ttattcaaca tgaccaagaa gatgtgctgc 5160
tgttcctaca acattggccg ggcgtggaac aagccctgtg aacagtgtcc catcccaagt 5220
acagatgagt ttgctacact ctgtggaagt caaaggccag gctttgtcat cgacatttat 5280
accggtttac ccgttgatat tgatgagtgc cgggagatcc caggggtctg tgaaaatgga 5340
gtgtgtatca acatggttgg cagcttccga tgtgaatgtc cagtgggatt cttctataat 5400
gacaagttgt tggtttgtga agatattgac gagtgtcaga acggcccagt gtgccagcgc 5460
aacgccgaat gcatcaacac tgcaggcagc taccgctgtg actgtaagcc cggctaccgc 5520
ttcacctcca caggacagtg caatgatcgt aatgaatgtc aagaaatccc caatatatgc 5580
agtcatgggc agtgcattga cacagttgga agcttttatt gcctttgcca cactggtttt 5640
aaaacaaatg atgaccaaac catgtgcttg gacataaatg aatgtgaaag agatgcctgt 5700
gggaatggaa cttgccggaa cacaattggt tccttcaact gccgctgcaa tcatggtttc 5760
atcctttctc acaacaatga ctgtatagat gttgatgaat gtgcaagtgg aaatgggaat 5820
ctttgcagaa atggccaatg cattaataca gtggggtctt tccagtgcca gtgcaatgaa 5880
ggctatgagg tggctccaga tgggaggacc tgtgtggata tcaatgaatg tcttctagaa 5940
cccagaaaat gtgcaccagg tacctgtcaa aacttggatg ggtcctacag atgcatttgc 6000
ccacctggat acagtcttca aaatgagaag tgtgaagata ttgatgagtg tgtcgaagag 6060
ccagaaattt gtgccctggg cacatgcagt aacactgaag gcagcttcaa atgtctgtgt 6120

-continued

```
ccagaagggt tttccttgtc ctccagtgga agaaggtgcc aagatttgcg aatgagctac  6180
tgttatgcga agtttgaagg aggaaagtgt tcatcaccca aatccagaaa tcactccaag  6240
caggaatgct gctgtgcctt gaagggagaa ggctggggag acccctgcga gctctgcccc  6300
acggaacctg atgaggcctt ccgccagata tgtccttatg gaagtgggat catcgtggga  6360
cctgatgatt cagcagttga tatggacgaa tgcaaagaac ccgatgtctg taaacatgga  6420
cagtgcatca atacagatgg ttcctatcgc tgcgagtgtc cctttggtta tattctagca  6480
gggaatgaat gtgtagatac tgatgaatgt tctgttggca atccttgtgg aaatggaacc  6540
tgcaagaatg tgattggagg ttttgaatgc acctgcgagg agggatttga gcccggtcca  6600
atgatgacat gtgaagatat aaatgaatgt gcccagaatc ctctgctctg tgccttccga  6660
tgtgtgaaca cttatgggtc atatgaatgc aaatgtcccg tgggatatgt gctcagagaa  6720
gaccgtagga tgtgcaaaga tgaggatgag tgtgaagagg gaaaacatga ctgtactgaa  6780
aaacaaatgg aatgcaagaa cctcattggc acatatatgt gcatctgtgg acccgggtat  6840
cagcggagac ctgatggaga aggctgtgta gatgagaatg aatgtcagac gaagccaggg  6900
atctgtgaga atgggcgctg cctcaacacc cgtgggagct acacctgtga gtgtaatgat  6960
gggtttaccg ccagccccaa ccaggacgag tgccttgaca atcgggaagg gtactgcttc  7020
acagaggtgc tacaaaacat gtgtcagatc ggctccagca acaggaaccc cgtcaccaaa  7080
tcggaatgct gctgtgacgg agggagaggc tggggtcccc actgtgagat ctgccctttc  7140
caggggactg tggctttcaa gaaactctgt ccccatggcc gaggattcat gaccaatgga  7200
gcagatatcg atgaatgcaa ggttattcac gatgtttgcc gaaatgggga atgtgtcaat  7260
gacagaggat catatcattg catttgtaaa actgggtaca ctccagatat aactgggact  7320
tcctgtgtag atctgaacga gtgcaaccag gctcccaaac cctgcaattt tatctgcaaa  7380
aacacagaag ggagttacca gtgttcatgc ccgaaaggct acattctgca agaggatgga  7440
aggagctgca aagatcttga tgagtgtgca accaagcaac acaactgcca gttcctatgt  7500
gttaacacca ttggcggctt cacatgcaaa tgtcctcccg gatttaccca acaccatacg  7560
tcctgcattg ataacaatga atgcacctct gacatcaatc tgtgcgggtc taagggcatt  7620
tgccagaaca ctcctggaag cttcacctgt gaatgccagc ggggattctc acttgatcag  7680
accggctcca gctgtgaaga cgtggacgag tgtgagggta accaccgctg ccagcatggc  7740
tgccagaaca tcattggggg ctacaggtgc agctgccccc agggctacct ccagcactac  7800
cagtggaacc agtgtgttga tgaaaacgaa tgcctcagcg ctcacatctg cggaggagcc  7860
tcctgtcaca acaccctggg gagctacaag tgcatgtgtc ccgccggctt ccagtatgaa  7920
cagttcagtg gaggatgcca agacatcaat gaatgtggct ctgcgcaggc cccctgcagc  7980
tatggctgtt ccaataccga gggcggttac ctgtgtggct gtccacctgg ttacttccgc  8040
ataggccaag ggcactgtgt ttctggaatg ggcatgggcc gaggaaaccc agagccacct  8100
gtcagtggtg aaatggatga caattcactc tccccagagg cttgttacga gtgtaagatc  8160
aatggctacc ccaaacgggg caggaaacgg agaagcacaa acgaaactga tgcctccaat  8220
atcgaggatc agtctgagac agaagccaat gtgagtcttg caagttggga tgttgagaag  8280
acagccatct ttgctttcaa tatttcccac gtcagtaaca aggttcgaat cctagaactc  8340
cttccagctc ttacaactct gacgaatcac aacagatact tgatcgaatc tggaaatgaa  8400
gatggcttct ttaaaatcaa ccaaaaggaa gggatcagct acctccactt cacaaagaag  8460
aagccagtgg ctggaaccta ttcattacaa atcagtagta ctccacttta taaaaagaaa  8520
gaacttaacc aactagaaga caaatatgac aaagactacc tcagtggtga actgggtgat  8580
aatctgaaga tgaaaatcca ggttttgctt cattaa                            8616

SEQ ID NO: 128         moltype = AA  length = 2871
FEATURE                Location/Qualifiers
source                 1..2871
                       mol_type = protein
                       organism = Homo sapiens
SEQUENCE: 128
MRRGRLLEIA LGFTVLLASY TSHGADANLE AGNVKETRAS RAKRRGGGGH DALKGPNVCG  60
SRYNAYCCPG WKTLPGGNQC IVPICRHSCG DGFCSRPNMC TCPSGQIAPS CGSRSIQHCN  120
IRCMNGGSCS DDHCLCQKGY IGTHCGQPVC ESGCLNGGRC VAPNRCACTY GFTGPQCERD  180
YRTGPCFTVI SNQMCQGQLS GIVCTKTLCC ATVGRAWGHP CEMCPAQPHP CRRGFIPNIR  240
TGACQDVDEC QAIPGLCQGG NCINTVGSFE CKCPAGHKLN EVSQKCEDID ECSTIPGICE  300
GGECTNTVSS YFCKCPPGFY TSPDGTRCID VRPGYCYTAL TNGRCSNQLP QSITKMQCCC  360
DAGRCWSPGV TVAPEMCPIR ATEDFNKLCS VPMVIPGRPE YPPPPLGPIP PVLPVPPGFP  420
PGPQIPVPRP PVEYLYPSRE PPRVLPVNVT DYCQLVRYLC QNGRCIPTPG SYRCECNKGF  480
QLDLRGECID VDECEKNPCA GGECINNQGS YTCQCRAGYQ STLTRTECRD IDECLQNGRI  540
CNNGRCINTD GSFHCVCNAG FHVTRDGKNC EDMDECSIRN MCLNGMCINE DGSFKCICKP  600
GFQLASDGRY CKDINECETP GICMNGRCVN TDGSYRCECF PGLAVGLDGR VCVDTHMRST  660
CYGGYKRGQC IKPLFGAVTK SECCCASTEY AFGEPCQPCP AQNSAEYQAL CSSGPGMTSA  720
GSDINECALD PDICPNGICE NLRGTYKCIC NSGYEVDSTG KNCVDINECV LNSLLCDNGQ  780
CRNTPGSFVC TCPKGFIYKP DLKTCEDIDE CESSPCINGV CKNSPGSFIC ECSSESTLDP  840
TKTICIETIK GTCWQTVIDG RCEININGAT LKSQCCSSLG AAWGSPCTLC QVDPICGKGY  900
SRIKGTQCED IDECEVFPGV CKNGLCVNTR GSFKCQCPSG MTLDATGRIC LDIRLETCFL  960
RYEDEECTLP IAGRHRMDAC CCSVGAAWGT EECEECPMRN TPEYEELCPR GPGFATKEIT  1020
NGKPFFKDIN ECKMIPSLCT HGKCRNTIGS FKCRCDSGFA LDSEERNCTD IDECRISPDL  1080
CGRGQCVNTP GDFECKCDEG YESGFMMMKN CMDIDECQRD PLLCRGGVCH NTEGSYRCEC  1140
PPGHQLSPNI SACIDINECE LSAHLCPNGR CVNLIGKYQC ACNPGYHSTP DRLFCVDIDE  1200
CSIMNGGCET FCTNSEGSYE CSCQPGFALM PDQRSCTDID ECEDNPNICD GGQCTNIPGE  1260
YRCLCYDGFM ASEDMKTCVD VNECDLNPNI CLSGTCENTK GSFICHCDMG YSGKKGKTGC  1320
TDINECEIGA HNCGKHAVCT NTAGSFKCSC SPGWIGDGIK CTDLDECSNG THMCSQHADC  1380
KNTMGSYRCL CKEGYTGDGF TCTDLDECSE NLNLCGNGQC LNAPGGYRCE CDMGFVPSAD  1440
GKACEDIDEC SLPNICVFGT CHNLPGLFRC ECEIGYELDR SGGNCTDVNE CLDPTTCISG  1500
NCVNTPGSYI CDCPPDFELN PTRVGCVDTR SGNCYLDIRP RGDNGDTACS NEIGVGVSKA  1560
SCCCSLGKAW GTPCEMCPAV NTSEYKILCP GGEGFRPNPI TVILEDIDEC QELPGLCQGG  1620
KCINTFGSFQ CRCPTGYYLN EDTRVCDDVN ECETPGICGP GTCYNTVGNY TCICPPDYMQ  1680
VNGGNNCMDM RRSLCYRNYY ADNQTCDGEL LFNMTKKMCC CSYNIGRAWN KPCEQCPIPS  1740
TDEFATLCGS QRPGFVIDIY TGLPVDIDEC REIPGVCENG VCINMVGSFR CECPVGFFYN  1800
```

-continued

```
DKLLVCEDID ECQNGPVCQR NAECINTAGS YRCDCKPGYR FTSTGQCNDR NECQEIPNIC  1860
SHGQCIDTVG SFYCLCHTGF KTNDDQTMCL DINECERDAC GNGTCRNTIG SFNCRCNHGF  1920
ILSHNNDCID VDECASGNGN LCRNGQCINT VGSFQCQCNE GYEVAPDGRT CVDINECLLE  1980
PRKCAPGTCQ NLDGSYRCIC PPGYSLQNEK CEDIDECVEE PEICALGTCS NTEGSFKCLC  2040
PEGFSLSSSG RRCQDLRMSY CYAKFEGGKC SSPKSRNHSK QECCCALKGE GWGDPCELCP  2100
TEPDEAFRQI CPYGSGIIVG PDDSAVDMDE CKEPDVCKHG QCINTDGSYR CECPFGYILA  2160
GNECVDTDEC SVGNPCGNGT CKNVIGGFEC TCEEGFEPGP MMTCEDINEC AQNPLLCAFR  2220
CVNTYGSYEC KCPVGYVLRE DRRMCKDEDE CEEGKHDCTE KQMECKNLIG TYMCICGPGY  2280
QRRPDGEGCV DENECQTKPG ICENGRCLNT RGSYTCECND GFTASPNQDE CLDNREGYCF  2340
TEVLQNMCQI GSSNRNPVTK SECCCDGGRG WGPHCEICPF QGTVAFKKLC PHGRGFMTNG  2400
ADIDECKVIH DVCRNGECVN DRGSYHCICK TGYTPDITGT SCVDLNECNQ APKPCNFICK  2460
NTEGSYQCSC PKGYILQEDG RSCKDLDECA TKQHNCQFLC VNTIGGFTCK CPPGFTQHHT  2520
SCIDNNECTS DINLCGSKGI CQNTPGSFTC ECQRGFSLDQ TGSSCEDVDE CEGNHRCQHG  2580
CQNIIGGYRC SCPQGYLQHY QWNQCVDENE CLSAHICGGA SCHNTLGSYK CMCPAGFQYE  2640
QFSGGCQDIN ECGSAQAPCS YGCSNTEGGY LCGCPPGYFR IGQGHCVSGM GMGRGNPEPP  2700
VSGEMDDNSL SPEACYECKI NGYPKRGRKR RSTNETDASN IEDQSETEAN VSLASWDVEK  2760
TAIFAFNISH VSNKVRILEL LPALTTLTNH NRYLIESGNE DGFFKINQKE GISYLHFTKK  2820
KPVAGTYSLQ ISSTPLYKKK ELNQLEDKYD KDYLSGELGD NLKMKIQVLL H           2871

SEQ ID NO: 129          moltype = DNA  length = 8520
FEATURE                 Location/Qualifiers
source                  1..8520
                        mol_type = genomic DNA
                        organism = Homo sapiens
SEQUENCE: 129
atggccgcgc acaggccggt ggaatgggtc caggccgtgg tcagccgctt cgacgagcag  60
cttccaataa aaacaggaca gcagaacaca cataccaaag tcagtactga gcacaacaag  120
gaatgtctaa tcaatatttc caaatacaag ttttctttgg ttataagcgg cctcactact  180
attttaaaga atgttaacaa tatgagaata tttggagaag ctgctgaaaa aaatttatat  240
ctctctcagt tgattatatt ggatacactg gaaaaatgtc ttgctgggca accaaaggac  300
acaatgagat tagatgaaac gatgctggtc aaacagttgc tgccagaaat ctgccatttt  360
cttcacacct gtcgtgaagg aaaccagcat gcagctgaac ttcggaattc tgcctctggg  420
gttttatttt ctctcagctg caacaacttc aatgcagtct ttagtcgcat ttctaccagg  480
ttacaggaat taactgtttg ttcagaagac aatgttgatg ttcatgatat agaattgtta  540
cagtatatca atgtggattg tgcaaaatta aaacgactcc tgaaggaaac agcattttaaa  600
tttaaagccc taaagaaggt tgcgcagtta gcagttataa atagcctgga aaaggcattt  660
tggaactggg tagaaaatta tccagatgaa tttacaaaac tataccagat cccacagact  720
gatatggctg aatgtgcaga aaagctattt gacttggtgg atggttttgc tgaaagcacc  780
aaacgtaaag cagcagtttg gccactacaa atcattctcc ttatcttgtg tccagaaata  840
atccaggata tatccaaaga cgtggttgat gaaaacaaca tgaataagaa gttatttctg  900
gacagtctac gaaaagctct tgctggccat ggaggaagta ggcagctgac agaaagtgct  960
gcaattgcct gtgtcaaact gtgtaaagca agtacttaca tcaattggga agataactct  1020
gtcattttcc tacttgttca gtccatggtg gttgatctta agaacctgct ttttaatcca  1080
agtaagccat tctcaagagg cagtcagcct gcagatgtgg atctaatgat tgactgcctt  1140
gtttcttgct ttcgtataag ccctcacaac aaccaacact ttaagatctg cctggctcag  1200
aattcacctt ctacatttca ctatgtgctg gtaaattcac tccatcgaat catcaccaat  1260
tccgcattgg attggtggcc taagattgat gctgtgtatt gtcactcggt tgaacttcga  1320
aatatgtttg gtgaaacact tcataaagca gtgcaaggtt gtggagcaca cccagcaata  1380
cgaatggcac cgagtcttac atttaaagaa aaagtaacaa gccttaaatt taaagaaaaa  1440
cctacagacc tggagacaag aagctataag tatcttctct tgtccatggt gaaactaatt  1500
catgcagatc caaagctctt gctttgtaat ccaagaaaac aggggcccga aacccaaggc  1560
agtacagcag aattaattac agggctcgtc caactggtcc ctcagtcaca catgccagag  1620
attgctcagg aagcaatgga ggctctgctg gttcttcatc agttagatag cattgatttg  1680
tggaatcctg atgctcctgt agaaacattt tgggagatta gctcacaaat gcttttttac  1740
atctgcaaga aattaactag tcatcaaatg cttagtagca cagaaattct caagtggttg  1800
cgggaaatat tgatctgcag gaataaattt cttcttaaaa ataagcaggc agatagaagt  1860
tcctgtcact ttctcctttt ttacggggta ggatgtgata ttccttctag tggaaatacc  1920
agtcaaatgt ccatggatca tgaagaatta ctacgtactc ctggagcctc tctccggaag  1980
ggaaaaggga actcctctat ggatagtgca gcaggatgca gcggaacccc cccgatttgc  2040
cgacaagccc agaccaaact agaagtggcc ctgtacatgt ttctgtggaa ccctgacact  2100
gaagctgttc tggttgccat gtcctgtttc cgccacctct gtgaggaagc agatatccgg  2160
tgtggggtgg atgaagtgtc agtgcataac ctcttgccca actataacac attcatggag  2220
tttgcctctg tcagcaatat gatgtcaaca ggaagagcag cacttcagaa aagagtgatg  2280
gcactgctga ggcgcattga gcatcccact gcaggaaaca ctgaggcttg ggaagataca  2340
catgcaaaat gggaacaagc aacaaagcta atccttaact atccaaaagc caaaatggaa  2400
gatggccagg ctgctgaaag ccttcacaag accattgtta agaggcgaat gtcccatgtg  2460
agtggaggag gatccataga tttgtctgac acagactccc tacaggaatg gatcaacatg  2520
actggcttcc tttgtgccct tgggggagtg tgcctccagc agagaagcaa ttctggcctg  2580
gcaacctata gcccacccat gggtccagtc agtgaacgta agggttctat gatttcagtg  2640
atgtcttcag agggaaacgc agatacacct gtcagcaaat ttatggatcg gctgttgtcc  2700
ttaatggtgt gtaaccatga gaaagtggga cttcaaatac ggaccaatgt taaggatctg  2760
gtgggtctag aattgagtcc tgctctgtat ccaatgctat ttaacaaatt gaagaatacc  2820
atcagcaagt tttttgactc ccaaggacag gttttattga ctgataccaa tactcaattt  2880
gtagaacaaa ccatagctat aatgaagaac ttgctagata atcatactga aggcagctct  2940
gaacatctag ggcaagctag cattgaaaca atgatgttaa atctggtcag gtatgttcgt  3000
gtgcttggga atatggtcca tgcaattcaa ataaaaacga aactgtgtca attagttgaa  3060
gtaatgatgg caaggagaga tgacctctca ttttgccaag agatgaaatt taggaataag  3120
atggtagaat acctgacaga ctgggttatg ggaacatcaa accaagcagc agatgatgat  3180
gtaaaatgtc ttacaagaga tttggaccag gcaagcatgg aagcagtagt ttcacttcta  3240
```

-continued gctggtctcc ctctgcagcc tgaagaagga gatggtgtgg aattgatgga agccaaatca 3300
cagttatttc ttaaatactt cacattattt atgaaccttt tgaatgactg cagtgaagtt 3360
gaagatgaaa gtgcgcaaac aggtggcagg aaacgtggca tgtctcggag gctggcatca 3420
ctgaggcact gtacggtcct tgcaatgtca aacttactca atgccaacgt agacagtggt 3480
ctcatgcact ccataggctt aggttaccac aaggatctcc agacaagagc tacatttatg 3540
gaagttctga caaaaatcct tcaacaaggc acagaatttg acacacttgc agaaacagta 3600
ttggctgatc ggtttgagag attggtggaa ctggtcacaa tgatgggtga tcaaggagaa 3660
ctccctatag cgatggctct ggccaatgtg gttccttgtt ctcagtggga tgaactagct 3720
cgagttctgg ttactctgtt tgattctcgg catttactct accaactgct ctggaacatg 3780
ttttctaaag aagtagaatt ggcagactcc atgcagactc tcttccgagg caacagcttg 3840
gccagtaaaa taatgacatt ctgtttcaag gtatatggtg ctacctatct acaaaaactc 3900
ctggatcctt tattacgaat tgtgatcaca tcctctgatt ggcaacatgt tagctttgaa 3960
gtggatccta ccaggttaga accatcagag agccttgagg aaaaccagcg gaacctcctt 4020
cagatgactg aaaagttctt ccatgccatc atcagttcct cctcagaatt cccccctcaa 4080
cttcgaagtg tgtgccactg tttataccag gcaacttgcc actccctact gaataaagct 4140
acagtaaaag aaaaaaagga aaacaaaaaa tcagtggtta gccagcgttt ccctcagaac 4200
agcatcggtg cagtaggaag tgccatgttc ctcagattta tcaatcctgc cattgtctca 4260
ccgtatgaag cagggatttt agataaaaag ccaccaccta gaatcgaaag gggcttgaag 4320
ttaatgtcaa agatacttca gagtattgcc aatcatgttc tcttcacaaa agaagaacat 4380
atgcggcctt tcaatgattt tgtgaaaagc aactttgatg cagcacgcag gtttttcctt 4440
gatatagcat ctgattgtcc tacaagtgat gcagtaaatc atagtctttc cttcataagt 4500
gacggcaatg tgcttgcttt acatcgtcta ctctggaaca atcaggagaa aattgggcag 4560
tatctttcca gcaacaggga tcataaagct gttggaagac gaccttttga taagatggca 4620
acacttcttg catacctggg tcctccagag cacaaacctg tggcagatac acactggtcc 4680
agccttaacc ttaccagttc aaagtttgag gaatttatga ctaggcatca ggtacatgaa 4740
aaagaagaat tcaaggcttt gaaaacgtta agtattttct accaagctgg gacttccaaa 4800
gctgggaatc ctatttttta ttatgttgca cggaggttca aaactggtca aatcaatggt 4860
gatttgctga tataccatgt cttactgact ttaaagccat attatgcaaa gccatatgaa 4920
attgtagtgg accttaccca taccgggcct agcaatcgct ttaaaacaga ctttctctct 4980
aagtggtttg ttgtttttcc tggctttgct tacgacaacg tctccgcagt ctatatctat 5040
aactgtaact cctgggtcag ggagtacacc aagtatcatg agcggctgct gactggcctc 5100
aaaggtagca aaaggcttgt tttcatagac tgtcctggga aactggctga gcacatagag 5160
catgaacaac agaaactacc tgctgccacc ttggctttag aagaggacct gaaggtattc 5220
cacaatgctc tcaagctagc tcacaaagac accaaagttt ccattaaagt tggttctact 5280
gctgtccaag taacttcagc agagcgaaca aaagtcctag ggcaatcagt ctttctaaat 5340
gacatttatt atgcttcgga aattgaagaa atctgcctag tagatgagaa ccagttcacc 5400
ttaaccattg caaaccaggg cacgccgctc accttcatgc accaggagtg tgaagccatt 5460
gtccagtcta tcattcatat ccggacccgc tgggaactgt cacagcccga ctctatcccc 5520
caacacacca agattcggcc aaaagatgtc cctgggacac tgctcaatat cgcattactt 5580
aatttaggca gttctgaccc gagtttacgg tcagctgcct ataatcttct gtgtgcctta 5640
acttgtacct ttaatttaaa aatcgagggc cagttactag agacatcagg tttatgtatc 5700
cctgccaaca acaccctctt tattgtctct attagtaaga cactggcagc caatgagcca 5760
cacctcacgt tagaattttt ggaagagtgt atttctggat ttagcaaatc tagtattgaa 5820
ttgaaacacc tttgtttgga atacatgact ccatggctgt caaatctagt tcgtttttgc 5880
aagcataatg atgatgccaa acgacaaaga gttactgcta ttcttgacaa gctgataaca 5940
atgaccatca atgaaaaaca gatgtaccca tctattcaag caaaaatatg ggaagcctt 6000
gggcagatta cagatctgct tgatgttgta ctagacagtt tcatcaaaac cagtgcaaca 6060
ggtggcttgg gatcaataaa agctgaggtg atggcagata ctgctgtagc tttggcttct 6120
ggaaatgtga aattggtttc aagcaaggtt attggaagga tgtgcaaaat aattgacaag 6180
acatgcttat ctccaactcc tactttagaa caacatctta tgtgggatga tattgctatt 6240
ttagcacgct acatgctgat gctgtccttc aacaattccc ttgatgtggc agctcatctt 6300
ccctacctct tccacgttgt tactttctta gtagccacag gtccgctctc ccttagagct 6360
tccacacatg gactggtcat taatatcatt cactctctgt gtacttgttc acagcttcat 6420
tttagtgaag agaccaagca agttttgaga ctcagtctga cagagttctc attacccaaa 6480
ttttacttgc tgtttggcat tagcaaagtc aagtcagctg ctgtcattgc cttccgttcc 6540
agttaccggg acaggtcatt ctctcctggc tcctatgaga gagagacttt tgctttgaca 6600
tccttggaaa cagtcacaga agctttgttg gagatcatgg aggcatgcat gagagatatt 6660
ccaacgtgca agtggctgga ccagtggaca gaactagctc aaagatttgc attccaatat 6720
aatccatccc tgcaaccaag agctcttgtt gtctttgggt gtattagcaa acgagtgtct 6780
catgggcaga taaagcagat aatccgtatt cttagcaagg cacttgagag ttgcttaaaa 6840
ggacctgaca cttacaacag tcaagttctg atagaagcta cagtaatagc actaaccaaa 6900
ttacagccac ttcttaataa ggactcgcct ctgcacaaag ccctcttttg ggtagctgtg 6960
gctgtgctgc agcttgatga ggtcaacttg tattcagcag gtaccgcact tcttgaacaa 7020
aacctgcata ctttagatag tctccgtata ttcaatgaca agagtccaga ggaagtattt 7080
atggcaatcc ggaatcctct ggagtggcac tgcaagcaaa tggatcattt tgttggactc 7140
aatttcaact ctaactttaa ctttgcattg gttggacacc ttttaaaagg gtacaggcat 7200
ccttcacctg ctattgttgc aagaacagtc agaattttac atacactact aactctggtt 7260
aacaaacaca gaaattgtga caaatttgaa gtgaatacac agagcgtggc ctacttagca 7320
gctttactta cagtgtctga agaagttcga agtcgctgca gcctaaaaca tagaaagtca 7380
cttcttctta ctgatatttc aatggaaaat gttcctatgg atacatatcc cattcatcat 7440
ggtgaccctt cctataggac actaaaggag actcagccat ggtcctctcc caaaggttct 7500
gaaggatacc ttgcagccac ctatccaact gtcggccaga ccagtccccg agccaggaaa 7560
tccatgagcc tggacatggg gcaaccttct caggccaaca ctaagaagtt gcttggaaca 7620
aggaaaagtt ttgatcactt gatatcagac acaaaggctc ctaaaaggca agaaatggaa 7680
tcagggatca caacaccccc caaaatgagg agagtagcag aaactgatta tgaaatggaa 7740
actcagagga tttcctcatc acaacagcac ccacatttac gtaaagtttc agtgtctgaa 7800
tcaaatgttc tcttggatga agaagtactt actgatccga agatccaggc gctgcttctt 7860
actgttctag ctacactggt aaaatatacc acagatgagt ttgatcaacg aattctttat 7920
gaatacttag cagaggccag tgttgtgttt cccaaagtct ttcctgttgt gcataatttg 7980

```
ttggactcta agatcaacac cctgttatca ttgtgccaag atccaaattt gttaaatcca  8040
atccatggaa ttgtgcagag tgtggtgtac catgaagaat ccccaccaca ataccaaaca  8100
tcttacctgc aaagttttgg ttttaatggc ttgtggcggt ttgcaggacc gttttcaaag  8160
caaacacaaa ttccagacta tgctgagctt attgttaagt ttcttgatgc cttgattgac  8220
acgtacctgc ctggaattga tgaagaaacc agtgaagaat ccctcctgac tcccacatct  8280
ccttaccctc ctgcactgca gagccagctt agtatcactg ccaaccttaa cctttctaat  8340
tccatgacct cacttgcaac ttcccagcat tccccaggaa tcgacaagga gaacgttgaa  8400
ctctccccta ccactggcca ctgtaacagt ggacgaactc gccacggatc cgcaagccaa  8460
gtgcagaagc aaagaagcgc tggcagtttc aaacgtaata gcattaagaa gatcgtgtga  8520

SEQ ID NO: 130         moltype = AA  length = 2839
FEATURE                Location/Qualifiers
source                 1..2839
                       mol_type = protein
                       organism = Homo sapiens
SEQUENCE: 130
MAAHRPVEWV QAVVSRFDEQ LPIKTGQQNT HTKVSTEHNK ECLINISKYK FSLVISGLTT  60
ILKNVNNMRI FGEAAEKNLY LSQLIILDTL EKCLAGQPKD TMRLDETMLV KQLLPEICHF  120
LHTCREGNQH AAELRNSASG VLFSLSCNNF NAVFSRISTR LQELTVCSED NVDVHDIELL  180
QYINVDCAKL KRLLKETAFK FKALKKVAQL AVINSLEKAF WNWVENYPDE FTKLYQIPQT  240
DMAECAEKLF DLVDGFAEST KRKAAVWPLQ IILLILCPEI IQDISKDVVD ENNMNKKLFL  300
DSLRKALAGH GGSRQLTESA AIACVKLCKA STYINWEDNS VIFLLVQSMV VDLKNLLFNP  360
SKPFSRGSQP ADVDLMIDCL VSCFRISPHN NQHFKICLAQ NSPSTFHYVL VNSLHRIITN  420
SALDWWPKID AVYCHSVELR NMFGETLHKA VQGCGAHPAI RMAPSLTFKE KVTSLKFKEK  480
PTDLETRSYK YLLLSMVKLI HADPKLLLCN PRKQGPETQG STAELITGLV QLVPQSHMPE  540
IAQEAMEALL VLHQLDSIDL WNPDAPVETF WEISSQMLFY ICKKLTSHQM LSSTEILKWL  600
REILICRNKF LLKNKQADRS SCHFLLFYGV GCDIPSSGNT SQMSMDHEEL LRTPGASLRK  660
GKGNSSMDSA AGCSGTPPIC RQAQTKLEVA LYMFLWNPDT EAVLVAMSCF RHLCEEADIR  720
CGVDEVSVHN LLPNYNTFME FASVSNMMST GRAALQKRVM ALLRRIEHPT AGNTEAWEDT  780
HAKWEQATKL ILNYPKAKME DGQAAESLHK TIVKRRMSHV SGGGSIDLSD TDSLQEWINM  840
TGFLCALGGV CLQQRSNSGL ATYSPPMGPV SERKGSMISV MSSEGNADTP VSKFMDRLLS  900
LMVCNHEKVG LQIRTNVKDL VGLELSPALY PMLFNKLKNT ISKFFDSQGQ VLLTDTNTQF  960
VEQTIAIMKN LLDNHTEGSS EHLGQASIET MMLNLVRYVR VLGNMVHAIQ IKTKLCQLVE  1020
VMMARRDDLS FCQEMKFRNK MVEYLTDWVM GTSNQAADDD VKCLTRDLDQ ASMEAVVSLL  1080
AGLPLQPEEG DGVELMEAKS QLFLKYFTLF MNLLNDCSEV EDESAQTGGR KRGMSRRLAS  1140
LRHCTVLAMS NLLNANVDSG LMHSIGLGYH KDLQTRATFM EVLTKILQQG TEFDTLAETV  1200
LADRFERLVE LVTMMGDQGE LPIAMALANV VPCSQWDELA RVLVTLFDSR HLLYQLLWNM  1260
FSKEVELADS MQTLFRGNSL ASKIMTFCFK VYGATYLQKL LDPLLRIVIT SSDWQHVSFE  1320
VDPTRLEPSE SLEENQRNLL QMTEKFFHAI ISSSSEFPPQ LRSVCHCLYQ ATCHSLLNKA  1380
TVKEKKENKK SVVSQRFPQN SIGAVGSAMF LRFINPAIVS PYEAGILDKK PPPRIERGLK  1440
LMSKILQSIA NHVLFTKEEH MRPFNDFVKS NFDAARRFFL DIASDCPTSD AVNHSLSFIS  1500
DGNVLALHRL LWNNQEKIGQ YLSSNRDHKA VGRRPFDKMA TLLAYLGPPE HKPVADTHWS  1560
SLNLTSSKFE EFMTRHQVHE KEEFKALKTL SIFYQAGTSK AGNPIFYYVA RRFKTGQING  1620
DLLIYHVLLT LKPYYAKPYE IVVDLTHTGP SNRFKTDFLS KWFVVFPGFA YDNVSAVYIY  1680
NCNSWVREYT KYHERLLTGL KGSKRLVFID CPGKLAEHIE HEQQKLPAAT LALEEDLKVF  1740
HNALKLAHKD TKVSIKVGST AVQVTSAERT KVLGQSVFLN DIYYASEIEE ICLVDENQFT  1800
LTIANQGTPL TFMHQECEAI VQSIIHIRTR WELSQPDSIP QHTKIRPKDV PGTLLNIALL  1860
NLGSSDPSLR SAAYNLLCAL TCTFNLKIEG QLLETSGLCI PANNTLFIVS ISKTLAANEP  1920
HLTLEFLEEC ISGFSKSSIE LKHLCLEYMT PWLSNLVRFC KHNDDAKRQR VTAILDKLIT  1980
MTINEKQMYP SIQAKIWGSL GQITDLLDVV LDSFIKTSAT GGLGSIKAEV MADTAVALAS  2040
GNVKLVSSKV IGRMCKIIDK TCLSPTPTLE QHLMWDDIAI LARYMLMLSF NNSLDVAAHL  2100
PYLFHVVTFL VATGPLSLRA STHGLVINII HSLCTCSQLH FSEETKQVLR LSLTEFSLPK  2160
FYLLFGISKV KSAAVIAFRS SYRDRSFSPG SYERETFALT SLETVTEALL EIMEACMRDI  2220
PTCKWLDQWT ELAQRFAFQY NPSLQPRALV VFGCISKRVS HGQIKQIIRI LSKALESCLK  2280
GPDTYNSQVL IEATVIALTK LQPLLNKDSP LHKALFWVAV AVLQLDEVNL YSAGTALLEQ  2340
NLHTLDSLRI FNDKSPEEVF MAIRNPLEWH CKQMDHFVGL NFNSNFNFAL VGHLLKGYRH  2400
PSPAIVARTV RILHTLLTLV NKHRNCDKFE VNTQSVAYLA ALLTVSEEVR SRCSLKHRKS  2460
LLLTDISMEN VPMDTYPIHH GDPSYRTLKE TQPWSSPKGS EGYLAATYPT VGQTSPRARK  2520
SMSLDMGQPS QANTKKLLGT RKSFDHLISD TKAPKRQEME SGITTPPKMR RVAETDYEME  2580
TQRISSSQQH PHLRKVSVSE SNVLLDEEVL TDPKIQALLL TVLATLVKYT TDEFDQRILY  2640
EYLAEASVVF PKVFPVVHNL LDSKINTLLS LCQDPNLLNP IHGIVQSVVY HEESPPQYQT  2700
SYLQSFGFNG LWRFAGPFSK QTQIPDYAEL IVKFLDALID TYLPGIDEET SEESLLTPTS  2760
PYPPALQSQL SITANLNLSN SMTSLATSQH SPGIDKENVE LSPTTGHCNS GRTRHGSASQ  2820
VQKQRSAGSF KRNSIKKIV                                              2839

SEQ ID NO: 131         moltype = DNA  length = 6051
FEATURE                Location/Qualifiers
source                 1..6051
                       mol_type = genomic DNA
                       organism = Homo sapiens
SEQUENCE: 131
atggcaaact tcctattacc tcggggcacc agcagcttcc gcaggttcac acgggagtcc  60
ctggcagcca tcgagaagcg catggcagag aagcaagccc gcggctcaac caccttgcag  120
gagagccgag aggggctgcc cgaggaggag gctccccggc cccagctgga cctgcaggcc  180
tccaaaaagc tgccagatct ctatggcaat ccaccccaag agctcatcgg agagcccctg  240
gaggacctgg acccettcta tagcacccaa aagactttca tcgtactgaa taaaggcaag  300
accatcttcc ggttcagtgc caccaacgcc ttgtatgtcc tcagtccctt ccaccccatc  360
cggagagcgg ctgtgaagat tctggttcac tcgctcttca acatgctcat catgtgcacc  420
atcctcacca actgcgtgtt catggcccag cacgaccctc caccctggac caagtatgtc  480
```

-continued gagtacacct tcaccgccat ttacaccttt gagtctctgg tcaagattct ggctcgaggc 540
ttctgcctgc acgcgttcac tttccttcgg gacccatgga actggctgga ctttagtgtg 600
attatcatgg catacacaac tgaatttgtg gacctgggca atgtctcagc cttacgcacc 660
ttccgagtcc tccgggccct gaaaactata tcagtcattt cagggctgaa gaccatcgtg 720
ggggccctga tccagtctgt gaagaagctg gctgatgtga tggtcctcac agtcttctgc 780
ctcagcgtct ttgccctcat cggcctgcag ctcttcatgg gcaacctaag gcacaagtgc 840
gtgcgcaact tcacagcgct caacggcacc aacggctccg tggaggccga cggcttggtc 900
tgggaatccc tggaccttta cctcagtgat ccagaaaatt acctgctcaa gaacggcacc 960
tctgatgtgt tactgtgtgg gaacagctct gacgctggga catgtccgga gggctaccgg 1020
tgcctaaagg caggcgagaa ccccgaccac ggctacacca gcttcgattc ctttgcctgg 1080
gcctttcttg cactcttccg cctgatgacg caggactgct gggagcgcct ctatcagcag 1140
accctcaggt ccgcagggaa gatctacatg atcttcttca tgcttgtcat cttcctgggg 1200
tccttctacc tggtgaacct gatcctggcc gtggtcgcaa tggcctatga ggagcaaaac 1260
caagccacca tcgctgagac cgaggagaag gaaaagcgct tccaggaggc catggaaatg 1320
ctcaagaaag aacacgaggc cctcaccatc aggggtgtgg ataccgtgtc ccgtagctcc 1380
ttggagatgt cccctttggc cccagtaaac agccatgaga gaagaagcaa gaggagaaaa 1440
cggatgtctt caggaactga ggagtgtggg gaggacaggc tccccaagtc tgactcagaa 1500
gatggtccca gagcaatgaa tcatctcagc ctcacccgtg gcctcagcag gacttctatg 1560
aagccacgtt ccagccgcgg gagcattttc acctttcgca ggcgagacct gggttctgaa 1620
gcagattttg cagatgatga aaacagcaca gcgggggaga gcgagagcca ccacacatca 1680
ctgctggtgc cctggcccct gcgccggacc agtgcccagg gacagcccag tcccggaacc 1740
tcggctcctg gccacgccct ccatggcaaa aagaacagca ctgtggactg caatggggtg 1800
gtctcattac tgggggcagg cgacccagag gccacatccc caggaagcca cctcctccgc 1860
cctgtgatgc tagagcaccc gccagacacg accacgccat cggaggagcc aggcgggccc 1920
cagatgctga cctcccaggc tccgtgtgta gatggcttcg aggagccagg agcacggcag 1980
cgggccctca gcgcagtcag cgtcctcacc agcgcactgg aagagttaga ggagtctcgc 2040
cacaagtgtc caccatgctg gaaccgtctc gcccagcgct acctgatctg ggagtgctgc 2100
ccgctgtgga tgtccatcaa gcagggagtg aagttggtgg tcatggaccc gtttactgac 2160
ctcaccatca ctatgtgcat cgtactcaac acactcttca tggcgctgga gcactacaac 2220
atgacaagtg aattcgagga gatgctgcag gtcggaaacc tggtcttcac agggattttc 2280
acagcagaga tgaccttcaa gatcattgcc ctcgacccct actactactt ccaacagggc 2340
tggaacatct tcgacagcat catcgtcatc cttagcctca tggagctggg cctgtcccgc 2400
atgagcaact tgtcggtgct gcgctccttc cgcctgctgc gggtcttcaa gctggccaaa 2460
tcatggccca ccctgaacac actcatcaag atcatcggga actcagtggg ggcactgggg 2520
aacctgacac tggtgctagc catcatcgtg ttcatctttg ctgtggtggg catgcagctc 2580
tttggcaaga actactcgga gctgagggac agcgactcag gcctgctgcc tcgctggcac 2640
atgatggact tctttcatgc cttcctcatc atcttccgca tcctctgtgg agagtggatc 2700
gagaccatgt gggactgcat ggaggtgtcg gggcagtcat tatgcctgct ggtcttcttg 2760
cttgttatgg tcattggcaa ccttgtggtc ctgaatctct tcctggcctt gctgctcagc 2820
tccttcagtg cagacaacct cacagcccct gatgaggaca gagagatgaa caacctccag 2880
ctggccctgg cccgcatcca gagggcctg cgctttgtca agcggaccac ctgggatttc 2940
tgctgtggtc tcctgcggca gcggcctcag aagcccgcag cccttgccgc ccagggccag 3000
ctgcccagct gcattgccac cccctactcc ccgccacccc cagagacgga gaaggtgcct 3060
cccacccgca aggaaacacg gtttgaggaa ggcgagcaac caggccaggg cacccccggg 3120
gatccagagc ccgtgtgtgt gcccatcgct gtggccgagt cagacacaga tgaccaagaa 3180
gaagatgagg agaacagcct gggcacggag gaggagtcca gcaagcagca ggaatcccag 3240
cctgtgtccg gtggcccaga ggcccctccg gattccagga cctggagcca ggtgtcagcg 3300
actgcctcct ctgaggccga ggccagtgca tctcaggccg actggcggca gcagtggaaa 3360
gcggaacccc aggccccagg gtgcggtgag accccagagg acagttgctc cgagggcagc 3420
acagcagaca tgaccaacac cgctgagctc ctggagcaga tccctgacct cggccaggat 3480
gtcaaggacc cagaggactg cttcactgaa ggctgtgtcc ggcgctgtcc ctgctgtgcg 3540
gtggacacca cacaggcccc agggaaggtc tggtggcggt tgcgcaagac ctgctaccac 3600
atcgtggagc acagctggtt cgagacattc atcatcttca tgatcctact cagcagtgga 3660
gcgctggcct tcgaggacat ctacctagag gagcggaaga ccatcaaggt tctgcttgag 3720
tatgccgaca agatgttcac atatgtcttc gtgctggaga tgctgctcaa gtgggtggcc 3780
tacggcttca agaagtactt caccaatgcc tggtgctggc tcgacttcct catcgtagac 3840
gtctctctgg tcagcctggt ggccaacacc ctgggctttg ccgagatggg ccccatcaag 3900
tcactgcgga cgctgcgtgc actccgtcct ctgagagctc tgtcacgatt tgagggcatg 3960
agggtggtgg tcaatgccct ggtgggcgcc atcccgtcca tcatgaacgt cctcctcgtc 4020
tgcctcatct tctggctcat cttcagcatc atgggcgtga acctctttgc ggggaagttt 4080
gggaggtgca tcaaccagac agagggagac ttgcctttga actacaccat cgtgaacaac 4140
aagagccagt gtgagtcctt gaacttgacc ggagaattgt actggaccaa ggtgaaagtc 4200
aactttgaca acgtgggggc cggtacctg gcccttctgc aggtggcaac atttaaaggc 4260
tggatggaca ttatgtatgc agctgtggac tccagggggt atgaagagca gcctcagtgg 4320
gaatacaacc tctacatgta catctatttt gtcattttca tcatctttgg gtctttcttc 4380
accctgaacc tctttattgg tgtcatcatt gacaacttca accaacagaa gaaaaagtta 4440
gggggccagg acatcttcat gacagaggag cagaagaagt actacaatgc catgaagaag 4500
ctgggctcca agaagcccca gaagcccatc ccacggcccc tgaacaagta ccagggcttc 4560
atattcgaca ttgtgaccaa gcaggccttt gacgtcacca tcatgtttct gatctgcttg 4620
aatatggtga ccatgatggt ggagacagat gaccaaagtc ctgagaaaat caacatcttg 4680
gccaagatca acctgctctt tgtggccatc ttcacaggcg agtgtattgt caagctggct 4740
gccctgcgcc actactactt caccaacagc tggaatatct tcgacttcgt ggttgtcatc 4800
ctctccatcg tgggcactgt gctctcggac atcatccaga agtacttctt ctccccgacg 4860
ctcttccgag tcatccgcct ggcccgaata ggccgcatcc tcagactgat ccgaggggcc 4920
aaggggatcc gcacgctgct ctttgccctc atgatgtccc tgcctgccct cttcaacatc 4980
gggctgctgc tcttcctcgt catgttcatc tactccatct ttggcatggc caacttcgct 5040
tatgtcaagt gggaggctgg catcgacgac atgttcaact tccagacctt cgccaacagc 5100
atgctgtgcc tcttccagat caccacgtcg gccggctggg atggcctcct cagccccatc 5160
ctcaacactg ggccgcccta ctgcgacccc actctgccca acagcaatgg ctctcggggg 5220

```
gactgcggga gcccagccgt gggcatcctc ttcttcacca cctacatcat catctccttc  5280
ctcatcgtgg tcaacatgta cattgccatc atcctggaga acttcagcgt ggccacggag  5340
gagagcaccg agcccctgag tgaggacgac ttcgatatgt tctatgagat ctgggagaaa  5400
tttgacccag aggccactca gtttattgag tattcggtcc tgtctgactt tgccgatgcc  5460
ctgtctgagc cactccgtat cgccaagccc aaccagataa gcctcatcaa catggacctg  5520
cccatggtga gtggggaccg catccattgc atggacattc tctttgcctt caccaaaagg  5580
gtcctggggg agtctgggga gatggacgcc ctgaagatcc agatggagga gaagttcatg  5640
gcagccaacc catccaagat ctcctacgag cccatcacca ccacactccg gcgcaagcac  5700
gaagaggtgt cggccatggt tatccagaga gccttccgca ggcacctgct gcaacgctct  5760
ttgaagcatg cctccttcct cttccgtcag caggcgggca gcggcctctc cgaagaggat  5820
gcccctgagc gagagggcct catcgcctac gtgatgagtg agaacttctc ccgacccctt  5880
ggcccaccct ccagctcctc catctcctcc acttccttcc caccctccta tgacagtgtc  5940
actagagcca ccagcgataa cctccaggtg cgggggtctg actacagcca cagtgaagat  6000
ctcgccgact tcccccccttc tccggacagg gaccgtgagt ccatcgtgtg a          6051
```

```
SEQ ID NO: 132          moltype = AA  length = 2016
FEATURE                 Location/Qualifiers
source                  1..2016
                        mol_type = protein
                        organism = Homo sapiens
SEQUENCE: 132
MANFLLPRGT SSFRRFTRES LAAIEKRMAE KQARGSTTLQ ESREGLPEEE APRPQLDLQA  60
SKKLPDLYGN PPQELIGEPL EDLDPFYSTQ KTFIVLNKGK TIFRFSATNA LYVLSPFHPI  120
RRAAVKILVH SLFNMLIMCT ILTNCVFMAQ HDPPPWTKYV EYTFTAIYTF ESLVKILARG  180
FCLHAFTFLR DPWNWLDFSV IIMAYTTEFV DLGNVSALRT FRVLRALKTI SVISGLKTIV  240
GALIQSVKKL ADVMVLTVFC LSVFALIGLQ LFMGNLRHKC VRNFTALNGT NGSVEADGLV  300
WESLDLYLSD PENYLLKNGT SDVLLCGNSS DAGTCPEGYR CLKAGENPDH GYTSFDSFAW  360
AFLALFRLMT QDCWERLYQQ TLRSAGKIYM IFFMLVIFLG SFYLVNLILA VVAMAYEEQN  420
QATIAETEEK EKRFQEAMEM LKKEHEALTI RGVDTVSRSS LEMSPLAPVN SHERRSKRRK  480
RMSSGTEECG EDRLPKSDSE DGPRAMNHLS LTRGLSRTSM KPRSSRGSIF TFRRRDLGSE  540
ADFADDENST AGESESHHTS LLVPWPLRRT SAQGQPSPGT SAPGHALHGK KNSTVDCNGV  600
VSLLGAGDPE ATSPGSHLLR PVMLEHPPDT TTPSEEPGGP QMLTSQAPCV DGFEEPGARQ  660
RALSAVSVLT SALEELEESR HKCPPCWNRL AQRYLIWECC PLWMSIKQGV KLVVMDPFTD  720
LTITMCIVLN TLFMALEHYN MTSEFEEMLQ VGNLVFTGIF TAEMTFKIIA LDPYYYFQQG  780
WNIFDSIIVI LSLMELGLSR MSNLSVLRSF RLLRVFKLAK SWPTLNTLIK IIGNSVGALG  840
NLTLVLAIIV FIFAVVGMQL FGKNYSELRD SDSGLLPRWH MMDFFHAFLI IFRILCGEWI  900
ETMWDCMEVS GQSLCLLVFL LVMVIGNLVV LNLFLALLLS SFSADNLTAP DEDREMNNLQ  960
LALARIQRGL RFVKRTTWDF CCGLLRQRPQ KPAALAAQGQ LPSCIATPYS PPPPETEKVP  1020
PTRKETRFEE GEQPGQGTPG DPEPVCVPIA VAESDTDDQE EDEENSLGTE EESSKQQESQ  1080
PVSGGPEAPP DSRTWSQVSA TASSEAEASA SQADWRQQWK AEPQAPGCGE TPEDSCSEGS  1140
TADMTNTAEL LEQIPDLGQD VKDPEDCFTE GCVRRCPCCA VDTTQAPGKV WWRLRKTCYH  1200
IVEHSWFETF IIFMILLSSG ALAFEDIYLE ERKTIKVLLE YADKMFTYVF VLEMLLKWVA  1260
YGFKKYFTNA WCWLDFLIVD VSLVSLVANT LGFAEMGPIK SLRTLRALRP LRALSRFEGM  1320
RVVVNALVGA IPSIMNVLLV CLIFWLIFSI MGVNLFAGKF GRCINQTEGD LPLNYTIVNN  1380
KSQCESLNLT GELYWTKVKV NFDNVGAGYL ALLQVATFKG WMDIMYAAVD SRGYEEQPQW  1440
EYNLYMYIYF VIFIIFGSFF TLNLFIGVII DNFNQQKKKL GGQDIFMTEE QKKYYNAMKK  1500
LGSKKPQKPI PRPLNKYQGF IFDIVTKQAF DVTIMFLICL NMVTMMVETD DQSPEKINIL  1560
AKINLLFVAI FTGECIVKLA ALRHYYFTNS WNIFDFVVVI LSIVGTVLSD IIQKYFFSPT  1620
LFRVIRLARI GRILRLIRGA KGIRTLLFAL MMSLPALFNI GLLLFLVMFI YSIFGMANFA  1680
YVKWEAGIDD MFNFQTFANS MLCLFQITTS AGWDGLLSPI LNTGPPYCDP TLPNSNGSRG  1740
DCGSPAVGIL FFTTYIIISF LIVVNMYIAI ILENFSVATE ESTEPLSEDD FDMFYEIWEK  1800
FDPEATQFIE YSVLSDFADA LSEPLRIAKP NQISLINMDL PMVSGDRIHC MDILFAFTKR  1860
VLGESGEMDA LKIQMEEKFM AANPSKISYE PITTTLRRKH EEVSAMVIQR AFRRHLLQRS  1920
LKHASFLFRQ QAGSGLSEED APEREGLIAY VMSENFSRPL GPPSSSSISS TSFPPSYDSV  1980
TRATSDNLQV RGSDYSHSED LADFPPSPDR DRESIV                          2016
```

```
SEQ ID NO: 133          moltype = DNA  length = 4002
FEATURE                 Location/Qualifiers
source                  1..4002
                        mol_type = genomic DNA
                        organism = Homo sapiens
SEQUENCE: 133
atgcaggcgc agcagctgcc ctacgagttt ttcagcgaag agaacgcgcc caagtggcgg  60
ggactactgg tgcctgcgct gaaaaaggtc caggggcaag ttcatcctac tctcgagtct  120
aatgatgatg ctcttcagta tgttgaagaa ttaattttgc aattattaaa tatgctatgc  180
caagctcagc cccgaagtgc ttcagatgta gaggaacgtg ttcaaaaaag tttccctcat  240
ccaattgata aatgggcaat agctgatgcc caatcagcta ttgaaaagag gaagcgaaga  300
aacccttat ctctcccagt agaaaaaatt catcctttat taaaggaggt cctaggttat  360
aaaattgacc accaggtttc tgtttacata gtagcagtct tagaatacat ttctgcagac  420
attttaaagc tggttgggaa ttatgtaaga aatatacggc attatgaaat tacaaaacaa  480
gatattaaag tggcaatgtg tgctgacaag gtattgatgg atatgtttca tcaagatgta  540
gaagatatta atatattatc tttaactgac gaagagcctt ccacctcagg agaacaaact  600
tactatgatt tggtaaaagc atttatggca gaaattcgac aatatataag ggaactaaat  660
ctaattataa aagtttttag agagcccttt gtctccaatt caaaattgtt ttcagctaat  720
gatgtagaaa atatatttag tcgcatagta gatatacatg aacttagtgt aaagttactg  780
ggccatatag aagatacagt agaaatgaca gatgaaggca gtccccatcc actagtagga  840
agctgctttg aagacttagc agaggaactg gcatttgatc catatgaatc gtatgctcga  900
gatattttgc gacctggttt tcatgatcgt ttccttagtc agttatcaaa gcctggggca  960
gcactttatt tgcagtcaat aggcgaaggt ttcaaagaag ctgttcaata tgttttaccc  1020
```

```
aggctgcttc tggcccctgt ttaccactgt ctccattact ttgaactttt gaagcagtta  1080
gaagaaaaaa gtgaagatca agaagacaag gaatgtttaa aacaagcaat aacagctttg  1140
cttaatgttc agagtggtat ggaaaaaata tgttctaaaa gtcttgcaaa acgaagactg  1200
agtgaatctg catgtcggtt ttatagtcag caaatgaagg ggaaacaact agcaatcaag  1260
aagatgaacg agattcagaa gaatattgat ggttgggagg gaaaagacat tggacagtgt  1320
tgtaatgaat ttataatgga aggaactctt acacgtgtag gagccaaaca tgagagacac  1380
atatttctct ttgatggctt aatgatttgc tgtaaatcaa atcatgggca gccaagactt  1440
cctggtgcta gcaatgcaga atatcgtctt aaagaaaagt tttttatgcg aaaggtacaa  1500
attaatgata aagatgacac caatgaatac aagcatgctt ttgaaataat tttaaaagat  1560
gaaaatagtg ttatattttc tgccaagtca gctgaagaga aaaacaattg gatggcagca  1620
ttgatatctt tacagtaccg gagtacactg gaaaggatgc ttgatgtaac aatgctacag  1680
gaagagaaag aggagcagat gaggctgcct agtgctgatg tttatagatt tgcagagcct  1740
gactctgaag agaatattat atttgaagag aacatgcagc ccaaggctgg aattccaatt  1800
atcaaagcag gaactgttat taaacttata gagaggctta cgtaccatat gtacgcagat  1860
cccaattttg ttcggacatt tcttacaaca tacagatcct tttgcaaacc tcaagaacta  1920
ctgagtctta taatagaaag gtttgaaatt ccagagcctg agccaacaga agctgatcgc  1980
atagctatag agaatggaga tcaacccttg agtgcagaac tgaaaagatt tagaaaagaa  2040
tatatacagc ctgtgcaact gcgagtatta aatgtatgtc ggcactgggt agagcaccac  2100
ttctatgatt ttgaaagaga tgcatatctt ttgcaacgaa tggaagaatt tattggaaca  2160
gtaagaggta aagcaatgaa aaaatgggtt gaatccatca ctaaaataat ccaaaggaaa  2220
aaaattgcaa gagacaatgg accaggtcat aatattacat ttcagagttc acctcccaca  2280
gttgagtggc atataagcag acctgggcac atagagactt ttgacctgct caccttacac  2340
ccaatagaaa ttgctcgaca actcacttta cttgaatcag atctataccg agctgtacag  2400
ccatcagaat tagttggaag tgtgtggaca aaagaagaca aagaaattaa ctctcctaat  2460
cttctgaaaa tgattcgaca taccaccaac ctcactctgt ggtttgagaa atgtattgta  2520
gaaactgaaa atttagaaga aagagtagct gtggtgagtc gaattattga gattctacaa  2580
gtctttcaag agttgaacaa ctttaatggt gtccttgagg ttgtcagtgc tatgaattca  2640
tcacctgttt acagactaga ccacacattt gagcaaatac caagtcgcca gaagaaaatt  2700
ttagaagaag ctcatgaatt gagtgaagat cactataaga aatatttggc aaaactcagg  2760
tctattaatc caccatgtgt gcctttcttt ggaatttatc tcactaatat cttgaaaaca  2820
gaagaaggca accctgaggt cctaaaaaga catggaaaag agcttataaa ctttagcaaa  2880
aggaggaaag tagcagaaat aacaggagag atccagcagt accaaaatca gccttactgt  2940
ttacgagtag aatcagatat caaaaggttc tttgaaaact tgaatccgat gggaaatagc  3000
atggagaagg aatttacaga ttatcttttc aacaaatccc tagaaataga accacgaaac  3060
cctaagcctc tcccaagatt tccaaaaaaa tatagctatc ccctaaaatc tcctggtgtt  3120
cgtccatcaa acccaagacc aggtaccatg aggcatccca cacctctgca gcaggagcca  3180
aggaaaatta gttatagtag gatccctgaa agtgaaacag aaagtacagc atctgcacca  3240
aattctccaa gaacaccgtt aacacctccg cctgcttctg gtgcttccag taccacagat  3300
gtttgcagtg tatttgattc cgatcattcg agcccttttc actcaagcaa tgataccgtc  3360
tttatccaag ttactctgcc ccatggccca agatctgctt ctgtatcatc tataagttta  3420
accaaaggca ctgatgaagt gcctgtccct cctcctgttc ctccacgaag acgaccagaa  3480
tctgccccag cagaatcttc accatctaag attatgtcta agcatttgga cagtccccca  3540
gccattcctc ctaggcaacc cacatcaaaa gcctattcac cacgatattc aatatcagac  3600
cggacctcta tctcagaccc tcctgaaagc cctcccttat taccaccacg agaacctgtg  3660
aggacacctg atgttttctc aagctcacca ctacatctcc aacctccccc tttgggcaaa  3720
aaaagtgacc atggcaatgc cttcttccca aacagccctt ccccctttac accacctcct  3780
cctcaaacac cttctcctca cggcacaaga aggcatctgc catcaccacc attgacacaa  3840
gaagtggacc ttcattccat tgctgggccg cctgttcctc cacgacaaag cacttctcaa  3900
catatcccta aactccctcc aaaaacttac aaaagggagc acacacaccc atccatgcac  3960
agagatggac caccactgtt ggagaatgcc cattcttcct ga                    4002

SEQ ID NO: 134          moltype = AA  length = 1333
FEATURE                 Location/Qualifiers
source                  1..1333
                        mol_type = protein
                        organism = Homo sapiens
SEQUENCE: 134
MQAQQLPYEF FSEENAPKWR GLLVPALKKV QGQVHPTLES NDDALQYVEE LILQLLNMLC  60
QAQPRSASDV EERVQKSFPH PIDKWAIADA QSAIEKRKRR NPLSLPVEKI HPLLKEVLGY  120
KIDHQVSVYI VAVLEYISAD ILKLVGNYVR NIRHYEITKQ DIKVAMCADK VLMDMFHQDV  180
EDINILSLTD EEPSTSGEQT YYDLVKAFMA EIRQYIRELN LIIKVFREPF VSNSKLFSAN  240
DVENIFSRIV DIHELSVKLL GHIEDTVEMT DEGSPHPLVG SCFEDLAEEL AFDPYESYAR  300
DILRPGFHDR FLSQLSKPGA ALYLQSIGEG FKEAVQYVLP RLLLAPVYHC LHYFELLKQL  360
EEKSEDQEDK ECLKQAITAL LNVQSGMEKI CSKSLAKRRL SESACRFYSQ QMKGKQLAIK  420
KMNEIQKNID GWEGKDIGQC CNEFIMEGTL TRVGAKHERH IFLFDGLMIC CKSNHGQPRL  480
PGASNAEYRL KEKFFMRKVQ INDKDDTNEY KHAFEIILKD ENSVIFSAKS AEEKNNWMAA  540
LISLQYRSTL ERMLDVTMLQ EEKEEQMRLP SADVYRFAEP DSEENIIFEE NMQPKAGIPI  600
IKAGTVIKLI ERLTYHMYAD PNFVRTFLTT YRSFCKPQEL LSLIIERFEI PEPEPTEADR  660
IAIENGDQPL SAELKRFRKE YIQPVQLRVL NVCRHWVEHH FYDFERDAYL LQRMEEFIGT  720
VRGKAMKKWV ESITKIIQRK KIARDNGPGH NITFQSSPPT VEWHISRPGH IETFDLLTLH  780
PIEIARQLTL LESDLYRAVQ PSELVGSVWT KEDKEINSPN LLKMIRHTTN LTLWFEKCIV  840
ETENLEERVA VVSRIIEILQ VFQELNNFNG VLEVVSAMNS SPVYRLDHTF EQIPSRQKKI  900
LEEAHELSED HYKKYLAKLR SINPPCVPFF GIYLTNILKT EEGNPEVLKR HGKELINFSK  960
RRKVAEITGE IQQYQNQPYC LRVESDIKRF FENLNPMGNS MEKEFTDYLF NKSLEIEPRN  1020
PKPLPRFPKK YSYPLKSPGV RPSNPRPGTM RHPTPLQQEP RKISYSRIPE SETESTASAP  1080
NSPRTPLTPP PASGASSTTD VCSVFDSDHS SPFHSSNDTV FIQVTLPHGP RSASVSSISL  1140
TKGTDEVPVP PPVPPRRRPE SAPAESSPSK IMSKHLDSPP AIPPRQPTSK AYSPRYSISD  1200
RTSISDPPES PPLLPPREPV RTPDVFSSSP LHLQPPPLGK KSDHGNAFFP NSPSPFTPPP  1260
PQTPSPHGTR RHLPSPPLTQ EVDLHSIAGP PVPPRQSTSQ HIPKLPPKTY KREHTHPSMH  1320
```

```
RDGPPLLENA HSS                                              1333

SEQ ID NO: 135          moltype = DNA  length = 3186
FEATURE                 Location/Qualifiers
source                  1..3186
                        mol_type = genomic DNA
                        organism = Homo sapiens
SEQUENCE: 135
atgccggggc cccggcgccc cgctggctcc cgcctgcgcc tgctcctgct cctgctgctg  60
ccgccgctgc tgctgctgct ccggggcagc cacgcgggca acctgacggt agccgtggta  120
ctgccgctgg ccaatacctc gtacccctgg tcgtgggcgc gcgtgggacc cgccgtggag  180
ctggccctgg cccaggtgaa ggcgcgcccc gacttgctgc cgggctggac ggtccgcacg  240
gtgctgggca gcagcgaaaa cgcgctgggc gtctgctccg acaccgcagc gcccctggcc  300
gcggtggacc tcaagtggga gcacaacccc gctgtgttcc tgggccccgg ctgcgtgtac  360
gccgccgccc cagtggggcg cttcaccgcg cactggcggg tcccgctgct gaccgccggc  420
gccccggcgc tgggcttcgg tgtcaaggac gagtatgcgc tgaccacccg cgcggggccc  480
agctacgcca agctggggga cttcgtggcg gcgctgcacc gacggctggg ctgggagcgc  540
caagcgctca tgctctacgc ctaccggccg ggtgacgaag agcactgctt cttcctcgtg  600
gaggggctgt tcatgcgggt ccgcgaccgc ctcaatatta cggtggacca cctggagttc  660
gccgaggacg acctcagcca ctacaccagg ctgctgcgga ccatgccgcg caaaggccga  720
gttatctaca tctgcagctc ccctgatgcc ttcagaaccc tcatgctcct ggccctggaa  780
gctggcttgt gtggggagga ctacgttttc ttccacctgg atatctttgg gcaaagcctg  840
caaggtggac agggccctgc tccccgcagg ccctgggaga gaggggatgg gcaggatgtc  900
agtgcccgcc aggcctttca ggctgccaaa atcattacat ataaagaccc agataatccc  960
gagtacttgg aattcctgaa gcagttaaaa cacctggcct atgagcagtt caacttcacc  1020
atggaggatg gcctggtgaa caccatccca gcatccttcc acgacgggct cctgctctat  1080
atccaggcag tgacggagac tctggcacat gggggaactg ttactgatgg ggagaacatc  1140
actcagcgga tgtggaaccg aagctttcaa ggtgtgacag gatacctgaa aattgatagc  1200
agtggcgatc gggaaacaga cttctccctc tgggatatgg atcccgagaa tggtgccttc  1260
agggttgtac tgaactacaa tgggacttcc caagagctgg tggctgtgtc ggggcgcaaa  1320
ctgaactggc ccctggggta ccctcctcct gacatcccca aatgtggctt tgacaacgaa  1380
gacccagcat gcaaccaaga tcacctttcc accctggagg tgctggcttt ggtgggcagc  1440
ctctccttgc tcggcattct gattgtctcc ttcttcatat acaggaagat gcagctggag  1500
aaggaactgg cctcggagct gtggcgggtg cgctgggagg acgttgagcc cagtagcctt  1560
gagaggcacc tgcggagtgc aggcagccgg ctgaccctga gcgggagagg ctccaattac  1620
ggctccctgc taaccacaga gggccagttc caagtctttg ccaagacagc atattataag  1680
ggcaacctcg tggctgtgaa acgtgtgaac cgtaaacgca ttgagctgac acgaaaagtc  1740
ctgtttgaac tgaagcatat gcgggatgtg cagaatgaac acctgaccag gtttgtggga  1800
gcctgcaccg acccccccaa tatctgcatc ctcacagagt actgtccccg tgggagcctg  1860
caggacattc tggagaatga gagcatcacc ctggactgga tgttccggta ctcactcacc  1920
aatgacatcg tcaagggcat gctgtttcta cacaatgggg ctatctgttc ccatgggaac  1980
ctcaagtcat ccaactgcgt ggtagatggg cgctttgtgc tcaagatcac cgactatggg  2040
ctggagagct tcagggacct ggacccagag caaggacaca ccgtttatgc caaaaagctg  2100
tggacggccc ctgagctcct gcgaatggct tcaccccctg tgcggggctc ccaggctggt  2160
gacgtataca gctttgggat catccttcag gagattgccc tgaggagtgg ggtcttccac  2220
gtggaaggtt tggacctgag ccccaaagag atcatcgagc gggtgactcg gggtgagcag  2280
ccccccttcc ggccctccct ggccctgcag agtcacctgg aggagttggg gctgctcatg  2340
cagcggtgct gggctgagga cccacaggag aggccaccat tccagcagat ccgcctgacg  2400
ttgcgcaaat ttaacaggga gaacagcagc aacatcctgg acaacctgct gtcccgcatg  2460
gagcagtacg cgaacaatct ggaggaactg gtggaggagc ggacccaggc atacctggag  2520
gagaagcgca aggctgaggc cctgctctac cagatcctgc ctcactcagt ggctgagcag  2580
ctgaagcgtg gggagacggt gcaggccgaa gcctttgaca gtgttaccat ctacttcagt  2640
gacattgtgg gtttcacagc gctgtcggcg gagagcacac ccatgcaggt ggtgaccctg  2700
ctcaatgacc tgtacacttg ctttgatgct gtcatagaca actttgatgt gtacaaggtg  2760
gagacaattg gcgatgccta catggtggtg tcagggctcc ctgtgcggaa cgggcggcta  2820
cacgcctgcg aggtagcccg catggccctg gcactgctgg atgctgtgcg ctccttccga  2880
atccgccacc ggccccagga gcagctgcgc ttgcgcattg gcatccacac aggacctgtg  2940
tgtgctggag tggtgggact gaagatgccc cgttactgtc tctttgggga tacagtcaac  3000
acagcctcaa gaatggagtc taatggggaa gccctgaaga tccacttgtc ttctgagacc  3060
aaggctgtcc tggaggagtt tggtggtttc gagctggagc ttcgagggga tgtagaaatg  3120
aagggcaaag gcaaggttcg gacctactgg ctccttgggg agaggggag tagcacccga  3180
ggctga                                                      3186

SEQ ID NO: 136          moltype = AA  length = 1061
FEATURE                 Location/Qualifiers
source                  1..1061
                        mol_type = protein
                        organism = Homo sapiens
SEQUENCE: 136
MPGPRRPAGS RLRLLLLLLL PPLLLLLRGS HAGNLTVAVV LPLANTSYPW SWARVGPAVE  60
LALAQVKARP DLLPGWTVRT VLGSSENALG VCSDTAAPLA AVDLKWEHNP AVFLGPGCVY  120
AAAPVGRFTA HWRVPLLTAG APALGFGVKD EYALTTRAGP SYAKLGDFVA ALHRRLGWER  180
QALMLYAYRP GDEEHCFFLV EGLFMRVRDR LNITVDHLEF AEDDLSHYTR LLRTMPRKGR  240
VIYICSSPDA FRTLMLLALE AGLCGEDYVF FHLDIFGQSL QGGQGPAPRR PWERGDGQDV  300
SARQAFQAAK IITYKDPDNP EYLEFLKQLK HLAYEQFNFT MEDGLVNTIP ASFHDGLLLY  360
IQAVTETLAH GGTVTDGENI TQRMWNRSFQ GVTGYLKIDS SGDRETDFSL WDMDPENGAF  420
RVVLNYNGTS QELVAVSGRK LNWPLGYPPP DIPKCGFDNE DPACNQDHLS TLEVLALVGS  480
LSLLGILIVS FFIYRKMQLE KELASELWRV RWEDVEPSSL ERHLRSAGSR LTLSGRGSNY  540
GSLLTTEGQF QVFAKTAYYK GNLVAVKRVN RKRIELTRKV LFELKHMRDV QNEHLTRFVG  600
```

```
ACTDPPNICI LTEYCPRGSL QDILENESIT LDWMFRYSLT NDIVKGMLFL HNGAICSHGN  660
LKSSNCVVDG RFVLKITDYG LESFRDLDPE QGHTVYAKKL WTAPELLRMA SPPVRGSQAG  720
DVYSFGIILQ EIALRSGVFH VEGLDLSPKE IIERVTRGEQ PPFRPSLALQ SHLEELGLLM  780
QRCWAEDPQE RPPFQQIRLT LRKFNRENSS NILDNLLSRM EQYANNLEEL VEERTQAYLE  840
EKRKAEALLY QILPHSVAEQ LKRGETVQAE AFDSVTIYFS DIVGFTALSA ESTPMQVVTL  900
LNDLYTCFDA VIDNFDVYKV ETIGDAYMVV SGLPVRNGRL HACEVARMAL ALLDAVRSFR  960
IRHRPQEQLR LRIGIHTGPV CAGVVGLKMP RYCLFGDTVN TASRMESNGE ALKIHLSSET  1020
KAVLEEFGGF ELELRGDVEM KGKGKVRTYW LLGERGSSTR G                      1061

SEQ ID NO: 137         moltype = DNA  length = 3927
FEATURE                Location/Qualifiers
source                 1..3927
                       mol_type = genomic DNA
                       organism = Homo sapiens
SEQUENCE: 137
atgaagccgg cgacaggact ttgggtctgg gtgagccttc tcgtggcggc ggggaccgtc  60
cagcccagcg attctcagtc agtgtgtgca ggaacggaga ataaactgag ctctctctct  120
gacctggaac agcagtaccg agccttgcgc aagtactatg aaaactgtga ggttgtcatg  180
ggcaacctgg agataaccag cattgagcac aaccgggacc tctccttcct gcggtctgtt  240
cgagaagtca caggctacgt gttagtggct cttaatcagt ttcgttacct gcctctggag  300
aatttacgca ttattcgtgg gacaaaactt tatgaggatc gatatgcctt ggcaatattt  360
ttaaactaca gaaaagatgg aaactttgga cttcaagaac ttggattaaa gaacttgaca  420
gaaatcctaa atggtggagt ctatgtagac cagaacaaat tcctttgtta tgcagacacc  480
attcattggc aagatattgt tcggaaccca tggccttcca acttgactct tgtgtcaaca  540
aatggtagtt caggatgtgg acgttgccat aagtcctgta ctggccgttg ctggggaccc  600
acagaaaatc attgccagac tttgacaagg acggtgtgtg cagaacaatg tgacggcaga  660
tgctacggac cttacgtcag tgactgctgc catcgagaat gtgctggagg ctgctcagga  720
cctaaggaca cagactgctt tgcctgcatg aatttcaatg acagtggagc atgtgttact  780
cagtgtcccc aaacctttgt ctacaatcca accacctttc aactggagca caatttcaat  840
gcaaagtaca catatggagc attctgtgtc aagaaatgtc cacataactt tgtggtagat  900
tccagttctt gtgtgcgtgc ctgccctagt tccaagatgg aagtagaaga aaatgggatt  960
aaaatgtgta aaccttgcac tgacatttgc ccaaaagctt gtgatggcat tggcacagga  1020
tcattgatgt cagctcagac tgtggattcc agtaacattg acaaattcat aaactgtacc  1080
aagatcaatg ggaatttgat ctttctagtc actggtattc atggggaccc ttacaatgca  1140
attgaagcca tagacccaga gaaactgaac gtctttcgga cagtcagaga gataacaggt  1200
ttcctgaaca tacagtcatg gccaccaaac atgactgact tcagtgtttt ttctaacctg  1260
gtgaccattg gtggaagagt actctatagt ggcctgtcct tgcttatcct caagcaacag  1320
ggcatcacct ctctacagtt ccagtccctg aaggaaatca gcgcaggaaa catctatatt  1380
actgacaaca gcaacctgtg ttattatcat accattaact ggacaacact cttcagcaca  1440
atcaaccaga gaatagtaat ccgggacaac agaaaagctg aaaattgtac tgctgaagga  1500
atggtgtgca accatctgtg ttccagtgat ggctgttggg gacctgggcc agaccaatgt  1560
ctgtcgtgtc gccgcttcag tagaggaagg atctgcatag agtcttgtaa cctctatgat  1620
ggtgaatttc gggagtttga gaatggctcc atctgtgtgg agtgtgaccc ccagtgtgag  1680
aagatggaag atggcctcct cacatgccat ggaccgggtc ctgacaactg tacaaagtgc  1740
tctcatttta aagatggccc aaactgtgtg gaaaaatgtc cagatggctt acaggggggca  1800
aacagtttca ttttcaagta tgctgatcca gatcgggagt gccacccatg ccatccaaac  1860
tgcacccaag ggtgtaacgg tcccactagt catgactgca tttactaccc atggacgggc  1920
cattccactt taccacaaca tgctagaact cccctgattg cagctggagt aattggtggg  1980
ctcttcattc tggtcattgt gggtctgaca tttgctgttt atgttagaag gaagagcatc  2040
aaaaagaaaa gagccttgag aagattcttg gaaacagagt tggtggaacc attaactccc  2100
agtggcacag cacccaatca agctcaactt cgtattttga aagaaactga gctgaagagg  2160
gtaaaagtcc ttggctcagg tgcttttgga acggtttata aaggtatttg ggtacctgaa  2220
ggagaaactg tgaagattcc tgtggctatt aagattctta atgagacaac tggtcccaag  2280
gcaaatgtgg agttcatgga tgaagctctg atcatggcaa gtatggatca tccacaccta  2340
gtccggttgc tgggtgtgtg tctgagccca accatccagc tggttactca acttatgccc  2400
catggctgcc tgttggagta tgtccacgag cacaaggata acattggatc acaactgctg  2460
cttaactggt gtgtccagat agctaaggga atgatgtacc tggaagaaag acgactcgtt  2520
catcgggatt tggcagcccg taatgtctta gtgaaatctc caaaccatgt gaaaatcaca  2580
gattttgggc tagccagact cttggaagga gatgaaaaag agtacaatgc tgatggagga  2640
aagatgccaa ttaaatggat ggctctggag tgtatacatt acaggaaatt cacccatcag  2700
agtgacgttt ggagctatgg agttactata tgggaactga tgacctttgg aggaaaaccc  2760
tatgatggaa ttccaacgcg agaaatccct gatttattag agaaaggaga acgtttgcct  2820
cagcctccca tctgcactat tgacgtttac atggtcatgg tcaaatgttg gatgattgat  2880
gctgacagta gacctaaatt taaggaactg gctgctgagt tttcaaggat ggctcgagac  2940
cctcaaagat acctagttat tcagggtgat gatcgtatga agcttcccag tccaaatgac  3000
agcaagttct ttcagaatct cttggatgaa gaggatttgg aagatatgat ggatgctgag  3060
gagtacttgg tccctcaggc tttcaacatc ccacctccca tctatacttc cagagcaaga  3120
attgactcga ataggagtga aattggacac agccctcctc ctgcctacac ccccatgtca  3180
ggaaaccagt ttgtataccg agatggaggt tttgctgctg aacaaggagt gtctgtgccc  3240
tacagagccc caactagcac aattccagaa gctcctgtgg cacagggtgc tactgctgag  3300
atttttgatg actcctgctg taatggcacc ctacgcaagc cagtggcacc ccatgtccaa  3360
gaggacagta gcacccagag gtacagtgct gaccccaccg tgtttgcccc agaacggagc  3420
ccacgaggag agctggatga ggaaggttac atgactccta tgcgagacaa acccaaacaa  3480
gaatacctga atccagtgga ggagaaccct tttgtttctc ggagaaaaaa tggagacctt  3540
caagcattgg ataatcccga atatcacaat gcatccaatg gtccacccaa ggccgaggat  3600
gagtatgtga atgagccact gtacctcaac acctttgcca acaccttggg aaaagctgag  3660
tacctgaaga acaacatact gtcaatgcca gagaaggcca agaaagcgtt tgacaaccct  3720
gactactgga accacagcct gccacctcgg agcacccttc agcacccaga ctacctgcag  3780
gagtacagca caaaatattt ttataaacag aatgggcgga tccggcctat tgtggcagag  3840
```

```
aatcctgaat acctctctga gttctccctg aagccaggca ctgtgctgcc gcctccacct  3900
tacagacacc ggaatactgt ggtgtaa                                      3927

SEQ ID NO: 138         moltype = AA  length = 1308
FEATURE                Location/Qualifiers
source                 1..1308
                       mol_type = protein
                       organism = Homo sapiens
SEQUENCE: 138
MKPATGLWVW VSLLVAAGTV QPSDSQSVCA GTENKLSSLS DLEQQYRALR KYYENCEVVM  60
GNLEITSIEH NRDLSFLRSV REVTGYVLVA LNQFRYLPLE NLRIIRGTKL YEDRYALAIF  120
LNYRKDGNFG LQELGLKNLT EILNGGVYVD QNKFLCYADT IHWQDIVRNP WPSNLTLVST  180
NGSSGCGRCH KSCTGRCWGP TENHCQTLTR TVCAEQCDGR CYGPYVSDCC HRECAGGCSG  240
PKDTDCFACM NFNDSGACVT QCPQTFVYNP TTFQLEHNFN AKYTYGAFCV KKCPHNFVVD  300
SSSCVRACPS SKMEVEENGI KMCKPCTDIC PKACDGIGTG SLMSAQTVDS SNIDKFINCT  360
KINGNLIFLV TGIHGDPYNA IEAIDPEKLN VFRTVREITG FLNIQSWPPN MTDFSVFSNL  420
VTIGGRVLYS GLSLLILKQQ GITSLQFQSL KEISAGNIYI TDNSNLCYYH TINWTTLFST  480
INQRIVIRDN RKAENCTAEG MVCNHLCSSD GCWGPGPDQC LSCRRFSRGR ICIESCNLYD  540
GEFREFENGS ICVECDPQCE KMEDGLLTCH GPGPDNCTKC SHFKDGPNCV EKCPDGLQGA  600
NSFIFKYADP DRECHPCHPN CTQGCNGPTS HDCIYYPWTG HSTLPQHART PLIAAGVIGG  660
LFILVIVGLT FAVYVRRKSI KKKRALRRFL ETELVEPLTP SGTAPNQAQL RILKETELKR  720
VKVLGSGAFG TVYKGIWVPE GETVKIPVAI KILNETTGPK ANVEFMDEAL IMASMDHPHL  780
VRLLGVCLSP TIQLVTQLMP HGCLLEYVHE HKDNIGSQLL LNWCVQIAKG MMYLEERRLV  840
HRDLAARNVL VKSPNHVKIT DFGLARLLEG DEKEYNADGG KMPIKWMALE CIHYRKFTHQ  900
SDVWSYGVTI WELMTFGGKP YDGIPTREIP DLLEKGERLP QPPICTIDVY MVMVKCWMID  960
ADSRPKFKEL AAEFSRMARD PQRYLVIQGD DRMKLPSPND SKFFQNLLDE EDLEDMMDAE  1020
EYLVPQAFNI PPPIYTSRAR IDSNRSEIGH SPPPAYTPMS GNQFVYRDGG FAAEQGVSVP  1080
YRAPTSTIPE APVAQGATAE IFDDSCCNGT LRKPVAPHVQ EDSSTQRYSA DPTVFAPERS  1140
PRGELDEEGY MTPMRDKPKQ EYLNPVEENP FVSRRKNGDL QALDNPEYHN ASNGPPKAED  1200
EYVNEPLYLN TFANTLGKAE YLKNNILSMP EKAKKAFDNP DYWNHSLPPR STLQHPDYLQ  1260
EYSTKYFYKQ NGRIRPIVAE NPEYLSEFSL KPGTVLPPPP YRHRNTVV               1308

SEQ ID NO: 139         moltype = DNA  length = 510
FEATURE                Location/Qualifiers
source                 1..510
                       mol_type = genomic DNA
                       organism = Homo sapiens
SEQUENCE: 139
atggacacca gaaataaggc ccagctcctt gtgctcctga ctcttctcag tgtgctcttc  60
tcacagactt cggcatggcc tctttacagg gcaccttctg ctctcaggtt gggtgacaga  120
atacccttg agggagcaaa tgaacctgat caagtttcat taaaagaaga cattgacatg  180
ttgcaaaatg cattagctga aaatgacaca ccctattatg atgtatccag aaatgccagg  240
catgctgatg gagttttcac cagtgacttc agtaaactct tgggtcaact ttctgccaaa  300
aagtaccttg agtctcttat gggaaaacgt gttagtaaca tctcagaaga ccctgtacca  360
gtcaaacgtc actcagatgc agtcttcact gacaactata cccgccttag aaaacaaatg  420
gctgtaaaga aatatttgaa ctcaattctg aatggaaaga ggagcagtga gggagaatct  480
cccgactttc cagaagagtt agaaaaatga                                   510

SEQ ID NO: 140         moltype = AA  length = 169
FEATURE                Location/Qualifiers
source                 1..169
                       mol_type = protein
                       organism = Homo sapiens
SEQUENCE: 140
MDTRNKAQLL VLLTLLSVLF SQTSAWPLYR APSALRLGDR IPFEGANEPD QVSLKEDIDM  60
LQNALAENDT PYYDVSRNAR HADGVFTSDF SKLLGQLSAK KYLESLMGKR VSNISEDPVP  120
VKRHSDAVFT DNYTRLRKQM AVKKYLNSIL NGKRSSEGES PDFPEELEK              169

SEQ ID NO: 141         moltype = DNA  length = 5808
FEATURE                Location/Qualifiers
source                 1..5808
                       mol_type = genomic DNA
                       organism = Homo sapiens
SEQUENCE: 141
atgggagatt cggagatggc agtctttggg gctgccgccc cctacctgcg caagtcagag  60
aaggagcggc tagaagcgca gaccaggcct tttgacctca agaaggatgt cttcgtgcct  120
gatgacaaac aggagtttgt caaggccaag atcgtgtctc gagagggtgg caaagtcact  180
gccgagactg agtatggcaa gacagtgacc gtgaaggagg accaggtgat gcagcagaac  240
ccacccaagt tcgacaaaat cgaggacatg gccatgctga ccttcctgca tgagcccgcg  300
gtgctctaca acctcaagga tcgctacggc tcctggatga tctacaccta ctcgggcctc  360
ttctgtgtca ccgtcaaccc ttacaagtgg ctgccggtgt acactcctga ggtggtggct  420
gcctaccggg gcaagaagag gagcgaggcc ccgccccaca tcttctccat ctccgacaac  480
gcctatcagt acatgctgac agacagagaa aaccagtcca tcctgatcac cggagaatcc  540
ggagcaggga agacagtcaa caccaagagg gtcatccagt actttgctgt tattgcagcc  600
attggggacc gcagcaagaa ggaccagagc ccgggcaagg gcaccctgga ggaccagatc  660
atccaggcca accctgctct ggaggccttt ggcaatgcca agaccgtccg gaacgacaac  720
tcctcccgct tcgggaaatt cattcgaatt catttggggg caacaggaaa gttggcatct  780
gcagacatag agacctatct tctggaaaaa tccagagtta ttttccagct gaaagcagag  840
agagattatc acattttcta ccaaatcctg tctaacaaaa agcctgagct gctggacatg  900
```

-continued

```
ctgctgatca ccaacaaccc ctacgattat gcattcatct cccaaggaga gaccaccgtg  960
gcctccattg atgacgctga ggagctcatg gccactgata acgcttttga tgtgctgggc  1020
ttcacttcag aggagaaaaa ctccatgtat aagctgacag gcgccatcat gcactttgga  1080
aacatgaagt tcaagctgaa gcagcgggag gagcaggcgg agccagacgg cactgaagag  1140
gctgacaagt ctgcctacct catggggctg aactcagccg acctgctcaa ggggctgtgc  1200
caccctcggg tgaaagtggg caatgagtac gtcaccaagg ggcagaatgt ccagcaggtg  1260
atatatgcca ctggggcact ggccaaggca gtgtatgaga ggatgttcaa ctggatggtg  1320
acgcgcatca atgccaccct ggagaccaag cagccacgcc agtacttcat aggagtcctg  1380
gacatcgctg gcttcgagat cttcgatttc aacagctttg agcagctctg catcaacttc  1440
accaacgaga agctgcagca gttcttcaac caccacatgt ttgtgctgga gcaggaggag  1500
tacaagaagg agggcatcga gtggacattc attgactttg gcatggacct gcaggcctgc  1560
attgacctca tcgagaagcc catgggcatc atgtccatcc tggaagagga gtgcatgttc  1620
cccaaggcca ccgacatgac cttcaaggcc aagctgtttg acaaccacct gggcaaatcc  1680
gccaacttcc agaagccacg aaatatcaag gggaagcctg aagcccactt ctccctgatc  1740
cactatgccg gcatcgtgga ctacaacatc attggctggc tgcagaagaa caaggatcct  1800
ctcaatgaga ctgtcgtggg cttgtatcag aagtcttccc tcaagttgct cagcaccctg  1860
tttgccaact atgctggggc tgatgcgcct attgagaagg gcaaaggcaa ggccaagaaa  1920
ggctcgtcct ttcagactgt gtcagctctg cacagggaaa atctgaacaa gctgatgacc  1980
aacttgcgct ccacccatcc ccactttgta cgttgtatca tccctaatga gacaaagtct  2040
ccaggcgtga tggacaaccc cctggtcatg caccagctgc gctgcaatgg tgtgctggag  2100
ggcatccgca tctgcaggaa aggcttcccc aaccgcatcc tctacgggga cttccggcag  2160
aggtatcgca tcctgaaccc agcggccatc cctgagggac agttcattga tagcaggaag  2220
ggggcagaga agctgctcag ctccctggac attgatcaca accagtacaa gtttggccac  2280
accaaggtgt tcttcaaggc cgggctgctg gggctgctgg aggaaatgag ggacgagagg  2340
ctgagccgca tcatcacgcg tatccaggcc cagtcccgag gtgtgctcgc cagaatggag  2400
tacaaaaagc tgctggaacg tagagactcc ctgctggtaa tccagtggaa cattcgggcc  2460
ttcatggggg tcaagaattg gccctggatg aagctctact tcaagatcaa gccgctgctg  2520
aagagtgcag aaagagagaa ggagatggcc tccatgaagg aggagttcac acgcctcaaa  2580
gaggcgctag agaagtccga ggctcgccgc aaggagctgg aggagaagat ggtgtccctg  2640
ctgcaggaga agaatgacct gcagctccaa gtgcaggcgg aacaagacaa cctggcagat  2700
gctgaggagc gctgtgatca gctgatcaaa aacaagattc agctggaggc taaggtgaag  2760
gagatgaacg agaggctgga ggatgaggag gagatgaatg ctgagctcac tgccaagaag  2820
cgcaagttgg aagatgagtg ctcagagctc aaaagggaca tcgatgatct ggagctgaca  2880
ctggccaaag tggagaagga gaaacacgca acagagaaca aggtgaaaaa cctgacagag  2940
gagatggctg ggctggatga gatcattgcc aagctgacca aggagaagaa agctctgcaa  3000
gaggcccacc aacaggctct ggatgacctt caggccgagg aggacaaggt caacaccctg  3060
actaaggcca aagtcaagct ggagcagcaa gtggatgatc tggaaggatc cctggagcaa  3120
gagaagaagg tgcgcatgga cctggagcga gcgaagcgga agctggaggg cgacctgaag  3180
ctgacccagg agagcatcat ggacctggag aatgacaagc agcagctgga tgagcggctg  3240
aaaaaaaaag actttgagct gaatgctctc aacgcaagga ttgaggatga acaggccctc  3300
ggcagccagc tgcagaagaa gctcaaggag cttcaggcac gcatcgagga gctggaggag  3360
gagctggagt ccgagcgcac cgccagggct aaggtggaga agctgcgctc agacctgtct  3420
cgggagctgg aggagatcag cgagcggctg gaagaggccg gcggggccac gtccgtgcag  3480
atcgagatga acaagaagcg cgaggccgag ttccagaaga tgcggcggga cctggaggag  3540
gccacgctgc agcacgaggc cactgccgcg gccctgcgca agaagcacgc cgacagcgtg  3600
gccgagctgg gcgagcagat cgacaacctg cagcgggtga agcagaagct ggagaaggag  3660
aagagcgagt tcaagctgga gctggatgac gtcacctcca acatggagca gatcatcaag  3720
gccaaggcta acctggagaa gatgtgccgg accttggaag accagatgaa tgagcaccgg  3780
agcaaggcgg aggagaccca gcgttctgtc aacgacctca ccagccagcg ggccaagttg  3840
caaaccgaga atggtgagct gtcccggcag ctggatgaga aggaggcact gatctcccag  3900
ctgacccgag gcaagctcac ctacacccag cagctggagg acctcaagag gcagctggag  3960
gaggaggtta aggcgaagaa cgccctggcc cacgcactgc agtcggcccg gcatgactgc  4020
gacctgctgc gggagcagta cgaggaggag acggaggcca aggccgagct gcagcgcgtc  4080
ctttccaagg ccaactcgga ggtggcccag tggaggacca agtatgagac ggacgccatt  4140
cagcggactg aggagctcga ggaggccaag aagaagctgg cccagcggct gcaggaagct  4200
gaggaggccg tggaggctgt taatgccaag tgctcctcgc tggagaagac caagcaccgg  4260
ctacagaatg agatcgagga cttgatggtg gacgtagagc gctccaatgc tgctgctgca  4320
gccctggaca agaagcagag gaacttcgac aagatcctgg ccgagtggaa gcagaagtat  4380
gaggagtcgc agtcggagct ggagtcctcg cagaaggagg ctcgctccct cagcacagag  4440
ctcttcaaac tcaagaacgc ctatgaggag tccctggaac atctggagac cttcaagcgg  4500
gagaacaaaa acctgcagga ggagatctcc gacttgactg agcagttggg ttccagcgga  4560
aagactatcc atgagctgga gaaggtccga aagcagctgg aggccgagaa gatggagctg  4620
cagtcagccc tggaggaggc cgaggcctcc ctggagcacg aggagggcaa gatcctccgg  4680
gcccagctgg agttcaacca gatcaaggca gagatcgagc ggaagctggc agagaaggac  4740
gaggagatgg aacaggccaa gcgcaaccac ctgcgggtgg tggactcgct gcagacctcc  4800
ctggacgcag agacacgcag ccgcaacgag gccctgaggg tgaagaagaa gatggaagga  4860
gacctcaatg agatggagat ccagctcagc cacgccaacc gcatggccgc cgaggcccag  4920
aagcaagtca agagcctcca gagcttgttg aaggacaccc agattcagct ggacgatgca  4980
gtccgtgcca acgacgacct gaaggagaac atcgccatcg tggagcggcg caacaacctg  5040
ctgcaggctg agctggagga gttgcgtgcc gtggtggagc agacagagcg gtcccggaag  5100
ctggcggagc aggagctgat tgagactagt gagcgggtgc agctgctgca ttcccagaac  5160
accagcctca tcaaccagaa gaagaagatg gatgctgacc tgtcccagct ccagactgaa  5220
gtggaggagg cagtgcagga gtgcaggaat gctgaggaga aggccaagaa ggccatcacg  5280
gatgccgcca tgatggcaga ggagctgaag aaggagcagg acaccagcgc ccacctggag  5340
cgcatgaaga agaacatgga acagaccatt aaggacctgc agcaccggct ggacgaagcc  5400
gagcagatcg ccctcaaggg cggcaagaag cagctgcaga agctggaagc gcgggtgcgg  5460
gagctggaga atgagctgga ggccgagcag aagcgcaacg cagagtcggt gaagggcatg  5520
aggaagagcg agcggcgcat caaggagctc acctaccaga cggaggagga caggaaaaac  5580
ctgctgcggc tgcaggacct ggtagacaag ctgcagctaa aggtcaaggc ctacaagcgc  5640
```

```
caggccgagg aggcggagga gcaagccaac accaacctgt ccaagttccg caaggtgcag  5700
cacgagctgg atgaggcaga ggagcgggcg gacatcgccg agtcccaggt caacaagctg  5760
cgggccaaga gccgtgacat tggcacgaag ggcttgaatg aggagtag               5808

SEQ ID NO: 142         moltype = AA  length = 1935
FEATURE                Location/Qualifiers
source                 1..1935
                       mol_type = protein
                       organism = Homo sapiens
SEQUENCE: 142
MGDSEMAVFG AAAPYLRKSE KERLEAQTRP FDLKKDVFVP DDKQEFVKAK IVSREGGKVT  60
AETEYGKTVT VKEDQVMQQN PPKFDKIEDM AMLTFLHEPA VLYNLKDRYG SWMIYTYSGL  120
FCVTVNPYKW LPVYTPEVVA AYRGKKRSEA PPHIFSISDN AYQYMLTDRE NQSILITGES  180
GAGKTVNTKR VIQYFAVIAA IGDRSKKDQS PGKGTLEDQI IQANPALEAF GNAKTVRNDN  240
SSRFGKFIRI HFGATGKLAS ADIETYLLEK SRVIFQLKAE RDYHIFYQIL SNKKPELLDM  300
LLITNNPYDY AFISQGETTV ASIDDAEELM ATDNAFDVLG FTSEEKNSMY KLTGAIMHFG  360
NMKFKLKQRE EQAEPDGTEE ADKSAYLMGL NSADLLKGLC HPRVKVGNEY VTKGQNVQQV  420
IYATGALAKA VYERMFNWMV TRINATLETK QPRQYFIGVL DIAGFEIFDF NSFEQLCINF  480
TNEKLQQFFN HHMFVLEQEE YKKEGIEWTF IDFGMDLQAC IDLIEKPMGI MSILEEECMF  540
PKATDMTFKA KLFDNHLGKS ANFQKPRNIK GKPEAHFSLI HYAGIVDYNI IGWLQKNKDP  600
LNETVVGLYQ KSSLKLLSTL FANYAGADAP IEKGKGKAKK GSSFQTVSAL HRENLNKLMT  660
NLRSTHPHFV RCIIPNETKS PGVMDNPLVM HQLRCNGVLE GIRICRKGFP NRILYGDFRQ  720
RYRILNPAAI PEGQFIDSRK GAEKLLSSLD IDHNQYKFGH TKVFFKAGLL GLLEEMRDER  780
LSRIITRIQA QSRGVLARME YKKLLERRDS LLVIQWNIRA FMGVKNWPWM KLYFKIKPLL  840
KSAEREKEMA SMKEEFTRLK EALEKSEARR KELEEKMVSL LQEKNDLQLQ VQAEQDNLAD  900
AEERCDQLIK NKIQLEAKVK EMNERLEDEE EMNAELTAKK RKLEDECSEL KRDIDDLELT  960
LAKVEKEKHA TENKVKNLTE EMAGLDEIIA KLTKEKKALQ EAHQQALDDL QAEEDKVNTL  1020
TKAKVKLEQQ VDDLEGSLEQ EKKVRMDLER AKRKLEGDLK LTQESIMDLE NDKQQLDERL  1080
KKKDFELNAL NARIEDEQAL GSQLQKKLKE LQARIEELEE ELESERTARA KVEKLRSDLS  1140
RELEEISERL EEAGGATSVQ IEMNKKREAE FQKMRRDLEE ATLQHEATAA ALRKKHADSV  1200
AELGEQIDNL QRVKQKLEKE KSEFKLELDD VTSNMEQIIK AKANLEKMCR TLEDQMNEHR  1260
SKAEETQRSV NDLTSQRAKL QTENGELSRQ LDEKEALISQ LTRGKLTYTQ QLEDLKRQLE  1320
EEVKAKNALA HALQSARHDC DLLREQYEEE TEAKAELQRV LSKANSEVAQ WRTKYETDAI  1380
QRTEELEEAK KKLAQRLQEA EEAVEAVNAK CSSLEKTKHR LQNEIEDLMV DVERSNAAAA  1440
ALDKKQRNFD KILAEWKQKY EESQSELESS QKEARSLSTE LFKLKNAYEE SLEHLETFKR  1500
ENKNLQEEIS DLTEQLGSSG KTIHELEKVR KQLEAEKMEL QSALEEAEAS LEHEEGKILR  1560
AQLEFNQIKA EIERKLAEKD EEMEQAKRNH LRVVDSLQTS LDAETRSRNE ALRVKKKMEG  1620
DLNEMEIQLS HANRMAAEAQ KQVKSLQSLL KDTQIQLDDA VRANDDLKEN IAIVERRNNL  1680
LQAELEELRA VVEQTERSRK LAEQELIETS ERVQLLHSQN TSLINQKKKM DADLSQLQTE  1740
VEEAVQECRN AEEKAKKAIT DAAMMAEELK KEQDTSAHLE RMKKNMEQTI KDLQHRLDEA  1800
EQIALKGGKK QLQKLEARVR ELENELEAEQ KRNAESVKGM RKSERRIKEL TYQTEEDRKN  1860
LLRLQDLVDK LQLKVKAYKR QAEEAEEQAN TNLSKFRKVQ HELDEAEERA DIAESQVNKL  1920
RAKSRDIGTK GLNEE                                                   1935

SEQ ID NO: 143         moltype = AA  length = 736
FEATURE                Location/Qualifiers
source                 1..736
                       mol_type = protein
                       note = Adeno-associated virus serotype 9
                       organism = Adeno-associated dependoparvovirus A
SEQUENCE: 143
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                  736

SEQ ID NO: 144         moltype = AA  length = 724
FEATURE                Location/Qualifiers
source                 1..724
                       mol_type = protein
                       note = Adeno-associated virus serotype 5
                       organism = Adeno-associated dependoparvovirus A
SEQUENCE: 144
MSFVDHPPDW LEEVGEGLRE FLGLEAGPPK PKPNQQHQDQ ARGLVLPGYN YLGPGNGLDR  60
GEPVNRADEV AREHDISYNE QLEAGDNPYL KYNHADAEFQ EKLADDTSFG GNLGKAVFQA  120
KKRVLEPFGL VEEGAKTAPT GKRIDDHFPK RKKARTEEDS KPSTSSDAEA GPSGSQQLQI  180
PAQPASSLGA DTMSAGGGGP LGDNNQGADG VGNASGDWHC DSTWMGDRVV TKSTRTWVLP  240
SYNNHQYREI KSGSVDGSNA NAYFGYSTPW GYFDFNRFHS HWSPRDWQRL INNYWGFRPR  300
SLRVKIFNIQ VKEVTVQDST TTIANNLTST VQVFTDDDYQ LPYVVGNGTE GCLPAFPPQV  360
FTLPQYGYAT LNRDNTENPT ERSSFFCLEY FPSKMLRTGN NFEFTYNFEE VPFHSSFAPS  420
```

```
QNLFKLANPL VDQYLYRFVS TNNTGGVQFN KNLAGRYANT YKNWFPGPMG RTQGWNLGSG  480
VNRASVSAFA TTNRMELEGA SYQVPPQPNG MTNNLQGSNT YALENTMIFN SQPANPGTTA  540
TYLEGNMLIT SESETQPVNR VAYNVGGQMA TNNQSSTTAP ATGTYNLQEI VPGSVWMERD  600
VYLQGPIWAK IPETGAHFHP SPAMGGFGLK HPPPMMLIKN TPVPGNITSF SDVPVSSFIT  660
QYSTGQVTVE MEWELKKENS KRWNPEIQYT NNYNDPQFVD FAPDSTGEYR TTRPIGTRYL  720
TRPL                                                              724

SEQ ID NO: 145          moltype = AA  length = 736
FEATURE                 Location/Qualifiers
REGION                  1..736
                        note = Recombinant AAV Capsid Protein
source                  1..736
                        mol_type = protein
                        organism = synthetic construct
SEQUENCE: 145
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT ISQVNGRPRD LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 146          moltype = AA  length = 736
FEATURE                 Location/Qualifiers
REGION                  1..736
                        note = Recombinant AAV Capsid Protein
source                  1..736
                        mol_type = protein
                        organism = synthetic construct
SEQUENCE: 146
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT IGYHKSGAAQ LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 147          moltype = AA  length = 736
FEATURE                 Location/Qualifiers
REGION                  1..736
                        note = Recombinant AAV Capsid Protein
source                  1..736
                        mol_type = protein
                        organism = synthetic construct
SEQUENCE: 147
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQNVSYQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 148          moltype = AA  length = 736
FEATURE                 Location/Qualifiers
REGION                  1..736
                        note = Recombinant AAV Capsid Protein
source                  1..736
                        mol_type = protein
```

```
                        organism = synthetic construct
SEQUENCE: 148
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSMVNQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                736

SEQ ID NO: 149          moltype = AA  length = 736
FEATURE                 Location/Qualifiers
REGION                  1..736
                        note = Recombinant AAV Capsid Protein
source                  1..736
                        mol_type = protein
                        organism = synthetic construct
SEQUENCE: 149
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQANYGQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                736

SEQ ID NO: 150          moltype = AA  length = 736
FEATURE                 Location/Qualifiers
REGION                  1..736
                        note = Recombinant AAV Capsid Protein
source                  1..736
                        mol_type = protein
                        organism = synthetic construct
SEQUENCE: 150
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQNVGTQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                736

SEQ ID NO: 151          moltype = AA  length = 736
FEATURE                 Location/Qualifiers
REGION                  1..736
                        note = Recombinant AAV Capsid Protein
source                  1..736
                        mol_type = protein
                        organism = synthetic construct
SEQUENCE: 151
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT IGYHKSGAAQ LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQNVSYQ AQTGWVQNQG  600
ILPGMVWQDR DVYLQGPIWA KIPHTDGNFH PSPLMGGFGM KHPPPQILIK NTPVPADPPT  660
```

```
AFNKDKLNSF ITQYSTGQVS VEIEWELQKE NSKRWNPEIQ YTSNYYKSNN VEFAVNTEGV  720
YSEPRPIGTR YLTRNL                                                  736

SEQ ID NO: 152          moltype = AA  length = 736
FEATURE                 Location/Qualifiers
REGION                  1..736
                        note = Recombinant AAV Capsid Protein
source                  1..736
                        mol_type = protein
                        organism = synthetic construct
SEQUENCE: 152
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNLNSM LIWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                  736

SEQ ID NO: 153          moltype = AA  length = 736
FEATURE                 Location/Qualifiers
REGION                  1..736
                        note = Recombinant AAV Capsid Protein
source                  1..736
                        mol_type = protein
                        organism = synthetic construct
SEQUENCE: 153
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNQDAS LLWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                  736

SEQ ID NO: 154          moltype = AA  length = 736
FEATURE                 Location/Qualifiers
REGION                  1..736
                        note = Recombinant AAV Capsid Protein
source                  1..736
                        mol_type = protein
                        organism = synthetic construct
SEQUENCE: 154
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNGMS FTWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                  736

SEQ ID NO: 155          moltype = AA  length = 736
FEATURE                 Location/Qualifiers
REGION                  1..736
                        note = Recombinant AAV Capsid Protein
source                  1..736
                        mol_type = protein
                        organism = synthetic construct
SEQUENCE: 155
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
```

```
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT IGYHKSGAAQ LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQANYGQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 156         moltype = AA  length = 736
FEATURE                Location/Qualifiers
REGION                 1..736
                       note = Recombinant AAV Capsid Protein
source                 1..736
                       mol_type = protein
                       organism = synthetic construct
SEQUENCE: 156
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT IGYHKSGAAQ LKFSVAGPSN MAVQGRNYIP  480
GPSYRQQRVS TTVTQNQDAS LLWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 157         moltype = AA  length = 736
FEATURE                Location/Qualifiers
REGION                 1..736
                       note = Recombinant AAV Capsid Protein
source                 1..736
                       mol_type = protein
                       organism = synthetic construct
SEQUENCE: 157
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT IGYHKSGAAQ LKFSVAGPSN MAVQGRNYIP  480
GPSYRQQRVS TTVTQNNGMS FTWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 158         moltype = AA  length = 736
FEATURE                Location/Qualifiers
REGION                 1..736
                       note = Recombinant AAV Capsid Protein
source                 1..736
                       mol_type = protein
                       organism = synthetic construct
SEQUENCE: 158
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNLNSM LIWPGASSWA LNGRNSLMNP GPAMASHKEG EDRFFPLSGS  540
LIFGKQGTGR DNVDADKVMI TNEEEIKTTN PVATESYGQV ATNHQANYGQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 159         moltype = AA  length = 726
```

```
FEATURE                Location/Qualifiers
REGION                 1..726
                       note = Recombinant AAV Capsid Protein
source                 1..726
                       mol_type = protein
                       organism = synthetic construct
SEQUENCE: 159
MSFVDHPPDW LEEVGEGLRE FLGLEAGPPK PKPNQQHQDQ ARGLVLPGYN YLGPGNGLDR  60
GEPVNRADEV AREHDISYNE QLEAGDNPYL KYNHADAEFQ EKLADDTSFG GNLGKAVFQA  120
KKRVLEPFGL VEEGAKTAPT GKRIDDHFPK RKKARTEEDS KPSTSSDAEA GPSGSQQLQI  180
PAQPASSLGA DTMSAGGGGP LGDNNQGADG VGNASGDWHC DSTWMGDRVV TKSTRTWALP  240
TYNNHLYKQI SNSTSGGSSN DNAYFGYSTP WGYFDFNRFH CHFSPRDWQR LINNNWGFRP  300
KRLNFKLFNI QVKEVTDNNG VKTIANNLTS TVQVFTDSDY QLPYVLGSAH EGCLPPFPAD  360
VFMIPQYGYL TLNDGSQAVG RSSFYCLEYF PSQMLRTGNN FQFSYEFENV PFHSSYAHSQ  420
SLDRLMNPLI DQYLYYLSKT INGSGQNQQT LKFSVAGPSN MAVQGRNYIP GPSYRQQRVS  480
TTVTQNNNSE FAWPGASSWA LNGRNSLMNP GPAMASHKEG EDRFFPLSGS LIFGKQGTGR  540
DNVDADKVMI TNEEEIKTTN PVATESYGQV ATNHQSAQAQ AQTGWVQNQG ILPGMVWQDR  600
DVYLQGPIWA KIPHTDGNFH PSPLMGGFGM KHPPPQILIK NTPVPADPPT AFNKDKLNSF  660
ITQYSTGQVS VEIEWELQKE NSKRWNPEIQ YTNNYNDPQF VDFAPDSTGE YRTTRPIGTR  720
YLTRPL                                                            726

SEQ ID NO: 160         moltype = AA  length = 725
FEATURE                Location/Qualifiers
REGION                 1..725
                       note = Recombinant AAV Capsid Protein
source                 1..725
                       mol_type = protein
                       organism = synthetic construct
SEQUENCE: 160
MAADGYLPDW LEDNLSEGIR EWWALKPGAP QPKANQQHQD NARGLVLPGY NYLGPGNGLD  60
RGEPVNRADE VAREHDISYN EQLEAGDNPY LKYNHADAEF QEKLADDTSF GGNLGKAVFQ  120
AKKRVLEPFG LVEEGAKTAP TGKRIDDHFP KRKKARTEED SKPSTSSDAE AGPSGSQQLQ  180
IPAQPASSLG ADTMSAGGGG PLGDNNQGAD GVGNASGDWH CDSTWMGDRV VTKSTRTWVL  240
PSYNNHQYRE IKSGSVDGSN ANAYFGYSTP WGYFDFNRFH SHWSPRDWQR LINNYWGFRP  300
RSLRVKIFNI QVKEVTVQDS TTTIANNLTS TVQVFTDDDY QLPYVVGNGT EGCLPAFPPQ  360
VFTLPQYGYA TLNRDNTENP TERSSFFCLE YFPSKMLRTG NNFEFTYNFE EVPFHSSFAP  420
SQNLFKLANP LVDQYLYRFV STNNTGGVQF NKNLAGRYAN TYKNWFPGPM GRTQGWNLGS  480
GVNRASVSAF ATTNRMELEG ASYQVPPQPN GMTNNLQGSN TYALENTMIF NSQPANPGTT  540
ATYLEGNMLI TSESETQPVN RVAYNVGGQM ATNNQSSTTA PATGTYNLQE IVPGSVWMER  600
DVYLQGPIWA KIPETGAHFH PSPAMGGFGL KHPPPMMLIK NTPVPGNITS FSDVPVSSFI  660
TQYSTGQVTV EMEWELKKEN SKRWNPEIQY TSNYYKSNNV EFAVNTEGVY SEPRPIGTRY  720
LTRNL                                                             725

SEQ ID NO: 161         moltype = AA  length = 725
FEATURE                Location/Qualifiers
REGION                 1..725
                       note = Recombinant AAV Capsid Protein
source                 1..725
                       mol_type = protein
                       organism = synthetic construct
SEQUENCE: 161
MSFVDHPPDW LEEVGEGLRE FLGLEAGPPK PKPNQQHQDQ ARGLVLPGYN YLGPGNGLDR  60
GEPVNRADEV AREHDISYNE QLEAGDNPYL KYNHADAEFQ EKLADDTSFG GNLGKAVFQA  120
KKRVLEPFGL VEEAAKTAPT GKRIDDHFPK RKKARTEEDS KPSTSSDAEA GPSGSQQLQI  180
PAQPASSLGA DTMSAGGGGP LGDNNQGADG VGNASGDWHC DSTWMGDRVV TKSTRTWVLP  240
SYNNHQYREI KSGSVDGSNA NAYFGYSTPW GYFDFNRFHS HWSPRDWQRL INNYWGFRPR  300
SLRVKIFNIQ VKEVTDNNGV KTIANNLTST VQVFTDSDYQ LPYVLGSAHE GCLPPFPADV  360
FMIPQYGYLT LNDGSQAVGR SSFYCLEYFP SQMLRTGNNF QFSYEFENVP FHSSYAHSQS  420
LDRLMNPLID QYLYYLSKTI NGSGQNQQTL KFSVAGPSNM AVQGRNYIPG PSYRQQRVST  480
TVTQNNNSEF AWPGASSWAL NGRNSLMNPG PAMASHKEGE DRFFPLSGSL IFGKQGTGRD  540
NVDADKVMIT NEEEIKTTNP VATESYGQVA TNHQSAQAQA QTGWVQNQGI LPGMVWQDRD  600
VYLQGPIWAK IPHTDGNFHP SPLMGGFGMK HPPPQILIKN TPVPADPPTA FNKDKLNSFI  660
TQYSTGQVSV EIEWELQKEN SKRWNPEIQY TSNYYKSNNV EFAVNTEGVY SEPRPIGTRY  720
LTRNL                                                             725

SEQ ID NO: 162         moltype = AA  length = 727
FEATURE                Location/Qualifiers
REGION                 1..727
                       note = Recombinant AAV Capsid Protein
source                 1..727
                       mol_type = protein
                       organism = synthetic construct
SEQUENCE: 162
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QEKLADDTSF GGNLGKAVFQ  120
AKKRVLEPFG LVEEGAKTAP TGKRIDDHFP KRKKARTEED SKPSTSSDAE AGPSGSQQLQ  180
IPAQPASSLG ADTMSAGGGG PLGDNNQGAD GVGNASGDWH CDSTWLGDRV ITTSTRTWAL  240
PTYNNHLYKQ ISNSTSGGSS NDNAYFGYST PWGYFDFNRF HCHFSPRDWQ RLINNNWGFR  300
PKRLNFKLFN IQVKEVTDNN GVKTIANNLT STVQVFTDSD YQLPYVLGSA HEGCLPPFPA  360
```

```
DVFMIPQYGY LTLNDGSQAV GRSSFYCLEY FPSQMLRTGN NFQFSYEFEN VPFHSSYAHS  420
QSLDRLMNPL IDQYLYYLSK TINGSGQNQQ TLKFSVAGPS NMAVQGRNYI PGPSYRQQRV  480
STTVTQNNNS EFAWPGASSW ALNGRNSLMN PGPAMASHKE GEDRFFPLSG SLIFGKQGTG  540
RDNVDADKVM ITNEEEIKTT NPVATESYGQ VATNHQSAQA QAQTGWVQNQ GILPGMVWQD  600
RDVYLQGPIW AKIPHTDGNF HPSPLMGGFG MKHPPPQILI KNTPVPADPP TAFNKDKLNS  660
FITQYSTGQV SVEIEWELQK ENSKRWNPEI QYTSNYYKSN NVEFAVNTEG VYSEPRPIGT  720
RYLTRNL                                                            727

SEQ ID NO: 163          moltype = AA  length = 736
FEATURE                 Location/Qualifiers
REGION                  1..736
                        note = Recombinant AAV Capsid Protein
source                  1..736
                        mol_type = protein
                        organism = synthetic construct
SEQUENCE: 163
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVT VEMEWELKKE NSKRWNPEIQ YTNNYNDPQF VDFAPDSTGE  720
YRTTRPIGTR YLTRPL                                                  736

SEQ ID NO: 164          moltype = AA  length = 726
FEATURE                 Location/Qualifiers
REGION                  1..726
                        note = Recombinant AAV Capsid Protein
source                  1..726
                        mol_type = protein
                        organism = synthetic construct
SEQUENCE: 164
MSFVDHPPDW LEEVGEGLRE FLGLEAGPPK PKPNQQHQDQ ARGLVLPGYN YLGPGNGLDR  60
GEPVNRADEV AREHDISYNE QLEAGDNPYL KYNHADAEFQ EKLADDTSFG GNLGKAVFQA  120
KKRVLEPFGL VEEGAKTAPT GKRIDDHFPK RKKARTEEDS KPSTSSDAEA GPSGSQQLQI  180
PAQPASSLGA DTMSAGGGGP LGDNNQGADG VGNASGDWHC DSTWMGDRVI TTSTRTWALP  240
TYNNHLYKQI SNSTSGGSSN DNAYFGYSTP WGYFDFNRFH CHFSPRDWQR LINNNWGFRP  300
KRLNFKLFNI QVKEVTDNNG VKTIANNLTS TVQVFTDSDY QLPYVLGSAH EGCLPPFPAD  360
VFMIPQYGYL TLNDGSQAVG RSSFYCLEYF PSQMLRTGNN FQFSYEFENV PFHSSFAHSQ  420
SLDRLMNPLI DQYLYYLSKT INGSGQNQQT LKFSVAGPSN MAVQGRNYIP GPSYRQQRVS  480
TTVTQNNNSE FAWPGASSWA LNGRNSLMNP GPAMASHKEG EDRFFPLSGS LIFGKQGTGR  540
DNVDADKVMI TNEEEIKTTN PVATESYGQV ATNHQSAQAQ AQTGWVQNQG ILPGMVWQDR  600
DVYLQGPIWA KIPHTDGNFH PSPLMGGFGM KHPPPQILIK NTPVPADPPT AFNKDKLNSF  660
ITQYSTGQVS VEIEWELQKE NSKRWNPEIQ YTSNYYKSNN VEFAVNTEGV YSEPRPIGTR  720
YLTRNL                                                             726

SEQ ID NO: 165          moltype = AA  length = 726
FEATURE                 Location/Qualifiers
REGION                  1..726
                        note = Recombinant AAV Capsid Protein
source                  1..726
                        mol_type = protein
                        organism = synthetic construct
SEQUENCE: 165
MSFVDHPPDW LEEVGEGLRE FLGLEAGPPK PKPNQQHQDQ ARGLVLPGYN YLGPGNGLDR  60
GEPVNRADEV AREHDISYNE QLEAGDNPYL KYNHADAEFQ EKLADDTSFG GNLGKAVFQA  120
KKRVLEPFGL VEEGAKTAPT GKRIDDHFPK RKKARTEEDS KPSTSSDAEA GPSGSQQLQI  180
PAQPASSLGA DTMSAGGGGP LGDNNQGADG VGNASGDWHC DSQWLGDRVI TTSTRTWALP  240
TYNNHLYKQI SNSTSGGSSN DNAYFGYSTP WGYFDFNRFH CHFSPRDWQR LINNNWGFRP  300
KRLNFKLFNI QVKEVTDNNG VKTIANNLTS TVQVFTDSDY QLPYVLGSAH EGCLPPFPAD  360
VFMIPQYGYL TLNDGSQAVG RSSFYCLEYF PSQMLRTGNN FQFSYEFENV PFHSSYAHSQ  420
SLDRLMNPLI DQYLYYLSKT INGSGQNQQT LKFSVAGPSN MAVQGRNYIP GPSYRQQRVS  480
TTVTQNNNSE FAWPGASSWA LNGRNSLMNP GPAMASHKEG EDRFFPLSGS LIFGKQGTGR  540
DNVDADKVMI TNEEEIKTTN PVATESYGQV ATNHQSAQAQ AQTGWVQNQG ILPGMVWQDR  600
DVYLQGPIWA KIPHTDGNFH PSPLMGGFGM KHPPPQILIK NTPVPADPPT AFNKDKLNSF  660
ITQYSTGQVS VEIEWELQKE NSKRWNPEIQ YTSNYYKSNN VEFAVNTEGV YSEPRPIGTR  720
YLTRNL                                                             726

SEQ ID NO: 166          moltype = AA  length = 726
FEATURE                 Location/Qualifiers
REGION                  1..726
                        note = Recombinant AAV Capsid Protein
source                  1..726
```

```
                        mol_type = protein
                        organism = synthetic construct
SEQUENCE: 166
MSFVDHPPDW LEEVGEGLRE FLGLEAGPPK PKPNQQHQDQ ARGLVLPGYN YLGPGNGLDR  60
GEPVNRADEV AREHDISYNE QLEAGDNPYL KYNHADAEFQ EKLADDTSFG GNLGKAVFQA  120
KKRVLEPFGL VEEGAKTAPT GKRIDDHFPK RKKARTEEDS KPSTSSDAEA GPSGSQQLQI  180
PAQPASSLGA DTMSAGGGGP LGDNNQGADG VGNASGDWHC DSQWLGDRVI TTSTRTWALP  240
TYNNHLYKQI SNSTSGGSSN DNAYFGYSTP WGYFDFNRFH CHFSPRDWQR LINNNWGFRP  300
KRLNFKLFNI QVKEVTDNNG VKTIANNLTS TVQVFTDSDY QLPYVLGSAH EGCLPPFPAD  360
VFMIPQYGYL TLNDGSQAVG RSSFYCLEYF PSQMLRTGNN FQFSYEFENV PFHSSYAHSQ  420
SLDRLMNPLI DQYLYYLSKT INGSGQNQQT LKFSVAGPSN MAVQGRNYIP GPSYRQQRVS  480
TTVTQNNNSE FAWPGASSWA LNGRNSLMNP GPAMASHKEG EDRFFPLSGS LIFGKQGTGR  540
DNVDADKVMI TNEEEIKTTN PVATESYGQV ATNHQSAQAQ AQTGWVQNQG ILPGMVWQDR  600
DVYLQGPIWA KIPHTDGNFH PSPLMGGFGM KHPPPQILIK NTPVPADPPT AFNKDKLNSF  660
ITQYSTGQVS VEIEWELQKE NSKRWNPEIQ YTNNYNDPQF VDFAPDSTGE YRTTRPIGTR  720
YLTRPL                                                             726

SEQ ID NO: 167          moltype = AA  length = 727
FEATURE                 Location/Qualifiers
REGION                  1..727
                        note = Recombinant AAV Capsid Protein
source                  1..727
                        mol_type = protein
                        organism = synthetic construct
SEQUENCE: 167
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEGAKTAP TGKRIDDHFP KRKKARTEED SKPSTSSDAE AGPSGSQQLQ  180
IPAQPASSLG ADTMSAGGGG PLGDNNQGAD GVGNASGDWH CDSTWMGDRV ITTSTRTWAL  240
PTYNNHLYKQ ISNSTSGGSS NDNAYFGYST PWGYFDFNRF HCHFSPRDWQ RLINNNWGFR  300
PKRLNFKLFN IQVKEVTDNN GVKTIANNLT STVQVFTDSD YQLPYVLGSA HEGCLPPFPA  360
DVFMIPQYGY LTLNDGSQAV GRSSFYCLEY FPSQMLRTGN NFQFSYEFEN VPFHSSYAHS  420
QSLDRLMNPL IDQYLYYLSK TINGSGQNQQ TLKFSVAGPS NMAVQGRNYI PGPSYRQQRV  480
STTVTQNNNS EFAWPGASSW ALNGRNSLMN PGPAMASHKE GEDRFFPLSG SLIFGKQGTG  540
RDNVDADKVM ITNEEEIKTT NPVATESYGQ VATNHQSAQA QAQTGWVQNQ GILPGMVWQD  600
RDVYLQGPIW AKIPHTDGNF HPSPLMGGFG MKHPPPQILI KNTPVPADPP TAFNKDKLNS  660
FITQYSTGQV TVEMEWELKK ENSKRWNPEI QYTSNYYKSN NVEFAVNTEG VYSEPRPIGT  720
RYLTRNL                                                            727

SEQ ID NO: 168          moltype = AA  length = 726
FEATURE                 Location/Qualifiers
REGION                  1..726
                        note = Recombinant AAV Capsid Protein
source                  1..726
                        mol_type = protein
                        organism = synthetic construct
SEQUENCE: 168
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QEKLADDTSF GGNLGKAVFQ  120
AKKRVLEPFG LVEEGAKTAP TGKRIDDHFP KRKKARTEED SKPSTSSDAE AGPSGSQQLQ  180
IPAQPASSLG ADTMSAGGGG PLGDNNQGAD GVGNASGDWH CDSTWMGDRV VTKSTRTWVL  240
PSYNNHQYRE IKSGSVDGSN ANAYFGYSTP WGYFDFNRFH CHFSPRDWQR LINNNWGFRP  300
KRLNFKLFNI QVKEVTDNNG VKTIANNLTS TVQVFTDSDY QLPYVLGSAH EGCLPPFPAD  360
VFMIPQYGYL TLNDGSQAVG RSSFYCLEYF PSQMLRTGNN FQFSYEFENV PFHSSYAHSQ  420
SLDRLMNPLI DQYLYYLSKT INGSGQNQQT LKFSVAGPSN MAVQGRNYIP GPSYRQQRVS  480
TTVTQNNNSE FAWPGASSWA LNGRNSLMNP GPAMASHKEG EDRFFPLSGS LIFGKQGTGR  540
DNVDADKVMI TNEEEIKTTN PVATESYGQV ATNHQSAQAQ AQTGWVQNQG ILPGMVWQDR  600
DVYLQGPIWA KIPHTDGNFH PSPLMGGFGM KHPPPQILIK NTPVPADPPT AFNKDKLNSF  660
ITQYSTGQVS VEIEWELQKE NSKRWNPEIQ YTSNYYKSNN VEFAVNTEGV YSEPRPIGTR  720
YLTRNL                                                             726

SEQ ID NO: 169          moltype = AA  length = 726
FEATURE                 Location/Qualifiers
REGION                  1..726
                        note = Recombinant AAV Capsid Protein
source                  1..726
                        mol_type = protein
                        organism = synthetic construct
SEQUENCE: 169
MSFVDHPPDW LEEVGEGLRE FLGLEAGPPK PKPNQQHQDQ ARGLVLPGYN YLGPGNGLDR  60
GEPVNRADEV AREHDISYNE QLEAGDNPYL KYNHADAEFQ EKLADDTSFG GNLGKAVFQA  120
KKRVLEPFGL VEEGAKTAPT GKRIDDHFPK RKKARTEEDS KPSTSSDAEA GPSGSQQLQI  180
PAQPASSLGA DTMSAGGGGP LGDNNQGADG VGNASGDWHC DSTWMGDRVV TKSTRTWALP  240
TYNNHLYKQI SNSTSGGSSN DNAYFGYSTP WGYFDFNRFH CHFSPRDWQR LINNNWGFRP  300
KRLNFKLFNI QVKEVTDNNG VKTIANNLTS TVQVFTDSDY QLPYVLGSAH EGCLPPFPAD  360
VFMIPQYGYL TLNDGSQAVG RSSFYCLEYF PSQMLRTGNN FQFSYEFENV PFHSSYAHSQ  420
SLDRLMNPLI DQYLYYLSKT INGSGQNQQT LKFSVAGPSN MAVQGRNYIP GPSYRQQRVS  480
TTVTQNNNSE FAWPGASSWA LNGRNSLMNP GPAMASHKEG EDRFFPLSGS LIFGKQGTGR  540
DNVDADKVMI TNEEEIKTTN PVATESYGQV ATNHQSAQAQ AQTGWVQNQG ILPGMVWQDR  600
```

-continued

```
DVYLQGPIWA KIPHTDGNFH PSPLMGGFGM KHPPPQILIK NTPVPADPPT AFNKDKLNSF  660
ITQYSTGQVS VEIEWELQKE NSKRWNPEIQ YTSNYYKSNN VEFAVNTEGV YSEPRPIGTR  720
YLTRNL                                                            726

SEQ ID NO: 170         moltype = AA  length = 736
FEATURE                Location/Qualifiers
REGION                 1..736
                       note = Recombinant AAV Capsid Protein
source                 1..736
                       mol_type = protein
                       organism = synthetic construct
SEQUENCE: 170
MAADGYLPDW LEDNLSEGIR EWWALKPGAP QPKANQQHQD NARGLVLPGY NYLGPGNGLD  60
RGEPVNRADE VAREHDISYN EQLEAGDNPY LKYNHADAEF QERLKEDTSF GGNLGKAVFQ  120
AKKRVLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGNASGDWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSKMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVT VEMEWELKKE NSKRWNPEIQ YTNNYNDPQF VDFAPDSTGE  720
YRTTRPIGTR YLTRNL                                                 736

SEQ ID NO: 171         moltype = AA  length = 735
FEATURE                Location/Qualifiers
REGION                 1..735
                       note = Recombinant AAV Capsid Protein
source                 1..735
                       mol_type = protein
                       organism = synthetic construct
SEQUENCE: 171
MSFVDHPPDW LEEVGEGLRE FLGLEAGPPK PKPNQQHQDQ ARGLVLPGYN YLGPGNGLDR  60
GEPVNAADAA ALEHDKAYDQ QLKAGDNPYL KYNHADAEFQ ERLKEDTSFG GNLGRAVFQA  120
KKRLLEPLGL VEEAAKTAPG KKRPVEQSPQ EPDSSAGIGK SGAQPAKKRL NFGQTGDTES  180
VPDPQPIGEP PAAPSGVGSL TMASGGGAPV ADNNEGADGV GSSSGNWHCD SQWLGDRVIT  240
TSTRTWALPT YNNHLYKQIS NSTSGGSSND NAYFGYSTPW GYFDFNRFHC HFSPRDWQRL  300
INNNWGFRPK RLNFKLFNIQ VKEVTDNNGV KTIANNLTST VQVFTDSDYQ LPYVLGSAHE  360
GCLPPFPADV FMIPQYGYLT LNDGSQAVGR SSFYCLEYFP SQMLRTGNNF QFSYEFENVP  420
FHSSYAHSQS LDRLMNPLID QYLYYLSKTI NGSGQNQQTL KFSVAGPSNM AVQGRNYIPG  480
PSYRQQRVST TVTQNNNSEF AWPGASSWAL NGRNSLMNPG PAMASHKEGE DRFFPLSGSL  540
IFGKQGTGRD NVDADKVMIT NEEEIKTTNP VATESYGQVA TNHQSAQAQA QTGWVQNQGI  600
LPGMVWQDRD VYLQGPIWAK IPHTDGNFHP SPLMGGFGMK HPPPQILIKN TPVPADPPTA  660
FNKDKLNSFI TQYSTGQVSV EIEWELQKEN SKRWNPEIQY TNNYNDPQFV DFAPDSTGEY  720
RTTRPIGTRY LTRPL                                                  735

SEQ ID NO: 172         moltype = AA  length = 735
FEATURE                Location/Qualifiers
REGION                 1..735
                       note = Recombinant AAV Capsid Protein
source                 1..735
                       mol_type = protein
                       organism = synthetic construct
SEQUENCE: 172
MSFVDHPPDW LEEVGEGLRE FLGLEAGPPK PKPNQQHQDQ ARGLVLPGYN YLGPGNGLDR  60
GEPVNRADEV AREHDISYNE QLEAGDNPYL KYNHADAEFQ EKLADDTSFG GNLGKAVFQA  120
KKRVLEPLGL VEEAAKTAPG KKRPVEQSPQ EPDSSAGIGK SGAQPAKKRL NFGQTGDTES  180
VPDPQPIGEP PAAPSGVGSL TMASGGGAPV ADNNEGADGV GSSSGNWHCD SQWLGDRVIT  240
TSTRTWALPT YNNHLYKQIS NSTSGGSSND NAYFGYSTPW GYFDFNRFHC HFSPRDWQRL  300
INNNWGFRPK RLNFKLFNIQ VKEVTDNNGV KTIANNLTST VQVFTDSDYQ LPYVLGSAHE  360
GCLPPFPADV FMIPQYGYLT LNDGSQAVGR SSFYCLEYFP SQMLRTGNNF QFSYEFENVP  420
FHSSYAHSQS LDRLMNPLID QYLYYLSKTI NGSGQNQQTL KFSVAGPSNM AVQGRNYIPG  480
PSYRQQRVST TVTQNNNSEF AWPGASSWAL NGRNSLMNPG PAMASHKEGE DRFFPLSGSL  540
IFGKQGTGRD NVDADKVMIT NEEEIKTTNP VATESYGQVA TNHQSAQAQA QTGWVQNQGI  600
LPGMVWQDRD VYLQGPIWAK IPHTDGNFHP SPLMGGFGMK HPPPQILIKN TPVPADPPTA  660
FNKDKLNSFI TQYSTGQVSV EIEWELKKEN SKRWNPEIQY TSNYYKSNNV EFAVNTEGVY  720
SEPRPIGTRY LTRNL                                                  735

SEQ ID NO: 173         moltype = AA  length = 726
FEATURE                Location/Qualifiers
REGION                 1..726
                       note = Recombinant AAV Capsid Protein
source                 1..726
                       mol_type = protein
                       organism = synthetic construct
SEQUENCE: 173
MSFVDHPPDW LEEVGEGLRE FLGLEAGPPK PKPNQQHQDQ ARGLVLPGYN YLGPGNGLDR  60
```

```
GEPVNRADEV AREHDISYNE QLEAGDNPYL KYNHADAEFQ EKLADDTSFG GNLGKAVFQA  120
KKRVLEPFGL VEEGAKTAPT GKRIDDHFPK RKKARTEEDS KPSTSSDAEA GPSGSQQLQI  180
PAQPASSLGA DTMSAGGGGP LGDNNQGADG VGNASGDWHC DSTWMGDRVV TKSTRTWALP  240
TYNNHLYKQI SNSTSGGSSN DNAYFGYSTP WGYFDFNRFH CHFSPRDWQR LINNNWGFRP  300
KRLNFKLFNI QVKEVTDNNG VKTIANNLTS TVQVFTDSDY QLPYVLGSAH EGCLPPFPAD  360
VFMIPQYGYL TLNDGSQAVG RSSFYCLEYF PSQMLRTGNN FQFSYEFENV PFHSSYAHSQ  420
SLDRLMNPLI DQYLYYLSKT INGSGQNQQT LKFSVAGPSN MAVQGRNYIP GPSYRQQRVS  480
TTVTQNNNSE FAWPGASSWA LNGRNSLMNP GPAMASHKEG EDRFFPLSGS LIFGKQGTGR  540
DNVDADKVMI TNEEEIKTTN PVATESYGQV ATNHQSAQAQ AQTGWVQNQG ILPGMVWQDR  600
DVYLQGPIWA KIPHTDGNFH PSPLMGGFGM KHPPPQILIK NTPVPADPPT AFNKDKLNSF  660
ITQYSTGQVS VEIEWELQKE NSKRWNPEIQ YTSNYYKSNN VEFAVNTEGV YSEPRPIGTR  720
YLTRNL                                                             726

SEQ ID NO: 174         moltype = AA  length = 726
FEATURE                Location/Qualifiers
REGION                 1..726
                       note = Recombinant AAV Capsid Protein
source                 1..726
                       mol_type = protein
                       organism = synthetic construct
SEQUENCE: 174
MSFVDHPPDW LEEVGEGLRE FLGLEAGPPK PKPNQQHQDQ ARGLVLPGYN YLGPGNGLDR  60
GEPVNRADEV AREHDISYNE QLEAGDNPYL KYNHADAEFQ EKLADDTSFG GNLGKAVFQA  120
KKRVLEPFGL VEEGAKTAPT GKRIDDHFPK RKKARTEEDS KPSTSSDAEA GPSGSQQLQI  180
PAQPASSLGA DTMSAGGGAP VADNNEGADG VGSSSGNWHC DSQWLGDRVI TTSTRTWALP  240
TYNNHLYKQI SNSTSGGSSN DNAYFGYSTP WGYFDFNRFH CHFSPRDWQR LINNNWGFRP  300
KRLNFKLFNI QVKEVTDNNG VKTIANNLTS TVQVFTDSDY QLPYVLGSAH EGCLPPFPAD  360
VFMIPQYGYL TLNDGSQAVG RSSFYCLEYF PSQMLRTGNN FQFSYEFENV PFHSSYAHSQ  420
SLDRLMNPLI DQYLYYLSKT INGSGQNQQT LKFSVAGPSN MAVQGRNYIP GPSYRQQRVS  480
TTVTQNNNSE FAWPGASSWA LNGRNSLMNP GPAMASHKEG EDRFFPLSGS LIFGKQGTGR  540
DNVDADKVMI TNEEEIKTTN PVATESYGQV ATNHQSAQAQ AQTGWVQNQG ILPGMVWQDR  600
DVYLQGPIWA KIPHTDGNFH PSPLMGGFGM KHPPPQILIK NTPVPADPPT AFNKDKLNSF  660
ITQYSTGQVS VEIEWELQKE NSKRWNPEIQ YTSNYYKSNN VEFAVNTEGV YSEPRPIGTR  720
YLTRNL                                                             726

SEQ ID NO: 175         moltype = AA  length = 726
FEATURE                Location/Qualifiers
REGION                 1..726
                       note = Recombinant AAV Capsid Protein
source                 1..726
                       mol_type = protein
                       organism = synthetic construct
SEQUENCE: 175
MSFVDHPPDW LEEVGEGLRE FLGLEAGPPK PKPNQQHQDQ ARGLVLPGYK YLGPGNGLDK  60
GEPVNAADAA ALEHDKAYDQ QLKAGDNPYL KYNHADAEFQ EKLADDTSFG GNLGKAVFQA  120
KKRVLEPFGL VEEGAKTAPT GKRIDDHFPK RKKARTEEDS KPSTSSDAEA GPSGSQQLQI  180
PAQPASSLGA DTMSAGGGAP VADNNEGADG VGSSSGNWHC DSQWLGDRVI TTSTRTWALP  240
TYNNHLYKQI SNSTSGGSSN DNAYFGYSTP WGYFDFNRFH CHFSPRDWQR LINNNWGFRP  300
KRLNFKLFNI QVKEVTDNNG VKTIANNLTS TVQVFTDSDY QLPYVLGSAH EGCLPPFPAD  360
VFMIPQYGYL TLNDGSQAVG RSSFYCLEYF PSQMLRTGNN FQFSYEFENV PFHSSYAHSQ  420
SLDRLMNPLI DQYLYYLSKT INGSGQNQQT LKFSVAGPSN MAVQGRNYIP GPSYRQQRVS  480
TTVTQNNNSE FAWPGASSWA LNGRNSLMNP GPAMASHKEG EDRFFPLSGS LIFGKQGTGR  540
DNVDADKVMI TNEEEIKTTN PVATESYGQV ATNHQSAQAQ AQTGWVQNQG ILPGMVWQDR  600
DVYLQGPIWA KIPHTDGNFH PSPLMGGFGM KHPPPQILIK NTPVPADPPT AFNKDKLNSF  660
ITQYSTGQVS VEIEWELQKE NSKRWNPEIQ YTSNYYKSNN VEFAVNTEGV YSEPRPIGTR  720
YLTRNL                                                             726

SEQ ID NO: 176         moltype = AA  length = 727
FEATURE                Location/Qualifiers
REGION                 1..727
                       note = Recombinant AAV Capsid Protein
source                 1..727
                       mol_type = protein
                       organism = synthetic construct
SEQUENCE: 176
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPFG LVEEGAKTAP TGKRIDDHFP KRKKARTEED SKPSTSSDAE AGPSGSQQLQ  180
IPAQPASSLG ADTMSAGGGG PLGDNNEGAD GVGSSSGNWH CDSQWLGDRV ITTSTRTWAL  240
PTYNNHLYKQ ISNSTSGGSS NDNAYFGYST PWGYFDFNRF HCHFSPRDWQ RLINNNWGFR  300
PKRLNFKLFN IQVKEVTDNN GVKTIANNLT STVQVFTDSD YQLPYVLGSA HEGCLPPFPA  360
DVFMIPQYGY LTLNDGSQAV GRSSFYCLEY FPSQMLRTGN NFQFSYEFEN VPFHSSYAHS  420
QSLDRLMNPL IDQYLYYLSK TINGSGQNQQ TLKFSVAGPS NMAVQGRNYI PGPSYRQQRV  480
STTVTQNNNS EFAWPGASSW ALNGRNSLMN PGPAMASHKE GEDRFFPLSG SLIFGKQGTG  540
RDNVDADKVM ITNEEEIKTT NPVATESYGQ VATNHQSAQA QAQTGWVQNQ GILPGMVWQD  600
RDVYLQGPIW AKIPHTDGNF HPSPLMGGFG MKHPPPQILI KNTPVPADPP TAFNKDKLNS  660
FITQYSTGQV SVEIEWELQK ENSKRWNPEI QYTSNYYKSN NVEFAVNTEG VYSEPRPIGT  720
RYLTRNL                                                            727
```

```
SEQ ID NO: 177          moltype = AA  length = 727
FEATURE                 Location/Qualifiers
REGION                  1..727
                        note = Recombinant AAV Capsid Protein
source                  1..727
                        mol_type = protein
                        organism = synthetic construct
SEQUENCE: 177
MAADGYLPDW LEDNLSEGIR EWWALKPGAP QPKANQQHQD NARGLVLPGY KYLGPGNGLD  60
KGEPVNAADA AALEHDKAYD QQLEAGDNPY LKYNHADAEF QEKLADDTSF GGNLGKAVFQ  120
AKKRVLEPFG LVEEGAKTAP TGKRIDDHFP KRKKARTEED SKPSTSSDAE AGPSGSQQLQ  180
IPAQPASSLG ADTMSAGGGG PLGDNNQGAD GVGNASGDWH CDSTWMGDRV VTTSTRTWAL  240
PTYNNHLYKQ ISNSTSGGSS NDNAYFGYST PWGYFDFNRF HCHFSPRDWQ RLINNNWGFR  300
PKRLNFKLFN IQVKEVTDNN GVKTIANNLT STVQVFTDSD YQLPYVLGSA HEGCLPPFPA  360
DVFMIPQYGY LTLNDGSQAV GRSSFYCLEY FPSQMLRTGN NFQFSYEFEN VPFHSSYAHS  420
QSLDRLMNPL IDQYLYYLSK TINGSGQNQQ TLKFSVAGPS NMAVQGRNYI PGPSYRQQRV  480
STTVTQNNNS EFAWPGASSW ALNGRNSLMN PGPAMASHKE GEDRFFPLSG SLIFGKQGTG  540
RDNVDADKVM ITNEEEIKTT NPVATESYGQ VATNHQSAQA QAQTGWVQNQ GILPGMVWQD  600
RDVYLQGPIW AKIPHTDGNF HPSPLMGGFG MKHPPPQILI KNTPVPADPP TAFNKDKLNS  660
FITQYSTGQV SVEIEWELQK ENSKRWNPEI QYTSNYYKSN NVEFAVNTEG VYSEPRPIGT  720
RYLTRNL                                                            727

SEQ ID NO: 178          moltype = AA  length = 735
FEATURE                 Location/Qualifiers
REGION                  1..735
                        note = Recombinant AAV Capsid Protein
source                  1..735
                        mol_type = protein
                        organism = synthetic construct
SEQUENCE: 178
MSFVDHPPDW LEEVGEGLRE FLGLEAGPPK PKPNQQHQDQ ARGLVLPGYN YLGPGNGLDR  60
GEPVNRADEV AREHDISYNE QLEAGDNPYL KYNHADAEFQ ERLKEDTSFG GNLGRAVFQA  120
KKRLLEPLGL VEEAAKTAPG KKRPVEQSPQ EPDSSAGIGK SGAQPAKKRL NFGQTGDTES  180
VPDPQPIGEP PAAPSGVGSL TMASGGGAPV ADNNEGADGV GSSSGNWHCD SQWLGDRVIT  240
TSTRTWALPT YNNHLYKQIS NSTSGGSSND NAYFGYSTPW GYFDFNRFHC HFSPRDWQRL  300
INNNWGFRPK RLNFKLFNIQ VKEVTDNNGV KTIANNLTST VQVFTDSDYQ LPYVLGSAHE  360
GCLPPFPADV FMIPQYGYLT LNDGSQAVGR SSFYCLEYFP SQMLRTGNNF QFSYEFENVP  420
FHSSYAHSQS LDRLMNPLID QYLYYLSKTI NGSGQNQQTL KFSVAGPSNM AVQGRNYIPG  480
PSYRQQRVST TVTQNNNSEF AWPGASSWAL NGRNSLMNPG PAMASHKEGE DRFFPLSGSL  540
IFGKQGTGRD NVDADKVMIT NEEEIKTTNP VATESYGQVA TNHQSAQAQA QTGWVQNQGI  600
LPGMVWQDRD VYLQGPIWAK IPHTDGNFHP SPLMGGFGMK HPPPQILIKN TPVPADPPTA  660
FNKDKLNSFI TQYSTGQVSV EIEWELQKEN SKRWNPEIQY TSNYYKSNNV EFAVNTEGVY  720
SEPRPIGTRY LTRNL                                                   735

SEQ ID NO: 179          moltype = AA  length = 736
FEATURE                 Location/Qualifiers
REGION                  1..736
                        note = Recombinant AAV Capsid Protein
source                  1..736
                        mol_type = protein
                        organism = synthetic construct
SEQUENCE: 179
MAADGYLPDW LEDNLSEGIR EWWALKPGAP QPKANQQHQD NARGLVLPGY NYLGPGNGLD  60
RGEPVNRADE VAREHDISYN EQLEAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                  736

SEQ ID NO: 180          moltype = AA  length = 736
FEATURE                 Location/Qualifiers
REGION                  1..736
                        note = Recombinant AAV Capsid Protein
source                  1..736
                        mol_type = protein
                        organism = synthetic construct
SEQUENCE: 180
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QEKLADDTSF GGNLGKAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
```

```
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 181         moltype = AA  length = 736
FEATURE                Location/Qualifiers
REGION                 1..736
                       note = Recombinant AAV Capsid Protein
source                 1..736
                       mol_type = protein
                       organism = synthetic construct
SEQUENCE: 181
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QEKLADDTSF GGNLGKAVFQ  120
AKKRVLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 182         moltype = AA  length = 735
FEATURE                Location/Qualifiers
REGION                 1..735
                       note = Recombinant AAV Capsid Protein
source                 1..735
                       mol_type = protein
                       organism = synthetic construct
SEQUENCE: 182
MSFVDHPPDW LEEVGEGLRE FLGLEAGPPK PKPNQQHQDQ ARGLVLPGYN YLGPGNGLDR  60
GEPVNAADAA ALEHDKAYDQ QLKAGDNPYL KYNHADAEFQ ERLKEDTSFG GNLGRAVFQA  120
KKRLLEPLGL VEEAAKTAPG KKRPVEQSPQ EPDSSAGIGK SGAQPAKKRL NFGQTGDTES  180
VPDPQPIGEP PAAPSGVGSL TMASGGGAPV ADNNEGADGV GSSSGNWHCD SQWLGDRVIT  240
TSTRTWALPT YNNHLYKQIS NSTSGGSSND NAYFGYSTPW GYFDFNRFHC HFSPRDWQRL  300
INNNWGFRPK RLNFKLFNIQ VKEVTDNNGV KTIANNLTST VQVFTDSDYQ LPYVLGSAHE  360
GCLPPFPADV FMIPQYGYLT LNDGSQAVGR SSFYCLEYFP SQMLRTGNNF QFSYEFENVP  420
FHSSYAHSQS LDRLMNPLID QYLYYLSKTI NGSGQNQQTL KFSVAGPSNM AVQGRNYIPG  480
PSYRQQRVST TVTQNNNSEF AWPGASSWAL NGRNSLMNPG PAMASHKEGE DRFFPLSGSL  540
IFGKQGTGRD NVDADKVMIT NEEEIKTTNP VATESYGQVA TNHQSAQAQA QTGWVQNQGI  600
LPGMVWQDRD VYLQGPIWAK IPHTDGNFHP SPLMGGFGMK HPPPQILIKN TPVPADPPTA  660
FNKDKLNSFI TQYSTGQVSV EIEWELQKEN SKRWNPEIQY TNNYNDPQFV DFAPDSTGEY  720
RTTRPIGTRY LTRPL                                                  735

SEQ ID NO: 183         moltype = AA  length = 736
FEATURE                Location/Qualifiers
REGION                 1..736
                       note = Recombinant AAV Capsid Protein
source                 1..736
                       mol_type = protein
                       organism = synthetic construct
SEQUENCE: 183
MAADGYLPDW LEDNLSEGIR EWWALKPGAP QPKANQQHQD NARGLVLPGY NYLGPGNGLD  60
RGEPVNRADE VAREHDISYN EQLEAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT IGYHKSGAAQ LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 184         moltype = AA  length = 736
FEATURE                Location/Qualifiers
REGION                 1..736
                       note = Recombinant AAV Capsid Protein
```

```
source                  1..736
                        mol_type = protein
                        organism = synthetic construct
SEQUENCE: 184
MAADGYLPDW LEDNLSEGIR EWWALKPGAP QPKANQQHQD NARGLVLPGY NYLGPGNGLD  60
RGEPVNRADE VAREHDISYN EQLEAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQANYGQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 185          moltype = AA  length = 736
FEATURE                 Location/Qualifiers
REGION                  1..736
                        note = Recombinant AAV Capsid Protein
source                  1..736
                        mol_type = protein
                        organism = synthetic construct
SEQUENCE: 185
MAADGYLPDW LEDNLSEGIR EWWALKPGAP QPKANQQHQD NARGLVLPGY NYLGPGNGLD  60
RGEPVNRADE VAREHDISYN EQLEAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT IGYHKSGAAQ LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQNVSYQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 186          moltype = AA  length = 736
FEATURE                 Location/Qualifiers
REGION                  1..736
                        note = Recombinant AAV Capsid Protein
source                  1..736
                        mol_type = protein
                        organism = synthetic construct
SEQUENCE: 186
MAADGYLPDW LEDNLSEGIR EWWALKPGAP QPKANQQHQD NARGLVLPGY NYLGPGNGLD  60
RGEPVNRADE VAREHDISYN EQLEAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNLNSM LIWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 187          moltype = AA  length = 736
FEATURE                 Location/Qualifiers
REGION                  1..736
                        note = Recombinant AAV Capsid Protein
source                  1..736
                        mol_type = protein
                        organism = synthetic construct
SEQUENCE: 187
MAADGYLPDW LEDNLSEGIR EWWALKPGAP QPKANQQHQD NARGLVLPGY NYLGPGNGLD  60
RGEPVNRADE VAREHDISYN EQLEAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT IGYHKSGAAQ LKFSVAGPSN MAVQGRNYIP  480
GPSYRQQRVS TTVTQNNNSE FAWPGASSWA LNGRNSLMNP GPAMASHKEG EDRFFPLSGS  540
```

```
LIFGKQGTGR DNVDADKVMI TNEEEIKTTN PVATESYGQV ATNHQANYGQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 188         moltype = AA  length = 736
FEATURE                Location/Qualifiers
REGION                 1..736
                       note = Recombinant AAV Capsid Protein
source                 1..736
                       mol_type = protein
                       organism = synthetic construct
SEQUENCE: 188
MAADGYLPDW LEDNLSEGIR EWWALKPGAP QPKANQQHQD NARGLVLPGY NYLGPGNGLD  60
RGEPVNRADE VAREHDISYN EQLEAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNLNSM LIWPGASSWA LNGRNSLMNP GPAMASHKEG EDRFFPLSGS  540
LIFGKQGTGR DNVDADKVMI TNEEEIKTTN PVATESYGQV ATNHQANYGQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 189         moltype = AA  length = 735
FEATURE                Location/Qualifiers
REGION                 1..735
                       note = Recombinant AAV Capsid Protein
source                 1..735
                       mol_type = protein
                       organism = synthetic construct
SEQUENCE: 189
MSFVDHPPDW LEEVGEGLRE FLGLEAGPPK PKPNQQHQDQ ARGLVLPGYN YLGPGNGLDR  60
GEPVNRADEV AREHDISYNE QLEAGDNPYL KYNHADAEFQ EKLADDTSFG GNLGKAVFQA  120
KKRVLEPLGL VEEAAKTAPG KKRPVEQSPQ EPDSSAGIGK SGAQPAKKRL NFGQTGDTES  180
VPDPQPIGEP PAAPSGVGSL TMASGGGAPV ADNNEGADGV GSSSGNWHCD SQWLGDRVIT  240
TSTRTWALPT YNNHLYKQIS NSTSGGSSND NAYFGYSTPW GYFDFNRFHC HFSPRDWQRL  300
INNNWGFRPK RLNFKLFNIQ VKEVTDNNGV KTIANNLTST VQVFTDSDYQ LPYVLGSAHE  360
GCLPPFPADV FMIPQYGYLT LNDGSQAVGR SSFYCLEYFP SQMLRTGNNF QFSYEFENVP  420
FHSSYAHSQS LDRLMNPLID QYLYYLSKTI GYHKSGAAQL KFSVAGPSNM AVQGRNYIPG  480
PSYRQQRVST TVTQNNNSEF AWPGASSWAL NGRNSLMNPG PAMASHKEGE DRFFPLSGSL  540
IFGKQGTGRD NVDADKVMIT NEEEIKTTNP VATESYGQVA TNHQSAQAQA QTGWVQNQGI  600
LPGMVWQDRD VYLQGPIWAK IPHTDGNFHP SPLMGGFGMK HPPPQILIKN TPVPADPPTA  660
FNKDKLNSFI TQYSTGQVSV EIEWELKKEN SKRWNPEIQY TSNYYKSNNV EFAVNTEGVY  720
SEPRPIGTRY LTRNL                                                  735

SEQ ID NO: 190         moltype = AA  length = 735
FEATURE                Location/Qualifiers
REGION                 1..735
                       note = Recombinant AAV Capsid Protein
source                 1..735
                       mol_type = protein
                       organism = synthetic construct
SEQUENCE: 190
MSFVDHPPDW LEEVGEGLRE FLGLEAGPPK PKPNQQHQDQ ARGLVLPGYN YLGPGNGLDR  60
GEPVNRADEV AREHDISYNE QLEAGDNPYL KYNHADAEFQ EKLADDTSFG GNLGKAVFQA  120
KKRVLEPLGL VEEAAKTAPG KKRPVEQSPQ EPDSSAGIGK SGAQPAKKRL NFGQTGDTES  180
VPDPQPIGEP PAAPSGVGSL TMASGGGAPV ADNNEGADGV GSSSGNWHCD SQWLGDRVIT  240
TSTRTWALPT YNNHLYKQIS NSTSGGSSND NAYFGYSTPW GYFDFNRFHC HFSPRDWQRL  300
INNNWGFRPK RLNFKLFNIQ VKEVTDNNGV KTIANNLTST VQVFTDSDYQ LPYVLGSAHE  360
GCLPPFPADV FMIPQYGYLT LNDGSQAVGR SSFYCLEYFP SQMLRTGNNF QFSYEFENVP  420
FHSSYAHSQS LDRLMNPLID QYLYYLSKTI NGSGQNQQTL KFSVAGPSNM AVQGRNYIPG  480
PSYRQQRVST TVTQNNNSEF AWPGASSWAL NGRNSLMNPG PAMASHKEGE DRFFPLSGSL  540
IFGKQGTGRD NVDADKVMIT NEEEIKTTNP VATESYGQVA TNHQANYGQA QTGWVQNQGI  600
LPGMVWQDRD VYLQGPIWAK IPHTDGNFHP SPLMGGFGMK HPPPQILIKN TPVPADPPTA  660
FNKDKLNSFI TQYSTGQVSV EIEWELKKEN SKRWNPEIQY TSNYYKSNNV EFAVNTEGVY  720
SEPRPIGTRY LTRNL                                                  735

SEQ ID NO: 191         moltype = AA  length = 735
FEATURE                Location/Qualifiers
REGION                 1..735
                       note = Recombinant AAV Capsid Protein
source                 1..735
                       mol_type = protein
                       organism = synthetic construct
SEQUENCE: 191
```

```
MSFVDHPPDW LEEVGEGLRE FLGLEAGPPK PKPNQQHQDQ ARGLVLPGYN YLGPGNGLDR  60
GEPVNRADEV AREHDISYNE QLEAGDNPYL KYNHADAEFQ EKLADDTSFG GNLGKAVFQA  120
KKRVLEPLGL VEEAAKTAPG KKRPVEQSPQ EPDSSAGIGK SGAQPAKKRL NFGQTGDTES  180
VPDPQPIGEP PAAPSGVGSL TMASGGGAPV ADNNEGADGV GSSSGNWHCD SQWLGDRVIT  240
TSTRTWALPT YNNHLYKQIS NSTSGGSSND NAYFGYSTPW GYFDFNRFHC HFSPRDWQRL  300
INNNWGFRPK RLNFKLFNIQ VKEVTDNNGV KTIANNLTST VQVFTDSDYQ LPYVLGSAHE  360
GCLPPFPADV FMIPQYGYLT LNDGSQAVGR SSFYCLEYFP SQMLRTGNNF QFSYEFENVP  420
FHSSYAHSQS LDRLMNPLID QYLYYLSKTI GYHKSGAAQL KFSVAGPSNM AVQGRNYIPG  480
PSYRQQRVST TVTQNNNSEF AWPGASSWAL NGRNSLMNPG PAMASHKEGE DRFFPLSGSL  540
IFGKQGTGRD NVDADKVMIT NEEEIKTTNP VATESYGQVA TNHQNVSYQA QTGWVQNQGI  600
LPGMVWQDRD VYLQGPIWAK IPHTDGNFHP SPLMGGFGMK HPPPQILIKN TPVPADPPTA  660
FNKDKLNSFI TQYSTGQVSV EIEWELKKEN SKRWNPEIQY TSNYYKSNNV EFAVNTEGVY  720
SEPRPIGTRY LTRNL                                                  735

SEQ ID NO: 192          moltype = AA  length = 735
FEATURE                 Location/Qualifiers
REGION                  1..735
                        note = Recombinant AAV Capsid Protein
source                  1..735
                        mol_type = protein
                        organism = synthetic construct
SEQUENCE: 192
MSFVDHPPDW LEEVGEGLRE FLGLEAGPPK PKPNQQHQDQ ARGLVLPGYN YLGPGNGLDR  60
GEPVNRADEV AREHDISYNE QLEAGDNPYL KYNHADAEFQ EKLADDTSFG GNLGKAVFQA  120
KKRVLEPLGL VEEAAKTAPG KKRPVEQSPQ EPDSSAGIGK SGAQPAKKRL NFGQTGDTES  180
VPDPQPIGEP PAAPSGVGSL TMASGGGAPV ADNNEGADGV GSSSGNWHCD SQWLGDRVIT  240
TSTRTWALPT YNNHLYKQIS NSTSGGSSND NAYFGYSTPW GYFDFNRFHC HFSPRDWQRL  300
INNNWGFRPK RLNFKLFNIQ VKEVTDNNGV KTIANNLTST VQVFTDSDYQ LPYVLGSAHE  360
GCLPPFPADV FMIPQYGYLT LNDGSQAVGR SSFYCLEYFP SQMLRTGNNF QFSYEFENVP  420
FHSSYAHSQS LDRLMNPLID QYLYYLSKTI NGSGQNQQTL KFSVAGPSNM AVQGRNYIPG  480
PSYRQQRVST TVTQNLNSML IWPGASSWAL NGRNSLMNPG PAMASHKEGE DRFFPLSGSL  540
IFGKQGTGRD NVDADKVMIT NEEEIKTTNP VATESYGQVA TNHQSAQAQA QTGWVQNQGI  600
LPGMVWQDRD VYLQGPIWAK IPHTDGNFHP SPLMGGFGMK HPPPQILIKN TPVPADPPTA  660
FNKDKLNSFI TQYSTGQVSV EIEWELKKEN SKRWNPEIQY TSNYYKSNNV EFAVNTEGVY  720
SEPRPIGTRY LTRNL                                                  735

SEQ ID NO: 193          moltype = AA  length = 735
FEATURE                 Location/Qualifiers
REGION                  1..735
                        note = Recombinant AAV Capsid Protein
source                  1..735
                        mol_type = protein
                        organism = synthetic construct
SEQUENCE: 193
MSFVDHPPDW LEEVGEGLRE FLGLEAGPPK PKPNQQHQDQ ARGLVLPGYN YLGPGNGLDR  60
GEPVNRADEV AREHDISYNE QLEAGDNPYL KYNHADAEFQ EKLADDTSFG GNLGKAVFQA  120
KKRVLEPLGL VEEAAKTAPG KKRPVEQSPQ EPDSSAGIGK SGAQPAKKRL NFGQTGDTES  180
VPDPQPIGEP PAAPSGVGSL TMASGGGAPV ADNNEGADGV GSSSGNWHCD SQWLGDRVIT  240
TSTRTWALPT YNNHLYKQIS NSTSGGSSND NAYFGYSTPW GYFDFNRFHC HFSPRDWQRL  300
INNNWGFRPK RLNFKLFNIQ VKEVTDNNGV KTIANNLTST VQVFTDSDYQ LPYVLGSAHE  360
GCLPPFPADV FMIPQYGYLT LNDGSQAVGR SSFYCLEYFP SQMLRTGNNF QFSYEFENVP  420
FHSSYAHSQS LDRLMNPLID QYLYYLSKTI GYHKSGAAQL KFSVAGPSNM AVQGRNYIPG  480
PSYRQQRVST TVTQNNNSEF AWPGASSWAL NGRNSLMNPG PAMASHKEGE DRFFPLSGSL  540
IFGKQGTGRD NVDADKVMIT NEEEIKTTNP VATESYGQVA TNHQANYGQA QTGWVQNQGI  600
LPGMVWQDRD VYLQGPIWAK IPHTDGNFHP SPLMGGFGMK HPPPQILIKN TPVPADPPTA  660
FNKDKLNSFI TQYSTGQVSV EIEWELKKEN SKRWNPEIQY TSNYYKSNNV EFAVNTEGVY  720
SEPRPIGTRY LTRNL                                                  735

SEQ ID NO: 194          moltype = AA  length = 735
FEATURE                 Location/Qualifiers
REGION                  1..735
                        note = Recombinant AAV Capsid Protein
source                  1..735
                        mol_type = protein
                        organism = synthetic construct
SEQUENCE: 194
MSFVDHPPDW LEEVGEGLRE FLGLEAGPPK PKPNQQHQDQ ARGLVLPGYN YLGPGNGLDR  60
GEPVNRADEV AREHDISYNE QLEAGDNPYL KYNHADAEFQ EKLADDTSFG GNLGKAVFQA  120
KKRVLEPLGL VEEAAKTAPG KKRPVEQSPQ EPDSSAGIGK SGAQPAKKRL NFGQTGDTES  180
VPDPQPIGEP PAAPSGVGSL TMASGGGAPV ADNNEGADGV GSSSGNWHCD SQWLGDRVIT  240
TSTRTWALPT YNNHLYKQIS NSTSGGSSND NAYFGYSTPW GYFDFNRFHC HFSPRDWQRL  300
INNNWGFRPK RLNFKLFNIQ VKEVTDNNGV KTIANNLTST VQVFTDSDYQ LPYVLGSAHE  360
GCLPPFPADV FMIPQYGYLT LNDGSQAVGR SSFYCLEYFP SQMLRTGNNF QFSYEFENVP  420
FHSSYAHSQS LDRLMNPLID QYLYYLSKTI NGSGQNQQTL KFSVAGPSNM AVQGRNYIPG  480
PSYRQQRVST TVTQNLNSML IWPGASSWAL NGRNSLMNPG PAMASHKEGE DRFFPLSGSL  540
IFGKQGTGRD NVDADKVMIT NEEEIKTTNP VATESYGQVA TNHQANYGQA QTGWVQNQGI  600
LPGMVWQDRD VYLQGPIWAK IPHTDGNFHP SPLMGGFGMK HPPPQILIKN TPVPADPPTA  660
FNKDKLNSFI TQYSTGQVSV EIEWELKKEN SKRWNPEIQY TSNYYKSNNV EFAVNTEGVY  720
SEPRPIGTRY LTRNL                                                  735
```

```
SEQ ID NO: 195          moltype = AA  length = 727
FEATURE                 Location/Qualifiers
REGION                  1..727
                        note = Recombinant AAV Capsid Protein
source                  1..727
                        mol_type = protein
                        organism = synthetic construct
SEQUENCE: 195
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPFG LVEEGAKTAP TGKRIDDHFP KRKKARTEED SKPSTSSDAE AGPSGSQQLQ  180
IPAQPASSLG ADTMSAGGGG PLGDNNEGAD GVGSSSGNWH CDSQWLGDRV ITTSTRTWAL  240
PTYNNHLYKQ ISNSTSGGSS NDNAYFGYST PWGYFDFNRF HCHFSPRDWQ RLINNNWGFR  300
PKRLNFKLFN IQVKEVTDNN GVKTIANNLT STVQVFTDSD YQLPYVLGSA HEGCLPPFPA  360
DVFMIPQYGY LTLNDGSQAV GRSSFYCLEY FPSQMLRTGN NFQFSYEFEN VPFHSSYAHS  420
QSLDRLMNPL IDQYLYYLSK TIGYHKSGAA QLKFSVAGPS NMAVQGRNYI PGPSYRQQRV  480
STTVTQNNNS EFAWPGASSW ALNGRNSLMN PGPAMASHKE GEDRFFPLSG SLIFGKQGTG  540
RDNVDADKVM ITNEEEIKTT NPVATESYGQ VATNHQSAQA QAQTGWVQNQ GILPGMVWQD  600
RDVYLQGPIW AKIPHTDGNF HPSPLMGGFG MKHPPPQILI KNTPVPADPP TAFNKDKLNS  660
FITQYSTGQV SVEIEWELQK ENSKRWNPEI QYTSNYYKSN NVEFAVNTEG VYSEPRPIGT  720
RYLTRNL                                                           727

SEQ ID NO: 196          moltype = AA  length = 727
FEATURE                 Location/Qualifiers
REGION                  1..727
                        note = Recombinant AAV Capsid Protein
source                  1..727
                        mol_type = protein
                        organism = synthetic construct
SEQUENCE: 196
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPFG LVEEGAKTAP TGKRIDDHFP KRKKARTEED SKPSTSSDAE AGPSGSQQLQ  180
IPAQPASSLG ADTMSAGGGG PLGDNNEGAD GVGSSSGNWH CDSQWLGDRV ITTSTRTWAL  240
PTYNNHLYKQ ISNSTSGGSS NDNAYFGYST PWGYFDFNRF HCHFSPRDWQ RLINNNWGFR  300
PKRLNFKLFN IQVKEVTDNN GVKTIANNLT STVQVFTDSD YQLPYVLGSA HEGCLPPFPA  360
DVFMIPQYGY LTLNDGSQAV GRSSFYCLEY FPSQMLRTGN NFQFSYEFEN VPFHSSYAHS  420
QSLDRLMNPL IDQYLYYLSK TINGSGQNQQ TLKFSVAGPS NMAVQGRNYI PGPSYRQQRV  480
STTVTQNNNS EFAWPGASSW ALNGRNSLMN PGPAMASHKE GEDRFFPLSG SLIFGKQGTG  540
RDNVDADKVM ITNEEEIKTT NPVATESYGQ VATNHQSAQA QAQTGWVQNQ GILPGMVWQD  600
RDVYLQGPIW AKIPHTDGNF HPSPLMGGFG MKHPPPQILI KNTPVPADPP TAFNKDKLNS  660
FITQYSTGQV SVEIEWELQK ENSKRWNPEI QYTSNYYKSN NVEFAVNTEG VYSEPRPIGT  720
RYLTRNL                                                           727

SEQ ID NO: 197          moltype = AA  length = 727
FEATURE                 Location/Qualifiers
REGION                  1..727
                        note = Recombinant AAV Capsid Protein
source                  1..727
                        mol_type = protein
                        organism = synthetic construct
SEQUENCE: 197
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPFG LVEEGAKTAP TGKRIDDHFP KRKKARTEED SKPSTSSDAE AGPSGSQQLQ  180
IPAQPASSLG ADTMSAGGGG PLGDNNEGAD GVGSSSGNWH CDSQWLGDRV ITTSTRTWAL  240
PTYNNHLYKQ ISNSTSGGSS NDNAYFGYST PWGYFDFNRF HCHFSPRDWQ RLINNNWGFR  300
PKRLNFKLFN IQVKEVTDNN GVKTIANNLT STVQVFTDSD YQLPYVLGSA HEGCLPPFPA  360
DVFMIPQYGY LTLNDGSQAV GRSSFYCLEY FPSQMLRTGN NFQFSYEFEN VPFHSSYAHS  420
QSLDRLMNPL IDQYLYYLSK TIGYHKSGAA QLKFSVAGPS NMAVQGRNYI PGPSYRQQRV  480
STTVTQNNNS EFAWPGASSW ALNGRNSLMN PGPAMASHKE GEDRFFPLSG SLIFGKQGTG  540
RDNVDADKVM ITNEEEIKTT NPVATESYGQ VATNHQNVSY QAQTGWVQNQ GILPGMVWQD  600
RDVYLQGPIW AKIPHTDGNF HPSPLMGGFG MKHPPPQILI KNTPVPADPP TAFNKDKLNS  660
FITQYSTGQV SVEIEWELQK ENSKRWNPEI QYTSNYYKSN NVEFAVNTEG VYSEPRPIGT  720
RYLTRNL                                                           727

SEQ ID NO: 198          moltype = AA  length = 727
FEATURE                 Location/Qualifiers
REGION                  1..727
                        note = Recombinant AAV Capsid Protein
source                  1..727
                        mol_type = protein
                        organism = synthetic construct
SEQUENCE: 198
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPFG LVEEGAKTAP TGKRIDDHFP KRKKARTEED SKPSTSSDAE AGPSGSQQLQ  180
IPAQPASSLG ADTMSAGGGG PLGDNNEGAD GVGSSSGNWH CDSQWLGDRV ITTSTRTWAL  240
```

```
PTYNNHLYKQ ISNSTSGGSS NDNAYFGYST PWGYFDFNRF HCHFSPRDWQ RLINNNWGFR  300
PKRLNFKLFN IQVKEVTDNN GVKTIANNLT STVQVFTDSD YQLPYVLGSA HEGCLPPFPA  360
DVFMIPQYGY LTLNDGSQAV GRSSFYCLEY FPSQMLRTGN NFQFSYEFEN VPFHSSYAHS  420
QSLDRLMNPL IDQYLYYLSK TINGSGQNQQ TLKFSVAGPS NMAVQGRNYI PGPSYRQQRV  480
STTVTQNLNS MLIWPGASSW ALNGRNSLMN PGPAMASHKE GEDRFFPLSG SLIFGKQGTG  540
RDNVDADKVM ITNEEEIKTT NPVATESYGQ VATNHQSAQA QAQTGWVQNQ GILPGMVWQD  600
RDVYLQGPIW AKIPHTDGNF HPSPLMGGFG MKHPPPQILI KNTPVPADPP TAFNKDKLNS  660
FITQYSTGQV SVEIEWELQK ENSKRWNPEI QYTSNYYKSN NVEFAVNTEG VYSEPRPIGT  720
RYLTRNL                                                            727

SEQ ID NO: 199          moltype = AA  length = 727
FEATURE                 Location/Qualifiers
REGION                  1..727
                        note = Recombinant AAV Capsid Protein
source                  1..727
                        mol_type = protein
                        organism = synthetic construct
SEQUENCE: 199
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPFG LVEEGAKTAP TGKRIDDHFP KRKKARTEED SKPSTSSDAE AGPSGSQQLQ  180
IPAQPASSLG ADTMSAGGGG PLGDNNEGAD GVGSSSGNWH CDSQWLGDRV ITTSTRTWAL  240
PTYNNHLYKQ ISNSTSGGSS NDNAYFGYST PWGYFDFNRF HCHFSPRDWQ RLINNNWGFR  300
PKRLNFKLFN IQVKEVTDNN GVKTIANNLT STVQVFTDSD YQLPYVLGSA HEGCLPPFPA  360
DVFMIPQYGY LTLNDGSQAV GRSSFYCLEY FPSQMLRTGN NFQFSYEFEN VPFHSSYAHS  420
QSLDRLMNPL IDQYLYYLSK TIGYHKSGAA QLKFSVAGPS NMAVQGRNYI PGPSYRQQRV  480
STTVTQNNNS EFAWPGASSW ALNGRNSLMN PGPAMASHKE GEDRFFPLSG SLIFGKQGTG  540
RDNVDADKVM ITNEEEIKTT NPVATESYGQ VATNHQANYG QAQTGWVQNQ GILPGMVWQD  600
RDVYLQGPIW AKIPHTDGNF HPSPLMGGFG MKHPPPQILI KNTPVPADPP TAFNKDKLNS  660
FITQYSTGQV SVEIEWELQK ENSKRWNPEI QYTSNYYKSN NVEFAVNTEG VYSEPRPIGT  720
RYLTRNL                                                            727

SEQ ID NO: 200          moltype = AA  length = 727
FEATURE                 Location/Qualifiers
REGION                  1..727
                        note = Recombinant AAV Capsid Protein
source                  1..727
                        mol_type = protein
                        organism = synthetic construct
SEQUENCE: 200
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPFG LVEEGAKTAP TGKRIDDHFP KRKKARTEED SKPSTSSDAE AGPSGSQQLQ  180
IPAQPASSLG ADTMSAGGGG PLGDNNEGAD GVGSSSGNWH CDSQWLGDRV ITTSTRTWAL  240
PTYNNHLYKQ ISNSTSGGSS NDNAYFGYST PWGYFDFNRF HCHFSPRDWQ RLINNNWGFR  300
PKRLNFKLFN IQVKEVTDNN GVKTIANNLT STVQVFTDSD YQLPYVLGSA HEGCLPPFPA  360
DVFMIPQYGY LTLNDGSQAV GRSSFYCLEY FPSQMLRTGN NFQFSYEFEN VPFHSSYAHS  420
QSLDRLMNPL IDQYLYYLSK TINGSGQNQQ TLKFSVAGPS NMAVQGRNYI PGPSYRQQRV  480
STTVTQNLNS MLIWPGASSW ALNGRNSLMN PGPAMASHKE GEDRFFPLSG SLIFGKQGTG  540
RDNVDADKVM ITNEEEIKTT NPVATESYGQ VATNHQANYG QAQTGWVQNQ GILPGMVWQD  600
RDVYLQGPIW AKIPHTDGNF HPSPLMGGFG MKHPPPQILI KNTPVPADPP TAFNKDKLNS  660
FITQYSTGQV SVEIEWELQK ENSKRWNPEI QYTSNYYKSN NVEFAVNTEG VYSEPRPIGT  720
RYLTRNL                                                            727

SEQ ID NO: 201          moltype = DNA  length = 5393
FEATURE                 Location/Qualifiers
misc_feature            1..5393
                        note = rAAV vector
source                  1..5393
                        mol_type = other DNA
                        organism = synthetic construct
SEQUENCE: 201
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctacgta gccatgctct  180
aggaagatcg gaattctcag tccattagga gccagtagcc tggaagatgt ctttacccc  240
agcatcagtt caagtggagc agcacataac tcttgccctc tgccttccaa gattctggtg  300
ctgagactta tggagtgtct tggaggttgc cttctgcccc ccaaccctgc tcccagctgg  360
ccctcccagg cctgggttgc tggcctctgc tttatcagga ttctcaagag ggacagctgg  420
tttatgttgc atgactgttc cctgcatatc tgctctggtt ttaaatagct tatctgagca  480
gctggaggac cacatgggct tatatggcgt ggggtacatg ttcctgtagc cttgtccctg  540
gcacctgcca aaatagcagc caacaccccc cacccccacc gccatccccc tgccccaccc  600
gtcccctgtc gcacattcct ccctccgcag ggctggctca ccaggcccca gcccacatgc  660
ctgcttaaag ccctctccat cctctgcctc acccagtccc cgctgagact gagcagacgc  720
ctccaggatc tgtcggcaga agctttattg cggtagttta tcacagttaa attgctaacg  780
cagtcagtgc ttctgacaca acagtctcga acttaagctg cagaagttgg tcgtgaggca  840
ctgggcaggt aagtatcaag gttacaagac aggtttaagg agaccaatag aaactgggct  900
tgtcgagaca gagaagactc ttgcgtttct gataggcacc tattggtctt actgacatcc  960
actttgcctt tctctccaca ggtgtccact cccagttcaa ttacagctct taaggctaga  1020
```

-continued gtacttaata cgactcacta taggctagcc tcgagatgga ttacaaggat gacgacgata 1080
agcctggtgt gactgttctc aagatgccgg agccagggaa gaaaccagtg tcagccttca 1140
acaagaagcc aaggtcagcg gaggtgaccg ctggcagtgc tgccgtgttc gaggctgaga 1200
cggagcggtc aggcgtgaag gtgcggtggc agcgggatgg cagcgacatc accgccaatg 1260
acaagtatgg tttggcagca gagggcaagc gacacacact gacagtgcgg gatgcgagcc 1320
ctgatgacca gggttcctac gcggtcattg caggctcctc aaaggtcaag tttgacctca 1380
aggtcacaga gccagcccct ccagagaagg cagaatctga agttgctcca ggagccccca 1440
aagaagtccc tgctccagcc actgagttgg aagaaagtgt ctcaagtcct gaagggtcag 1500
tctcggtaac ccaggatggc tcagctgcag agcatcaggg agcccctgat gaccctattg 1560
gcctctttct gatgcgacca caggatggtg aggtgaccgt gggcggcagc attgtcttct 1620
cagcccgagt ggctggggcc agcctcctga aaccgcctgt ggtcaagtgg ttcaagggca 1680
agtgggtgga cctgagcagc aaagtgggcc agcacctgca gctgcatgac agctatgaca 1740
gagccagcaa ggtctacttg tttgagttgc acatcacaga tgctcagacc acttctgctg 1800
ggggctaccg ctgtgaggtg tctaccaagg acaaatttga cagctgtaac ttcaacctca 1860
ctgtccatga ggccattggt tctggagacc tggacctcag atcagctttc cgacgcacga 1920
gcctggcggg agcaggtcgg agaaccagtg acagccatga agatgctggg actctggact 1980
ttagttccct gctgaagaag agagacagtt tccggaggga ctcaaagctg gaggcacctg 2040
ctgaagaaga cgtgtgggag atcctgagac aggcaccgcc gtcagaatat gagcgcatcg 2100
ccttccagca cggagtcaca gaccttcgag gcatgctgaa gaggctcaag ggcatgaagc 2160
aggatgaaaa gaagagcaca gcctttcaga agaagctgga gcctgcctac caggtaaaca 2220
agggccacaa gattcggctt actgtggaac tggctgatcc ggacgccgaa gtcaagtggc 2280
ttaagaatgg acaggagatc cagatgagtg gcagcaagta catcttcgag tccgtcggtg 2340
ccaagcgcac cctgaccatc agccagtgct cactggctga cgacgcagcc taccagtgtg 2400
tggtgggggg cgagaagtgc agcacggagc tctttgtcaa agagcccccg gtgctgatca 2460
ctcggtccct ggaagaccag ctggtgatgg tgggtcagcg ggtggagttt gagtgtgagg 2520
tctcagaaga aggggcccaa gtcaaatggc tgaaggatgg ggttgagctg acacgtgagg 2580
agaccttcaa ataccggttc aagaaaagatg ggcggaaaca ccacttgatc atcaatgaag 2640
caaccctgga ggatgcagga cactatgcag tacgcacaag tggaggccag tcactggctg 2700
agctcattgt gcaagagaag aagttggagg tataccaaag catcgcggac ctggcagtgg 2760
gagccaagga ccaggctgtg tttaagtgtg aggtttcaga tgagaatgta cgcggcgtgt 2820
ggctgaagaa tgggaaggaa ctggtgcctg acaaccgcat aaaggtgtcc catataggcc 2880
gggtccacaa actgaccatt gacgatgtca cacctgctga tgaggctgac tacagctttg 2940
tccctgaagg gtttgcctgc aacctgtctg ccaagctcca cttcatggag gtcaagattg 3000
actttgtgcc taggcaggaa cctcccaaga tccacttgga ttgtcccggc agcacaccag 3060
acaccattgt ggttgttgct gggaacaagt tacgcctgga tgtccctatt tctggagacc 3120
ctgctcccac tgtggtctgg cagaagactg taacacaggg gaagaaggcc tcaactgggc 3180
cacaccctga tgccccagaa gatgctggtg ctgatgagga gtgggtgttt gataagaagc 3240
tgttgtgtga gactgagggc cggtccgggg tggagaccac caaagaccgc agcgtcttta 3300
cagtcgaagg ggcagagaag gaagatgaag gtgtctacac agtcacagta aagaaccccg 3360
tgggcgagga ccaggtcaac ctcacagtca aggtcatcga tgtcccagat gctcctgcgg 3420
cccctaagat cagcaacgtg ggcgaggact cctgcactgt gcagtgggaa ccgcctgcct 3480
atgatggcgg gcagccggtc ctgggataca tcctggagcg caagaagaaa aagagctaca 3540
ggtggatgag gctcaacttt gatctgctgc gggagctgag ccacgaggcg aggcgcatga 3600
tcgagggtgt agcctatgag atgcgagtct acgcagtcaa tgccgtggga atgtccaggc 3660
ccagccctgc ctctcagccc ttcatgccta ttgggccccc tggcgaacca acccacttgg 3720
ctgtggagga tgtgtcagac accactgtct cactcaagtg gcggccccca gagcgcgtgg 3780
gggccggtgg cctggacgga tacagcgtgg agtactgcca ggagggatgc tccgagtgga 3840
cacctgctct gcaggggctg acagagcgca catcgatgct ggtgaaggac ctacccactg 3900
gggcacggct gctgttccga gtacgggcac acaatgtggc aggtcctgga ggccctatcg 3960
tcaccaagga gcctgtgaca gtgcaggaga tactgcaacg accacggctc caactgccca 4020
gacacctgcg ccagaccatc cagaagaaag ttggggagcc tgtgaacctc ctcatccctt 4080
tccagggcaa accccggcct caggtgacct ggaccaaaga ggggcagccc ctggcaggtg 4140
aggaggtgag catccggaac agccccacag acacgatctt gttcatccga gctgcccgcc 4200
gcacccactc gggcacctac caggtgacag ttcgcattga gaacatggag gacaaggcaa 4260
cgctgatcct gcagattgtg gacaagccaa gtcctcccca ggatatccgg atcgttgaga 4320
cttggggttt caatgtggct ctggagtgga agccacccca agatgatggc aatacagaga 4380
tctggggtta tactgtacag aaagctgaca agaagaccat ggagtggttc acggttttgg 4440
aacactaccg acgcactcac tgtgtggtat cagagcttat cattggcaat ggctactact 4500
tccgggtctt cagccataac atggtgggtt ccagtgacaa agctgccgcc accaaggagc 4560
cagtctttat tccaagacca ggcatcacat atgagccacc caaatacaag gccctggact 4620
tctctgaggc cccaagcttc acccagccct tggcaaatcg ctccatcatt gcaggctata 4680
atgccatcct ctgctgtgct gtccgaggta gtcctaagcc caagatttcc tggttcaaga 4740
atggcctgga tctgggagaa gatgctcgct tccgcatgtt ctgcaagcag ggagtattga 4800
ccctggagat caggaaaccc tgcccctatg atggtggtgt ctatgtctgc agggccacca 4860
acttgcaggg cgaggcacag tgtgagtgcc gcctggaggt gcgagttcct cagtgaccag 4920
ggatccgtcg acgcggccgc ttccctttag tgagggttaa tgcttcgagc agacatgata 4980
agatacattg atgagtttgg acaaaccaca actagaatgc agtgaaaaaa atgctttatt 5040
tgtgaaattt gtgatgctat tgctttattt gtaaccatta taagctgcaa taaacaagtt 5100
aacaacaaca attgcattca ttttatgttt caggttcagg gggagatgtg ggaggttttt 5160
taaagcaagt aaaacctcta caaatgtggt aaattcccga ttaggatctt cctagagcat 5220
ggctacgtag ataagtagca tggcgggtta atcattaact acaaggaacc cctagtgatg 5280
gagttggcca ctccctctct gcgcgctcgc tcgctcactg aggccgggcg accaaaggtc 5340
gcccgacgcc cgggctttgc ccgggcggcc tcagtgagcg agcgagcgcg cag 5393

GENE THERAPY VECTORS FOR TREATING HEART DISEASE

CROSS REFERENCE TO RELATED APPLICATIONS

This application is a continuation of U.S. patent application Ser. No. 17/581,576, filed on Jan. 21, 2022; which is a continuation of U.S. patent application Ser. No. 17/383,138, filed on Jul. 22, 2021; which is a divisional of U.S. patent application Ser. No. 17/210,882, filed on Mar. 24, 2021, issued as U.S. Pat. No. 11,129,908; which is a continuation of International PCT Application No. PCT/US2021/017699, filed on Feb. 11, 2021; which claims the benefit of U.S. Provisional Patent Application No. 63/047,633, filed on Jul. 2, 2020, and U.S. Provisional Patent Application No. 62/976,160, filed on Feb. 13, 2020, the contents of each of which are hereby incorporated by reference in their entireties.

REFERENCE TO SEQUENCE LISTING

Sequence Listing associated with this application is provided electronically in XML file format and is hereby incorporated by reference into the specification. The name of the XML file containing the Sequence Listing is TENA_015_06US_SeqList_ST26.xml. The XML file is 419,688 bytes, was created on Jul. 26, 2023, and is being submitted electronically via the USPTO Patent Center.

TECHNICAL FIELD

The present disclosure relates to compositions and methods for the treatment or prevention of heart disease (e.g., cardiomyopathy) in a subject. In particular, the present disclosure relates to a vector comprising a cardiac-specific promoter operability linked to a therapeutic gene product for the treatment of heart disease (e.g., cardiomyopathy).

BACKGROUND

Gene therapy approaches for the treatment of heart disease often employ vectors configured to effectively transduce cardiac cells and to express a transgene in a cardiac-tissue specific manner. Adeno-associated virus (AAV) vectors, cardiac-specific promoters, or both in combination, may be used to deliver a polynucleotide encoding a gene product (e.g. a therapeutic protein) to heart tissue and thereby express the gene product in that tissue to treat the heart disease. Cardiac-specific promoters include desmin (Des), alpha-myosin heavy chain (α-MHC), myosin light chain 2 (MLC-2) and cardiac troponin C (TNNC1 or cTnC) promoters, as well as the 600 base pair cardiac troponin T (TNNT2) promoter. The delivery of polynucleotides encoding large proteins remains challenging, however, due in part to the packaging limit of viral vectors.

Given these challenges, there remains a need in the art for improved gene therapy vectors for heart disease.

SUMMARY

The present disclosure relates generally to compositions and methods for the treatment or prevention of heart disease (e.g. cardiomyopathy). In a first aspect, the present disclosure provides vectors comprising a promoter, optionally a cardiac-specific promoter, operably linked to a polynucleotide encoding a therapeutic gene product for the treatment of prevention of heart disease, e.g., cardiomyopathy. The vector may be an adeno-associated viral (AAV) vector.

In some aspects, the present disclosure provides a cardiac troponin T promoter, comprising a polynucleotide having between 300 bp and 500 bp. In some embodiments, the polynucleotide comprises a sequence that shares at least 80%, at least 90%, or at least 100% identity to any one of SEQ ID NOs: 1-85. In some embodiments, the polynucleotide comprises a sequence that shares at least 80%, at least 90%, or at least 100% identity to SEQ ID NO: 1. In some embodiments, the polynucleotide comprises a sequence that shares at least 80%, at least 90%, or at least 100% identity to SEQ ID NO: 3. In some embodiments, the polynucleotide shares at least 80%, 90%, 95%, 96%, 97%, 98%, 99%, or and 100% sequence identity with a genomic polynucleotide sequence upstream of and including the transcription start site of a troponin T gene. In some embodiments, the polynucleotide shares at least 80%, 90%, 95%, 96%, 97%, 98%, 99%, or and 100% sequence identity with a genomic polynucleotide sequence −450 bp to +1 bp relative to the transcription start site of a troponin T gene. In some embodiments, the polynucleotide shares at least 80%, 90%, 95%, 96%, 97%, 98%, 99%, or and 100% sequence identity with a genomic polynucleotide sequence −350 bp to +1 bp relative to the transcription start site of a troponin T gene. In some embodiments, the polynucleotide shares at least 80%, 90%, 95%, 96%, 97%, 98%, 99%, or and 100% sequence identity with a genomic polynucleotide sequence −250 bp to +1 bp relative to the transcription start site of a troponin T gene. In some embodiments, the polynucleotide shares at least 80%, 90%, 95%, 96%, 97%, 98%, 99%, or and 100% sequence identity with a genomic polynucleotide sequence −450 bp to +50 bp relative to the transcription start site of a troponin T gene. In some embodiments, the polynucleotide shares at least 80%, 90%, 95%, 96%, 97%, 98%, 99%, or and 100% sequence identity with a genomic polynucleotide sequence −350 bp to +50 bp relative to the transcription start site of a troponin T gene. In some embodiments, the polynucleotide shares at least 80%, 90%, 95%, 96%, 97%, 98%, 99%, or and 100% sequence identity with a genomic polynucleotide sequence −250 bp to +50 bp relative to the transcription start site of a troponin T gene. In some embodiments, the troponin T gene is a human troponin T gene.

In some embodiments, the promoter is a muscle-specific promoter. In some embodiments, the promoter is a cardiac cell-specific promoter. In some embodiments, the promoter is a cardiomyocyte-specific promoter. In some embodiments, the promoter has the same cell-type specificity as a native troponin T promoter of about 600 bp. In some embodiments, the promoter described herein has the same cell-type specificity as a reference promoter comprising SEQ ID NO: 1. In some embodiments, the promoter expresses a gene product operatively linked thereto at least about 10%, at least about 20%, at least about 30% more than a native troponin T promoter. In some embodiments, the promoter described herein expresses a gene product operatively linked thereto at least about 10%, at least about 20%, at least about 30% more than a reference promoter comprising SEQ ID NO: 1.

In some aspects, the present disclosure provides a vector comprising any one of the promoters described herein operatively linked to a polynucleotide encoding a gene product. In some embodiments the vector is a viral vector. In some embodiments, the viral vector is an adeno-associated virus vector (AAV). In some embodiments, the viral vector has a packaging limit of at most about 5.5 kb.

In some embodiments, the gene product is selected from MYBPC3, KCNH2, TRPM4, DSG2, and ATP2A2 protein. In some embodiments, the gene product is selected from CACNA1C, DMD, DMPK, EPG5, EVC, EVC2, FBN1, NF1, SCN5A, SOS1, NPR1, ERBB4, VIP, and MYH7 proteins. In some embodiments, the gene product is a Cas9, optionally selected from SpCas9, St1Cas9, and SaCas9.

In some embodiments, the vector described herein comprises a polynucleotide encoding a second gene product. In some embodiments, the second gene product is a functional RNA, optionally a microRNA or a guide RNA.

In some aspects, the present disclosure provides an isolated cell comprising any one of the promoters described herein. In some embodiments, the isolated cell is an induced pluripotent stem cell or an isolated cardiomyocyte.

In some aspects, the present disclosure provides a pharmaceutical composition comprising any one of the vectors described herein.

In some aspects, the present disclosure provides a cell therapy composition comprising any one of the isolated cells described herein.

In some aspects, the present disclosure provides a recombinant adeno-associated virus (AAV) vector genome, comprising a MYBPC3 polynucleotide encoding a MYBPC3 protein, or a functional variant thereof, and a promoter, wherein the promoter is a polynucleotide having between 300 bp and 500 bp. In some embodiments, the polynucleotide comprises a sequence that shares at least 80%, at least 90%, or at least 100% identity to any one of SEQ ID NOs: 1-85. In some embodiments, the polynucleotide comprises a sequence that shares at least 80%, at least 90%, or at least 100% identity to any one of SEQ ID NO: 1. In some embodiments, the polynucleotide comprises a sequence that shares at least 80%, at least 90%, or at least 100% identity to any one of SEQ ID NO: 3. In some embodiments, the polynucleotide shares at least 80%, 90%, 95%, 96%, 97%, 98%, 99%, or and 100% sequence identity with a genomic polynucleotide sequence upstream of and including the transcription start site of a troponin T gene. In some embodiments, the polynucleotide shares at least 80%, 90%, 95%, 96%, 97%, 98%, 99%, or and 100% sequence identity with a genomic polynucleotide sequence −450 bp to +1 bp relative to the transcription start site of a troponin T gene. In some embodiments, the polynucleotide shares at least 80%, 90%, 95%, 96%, 97%, 98%, 99%, or and 100% sequence identity with a genomic polynucleotide sequence −350 bp to +1 bp relative to the transcription start site of a troponin T gene. In some embodiments, the polynucleotide shares at least 80%, 90%, 95%, 96%, 97%, 98%, 99%, or and 100% sequence identity with a genomic polynucleotide sequence −250 bp to +1 bp relative to the transcription start site of a troponin T gene. In some embodiments, the polynucleotide shares at least 80%, 90%, 95%, 96%, 97%, 98%, 99%, or and 100% sequence identity with a genomic polynucleotide sequence −450 bp to +50 bp relative to the transcription start site of a troponin T gene. In some embodiments, the polynucleotide shares at least 80%, 90%, 95%, 96%, 97%, 98%, 99%, or and 100% sequence identity with a genomic polynucleotide sequence −350 bp to +50 bp relative to the transcription start site of a troponin T gene. In some embodiments, the polynucleotide shares at least 80%, 90%, 95%, 96%, 97%, 98%, 99%, or and 100% sequence identity with a genomic polynucleotide sequence −250 bp to +50 bp relative to the transcription start site of a troponin T gene. In some embodiments, the troponin T gene is a human troponin T gene.

In some embodiments, the promoter is a muscle-specific promoter. In some embodiments, the promoter is a cardiac cell-specific promoter. In some embodiments, the promoter is a cardiomyocyte-specific promoter. In some embodiments, the promoter has the same cell-type specificity as a native troponin T promoter of about 600 bp. In some embodiments, the promoter has the same cell-type specificity as a reference promoter comprising SEQ ID NO: 1. In some embodiments, the promoter expresses a gene product operatively linked thereto at least about 10%, at least about 20%, at least about 30% more than a native troponin T promoter. In some embodiments, the promoter expresses a gene product operatively linked thereto at least about 10%, at least about 20%, at least about 30% more than a reference promoter comprising SEQ ID NO: 1.

In some embodiments, the recombinant adeno-associated virus (AAV) vector genome described herein comprises a MYBPC3 polynucleotide encoding a MYBPC3 protein. In some embodiments, the MYBPC3 polynucleotide comprises at least about 3.5 kB. In some embodiments, the MYBPC3 polynucleotide comprises about 3.8 kB. In some embodiments, the MYBPC3 is a full-length MYBPC3. In some embodiments, the MYBPC3 is a truncated MYBPC3.

In some embodiments, the rAAV vector genome described herein expresses MYBPC3. In some embodiments, the rAAV vector genome expresses MYBPC3 at about the same level as a reference AAV vector comprising a native troponin T promoter of about 600 bp. In some embodiments, the rAAV vector genome expresses MYBPC3 at a level at least about 10% greater than a reference AAV vector comprising a native troponin T promoter of about 600 bp. In some embodiments, the rAAV vector genome expresses MYBPC3 at a level at least about 20% greater than a reference AAV vector comprising a native troponin T promoter of about 600 bp.

In some aspects, the present disclosure provides a recombinant adeno-associated virus (AAV) vector genome, comprising an expression cassette comprising, in 5' to 3' order, a 5' segment comprising a promoter; a polynucleotide encoding a gene product; and a 3' segment comprising a polyA signal, the expression cassette optionally flanked by one or both of a 5' inverted terminal repeat (ITR) and a 3' ITR, wherein the polynucleotide encoding the gene product comprises between 3 kb and 11 kb, between 3 kb and 5 kb, between 3.5 kb and 4.5 kb, or between 3.7 kb and 4 kb; and wherein: a) the 5' segment and the 3' segment together comprise at most 0.8 kbp or at most 0.9 kbp; b) the 5' ITR, 5' segment, the 3' segment, and 3' ITR together comprise or at most 1.2 kbp, at most 1.3 kbp; and/or c) the vector genome comprises at most 4.7 kbp, at most 4.8 kbp, at most 4.9 kbp, or at most 5.0 kbp. In some embodiments, the 5' segment comprises at most 500 bp or at most 480 bp. In some embodiments, the 3' segment comprises at most 200 bp or at most 150 bp.

In some embodiments, the rAAV vector genome comprises a polynucleotide encoding a gene product comprising 3.7 kbp to 3.9 kbp, optionally 3.8 kbp. In some embodiments, the gene product is MYBPC3, or a functional variant thereof. In some embodiments, the gene product is MYBPC3. In some embodiments, the polynucleotide encoding MYBPC3 shares at least 90% identity to SEQ ID NO: 86. In some embodiments, the polynucleotide encoding MYBPC3 share at least 95% identify to SEQ ID NO: 86. In some embodiments the polynucleotide encoding MYBPC3 is SEQ ID NO: 86. In some embodiments, MYBPC3 shares at least 90% identity to the polypeptide sequence of SEQ ID NO: 103. In some embodiments, MYBPC3 shares at least 95% identity to the polypeptide sequence of SEQ ID NO: 103. In some embodiments, MYBPC3 shares 100% identity to the polypeptide sequence of SEQ ID NO: 103.

In some embodiments, the rAAV vector genome comprises a promoter, wherein the promoter is a polynucleotide having between 300 bp and 500 bp. In some embodiments the promoter comprises a sequence that shares at least 80% identity to SEQ ID NO:1-85. In some embodiments the promoter comprises a sequence that shares at least 90% identity to SEQ ID NO:1-85. In some embodiments the promoter comprises a sequence that shares at least 100% identity to SEQ ID NO:1-85.

In some embodiments, the rAAV vector genome comprises a polyA signal. In some embodiments, the polyA signal comprises, consists essentially of, or consists of a sequence that shares at least 90% identity to SEQ ID NO: 92. In some embodiments, the polyA signal comprises, consists essentially of, or consists of a sequence that shares at least 95% identity to SEQ ID NO: 92. In some embodiments, the polyA signal is SEQ ID NO: 92.

In some embodiments, the rAAV vector genome comprises a 5' segment. In some embodiments, the 5' segment shares at least 80% identity to SEQ ID NO: 93. In some embodiments, the 5' segment shares at least 90% identity to SEQ ID NO: 93. In some embodiments, the 5' segment shares at least 95% identity to SEQ ID NO: 93. In some embodiments, the 5' segment is SEQ ID NO: 93.

In some embodiments, the rAAV vector genome comprises a 3' segment. In some embodiments, the 3' segment shares at least 80% identity to SEQ ID NO: 94. In some embodiments, the 3' segment shares at least 90% identity to SEQ ID NO: 94. In some embodiments, the 3' segment shares at least 95% identity to SEQ ID NO: 94. In some embodiments, the 3' segment is SEQ ID NO: 94.

In some embodiments, the rAAV vector genome comprises an expression cassette. In some embodiments, the expression cassette shares at least 80% identity to SEQ ID NO: 95. In some embodiments, the expression cassette shares at least 90% identity to SEQ ID NO: 95. In some embodiments, the expression cassette shares at least 95% identity to SEQ ID NO: 95. In some embodiments, the expression cassette is SEQ ID NO: 95.

In some embodiments, the rAAV genome comprises an expression cassette that is flanked by one or both of a 5' inverted terminal repeat (ITR) and a 3' ITR. In some embodiments, the 5' ITR comprises a sequence that shares 95% identity to SEQ ID NO: 96. In some embodiments, the 3' ITR comprises a sequence that shares at least 95% identity to SEQ ID NO: 97.

In some aspects, the present disclosure provides a recombinant AAV (rAAV) virion. In some embodiments the rAAV virion comprises any one of the rAAV vector genomes described herein and an AAV capsid protein.

In some aspects, the present disclosure provides a method of expressing a MYBPC3 protein in a cell, comprising transducing the cell with an rAAV virion described herein or any one of the rAAV vector genomes described herein. In some embodiments, the cell is a MYBPC3$^{-/-}$ cell. In some embodiments, the cell comprises an inactivating mutation in one or both copies of the endogenous MYBPC3 gene.

In some aspects, the present disclosure provides a method of treating and/or preventing a cardiomyopathy in a subject in need thereof, comprising administering the rAAV virion described herein or any one of the rAAV vector genomes described herein to the subject, wherein optionally the subject suffers from or is at risk for cardiomyopathy.

In some aspects, the present disclosure provides a method of expressing a MYBPC3 protein in the heart of a subject in need thereof, comprising administering the rAAV virion described herein or any one of the rAAV vector genomes described herein to the subject, optionally a subject suffering from or at risk for cardiomyopathy, wherein optionally the subject suffers from or is at risk for cardiomyopathy.

In some embodiments, administration of the AAV vector causes specific expression of MYBPC3 in the heart of the subject. In some embodiments, administration of the AAV vector causes low or undetectable expression of MYBPC3 in the skeletal tissue, brain, and/or liver of the subject, wherein optionally the subject suffers from or is at risk for cardiomyopathy.

In some aspects, the present disclosure provides a method of treating a disease caused by a MYBPC3 mutation in a subject in need thereof, comprising administering the rAAV virion described or any one of the rAAV vector genomes described herein to the subject, wherein optionally the subject suffers from or is at risk for cardiomyopathy.

In some aspects, the present disclosure provides a method of increasing MYBPC3 activity and/or increasing cardiac function in the heart of a subject in need thereof, comprising administering the rAAV virion described herein or any one of the rAAV vector genomes described herein to the subject, wherein optionally the subject suffers from or is at risk for cardiomyopathy.

In some embodiments, the methods described herein treats the cardiomyopathy. In some embodiments, the methods described herein prevents the cardiomyopathy. In some embodiments, the cardiomyopathy is hypertrophic cardiomyopathy.

In some embodiments, the methods described herein comprise intravenous administration of the rAAV virion described herein or any one of the rAAV vector genomes described herein to the subject. In some embodiments, the methods described herein comprise intracardiac administration of the rAAV virion described herein or any one of the rAAV vector genomes described herein to the subject. In some embodiments, the methods described herein comprise direct injection of the rAAV virion described herein or any one of the rAAV vector genomes described herein to the subject. In some embodiments, the methods described herein comprise administering a dose of about $10^{11}$ to about $10^{14}$ rAAV virions per kg or viral genomes per kg.

In some embodiments, the subject is a mammal. In some embodiments, the subject is a human. In some embodiments, the subject is an adult.

In some embodiments, the pharmaceutical compositions described herein are for use as a medicament in therapeutic or prophylactic treatment of heart disease, e.g. cardiomyopathies.

DETAILED DESCRIPTION

Figure 1A:
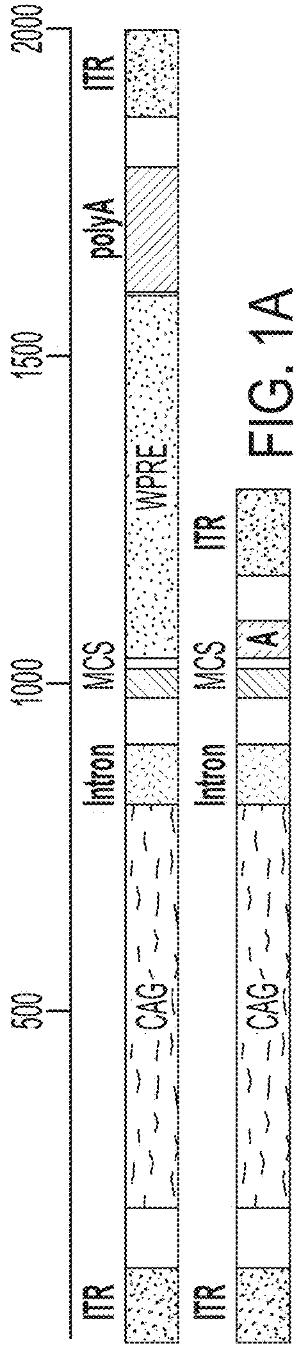
FIG. 1A shows maps of insert sequences for AAV vector genomes adapted for large cargoes, showing deletion or truncation of two cis-regulatory elements.

The present disclosure provides compositions and methods for gene therapy in cardiac cells and/or with large genes. The disclosed polynucleotides and vectors may be used in treatment or prevention of disease (e.g. heart disease, such as cardiomyopathy). The present disclosure provides cardiac-specific promoters, expression cassettes, recombinant adeno-associated virus (rAAV) viral genomes, rAAV virions, pharmaceutical compositions, and methods of use. The expression cassettes and rAAV viral genomes may comprise a cardiac-specific promoter operably linked to a polynucleotide encoding a gene product. The gene product may be a therapeutic gene product, such therapeutic gene product used to treat and/or prevent heart disease, e.g. cardiomyopathy. The disclosure further provides rAAV viral genomes and expression cassettes engineered to deliver and express a large gene product. In some embodiments, the vector genome comprises a polynucleotide encoding a MYBPC3 polypeptide, or a functional variant thereof and a promoter. In some embodiments, the promoter is a cardiac troponin T promoter (i.e., a TNNT2 promoter). In some embodiments, the rAAV vector genome comprises an expression cassette comprising a polynucleotide encoding a gene product, e.g. MYBPC3 and a promoter, e.g. TNNT2 promoter, flanked by one or more inverted terminal repeat polynucleotide sequences. In some embodiments, the rAAV virion comprises a polynucleotide comprising an rAAV vector genome as described herein and an AAV capsid protein. The present disclosure also provides pharmaceutical compositions comprising the vector genomes, rAAV vector genomes, and rAAV virions described herein. Also provided are methods of treating and/or preventing a cardiomyopathy in a subject comprising administering the rAAV virions or vector genomes described herein.

Other embodiments, features, and advantages of the invention will be apparent from and encompassed by the following detailed description and claims.

I. Definitions

As used in this specification and the appended claims, the singular forms "a," "an" and "the" include plural references unless the content clearly dictates otherwise.

As used in this specification, the term "and/or" is used in this disclosure to mean either "and" or "or" unless indicated otherwise.

Throughout this specification, unless the context requires otherwise, the words "comprise", or variations such as "comprises" or "comprising", will be understood to imply the inclusion of a stated element or integer or group of elements or integers but not the exclusion of any other element or integer or group of elements or integers.

As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The terms "polynucleotide" and "nucleic acid," used interchangeably herein, refer to a polymeric form of nucleotides of more than about 100 nucleotides, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as "oligomers" or "oligos" and may be isolated from genes, or chemically synthesized by methods known in the art. The terms "polynucleotide" and "nucleic acid" should be understood to include, as applicable to the embodiments being described, single-stranded (such as sense or antisense) and double-stranded polynucleotides.

The term "promoter" as used herein refers a polynucleotide sequence that has one or more recognition site(s) to which an RNA polymerase binds, such that in a host or target cell, an RNA polymerase may initiate and transcribe a polynucleotide sequence "downstream" of the promoter into an RNA. Similarly stated, a "promoter" is operably linked or operatively linked to a polynucleotide sequence if in a host or target cell in which the promoter is active, an RNA polymerase initiates transcription of the polynucleotide at a transcription state site. Promoters operative in mammalian cells generally comprise an AT-rich region located approximately 25 to 30 bases upstream from the site where transcription is initiated and/or another sequence found 70 to 80 bases upstream from the start of transcription, a CNCAAT region where N may be any nucleotide.

The terms "upstream" and "upstream end" refer to a portion of a polynucleotide that is, with reference to a transcription start site (TSS), 5' to the TSS on the sense strand (or coding strand) of the polynucleotide; and 3' to the TSS on the antisense strand of the polynucleotide. The terms "downstream" and "downstream end" refer to a portion of a polynucleotide that is, with reference to a TSS, 3' to TSS on the sense strand (or coding strand) of the polynucleotide; and 5' to the TSS on the antisense strand of the polynucleotide. Thus, a deletion from the upstream end of a promoter is a deletion of one or more base pairs in the non-transcribed region of the polynucleotide, 5' to the TSS on the sense strand (or equivalently, 3' to the TSS on the antisense strand). A deletion from the downstream end of a promoter is a deletion of one or more base pairs in the transcribed region of the polynucleotide, 3' to the TSS on the sense strand (or equivalently, 5' to the TSS on the antisense strand).

As used herein, the term "transgene" refers to a nucleic acid sequence encoding a protein or RNA (e.g., a therapeutic protein), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

The term "sequence identity" refers to the percentage of bases or amino acids between two polynucleotide or polypeptide sequences that are the same, and in the same relative position. As such one polynucleotide or polypeptide sequence has a certain percentage of sequence identity compared to another polynucleotide or polypeptide sequence. For sequence comparison, typically one sequence acts as a reference sequence, to which test sequences are compared. The term "reference sequence" refers to a molecule to which a test sequence is compared.

Methods of sequence alignment for comparison and determination of percent sequence identity is well known in the art. Optimal alignment of sequences for comparison can be conducted, e.g., by the homology alignment algorithm of Needleman and Wunsch, *J. Mol. Biol.* 48:443 (1970), by the search for similarity method of Pearson and Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, WI), by manual alignment and visual inspection (see, e.g., Brent et al., Current Protocols in Molecular Biology (2003)), by use of algorithms know in the art including the BLAST and BLAST 2.0 algorithms, which are described in Altschul et al., *Nuc. Acids Res.* 25:3389-3402 (1977); and Altschul et al., *J. Mol. Biol.* 215:403-410 (1990), respectively. Software for performing BLAST analyses is publicly available through the National Center for Biotechnology Information.

In some embodiments, the determination of the percentage of sequence identity may take place after a local alignment. Such alignments are well known in the art, for instance the service EMBOSS Matcher identifies local similarities between two sequences using an algorithm based on the LALIGN application, version 2.0u4. In an example, the identity between two nucleic acid sequences may be calculated using the service Matcher (EMBOSS) set to the default parameters, e.g. matrix (DNAfull), gap open (16), gap extend (4), alternative matches (1).

An "expression cassette" or "expression construct" refers to a DNA polynucleotide sequence operably linked to a promoter. "Operably linked" or "operatively linked" refers to a juxtaposition wherein the components so described are in a relationship permitting them to function in their intended manner. For instance, a promoter is operably linked to a polynucleotide sequence if the promoter affects the transcription or expression of the polynucleotide sequence.

As used herein, the term "delivery", which is used interchangeably with "transduction," refers to the process by which exogenous nucleic acid molecules are transferred into a cell such that they are located inside the cell. Delivery of nucleic acids is a distinct process from expression of nucleic acids.

The term "modified" refers to a substance or compound (e.g., a cell, a polynucleotide sequence, and/or a polypeptide sequence) that has been altered or changed as compared to the corresponding unmodified substance or compound.

The term "sample" refers to a biological composition (e.g., a cell or a portion of a tissue) that is subjected to analysis and/or genetic modification. In some embodiments, a sample is a "primary sample" in that it is obtained directly from a subject; in some embodiments, a "sample" is the result of processing of a primary sample, for example to remove certain components and/or to isolate or purify certain components of interest.

The term "gene" or "recombinant gene" refers to a nucleic acid comprising an open reading frame encoding a polypeptide, including both exon and (optionally) intron sequences.

The term "transfection" refers to the uptake of foreign DNA by a cell. A cell has been "transfected" when exogenous DNA has been introduced inside the cell membrane. A number of transfection techniques are generally known in the art. See, e.g., Graham et al., *Virology* 52:456 (1973); Sambrook et al., Molecular Cloning: A Laboratory Manual (1989); Davis et al., Basic Methods in Molecular Biology (1986); Chu et al., *Gene* 13:197 (1981). Such techniques can be used to introduce one or more exogenous DNA moieties, such as a nucleotide integration vector and other nucleic acid molecules, into suitable host cells. The term captures chemical and electrical transfection procedures.

The term "expression" refers to the process by which a nucleic acid is translated into peptides or is transcribed into RNA, which, for example, can be translated into peptides, polypeptides or proteins. If the nucleic acid is derived from genomic DNA, expression may, if an appropriate eukaryotic host cell or organism is selected, include splicing of the mRNA. For heterologous nucleic acid to be expressed in a host cell, it must initially be delivered into the cell and then, once in the cell, ultimately reside in the nucleus.

The term "gene therapy" involves the transfer of heterologous DNA to cells of a mammal, particularly a human, with a disorder or conditions for which therapy or diagnosis is sought. The DNA is introduced into the selected target cells in a manner such that the heterologous DNA is expressed and a therapeutic product encoded thereby is produced. Alternatively, the heterologous DNA may in some manner mediate expression of DNA that encodes the therapeutic product; it may encode a product, such as a peptide or RNA that in some manner mediates, directly or indirectly, expression of a therapeutic product. Gene therapy may also be used to deliver nucleic acid encoding a gene product to replace a defective gene or supplement a gene product produced by the mammal or the cell in which it is introduced. The introduced nucleic acid may encode a therapeutic gene product that is not normally produced in the mammalian host or that is not produced in therapeutically effective amounts or at a therapeutically useful time. The heterologous DNA encoding the therapeutic product may be modified prior to introduction into the cells of the afflicted host in order to enhance or otherwise alter the product or expression thereof.

As used herein, a "heterologous" polynucleotide or nucleic acid refers to a polynucleotide or portion of a polynucleotide derived from a source other than the host organism or, for a viral vector, the native, non-recombinant virus. Examples of heterologous DNA include, but are not limited to, DNA that encodes traceable marker proteins, such as a protein that confers drug resistance, DNA that encodes therapeutically effective substances, such as anti-cancer agents, enzymes and hormones, and DNA that encodes other types of proteins, such as antibodies.

The term "wild type" refers to the naturally-occurring polynucleotide sequence encoding a protein, or a portion thereof, or protein sequence, or portion thereof, respectively, as it normally exists in vivo in a normal or healthy subject.

The term "variant" refers to a protein or nucleic acid having one or more genetic changes (e.g. insertions, deletions, substitutions, or the like) that returns all or substantially all of the functions of the reference protein or nucleic acid. For example, a variant of a therapeutic protein retains the same or substantially the same activity and/or provides the same or substantially the same therapeutic benefit to a subject in need thereof. A variant of a promoter sequence retains the ability to initiate transcription at the same or substantially the same level as the reference promoter, and retains the same or substantially the same cell type specificity. In particular embodiments, polynucleotides variants have at least or about 50%, 55%, 60%, 65%, 70%, 71%, 72%, 73%, 74%, 75%,76%, 77%, 78%, 79%, 80%, 81%, 82%, 83%, 84%,85%, 86%, 87%, 88%, 89%, 90%, 91%, 92%, 93%, 94%, 95%, 96%, 97%, 98%, 99% or 100% sequence identity to a reference sequence. In particular embodiments, protein variants have at least or about 50%, 55%, 60%, 65%, 70%, 71%, 72%, 73%, 74%, 75%,76%, 77%, 78%, 79%, 80%, 81%, 82%, 83%, 84%,85%, 86%, 87%, 88%, 89%, 90%, 91%, 92%, 93%, 94%, 95%, 96%, 97%, 98%, 99% or 100% sequence identity to a reference sequence.

The term "subject" includes animals, such as e.g. mammals. In some embodiments, the mammal is a primate. In some embodiments, the mammal is a human. In some embodiments, subjects are livestock such as cattle, sheep, goats, cows, swine, and the like; or domesticated animals such as dogs and cats. In some embodiments (e.g., particularly in research contexts) subjects are rodents (e.g., mice, rats, hamsters), rabbits, primates, or swine such as inbred pigs and the like. The terms "subject" and "patient" are used interchangeably herein.

The term "administering" to a subject is a procedure by which one or more delivery agents, together or separately, are introduced into or applied onto a subject such that target cells which are present in the subject are eventually contacted with the agent.

"Treating" as used herein refers to delivering an agent or composition to a subject to affect a physiologic outcome.

As used herein, the term "gene product" refers to the a protein or nucleic acid produced by the transcription of a polynucleotide and, in the case of a protein gene product, the subsequent translation of transcript into a protein. A "therapeutic gene product" refers to a gene product that provides a therapeutic physiological effect or benefit to a subject in need when expressed in a therapeutic amount in a subject.

As used herein, the term "therapeutic protein" refers to a protein or polypeptide that provides a therapeutic physiological effect or benefit to a subject in need when expressed or administered in a therapeutic amount in a subject. In some embodiments, treatment with a therapeutic protein or a vector that expresses a therapeutic protein provides a therapeutic physiological effect or benefit to a subject with heart disease (e.g., a subject with cardiomyopathy). Illustrative therapeutic proteins for the treatment of heart disease are provided in Table 2.

As used herein, the term "cardiomyopathy" refers to the deterioration of the function of the myocardium (i.e., the actual heart muscle) for any reason. Subjects with cardiomyopathy are often at risk of arrhythmia or sudden cardiac death or both.

As used herein, the term "hypertrophic cardiomyopathy" refers to a disease of the heart and myocardium in which a portion of the myocardium is hypertrophied.

As used herein, the term "familial hypertrophic cardiomyopathy" refers to a genetic disorder characterized by increased growth (i.e., hypertrophy) in thickness of the wall of the left ventricle.

As used herein, the term "effective amount" refers to the minimum amount of an agent or composition required to result in a particular physiological effect. The effective amount of a particular agent may be represented in a variety of ways based on the nature of the agent, such as mass/ volume, # of cells/volume, particles/volume, (mass of the agent)/(mass of the subject), # of cells/(mass of subject), or particles/(mass of subject). The effective amount of a particular agent may also be expressed as the half-maximal effective concentration ($EC_{50}$), which refers to the concentration of an agent that results in a magnitude of a particular physiological response that is half-way between a reference level and a maximum response level.

II. Polynucleotides

In some embodiments, the present disclosure provides polynucleotide sequences for the treatment and/or prevention of heart disease (e.g., cardiomyopathy). In some embodiments, the polynucleotide sequences comprise a cardiac-specific promoter operatively linked to a polynucleotide encoding one or more therapeutic gene products for the treatment and/or prevention of cardiomyopathy.

Polynucleotides refer to a polymeric form of nucleotides of at least 5, at least 10, at least 15, at least 20, at least 25, at least 30, at least 40, at least 50, at least 100, at least 200, at least 300, at least 400, at least 500, at least 1000, at least 5000, at least 10000, or at least 15000 or more nucleotides in length, either ribonucleotides or deoxyribonucleotides or a modified form of either type of nucleotide, as well as all intermediate lengths. "Intermediate lengths," in this context, means any length between the quoted values, such as 6, 7, 8, 9, etc., 101, 102, 103, etc.; 151, 152, 153, etc.; 201, 202, 203, etc.

As a result of the degeneracy of the genetic code, there are many nucleotide sequences that encode a polypeptide, or fragment of variant thereof, as described herein. Some of these polynucleotides bear minimal homology to the nucleotide sequence of any native gene. Nonetheless, polynucleotides that vary due to differences in codon usage are specifically contemplated in particular embodiments, for example polynucleotides that are optimized for human and/or primate codon selection. Further, alleles of the genes comprising the polynucleotide sequences provided herein may also be used. Alleles are endogenous genes that are altered as a result of one or more mutations, such as deletions, additions and/or substitutions of nucleotides.

The polynucleotides contemplated herein, regardless of the length of the coding sequence itself, may be combined with other DNA sequences, such as promoters and/or enhancers, untranslated regions (UTRs), signal sequences, Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, and polynucleotides encoding self-cleaving polypeptides, epitope tags, as disclosed elsewhere herein or as known in the art.

Polynucleotides can be prepared, manipulated and/or expressed using any of a variety of well-established techniques known and available in the art.

In some embodiments, the polynucleotide sequence is a promoter. In some embodiments, the polynucleotide sequence is a promoter operatively linked to a polynucleotide encoding a therapeutic gene product for the treatment or prevention of heart disease (e.g., cardiomyopathy).

In some embodiments, the vector comprises a cardiac-specific promoter which is operably linked to a polynucleotide encoding a therapeutic gene product (e.g., encoding a therapeutic protein, e.g., MYBPC3 protein). As used herein, a "cardiac-specific promoter" refers to a promoter whose activity in cardiac cells is at least 2-fold higher than in any other non-cardiac cell type. Preferably, a cardiac-specific promoter suitable for being used in the vector of the invention has an activity in cardiac cells which is at least 5-fold, at least 10-fold, at least 15-fold, at least 20-fold, at least 25-fold, or at least 50-fold higher compared to its activity in a non-cardiac cell type.

In some embodiments, the vector comprises a cardiomyocyte-specific promoter which is operably linked to a polynucleotide encoding a therapeutic gene product (e.g., MYBPC3 protein). A "cardiomyocyte-specific promoter", as used herein, specifies a promoter whose activity in cardiomyocytes is at least 2-fold higher than in any other non-cardiac cell type or cardiac cell which is not a cardiomyocyte. Preferably, a cardiomyocyte-specific promoter suitable for being used in the vector of the present disclosure has an activity in cardiomyocytes which is at least 5-fold, at least 10-fold, at least 15-fold, at least 20-fold, at least 25-fold, or at least 50-fold higher compared to its activity in a non-cardiac cell type or a cardiac cell type which is not a cardiomyocyte.

In some embodiments, the cardiac-specific or cardiomyocyte-specific promoter is a human promoter. Examples of cardiac-specific or cardiomyocyte-specific promoter include, but are not limited to, the alpha myosin heavy chain promoter, the myosin light chain 2v promoter, the alpha myosin heavy chain promoter, the alpha-cardiac actin promoter, the alpha-tropomyosin promoter, the cardiac troponin C promoter, the cardiac troponin I promoter, the cardiac myosin-binding protein C promoter, and the sarco/endoplasmic reticulum $Ca^{2+}$ATPase (SERCA) promoter (e.g. isoform 2 of SERCA2).

In some embodiments, the cardiac-specific promoter is the cardiac TNNT2 promoter. In some embodiments, the cardiac TNNT2 promoter is modified, e.g., by the deletion, insertion, or substitution of polynucleotides. Illustrative polynucleotide sequences of the cardiac TNNT2 promoter are shown in Table 1 below. The transcription start site (TSS) of the TNNT2 promoters are bolded and underlined.

TABLE 1

Illustrative TNNT2 promoters

| Name | DNA Sequence | SEQ ID NO. |
|---|---|---|
| TNNT2p-600 | GTCATGGAGAAGACCCACCTTGCAG<br>ATGTCCTCACTGGGGCTGGCAGAGC<br>CGGCAACCTGCCTAAGGCTGCTCAG<br>TCCATTAGGAGCCAGTAGCCTGGAA<br>GATGTCTTTACCCCCAGCATCAGTT<br>CAAGTGGAGCAGCACATAACTCTTG<br>CCCTCTGCCTTCCAAGATTCTGGTG<br>CTGAGACTTATGGAGTGTCTTGGAG<br>GTTGCCTTCTGCCCCCCAACCCTGC<br>TCCCAGCTGGCCCTCCCAGGCCTGG<br>GTTGCTGGCCTCTGCTTTATCAGGA<br>TTCTCAAGAGGGACAGCTGGTTTAT<br>GTTGCATGACTGTTCCCTGCATATC<br>TGCTCTGGTTTTAAATAGCTTATCT<br>GAGCAGCTGGAGGACCACATGGGCT<br>TATATGGCGTGGGGTACATGTTCCT<br>GTAGCCTTGTCCCTGGCACCTGCCA<br>AAATAGCAGCCAACACCCCCCACCC<br>CCACCGCCATCCCCCTGCCCCACCC<br>GTCCCCTGTCGCACATTCCTCCCTC<br>CGCAGGGCTGGCTCACCAGGCCCCA<br>GCCCACATGCCTGCTTAAAGCCCT**C**<br>**TCCATC**CTCTGCCTCACCCAGTCCC<br>CGCTGAGACTGAGCAGACGCCTCCA | 1 |
| TNNT2p-500 | GATGTCTTTACCCCCAGCATCAGTT<br>CAAGTGGAGCAGCACATAACTCTTG<br>CCCTCTGCCTTCCAAGATTCTGGTG<br>CTGAGACTTATGGAGTGTCTTGGAG | 2 |

TABLE 1-continued

| Illustrative TNNT2 promoters | | |
|---|---|---|
| Name | DNA Sequence | SEQ ID NO. |
| | GTTGCCTTCTGCCCCCCAACCCTGC TCCCAGCTGGCCCTCCCAGGCCTGG GTTGCTGGCCTCTGCTTTATCAGGA TTCTCAAGAGGGACAGCTGGTTTAT GTTGCATGACTGTTCCCTGCATATC TGCTCTGGTTTTAAATAGCTTATCT GAGCAGCTGGAGGACCACATGGGCT TATATGGCGTGGGGTACATGTTCCT GTAGCCTTGTCCCTGGCACCTGCCA AAATAGCAGCCAACACCCCCCACCC CCACCGCCATCCCCCTGCCCCACCC GTCCCCTGTCGCACATTCCTCCCTC CGCAGGGCTGGCTCACCAGGCCCCA GCCCACATGCCTGCTTAAAGCCCTC **TCCATC**CTCTGCCTCACCCAGTCCC CGCTGAGACTGAGCAGACGCCTCCA | |
| TNNT2p-400 | GTTGCCTTCTGCCCCCCAACCCTGC TCCCAGCTGGCCCTCCCAGGCCTGG GTTGCTGGCCTCTGCTTTATCAGGA TTCTCAAGAGGGACAGCTGGTTTAT GTTGCATGACTGTTCCCTGCATATC TGCTCTGGTTTTAAATAGCTTATCT GAGCAGCTGGAGGACCACATGGGCT TATATGGCGTGGGGTACATGTTCCT GTAGCCTTGTCCCTGGCACCTGCCA AAATAGCAGCCAACACCCCCCACCC CCACCGCCATCCCCCTGCCCCACCC GTCCCCTGTCGCACATTCCTCCCTC CGCAGGGCTGGCTCACCAGGCCCCA GCCCACATGCCTGCTTAAAGCCCTC **TCCATC**CTCTGCCTCACCCAGTCCC CGCTGAGACTGAGCAGACGCCTCCA | 3 |
| TNNT2p-300 | GTTGCATGACTGTTCCCTGCATATC TGCTCTGGTTTTAAATAGCTTATCT GAGCAGCTGGAGGACCACATGGGCT TATATGGCGTGGGGTACATGTTCCT GTAGCCTTGTCCCTGGCACCTGCCA AAATAGCAGCCAACACCCCCCACCC CCACCGCCATCCCCCTGCCCCACCC GTCCCCTGTCGCACATTCCTCCCTC CGCAGGGCTGGCTCACCAGGCCCCA GCCCACATGCCTGCTTAAAGCCCTC **TCCATC**CTCTGCCTCACCCAGTCCC CGCTGAGACTGAGCAGACGCCTCCA | 4 |

In some embodiments, the cardiac TNNT2 promoter is modified to comprise a polynucleotide sequence of between about 200 and 500 base pairs, between about 250 and 500 base pairs, between about 300 to 500 base pairs, between about 350 to 500 base pairs, between about 400 to 500 base pairs, between about 450 to 500 base pairs, between about 200 and 450 base pairs, between about 200 and 400 base pairs, between about 200 and 350 base pairs, between about 200 and 300 base pairs, and between about 200 and 250 base pairs in length. In some embodiments, the modified cardiac TNNT2 promoter comprises a polynucleotide sequence of between about 350 base pairs to about 450 base pairs, between about 375 base pairs to about 425 base pairs, between about 375 base pairs to about 400 base pairs, between about 375 base pairs to about 425 base pairs, between about 400 base pairs to about 425 base pairs, or between about 400 base pairs to about 450 base pairs. In some embodiments, the cardiac TNNT2 promoter comprises a polynucleotide sequence of about 400 base pairs.

In a particular embodiment, the modified cardiac troponin T promoter comprises between 300 bp and 500 bp of SEQ ID NO: 1. For instance, the modified cardiac troponin T promoter may comprise SEQ ID NO: 3. In some examples, the 300 bp-500 bp sequence may be linked to further polynucleotide sequences but may not be linked to additional sequences derived from SEQ ID NO: 1. For example, in an embodiment, the modified cardiac troponin T promoter may include no more than 500 bp of SEQ ID NO: 1 but may include additional unrelated polynucleotide sequences. In another example, the modified cardiac troponin T promoter may include SEQ ID NO: 3, no additional sequences derived from SEQ ID NO: 1, but may include additional unrelated polynucleotide sequences.

In some embodiments, the cardiac TNNT2 promoter is modified by the deletion of polynucleotides. A modification may include one, two, three or more internal deletions. Each deletion may be a deletion of 1 base pair, 2 base pairs, 3 base pairs, 4 base pairs, 5 base pairs, 10 base pairs, 15 base pairs, 20 base pairs, 25 base pairs, 30 base pairs, 40 base pairs, 50 base pairs, 60 base pairs, 70 base pairs, 80 base pairs, 90 base pairs, 100 base pairs, 125 base pairs, 150 base pairs, 175 base pairs, 200 base pairs, 225 base pairs, 250 base pairs, 275 base pairs, or 300 base pairs with respect to a reference cardiac TNNT2 promoter (SEQ ID NO: 1) having about 600 base pairs.

In some embodiments, the TNNT2 promoter is modified by the deletion of polynucleotides from the upstream end of the promoter with respect to a reference cardiac TNNT2 promoter (SEQ ID NO: 1) having about 600 base pairs. A modification may include the deletion of 1 base pair, 2 base pairs, 3 base pairs, 4 base pairs, 5 base pairs, 10 base pairs, 15 base pairs, 20 base pairs, 25 base pairs, 30 base pairs, 40 base pairs, 50 base pairs, 60 base pairs, 70 base pairs, 80 base pairs, 90 base pairs, 100 base pairs, 125 base pairs, 150 base pairs, 175 base pairs, 200 base pairs, 225 base pairs, 250 base pairs, 275 base pairs, or 300 base pairs from the upstream end of the promoter with respect to a reference cardiac TNNT2 promoter (SEQ ID NO: 1) having about 600 base pairs. In some embodiments, the modification is a 200 base pair deletion from the upstream end of the promoter with respect to a reference cardiac TNNT2 promoter (SEQ ID NO: 1) having about 600 base pairs.

In some embodiments, the cardiac TNNT2 promoter is modified by the deletion of polynucleotides from the downstream end of the promoter with respect to a reference cardiac TNNT2 promoter (SEQ ID NO: 1) having about 600 base pairs. A modification may include the deletion of 1 base pair, 2 base pairs, 3 base pairs, 4 base pairs, 5 base pairs, 10 base pairs, 15 base pairs, 20 base pairs, 25 base pairs, 30 base pairs, 40 base pairs, 50 base pairs, 60 base pairs, 70 base pairs, 80 base pairs, 90 base pairs, 100 base pairs, 125 base pairs, 150 base pairs, 175 base pairs, 200 base pairs, 225 base pairs, 250 base pairs, 275 base pairs, or 300 base pairs from the downstream end of the promoter with respect to a reference cardiac TNNT2 promoter (SEQ ID NO: 1) having about 600 base pairs.

In some embodiments, the cardiac TNNT2 promoter is modified by an internal deletion of polynucleotides. A modification may include the internal deletion of 1 base pair, 2 base pairs, 3 base pairs, 4 base pairs, 5 base pairs, 10 base pairs, 15 base pairs, 20 base pairs, 30 base pairs, 40 base pairs, 50 base pairs, 60 base pairs, 70 base pairs, 80 base pairs, 90 base pairs, 100 base pairs, 125 base pairs, 150 base pairs, 175 base pairs, 200 base pairs, 225 base pairs, 250 base pairs, 275 base pairs, or 300 base pairs with respect to a reference cardiac TNNT2 promoter (SEQ ID NO: 1).

In some embodiments, the cardiac TNNT2 promoter is modified by the insertion of polynucleotides. A modification may include the insertion of 1 base pair, 2 base pairs, 3 base pairs, 4 base pairs, 5 base pairs, 10 base pairs, 15 base pairs, 20 base pairs, 25 base pairs, 30 base pairs, 35 base pairs, 40 base pairs, 45 base pairs, 50 base pairs, 55 base pairs, 60 base pairs, 65 base pairs, 70 base pairs, 75 base pairs, 80, base pairs, 85 base pairs, 90 base pairs, 100 base pairs, 125 base pairs, 150 base pairs, 175 base pairs, 200 base pairs, 225 base pairs, 250 base pairs, 275 base pairs, or 300 base pairs with respect to a reference cardiac TNNT2 promoter (SEQ ID NO: 1) .

In some embodiments, the cardiac TNNT2 promoter is modified by the substitution of polynucleotides. A modification may include the substitution of 1 base pair, 2 base pairs, 3 base pairs, 4 base pairs, 5 base pairs, 6 base pairs, 7 base pairs, 8 base pairs, 9 base pairs, or 10 base pairs with respect to a reference cardiac TNNT2 promoter (SEQ ID NO: 1).

In some embodiments, the polynucleotide sequence of the TNNT2 promoter shares at least 80%, 90%, 95%, 96%, 97%, 98%, 99%, or 100% sequence identity with the polynucleotide sequence −450 base pairs to +1 base pairs relative to the transcription start site of the human TNNT2 gene. In some embodiments, the polynucleotide sequence of the TNNT2 promoter shares at least 80%, 90%, 95%, 96%, 97%, 98%, 99%, or and 100% sequence identity with the polynucleotide sequence −350 base pairs to +1 base pairs relative to the transcription start site of the human TNNT2 gene. In some embodiments, the polynucleotide sequence of the TNNT2 promoter shares at least 80%, 90%, 95%, 96%, 97%, 98%, 99%, or and 100% sequence identity with the polynucleotide sequence −250 base pairs to +1 base pairs relative to the transcription start site of the human TNNT2 gene.

In some embodiments, the polynucleotide sequence of the cardiac TNNT2 promoter shares at least 80%, 90%, 95%, 96%, 97%, 98%, 99%, or and 100% sequence identity with the polynucleotide sequence −450 base pairs to +50 base pairs relative to the transcription start site of the TNNT2 gene. In some embodiments, the polynucleotide sequence of the cardiac TNNT2 promoter shares at least 80%, 90%, 95%, 96%, 97%, 98%, 99%, or and 100% sequence identity with the polynucleotide sequence −350 base pairs to +50 base pairs relative to the transcription start site of the TNNT2 gene. In some embodiments, the polynucleotide sequence of the cardiac TNNT2 promoter shares at least 80%, 90%, 95%, 96%, 97%, 98%, 99%, or and 100% sequence identity with the polynucleotide sequence −250 base pairs to +5 base pairs relative to the transcription start site of the TNNT2 gene.

In some embodiments, the cardiac TNNT2 promoter comprises a polynucleotide comprising a sequence that shares at least 80%, 90%, 95%, 96%, 97%, 98%, 99%, or and 100% identity to any one of SEQ ID NOs: 1-85. In some embodiments, the polynucleotide comprises a sequence that shares at least 80% identity to any one of SEQ ID NOS: 1-85. In some embodiments, the polynucleotide comprises a sequence that shares at least 90% identity to any one of SEQ ID NOS: 1-85. In some embodiments, the polynucleotide comprises a sequence that shares at least 100% identity to any one of SEQ ID NOS: 1-85. In some embodiments, the polynucleotide comprises a sequence that shares at least 80% identity to SEQ ID NO: 1. In some embodiments, the polynucleotide comprises a sequence that shares at least 90% identity to SEQ ID NO: 1. In some embodiments, the polynucleotide comprises a sequence that shares at least 100% identity to SEQ ID NO: 1. In some embodiments, the polynucleotide comprises a sequence that shares at least 80% identity to SEQ ID NO: 3. In some embodiments, the polynucleotide comprises a sequence that shares at least 90% identity to SEQ ID NO: 3. In some embodiments, the polynucleotide comprises a sequence that shares at least 100% identity to SEQ ID NO: 3.

B. Illustrative Gene Products (Proteins)

The promoters of the disclosure may be operatively linked to a polynucleotide comprising a sequence encoding a gene product (e.g., protein or nucleic acid). In some embodiments, the gene product is a therapeutic protein. The therapeutic protein may be any of the native human proteins listed in Table 2, or functional homologs or variants thereof. The promoters of the disclosure are particularly suited for use with large genes that may otherwise be expressed at low levels or not be expressed when delivered by a viral vector. An advantage of some embodiments disclosed herein lies in the ability to express a therapeutic protein (particularly a large therapeutic protein) in a viral vector having limited packaging capacity, e.g., an AAV vector. A "large" protein is any protein whose size impacts expression in a selected vector. Generally, "large" therapeutic proteins comprise at least about 1000 or more amino acids—that is, the protein is encoded by a polynucleotide sequence of about 3 kbps or greater. Illustrative proteins, including large proteins, are provided in Table 2 below.

TABLE 2

Illustrative Proteins

| Gene Name | Gene Symbol | NCBI Gene ID | UniProt ID |
|---|---|---|---|
| Myosin-binding protein C | MYBPC3 | 4607 | Q14896 |
| Potassium voltage-gated channel subfamily H member 2 | KCNH2 | 3757 | Q12809 |
| Transient receptor potential cation channel subfamily M member 4 | TRPM4 | 54795 | Q8TD43 |
| Desmoglein-2 | DSG2 | 1829 | Q14126 |
| ATPase sarcoplasmic/endoplasmic reticulum calcium transporting 2 | ATP2A2 | 488 | P16615 |
| Calcium voltage-gated channel subunit alpha 1C | CACNA1C | 775 | Q13936 |
| Dystrophin | DMD | 1756 | P11532 |
| DM1 protein kinase | DMPK | 1760 | Q09013 |
| Ectopic P granules protein 5 homolog | EPG5 | 57724 | Q9HCE0 |
| EvC ciliary complex subunit 1 | EVC | 2121 | P57679 |
| Limbin | EVC2 | 132884 | Q86UK5 |
| Fibrillin-1 | FBN1 | 2200 | P35555 |
| Neurofibromin | NF1 | 4763 | P21359 |
| Sodium channel protein type 5 subunit alpha | SCN5A | 6331 | Q14524 |
| Son of sevenless homolog 1 | SOS1 | 6654 | Q07889 |
| Natriuretic peptide receptor 1 | NPR1 | 4881 | P16066 |
| Receptor tyrosine-protein kinase erbB-4 | ERBB4 | 2066 | Q15303 |
| Vasoactive intestinal peptide | VIP | 7432 | P01282 |
| Beta-myosin heavy chain | MYH7 | 4625 | P12883 |

Various therapeutic polynucleotides, or therapeutic proteins encoded by polynucleotides, having lengths of 3 kilobases or greater are expressed more effectively when operatively linked to a modified TNNT2 promoter of the disclosure compared to a TNNT2 promoter of about 600 base pairs. The promoters of the disclosure are useful in expression of, at least, the following: a) large genes in which loss-of-function mutations result in cardiomyopathy (gene replacement therapy); b) large genes whose expression in cardiomyocytes is cardioprotective; c) combinations of genes whose co-expression in cardiomyocytes is beneficial; and d) tools for cardiomyocyte-specific genome editing. A "large" gene is any gene whose size impacts expression in a selected vector. Generally, "large" therapeutic genes encode proteins that comprise at least about 1000 or more amino acids—that is, the gene comprises a polynucleotide sequence of about 3 kbps or greater. In further embodiments, the vectors and promoters of the disclosure are used in treatment of the diseases or disorders list in Table 3, where the polynucleotide encodes the therapeutic protein indicated in the table.

TABLE 3

Illustrative Therapeutic Gene Products for Heart Disease

| Condition | Therapeutic Gene Product | Gene Size (kb) |
|---|---|---|
| Timothy syndrome | CACNA1C | 6.663 |
| Becker muscular dystrophy | DMD | 11.055 |
| Duchenne muscular dystrophy | DMD | 11.055 |
| Myotonic dystrophy type 1 | DMPK | 4.653 |
| Vici syndrome | EPG5 | 7.737 |
| Ellis-Van Creveld syndrome | EVC | 2.976 |
| Ellis-Van Creveld syndrome | EVC2 | 3.924 |
| Marfan syndrome | FBN1 | 8.613 |
| Long QT Syndrome | KCNH2 | 3.477 |
| Neurofibromatosis Noonan syndrome | NF1 | 3.517 |
| Brugada Syndrome | SCN5A | 6.048 |
| Long QT Syndrome | SCN5A | 6.048 |
| Paroxysmal ventricular fibrillation 1 | SCN5A | 6.048 |
| Progressive familial heart block type 1A | SCN5A | 6.048 |
| Noonan syndrome | SOS1 | 3.999 |
| Progressive familial heart block type 1B | TRPM4 | 3.642 |
| Acute decompensated heart failure (ADHF) | NPR1 | 3.183 |
| Congestive Heart Failure (CHF) | ERBB4 | 3.924 |
| Congestive Heart Failure (CHF) | VIP analog* | 3.729 |
| Hypertrophic cardiomyopathy | MYBPC3 | 3.822 |
| Left Ventricular Noncompaction Cardiomyopathy | MYBPC3 | 3.822 |
| Hypertrophic cardiomyopathy | MYH7 | 5.805 |
| Left Ventricular Noncompaction Cardiomyopathy | MYH7 | 5.805 |

*VIP fused to an ELP biopolymer (e.g., PB1046) to increase stability in vivo

MYBPC3 is a gene expressed in cardiac cells. Various mutations in MYBPC3 are known to cause hypertrophic cardiomyopathy. Almost half of all mutations causative for hypertrophic cardiomyopathy result in truncations, via nonsense, frameshift or splice-site mutations (Marian and Braunwald, Circ. Res. 121:749-770 (2017); Walsh et al., Genet. Med. 19:192-203 (2017). mRNAs containing premature stop codons are subjected to surveillance and degradation by nonsense-mediated decay machinery. This is consistent with decreased levels of mutant RNAs in analysis of cardiac tissue from hypertrophic cardiomyopathy patients who have received myectomies (Marston et al., Circ. Res. 105:219-222 (2009); van Dijk et al., Circulation 119:1473-1483 (2009); Helms et al., Circ. Cardiovasc. Genet. 7:434-443 (2014). Further, any resultant truncated polypeptides appear sensitive to the ubiquitin-proteasome degradation system. In patient myectomy samples, no truncated protein was observed for nine distinct mutations (Rottbauer et al., J. Clin. Invest. 100:475-482 (1997); Moolman et al., Circulation 101:1396-1402 (2000); Marston et al., Circ. Res. 105: 219-222 (2009); van Dijk et al., Circ. Heart Fail 5:36-46 (2012)). Even though it appears that the wild-type MYBPC3 allele in heterozygous patients is slightly upregulated, the total amount of MYBPC3 protein incorporated into sarcomeres falls significantly below normal at ~65% (Marston et al., Circ. Res. 105:219-222 (2009); van Dijk et al., Circ. Heart Fail 5:36-46 (2012); McNamara et al., PLoS One 12:e0180064 (2017)). Thus, the sarcomeric pathophysiology of hypertrophic cardiomyopathy patients with MYBPC3 truncating mutations appears to be due to haploinsufficiency.

In some embodiments, the disclosure provides a vector comprising a polynucleotide sequence that encodes the MYBPC3 protein, operatively linked to a modified cardiac TNNT2 promoter. Similarly stated, in some embodiments, the polynucleotide sequence operatively linked to the cardiac-specific promoter (e.g., a modified cardiac TNNT2 promoter) is MYBPC3, or a mutant, variant, or fragment thereof. In humans, the MYBPC3 gene encodes the MYBPC3 protein (also known as MyBP-C), which regulates the cardiac sarcomere, the basic unit of muscle contraction. The cardiac muscle sarcomere consists of thick and thin filaments, and MYBPC3 attaches to the thick filaments to prevent premature degradation. Illustrative MYBPC3 polynucleotide sequences are shown in Table 4A below. In some embodiments, the polynucleotide encoding MYBPC3 shares at least 85%, 90%, 95%, 99%, or 100% identity to any one of SEQ ID NOs: 86-89. Illustrative MYBPC3 protein sequences are shown in Table 4B. In some embodiments, the vector genome encodes an MYBPC3 protein that shares at least 85%, 90%, 95%, 99%, or 100% identity to any one of SEQ ID NOs: 103-106.

TABLE 4A

Illustrative MYBPC3 Polynucleotide Sequences

| Name | DNA Sequence | SEQ ID NO. |
|---|---|---|
| MYBPC3 | ATGCCTGAGCCGGGGAAGAAGCCAGTCTCA | 86 |
| | GCTTTTAGCAAGAAGCCACGGTCAGTGGAA | |
| | GTGGCCGCAGGCAGCCCTGCCGTGTTCGAG | |
| | GCCGAGACAGAGCGGGCAGGAGTGAAGGTG | |
| | CGCTGGCAGCGCGGAGGCAGTGACATCAGC | |
| | GCCAGCAACAAGTACGGCCTGGCCACAGAG | |
| | GGCACACGGCATACGCTGACAGTGCGGGAA | |
| | GTGGGCCCTGCCGACCAGGGATCTTACGCA | |
| | GTCATTGCTGGCTCCTCCAAGGTCAAGTTC | |
| | GACCTCAAGGTCATAGAGGCAGAGAAGGCA | |
| | GAGCCCATGCTGGCCCCTGCCCCTGCCCCT | |
| | GCTGAGGCCACTGGAGCCCCTGGAGAAGCC | |
| | CCGGCCCCAGCCGCTGAGCTGGGAGAAAGT | |
| | GCCCCAAGTCCCAAAGGGTCAAGCTCAGCA | |
| | GCTCTCAATGGTCCTACCCCTGGAGCCCCC | |
| | GATGACCCCATTGGCCTCTTCGTGATGCGG | |
| | CCACAGGATGGCGAGGTGACCGTGGGTGGC | |
| | AGCATCACCTTCTCAGCCCGCGTGGCCGGC | |
| | GCCAGCCTCCTGAAGCCGCCTGTGGTCAAG | |
| | TGGTTCAAGGGCAAATGGGTGGACCTGAGC | |
| | AGCAAGGTGGGCCAGCACCTGCAGCTGCAC | |
| | GACAGCTACGACCGCGCCAGCAAGGTCTAT | |
| | CTGTTCGAGCTGCACATCACCGATGCCCAG | |
| | CCTGCCTTCACTGGCAGCTACCGCTGTGAG | |
| | GTGTCCACCAAGGACAAATTTGACTGCTCC | |
| | AACTTCAATCTCACTGTCCACGAGGCCATG | |
| | GGCACCGGAGACCTGGACCTCCTATCAGCC | |
| | TTCCGCCGCACGAGCCTGGCTGGAGGTGGT | |
| | CGGCGGATCAGTGATAGCCATGAGGACACT | |
| | GGGATTCTGGACTTCAGCTCACTGCTGAAA | |
| | AAGAGAGACAGTTTCCGGACCCCGAGGGAC | |
| | TCGAAGCTGGAGGCACCAGCAGAGGAGGAC | |
| | GTGTGGGAGATCCTACGGCAGGCACCCCCA | |
| | TCTGAGTACGAGCGCATCGCCTTCCAGTAC | |
| | GGCGTCACTGACCTGCGCGGCATGCTAAAG | |
| | AGGCTCAAGGGCATGAGGCGCGATGAGAAG | |
| | AAGAGCACAGCCTTTCAGAAGAAGCTGGAG | |
| | CCGGCCTACCAGGTGAGCAAAGGCCACAAG | |
| | ATCCGGCTGACCGTGGAACTGGCTGACCAT | |
| | GACGCTGAGGTCAAATGGCTCAAGAATGGC | |
| | CAGGAGATCCAGATGAGCGGCAGCAAGTAC | |
| | ATCTTTGAGTCCATCGGTGCCAAGCGTACC | |
| | CTGACCATCAGCCAGTGCTCATTGGCGGAC | |
| | GACGCAGCCTACCAGTGCGTGGTGGGTGGC | |
| | GAGAAGTGTAGCACGGAGCTCTTTGTGAAA | |
| | GAGCCCCCTGTGCTCATCACGCGCCCCTTG | |
| | GAGGACCAGCTGGTGATGGTGGGGCAGCGG | |

TABLE 4A-continued

Illustrative MYBPC3 Polynucleotide Sequences

| Name | DNA Sequence | SEQ ID NO. |
|---|---|---|
| | GTGGAGTTTGAGTGTGAAGTATCGGAGGAG<br>GGGGCGCAAGTCAAATGGCTGAAGGACGGG<br>GTGGAGCTGACCCGGGAGGAGACCTTCAAA<br>TACCGGTTCAAGAAGGACGGGCAGAGACAC<br>CACCTGATCATCAACGAGGCCATGCTGGAG<br>GACGCGGGGCACTATGCACTGTGCACTAGC<br>GGGGGCCAGGCGCTGGCTGAGCTCATTGTG<br>CAGGAAAAGAAGCTGGAGGTGTACCAGAGC<br>ATCGCAGACCTGATGGTGGGCGCAAAGGAC<br>CAGGCGGTGTTCAAATGTGAGGTCTCAGAT<br>GAGAATGTTCGGGGTGTGTGGCTGAAGAAT<br>GGGAAGGAGCTGGTGCCCGACAGCCGCATA<br>AAGGTGTCCCACATCGGGCGGGTCCACAAA<br>CTGACCATTGACGACGTCACACCTGCCGAC<br>GAGGCTGACTACAGCTTTGTGCCCGAGGGC<br>TTCGCCTGCAACCTGTCAGCCAAGCTCCAC<br>TTCATGGAGGTCAAGATTGACTTCGTACCC<br>AGGCAGGAACCTCCCAAGATCCACCTGGAC<br>TGCCCAGGCCGCATACCAGACACCATTGTG<br>GTTGTAGCTGGAAATAAGCTACGTCTGGAC<br>GTCCCTATCTCTGGGGACCCCGCTCCCACT<br>GTGATCTGGCAGAAGGCTATCACGCAGGGG<br>AATAAGGCCCCAGCCAGGCCAGCCCCAGAT<br>GCCCCAGAGGACACAGGTGACAGCGATGAG<br>TGGGTGTTTGACAAGAAGCTGCTGTGTGAG<br>ACCGAGGGCCGGGTCCGCGTGGAGACCACC<br>AAGGACCGCAGCATCTTCACGGTCGAGGGG<br>GCAGAGAAGGAAGATGAGGGCGTCTACACG<br>GTCACAGTGAAGAACCCTGTGGGCGAGGAC<br>CAGGTCAACCTCACAGTCAAGGTCATCGAC<br>GTGCCAGACGCACCTGCGGCCCCCAAGATC<br>AGCAACGTGGGAGAGGACTCCTGCACAGTA<br>CAGTGGGAGCCGCCTGCCTACGATGGCGGG<br>CAGCCCATCCTGGGCTACATCCTGGAGCGC<br>AAGAAGAAGAAGAGCTACCGGTGGATGCGG<br>CTGAACTTCGACCTGATTCAGGAGCTGAGT<br>CATGAAGCGCGGCGCATGATCGAGGGCGTG<br>GTGTACGAGATGCGCGTCTACGCGGTCAAC<br>GCCATCGGCATGTCCAGGCCCAGCCCTGCC<br>TCCCAGCCCTTCATGCCTATCGGTCCCCCC<br>AGCGAACCCACCCACCTGGCAGTAGAGGAC<br>GTCTCTGACACCACGGTCTCCCTCAAGTGG<br>CGGCCCCCAGAGCGCGTGGGAGCAGGAGGC<br>CTGGATGGCTACAGCGTGGAGTACTGCCCA<br>GAGGGCTGCTCAGAGTGGGTGGCTGCCCTG<br>CAGGGGCTGACAGAGCACACATCGATACTG<br>GTGAAGGACCTGCCCACGGGGGCCCGGCTG<br>CTTTTCCGAGTGCGGGCACACAATATGGCA<br>GGGCCTGGAGCCCCTGTTACCACCACGGAG<br>CCGGTGACAGTGCAGGAGATCCTGCAACGG<br>CCACGGCTTCAGCTGCCCAGGCACCTGCGC<br>CAGACCATTCAGAAGAAGGTCGGGGAGCCT<br>GTGAACCTTCTCATCCCTTTCCAGGGCAAG<br>CCCCGGCCTCAGGTGACCTGGACCAAAGAG<br>GGGCAGCCCCTGGCAGGCGAGGAGGTGAGC<br>ATCCGCAACAGCCCCACAGACACCATCCTG<br>TTCATCCGGGCCGCTCGCCGCGTGCATTCA<br>GGCACTTACCAGGTGACGGTGCGCATTGAG<br>AACATGGAGGACAAGGCCACGCTGGTGCTG<br>CAGGTTGTTGACAAGCCAAGTCCTCCCCAG<br>GATCTCCGGGTGACTGACGCCTGGGGTCTT<br>AATGTGGCTCTGGAGTGGAAGCCACCCCAG<br>GATGTCGGCAACACGGAACTCTGGGGGTAC<br>ACAGTGCAGAAAGCCGACAAGAAGACCATG<br>GAGTGGTTCACCGTCTTGGAGCATTACCGC<br>CGCACCCACTGCGTGGTGCCAGAGCTCATC<br>ATTGGCAATGGCTACTACTTCCGCGTCTTC<br>AGCCAGAATATGGTTGGCTTTAGTGACAGA<br>GCGGCCACCACCAAGGAGCCCGTCTTTATC<br>CCCAGACCAGGCATCACCTATGAGCCACCC<br>AACTATAAGGCCCTGGACTTCTCCGAGGCC<br>CCAAGCTTCACCCAGCCCCTGGTGAACCGC<br>TCGGTCATCGCGGGCTACACTGCTATGCTC<br>TGCTGTGCTGTCCGGGGTAGCCCCAAGCCC<br>AAGATTTCCTGGTTCAAGAATGGCCTGGAC | |

TABLE 4A-continued

Illustrative MYBPC3 Polynucleotide Sequences

| Name | DNA Sequence | SEQ ID NO. |
|---|---|---|
| | CTGGGAGAAGACGCCCGCTTCCGCATGTTC<br>AGCAAGCAGGGAGTGTTGACTCTGGAGATT<br>AGAAAGCCCTGCCCCTTTGACGGGGGCATC<br>TATGTCTGCAGGGCCACCAACTTACAGGGC<br>GAGGCACGGTGTGAGTGCCGCCTGGAGGTG<br>CGAGTGCCTCAGTAA | |
| MYBPC3-de1C3 | ATGCCTGAGCCGGGGAAGAAGCCAGTCTCA<br>GCTTTTAGCAAGAAGCCACGGTCAGTGGAA<br>GTGGCCGCAGGCAGCCCTGCCGTGTTCGAG<br>GCCGAGACAGAGCGGGCAGGAGTGAAGGTG<br>CGCTGGCAGCGCGGAGGCAGTGACATCAGC<br>GCCAGCAACAAGTACGGCCTGGCCACAGAG<br>GGCACACGGCATACGCTGACAGTGCGGGAA<br>GTGGGCCCTGCCGACCAGGGATCTTACGCA<br>GTCATTGCTGGCTCCTCCAAGGTCAAGTTC<br>GACCTCAAGGTCATAGAGGCAGAGAAGGCA<br>GAGCCCATGCTGGCCCCTGCCCCTGCCCCT<br>GCTGAGGCCACTGGAGCCCCTGGAGAAGCC<br>CCGGCCCCAGCCGCTGAGCTGGGAGAAAGT<br>GCCCCAAGTCCCAAAGGGTCAAGCTCAGCA<br>GCTCTCAATGGTCCTACCCCTGGAGCCCCC<br>GATGACCCCATTGGCCTCTTCGTGATGCGG<br>CCACAGGATGGCGAGGTGACCGTGGGTGGC<br>AGCATCACCTTCTCAGCCCGCGTGGCCGGC<br>GCCAGCCTCCTGAAGCCGCCTGTGGTCAAG<br>TGGTTCAAGGGCAAATGGGTGGACCTGAGC<br>AGCAAGGTGGGCCAGCACCTGCAGCTGCAC<br>GACAGCTACGACCGCGCCAGCAAGGTCTAT<br>CTGTTCGAGCTGCACATCACCGATGCCCAG<br>CCTGCCTTCACTGGCAGCTACCGCTGTGAG<br>GTGTCCACCAAGGACAAATTTGACTGCTCC<br>AACTTCAATCTCACTGTCCACGAGGCCATG<br>GGCACCGGAGACCTGGACCTCCTATCAGCC<br>TTCCGCCGCACGAGCCTGGCTGGAGGTGGT<br>CGGCGGATCAGTGATAGCCATGAGGACACT<br>GGGATTCTGGACTTCAGCTCACTGCTGAAA<br>AAGAGAGACAGTTTCCGGACCCCGAGGGAC<br>TCGAAGCTGGAGGCACCAGCAGAGGAGGAC<br>GTGTGGGAGATCCTACGGCAGGCACCCCCA<br>TCTGAGTACGAGCGCATCGCCTTCCAGTAC<br>GGCGTCACTGACCTGCGCGGCATGCTAAAG<br>AGGCTCAAGGGCATGAGGCGCGATGAGAAG<br>AAGAGCACAGCCTTTCAGAAGAAGCTGGAG<br>CCGGCCTACCAGGTGAGCAAAGGCCACAAG<br>ATCCGGCTGACCGTGGAACTGGCTGACCAT<br>GACGCTGAGGTCAAATGGCTCAAGAATGGC<br>CAGGAGATCCAGATGAGCGGCAGCAAGTAC<br>ATCTTTGAGTCCATCGGTGCCAAGCGTACC<br>CTGACCATCAGCCAGTGCTCATTGGCGGAC<br>GACGCAGCCTACCAGTGCGTGGTGGGTGGC<br>GAGAAGTGTAGCACGGAGCTCTTTGTGAAA<br>GAGCCCCCTGTGTACCAGAGCATCGCAGAC<br>CTGATGGTGGGCGCAAAGGACCAGGCGGTG<br>TTCAAATGTGAGGTCTCAGATGAGAATGTT<br>CGGGGTGTGTGGCTGAAGAATGGGAAGGAG<br>CTGGTGCCCGACAGCCGCATAAAGGTGTCC<br>CACATCGGGCGGGTCCACAAACTGACCATT<br>GACGACGTCACACCTGCCGACGAGGCTGAC<br>TACAGCTTTGTGCCCGAGGGCTTCGCCTGC<br>AACCTGTCAGCCAAGCTCCACTTCATGGAG<br>GTCAAGATTGACTTCGTACCCAGGCAGGAA<br>CCTCCCAAGATCCACCTGGACTGCCCAGGC<br>CGCATACCAGACACCATTGTGGTTGTAGCT<br>GGAAATAAGCTACGTCTGGACGTCCCTATC<br>TCTGGGGACCCCGCTCCCACTGTGATCTGG<br>CAGAAGGCTATCACGCAGGGGAATAAGGCC<br>CCAGCCAGGCCAGCCCCAGATGCCCCAGAG<br>GACACAGGTGACAGCGATGAGTGGGTGTTT<br>GACAAGAAGCTGCTGTGTGAGACCGAGGGC<br>CGGGTCCGCGTGGAGACCACCAAGGACCGC<br>AGCATCTTCACGGTCGAGGGGGCAGAGAAG<br>GAAGATGAGGGCGTCTACACGGTCACAGTG<br>AAGAACCCTGTGGGCGAGGACCAGGTCAAC<br>CTCACAGTCAAGGTCATCGACGTGCCAGAC | 87 |

TABLE 4A-continued

Illustrative MYBPC3 Polynucleotide Sequences

| Name | DNA Sequence | SEQ ID NO. |
|---|---|---|
| | GCACCTGCGGCCCCCAAGATCAGCAACGTG<br>GGAGAGGACTCCTGCACAGTACAGTGGGAG<br>CCGCCTGCCTACGATGGCGGGCAGCCCATC<br>CTGGGCTACATCCTGGAGCGCAAGAAGAAG<br>AAGAGCTACCGGTGGATGCGGCTGAACTTC<br>GACCTGATTCAGGAGCTGAGTCATGAAGCG<br>CGGCGCATGATCGAGGGCGTGGTGTACGAG<br>ATGCGCGTCTACGCGGTCAACGCCATCGGC<br>ATGTCCAGGCCCAGCCCTGCCTCCCAGCCC<br>TTCATGCCTATCGGTCCCCCCAGCGAACCC<br>ACCCACCTGGCAGTAGAGGACGTCTCTGAC<br>ACCACGGTCTCCCTCAAGTGGCGGCCCCCA<br>GAGCGCGTGGGAGCAGGAGGCCTGGATGGC<br>TACAGCGTGGAGTACTGCCCAGAGGGCTGC<br>TCAGAGTGGGTGGCTGCCCTGCAGGGGCTG<br>ACAGAGCACACATCGATACTGGTGAAGGAC<br>CTGCCCACGGGGGCCCGGCTGCTTTTCCGA<br>GTGCGGGCACACAATATGGCAGGGCCTGGA<br>GCCCCTGTTACCACCACGGAGCCGGTGACA<br>GTGCAGGAGATCCTGCAACGGCCACGGCTT<br>CAGCTGCCCAGGCACCTGCGCCAGACCATT<br>CAGAAGAAGGTCGGGGAGCCTGTGAACCTT<br>CTCATCCCTTTCCAGGGCAAGCCCCGGCCT<br>CAGGTGACCTGGACCAAAGAGGGGCAGCCC<br>CTGGCAGGCGAGGAGGTGAGCATCCGCAAC<br>AGCCCCACAGACACCATCCTGTTCATCCGG<br>GCCGCTCGCCGCGTGCATTCAGGCACTTAC<br>CAGGTGACGGTGCGCATTGAGAACATGGAG<br>GACAAGGCCACGCTGGTGCTGCAGGTTGTT<br>GACAAGCCAAGTCCTCCCCAGGATCTCCGG<br>GTGACTGACGCCTGGGGTCTTAATGTGGCT<br>CTGGAGTGGAAGCCACCCCAGGATGTCGGC<br>AACACGGAACTCTGGGGGTACACAGTGCAG<br>AAAGCCGACAAGAAGACCATGGAGTGGTTC<br>ACCGTCTTGGAGCATTACCGCCGCACCCAC<br>TGCGTGGTGCCAGAGCTCATCATTGGCAAT<br>GGCTACTACTTCCGCGTCTTCAGCCAGAAT<br>ATGGTTGGCTTTAGTGACAGAGCGGCCACC<br>ACCAAGGAGCCCGTCTTTATCCCCAGACCA<br>GGCATCACCTATGAGCCACCCAACTATAAG<br>GCCCTGGACTTCTCCGAGGCCCCAAGCTTC<br>ACCCAGCCCCTGGTGAACCGCTCGGTCATC<br>GCGGGCTACACTGCTATGCTCTGCTGTGCT<br>GTCCGGGGTAGCCCCAAGCCCAAGATTTCC<br>TGGTTCAAGAATGGCCTGGACCTGGGAGAA<br>GACGCCCGCTTCCGCATGTTCAGCAAGCAG<br>GGAGTGTTGACTCTGGAGATTAGAAAGCCC<br>TGCCCCTTTGACGGGGGCATCTATGTCTGC<br>AGGGCCACCAACTTACAGGGCGAGGCACGG<br>TGTGAGTGCCGCCTGGAGGTGCGAGTGCCT<br>CAGTAA | |
| MYBPC3-delC4 | ATGCCTGAGCCGGGGAAGAAGCCAGTCTCA<br>GCTTTTAGCAAGAAGCCACGGTCAGTGGAA<br>GTGGCCGCAGGCAGCCCTGCCGTGTTCGAG<br>GCCGAGACAGAGCGGGCAGGAGTGAAGGTG<br>CGCTGGCAGCGCGGAGGCAGTGACATCAGC<br>GCCAGCAACAAGTACGGCCTGGCCACAGAG<br>GGCACACGGCATACGCTGACAGTGCGGGAA<br>GTGGGCCCTGCCGACCAGGGATCTTACGCA<br>GTCATTGCTGGCTCCTCCAAGGTCAAGTTC<br>GACCTCAAGGTCATAGAGGCAGAGAAGGCA<br>GAGCCCATGCTGGCCCCTGCCCCTGCCCCT<br>GCTGAGGCCACTGGAGCCCCTGGAGAAGCC<br>CCGGCCCCAGCCGCTGAGCTGGGAGAAAGT<br>GCCCCAAGTCCCAAAGGGTCAAGCTCAGCA<br>GCTCTCAATGGTCCTACCCCTGGAGCCCCC<br>GATGACCCCATTGGCCTCTTCGTGATGCGG<br>CCACAGGATGGCGAGGTGACCGTGGGTGGC<br>AGCATCACCTTCTCAGCCCGCGTGGCCGGC<br>GCCAGCCTCCTGAAGCCGCCTGTGGTCAAG<br>TGGTTCAAGGGCAAATGGGTGGACCTGAGC<br>AGCAAGGTGGGCCAGCACCTGCAGCTGCAC<br>GACAGCTACGACCGCGCCAGCAAGGTCTAT<br>CTGTTCGAGCTGCACATCACCGATGCCCAG | 88 |

TABLE 4A-continued

Illustrative MYBPC3 Polynucleotide Sequences

| Name | DNA Sequence | SEQ ID NO. |
|---|---|---|
| | CCTGCCTTCACTGGCAGCTACCGCTGTGAG<br>GTGTCCACCAAGGACAAATTTGACTGCTCC<br>AACTTCAATCTCACTGTCCACGAGGCCATG<br>GGCACCGGAGACCTGGACCTCCTATCAGCC<br>TTCCGCCGCACGAGCCTGGCTGGAGGTGGT<br>CGGCGGATCAGTGATAGCCATGAGGACACT<br>GGGATTCTGGACTTCAGCTCACTGCTGAAA<br>AAGAGAGACAGTTTCCGGACCCCGAGGGAC<br>TCGAAGCTGGAGGCACCAGCAGAGGAGGAC<br>GTGTGGGAGATCCTACGGCAGGCACCCCCA<br>TCTGAGTACGAGCGCATCGCCTTCCAGTAC<br>GGCGTCACTGACCTGCGCGGCATGCTAAAG<br>AGGCTCAAGGGCATGAGGCGCGATGAGAAG<br>AAGAGCACAGCCTTTCAGAAGAAGCTGGAG<br>CCGGCCTACCAGGTGAGCAAAGGCCACAAG<br>ATCCGGCTGACCGTGGAACTGGCTGACCAT<br>GACGCTGAGGTCAAATGGCTCAAGAATGGC<br>CAGGAGATCCAGATGAGCGGCAGCAAGTAC<br>ATCTTTGAGTCCATCGGTGCCAAGCGTACC<br>CTGACCATCAGCCAGTGCTCATTGGCGGAC<br>GACGCAGCCTACCAGTGCGTGGTGGGTGGC<br>GAGAAGTGTAGCACGGAGCTCTTTGTGAAA<br>GAGCCCCCTGTGCTCATCACGCGCCCCTTG<br>GAGGACCAGCTGGTGATGGTGGGGCAGCGG<br>GTGGAGTTTGAGTGTGAAGTATCGGAGGAG<br>GGGGCGCAAGTCAAATGGCTGAAGGACGGG<br>GTGGAGCTGACCCGGGAGGAGACCTTCAAA<br>TACCGGTTCAAGAAGGACGGGCAGAGACAC<br>CACCTGATCATCAACGAGGCCATGCTGGAG<br>GACGCGGGGCACTATGCACTGTGCACTAGC<br>GGGGGCCAGGCGCTGGCTGAGCTCATTGTG<br>CAGGAAAAGAAGCTGGAGCCTCCCAAGATC<br>CACCTGGACTGCCCAGGCCGCATACCAGAC<br>ACCATTGTGGTTGTAGCTGGAAATAAGCTA<br>CGTCTGGACGTCCCTATCTCTGGGGACCCC<br>GCTCCCACTGTGATCTGGCAGAAGGCTATC<br>ACGCAGGGGAATAAGGCCCCAGCCAGGCCA<br>GCCCCAGATGCCCCAGAGGACACAGGTGAC<br>AGCGATGAGTGGGTGTTTGACAAGAAGCTG<br>CTGTGTGAGACCGAGGGCCGGGTCCGCGTG<br>GAGACCACCAAGGACCGCAGCATCTTCACG<br>GTCGAGGGGGCAGAGAAGGAAGATGAGGGC<br>GTCTACACGGTCACAGTGAAGAACCCTGTG<br>GGCGAGGACCAGGTCAACCTCACAGTCAAG<br>GTCATCGACGTGCCAGACGCACCTGCGGCC<br>CCCAAGATCAGCAACGTGGGAGAGGACTCC<br>TGCACAGTACAGTGGGAGCCGCCTGCCTAC<br>GATGGCGGGCAGCCCATCCTGGGCTACATC<br>CTGGAGCGCAAGAAGAAGAAGAGCTACCGG<br>TGGATGCGGCTGAACTTCGACCTGATTCAG<br>GAGCTGAGTCATGAAGCGCGGCGCATGATC<br>GAGGGCGTGGTGTACGAGATGCGCGTCTAC<br>GCGGTCAACGCCATCGGCATGTCCAGGCCC<br>AGCCCTGCCTCCCAGCCCTTCATGCCTATC<br>GGTCCCCCCAGCGAACCCACCCACCTGGCA<br>GTAGAGGACGTCTCTGACACCACGGTCTCC<br>CTCAAGTGGCGGCCCCCAGAGCGCGTGGGA<br>GCAGGAGGCCTGGATGGCTACAGCGTGGAG<br>TACTGCCCAGAGGGCTGCTCAGAGTGGGTG<br>GCTGCCCTGCAGGGGCTGACAGAGCACACA<br>TCGATACTGGTGAAGGACCTGCCCACGGGG<br>GCCCGGCTGCTTTTCCGAGTGCGGGCACAC<br>AATATGGCAGGGCCTGGAGCCCCTGTTACC<br>ACCACGGAGCCGGTGACAGTGCAGGAGATC<br>CTGCAACGGCCACGGCTTCAGCTGCCCAGG<br>CACCTGCGCCAGACCATTCAGAAGAAGGTC<br>GGGGAGCCTGTGAACCTTCTCATCCCTTTC<br>CAGGGCAAGCCCCGGCCTCAGGTGACCTGG<br>ACCAAAGAGGGGCAGCCCCTGGCAGGCGAG<br>GAGGTGAGCATCCGCAACAGCCCCACAGAC<br>ACCATCCTGTTCATCCGGGCCGCTCGCCGC<br>GTGCATTCAGGCACTTACCAGGTGACGGTG<br>CGCATTGAGAACATGGAGGACAAGGCCACG<br>CTGGTGCTGCAGGTTGTTGACAAGCCAAGT<br>CCTCCCCAGGATCTCCGGGTGACTGACGCC | |

TABLE 4A-continued

Illustrative MYBPC3 Polynucleotide Sequences

| Name | DNA Sequence | SEQ ID NO. |
|---|---|---|
| | TGGGGTCTTAATGTGGCTCTGGAGTGGAAG<br>CCACCCCAGGATGTCGGCAACACGGAACTC<br>TGGGGGTACACAGTGCAGAAAGCCGACAAG<br>AAGACCATGGAGTGGTTCACCGTCTTGGAG<br>CATTACCGCCGCACCCACTGCGTGGTGCCA<br>GAGCTCATCATTGGCAATGGCTACTACTTC<br>CGCGTCTTCAGCCAGAATATGGTTGGCTTT<br>AGTGACAGAGCGGCCACCACCAAGGAGCCC<br>GTCTTTATCCCCAGACCAGGCATCACCTAT<br>GAGCCACCCAACTATAAGGCCCTGGACTTC<br>TCCGAGGCCCCAAGCTTCACCCAGCCCCTG<br>GTGAACCGCTCGGTCATCGCGGGCTACACT<br>GCTATGCTCTGCTGTGCTGTCCGGGGTAGC<br>CCCAAGCCCAAGATTTCCTGGTTCAAGAAT<br>GGCCTGGACCTGGGAGAAGACGCCCGCTTC<br>CGCATGTTCAGCAAGCAGGGAGTGTTGACT<br>CTGGAGATTAGAAAGCCCTGCCCCTTTGAC<br>GGGGGCATCTATGTCTGCAGGGCCACCAAC<br>TTACAGGGCGAGGCACGGTGTGAGTGCCGC<br>CTGGAGGTGCGAGTGCCTCAGTAA | |
| MYBPC3-delC4b | ATGCCTGAGCCGGGGAAGAAGCCAGTCTCA<br>GCTTTTAGCAAGAAGCCACGGTCAGTGGAA<br>GTGGCCGCAGGCAGCCCTGCCGTGTTCGAG<br>GCCGAGACAGAGCGGGCAGGAGTGAAGGTG<br>CGCTGGCAGCGCGGAGGCAGTGACATCAGC<br>GCCAGCAACAAGTACGGCCTGGCCACAGAG<br>GGCACACGGCATACGCTGACAGTGCGGGAA<br>GTGGGCCCTGCCGACCAGGGATCTTACGCA<br>GTCATTGCTGGCTCCTCCAAGGTCAAGTTC<br>GACCTCAAGGTCATAGAGGCAGAGAAGGCA<br>GAGCCCATGCTGGCCCCTGCCCCTGCCCCT<br>GCTGAGGCCACTGGAGCCCCTGGAGAAGCC<br>CCGGCCCCAGCCGCTGAGCTGGGAGAAAGT<br>GCCCCAAGTCCCAAAGGGTCAAGCTCAGCA<br>GCTCTCAATGGTCCTACCCCTGGAGCCCCC<br>GATGACCCCATTGGCCTCTTCGTGATGCGG<br>CCACAGGATGGCGAGGTGACCGTGGGTGGC<br>AGCATCACCTTCTCAGCCCGCGTGGCCGGC<br>GCCAGCCTCCTGAAGCCGCCTGTGGTCAAG<br>TGGTTCAAGGGCAAATGGGTGGACCTGAGC<br>AGCAAGGTGGGCCAGCACCTGCAGCTGCAC<br>GACAGCTACGACCGCGCCAGCAAGGTCTAT<br>CTGTTCGAGCTGCACATCACCGATGCCCAG<br>CCTGCCTTCACTGGCAGCTACCGCTGTGAG<br>GTGTCCACCAAGGACAAATTTGACTGCTCC<br>AACTTCAATCTCACTGTCCACGAGGCCATG<br>GGCACCGGAGACCTGGACCTCCTATCAGCC<br>TTCCGCCGCACGAGCCTGGCTGGAGGTGGT<br>CGGCGGATCAGTGATAGCCATGAGGACACT<br>GGGATTCTGGACTTCAGCTCACTGCTGAAA<br>AAGAGAGACAGTTTCCGGACCCCGAGGGAC<br>TCGAAGCTGGAGGCACCAGCAGAGGAGGAC<br>GTGTGGGAGATCCTACGGCAGGCACCCCCA<br>TCTGAGTACGAGCGCATCGCCTTCCAGTAC<br>GGCGTCACTGACCTGCGCGGCATGCTAAAG<br>AGGCTCAAGGGCATGAGGCGCGATGAGAAG<br>AAGAGCACAGCCTTTCAGAAGAAGCTGGAG<br>CCGGCCTACCAGGTGAGCAAAGGCCACAAG<br>ATCCGGCTGACCGTGGAACTGGCTGACCAT<br>GACGCTGAGGTCAAATGGCTCAAGAATGGC<br>CAGGAGATCCAGATGAGCGGCAGCAAGTAC<br>ATCTTTGAGTCCATCGGTGCCAAGCGTACC<br>CTGACCATCAGCCAGTGCTCATTGGCGGAC<br>GACGCAGCCTACCAGTGCGTGGTGGGTGGC<br>GAGAAGTGTAGCACGGAGCTCTTTGTGAAA<br>GAGCCCCCTGTGCTCATCACGCGCCCCTTG<br>GAGGACCAGCTGGTGATGGTGGGGCAGCGG<br>GTGGAGTTTGAGTGTGAAGTATCGGAGGAG<br>GGGGCGCAAGTCAAATGGCTGAAGGACGGG<br>GTGGAGCTGACCCGGGAGGAGACCTTCAAA<br>TACCGGTTCAAGAAGGACGGGCAGAGACAC<br>CACCTGATCATCAACGAGGCCATGCTGGAG<br>GACGCGGGGCACTATGCACTGTGCACTAGC<br>GGGGGCCAGGCGCTGGCTGAGCTCATTGTG | 89 |

TABLE 4A-continued

Illustrative MYBPC3 Polynucleotide Sequences

| Name | DNA Sequence | SEQ ID NO. |
|---|---|---|
| | CAGGAAAAGAAGCTGGAGCCCAGGCAGGAA<br>CCTCCCAAGATCCACCTGGACTGCCCAGGC<br>CGCATACCAGACACCATTGTGGTTGTAGCT<br>GGAAATAAGCTACGTCTGGACGTCCCTATC<br>TCTGGGGACCCCGCTCCCACTGTGATCTGG<br>CAGAAGGCTATCACGCAGGGGAATAAGGCC<br>CCAGCCAGGCCAGCCCCAGATGCCCCAGAG<br>GACACAGGTGACAGCGATGAGTGGGTGTTT<br>GACAAGAAGCTGCTGTGTGAGACCGAGGGC<br>CGGGTCCGCGTGGAGACCACCAAGGACCGC<br>AGCATCTTCACGGTCGAGGGGGCAGAGAAG<br>GAAGATGAGGGCGTCTACACGGTCACAGTG<br>AAGAACCCTGTGGGCGAGGACCAGGTCAAC<br>CTCACAGTCAAGGTCATCGACGTGCCAGAC<br>GCACCTGCGGCCCCCAAGATCAGCAACGTG<br>GGAGAGGACTCCTGCACAGTACAGTGGGAG<br>CCGCCTGCCTACGATGGCGGGCAGCCCATC<br>CTGGGCTACATCCTGGAGCGCAAGAAGAAG<br>AAGAGCTACCGGTGGATGCGGCTGAACTTC<br>GACCTGATTCAGGAGCTGAGTCATGAAGCG<br>CGGCGCATGATCGAGGGCGTGGTGTACGAG<br>ATGCGCGTCTACGCGGTCAACGCCATCGGC<br>ATGTCCAGGCCCAGCCCTGCCTCCCAGCCC<br>TTCATGCCTATCGGTCCCCCCAGCGAACCC<br>ACCCACCTGGCAGTAGAGGACGTCTCTGAC<br>ACCACGGTCTCCCTCAAGTGGCGGCCCCCA<br>GAGCGCGTGGGAGCAGGAGGCCTGGATGGC<br>TACAGCGTGGAGTACTGCCCAGAGGGCTGC<br>TCAGAGTGGGTGGCTGCCCTGCAGGGGCTG<br>ACAGAGCACACATCGATACTGGTGAAGGAC<br>CTGCCCACGGGGGCCCGGCTGCTTTTCCGA<br>GTGCGGGCACACAATATGGCAGGGCCTGGA<br>GCCCCTGTTACCACCACGGAGCCGGTGACA<br>GTGCAGGAGATCCTGCAACGGCCACGGCTT<br>CAGCTGCCCAGGCACCTGCGCCAGACCATT<br>CAGAAGAAGGTCGGGGAGCCTGTGAACCTT<br>CTCATCCCTTTCCAGGGCAAGCCCCGGCCT<br>CAGGTGACCTGGACCAAAGAGGGGCAGCCC<br>CTGGCAGGCGAGGAGGTGAGCATCCGCAAC<br>AGCCCCACAGACACCATCCTGTTCATCCGG<br>GCCGCTCGCCGCGTGCATTCAGGCACTTAC<br>CAGGTGACGGTGCGCATTGAGAACATGGAG<br>GACAAGGCCACGCTGGTGCTGCAGGTTGTT<br>GACAAGCCAAGTCCTCCCCAGGATCTCCGG<br>GTGACTGACGCCTGGGGTCTTAATGTGGCT<br>CTGGAGTGGAAGCCACCCCAGGATGTCGGC<br>AACACGGAACTCTGGGGGTACACAGTGCAG<br>AAAGCCGACAAGAAGACCATGGAGTGGTTC<br>ACCGTCTTGGAGCATTACCGCCGCACCCAC<br>TGCGTGGTGCCAGAGCTCATCATTGGCAAT<br>GGCTACTACTTCCGCGTCTTCAGCCAGAAT<br>ATGGTTGGCTTTAGTGACAGAGCGGCCACC<br>ACCAAGGAGCCCGTCTTTATCCCCAGACCA<br>GGCATCACCTATGAGCCACCCAACTATAAG<br>GCCCTGGACTTCTCCGAGGCCCCAAGCTTC<br>ACCCAGCCCCTGGTGAACCGCTCGGTCATC<br>GCGGGCTACACTGCTATGCTCTGCTGTGCT<br>GTCCGGGGTAGCCCCAAGCCCAAGATTTCC<br>TGGTTCAAGAATGGCCTGGACCTGGGAGAA<br>GACGCCCGCTTCCGCATGTTCAGCAAGCAG<br>GGAGTGTTGACTCTGGAGATTAGAAAGCCC<br>TGCCCCTTTGACGGGGGCATCTATGTCTGC<br>AGGGCCACCAACTTACAGGGCGAGGCACGG<br>TGTGAGTGCCGCCTGGAGGTGCGAGTGCCT<br>CAGTAA | |

TABLE 4B

Illustrative MYBPC3 Protein Sequences

| Name | Protein Sequence | SEQ ID NO. |
|---|---|---|
| MYBPC3 | MPEPGKKPVSAFSKKPRSVEVAAGS<br>PAVFEAETERAGVKVRWQRGGSDIS<br>ASNKYGLATEGTRHTLTVREVGPAD<br>QGSYAVIAGSSKVKFDLKVIEAEKA<br>EPMLAPAPAPAEATGAPGEAPAPAA<br>ELGESAPSPKGSSSAALNGPTPGAP<br>DDPIGLFVMRPQDGEVTVGGSITFS<br>ARVAGASLLKPPVVKWFKGKWVDLS<br>SKVGQHLQLHDSYDRASKVYLFELH<br>ITDAQPAFTGSYRCEVSTKDKFDCS<br>NFNLTVHEAMGTGDLDLLSAFRRTS<br>LAGGGRRISDSHEDTGILDFSSLLK<br>KRDSFRTPRDSKLEAPAEEDVWEIL<br>RQAPPSEYERIAFQYGVTDLRGMLK<br>RLKGMRRDEKKSTAFQKKLEPAYQV<br>SKGHKIRLTVELADHDAEVKWLKNG<br>QEIQMSGSKYIFESIGAKRTLTISQ<br>CSLADDAAYQCVVGGEKCSTELFVK<br>EPPVLITRPLEDQLVMVGQRVEFEC<br>EVSEEGAQVKWLKDGVELTREETFK<br>YRFKKDGQRHHLIINEAMLEDAGHY<br>ALCTSGGQALAELIVQEKKLEVYQS<br>IADLMVGAKDQAVFKCEVSDENVRG<br>VWLKNGKELVPDSRIKVSHIGRVHK<br>LTIDDVTPADEADYSFVPEGFACNL<br>SAKLHFMEVKIDFVPRQEPPKIHLD<br>CPGRIPDTIVVVAGNKLRLDVPISG<br>DPAPTVIWQKAITQGNKAPARPAPD<br>APEDTGDSDEWVFDKKLLCETEGRV<br>RVETTKDRSIFTVEGAEKEDEGVYT<br>VTVKNPVGEDQVNLTVKVIDVPDAP<br>AAPKISNVGEDSCTVQWEPPAYDGG<br>QPILGYILERKKKKSYRWMRLNFDL<br>IQELSHEARRMIEGVVYEMRVYAVN<br>AIGMSRPSPASQPFMPIGPPSEPTH<br>LAVEDVSDTTVSLKWRPPERVGAGG<br>LDGYSVEYCPEGCSEWVAALQGLTE<br>HTSILVKDLPTGARLLFRVRAHNMA<br>GPGAPVTTTEPVTVQEILQRPRLQL<br>PRHLRQTIQKKVGEPVNLLIPFQGK<br>PRPQVTWTKEGQPLAGEEVSIRNSP<br>TDTILFIRAARRVHSGTYQVTVRIE<br>NMEDKATLVLQVVDKPSPPQDLRVT<br>DAWGLNVALEWKPPQDVGNTELWGY<br>TVQKADKKTMEWFTVLEHYRRTHCV<br>VPELIIGNGYYFRVFSQNMVGFSDR<br>AATTKEPVFIPRPGITYEPPNYKAL<br>DFSEAPSFTQPLVNRSVIAGYTAML<br>CCAVRGSPKPKISWFKNGLDLGEDA<br>RFRMFSKQGVLTLEIRKPCPFDGGI<br>YVCRATNLQGEARCECRLEVRVPQ | 103 |
| MYBPC3-delC3 | MPEPGKKPVSAFSKKPRSVEVAAGS<br>PAVFEAETERAGVKVRWQRGGSDIS<br>ASNKYGLATEGTRHTLTVREVGPAD<br>QGSYAVIAGSSKVKFDLKVIEAEKA<br>EPMLAPAPAPAEATGAPGEAPAPAA<br>ELGESAPSPKGSSSAALNGPTPGAP<br>DDPIGLFVMRPQDGEVTVGGSITFS<br>ARVAGASLLKPPVVKWFKGKWVDLS<br>SKVGQHLQLHDSYDRASKVYLFELH<br>ITDAQPAFTGSYRCEVSTKDKFDCS<br>NFNLTVHEAMGTGDLDLLSAFRRTS<br>LAGGGRRISDSHEDTGILDFSSLLK<br>KRDSFRTPRDSKLEAPAEEDVWEIL<br>RQAPPSEYERIAFQYGVTDLRGMLK<br>RLKGMRRDEKKSTAFQKKLEPAYQV<br>SKGHKIRLTVELADHDAEVKWLKNG<br>QEIQMSGSKYIFESIGAKRTLTISQ<br>CSLADDAAYQCVVGGEKCSTELFVK<br>EPPVYQSIADLMVGAKDQAVFKCEV<br>SDENVRGVWLKNGKELVPDSRIKVS<br>HIGRVHKLTIDDVTPADEADYSFVP<br>EGFACNLSAKLHFMEVKIDFVPRQE<br>PPKIHLDCPGRIPDTIVVVAGNKLR | 104 |

TABLE 4B-continued

Illustrative MYBPC3 Protein Sequences

| Name | Protein Sequence | SEQ ID NO. |
|---|---|---|
| | LDVPISGDPAPTVIWQKAITQGNKA<br>PARPAPDAPEDTGDSDEWVFDKKLL<br>CETEGRVRVETTKDRSIFTVEGAEK<br>EDEGVYTVTVKNPVGEDQVNLTVKV<br>IDVPDAPAAPKISNVGEDSCTVQWE<br>PPAYDGGQPILGYILERKKKKSYRW<br>MRLNFDLIQELSHEARRMIEGVVYE<br>MRVYAVNAIGMSRPSPASQPFMPIG<br>PPSEPTHLAVEDVSDTTVSLKWRPP<br>ERVGAGGLDGYSVEYCPEGCSEWVA<br>ALQGLTEHTSILVKDLPTGARLLFR<br>VRAHNMAGPGAPVTTTEPVTVQEIL<br>QRPRLQLPRHLRQTIQKKVGEPVNL<br>LIPFQGKPRPQVTWTKEGQPLAGEE<br>VSIRNSPTDTILFIRAARRVHSGTY<br>QVTVRIENMEDKATLVLQVVDKPSP<br>PQDLRVTDAWGLNVALEWKPPQDVG<br>NTELWGYTVQKADKKTMEWFTVLEH<br>YRRTHCVVPELIIGNGYYFRVFSQN<br>MVGFSDRAATTKEPVFIPRPGITYE<br>PPNYKALDFSEAPSFTQPLVNRSVI<br>AGYTAMLCCAVRGSPKPKISWFKNG<br>LDLGEDARFRMFSKQGVLTLEIRKP<br>CPFDGGIYVCRATNLQGEARCECRL<br>EVRVPQ | |
| MYBPC3-delC4 | MPEPGKKPVSAFSKKPRSVEVAAGS<br>PAVFEAETERAGVKVRWQRGGSDIS<br>ASNKYGLATEGTRHTLTVREVGPAD<br>QGSYAVIAGSSKVKFDLKVIEAEKA<br>EPMLAPAPAPAEATGAPGEAPAPAA<br>ELGESAPSPKGSSSAALNGPTPGAP<br>DDPIGLFVMRPQDGEVTVGGSITFS<br>ARVAGASLLKPPVVKWFKGKWVDLS<br>SKVGQHLQLHDSYDRASKVYLFELH<br>ITDAQPAFTGSYRCEVSTKDKFDCS<br>NFNLTVHEAMGTGDLDLLSAFRRTS<br>LAGGGRRISDSHEDTGILDFSSLLK<br>KRDSFRTPRDSKLEAPAEEDVWEIL<br>RQAPPSEYERIAFQYGVTDLRGMLK<br>RLKGMRRDEKKSTAFQKKLEPAYQV<br>SKGHKIRLTVELADHDAEVKWLKNG<br>QEIQMSGSKYIFESIGAKRTLTISQ<br>CSLADDAAYQCVVGGEKCSTELFVK<br>EPPVLITRPLEDQLVMVGQRVEFEC<br>EVSEEGAQVKWLKDGVELTREETFK<br>YRFKKDGQRHHLIINEAMLEDAGHY<br>ALCTSGGQALAELIVQEKKLEPPKI<br>HLDCPGRIPDTIVVVAGNKLRLDVP<br>ISGDPAPTVIWQKAITQGNKAPARP<br>APDAPEDTGDSDEWVFDKKLLCETE<br>GRVRVETTKDRSIFTVEGAEKEDEG<br>VYTVTVKNPVGEDQVNLTVKVIDVP<br>DAPAAPKISNVGEDSCTVQWEPPAY<br>DGGQPILGYILERKKKKSYRWMRLN<br>FDLIQELSHEARRMIEGVVYEMRVY<br>AVNAIGMSRPSPASQPFMPIGPPSE<br>PTHLAVEDVSDTTVSLKWRPPERVG<br>AGGLDGYSVEYCPEGCSEWVAALQG<br>LTEHTSILVKDLPTGARLLFRVRAH<br>NMAGPGAPVTTTEPVTVQEILQRPR<br>LQLPRHLRQTIQKKVGEPVNLLIPF<br>QGKPRPQVTWTKEGQPLAGEEVSIR<br>NSPTDTILFIRAARRVHSGTYQVTV<br>RIENMEDKATLVLQVVDKPSPPQDL<br>RVTDAWGLNVALEWKPPQDVGNTEL<br>WGYTVQKADKKTMEWFTVLEHYRRT<br>HCVVPELIIGNGYYFRVFSQNMVGF<br>SDRAATTKEPVFIPRPGITYEPPNY<br>KALDFSEAPSFTQPLVNRSVIAGYT<br>AMLCCAVRGSPKPKISWFKNGLDLG<br>EDARFRMFSKQGVLTLEIRKPCPFD<br>GGIYVCRATNLQGEARCECRLEVRV<br>PQ | 105 |

TABLE 4B-continued

Illustrative MYBPC3 Protein Sequences

| Name | Protein Sequence | SEQ ID NO. |
|---|---|---|
| MYBPC3-delC4b | MPEPGKKPVSAFSKKPRSVEVAAGS PAVFEAETERAGVKVRWQRGGSDIS ASNKYGLATEGTRHTLTVREVGPAD QGSYAVIAGSSKVKFDLKVIEAEKA EPMLAPAPAPAEATGAPGEAPAPAA ELGESAPSPKGSSSAALNGPTPGAP DDPIGLFVMRPQDGEVTVGGSITFS ARVAGASLLKPPVVKWFKGKWVDLS SKVGQHLQLHDSYDRASKVYLFELH ITDAQPAFTGSYRCEVSTKDKFDCS NFNLTVHEAMGTGDLDLLSAFRRTS LAGGGRRISDSHEDTGILDFSSLLK KRDSFRTPRDSKLEAPAEEDVWEIL RQAPPSEYERIAFQYGVTDLRGMLK RLKGMRRDEKKSTAFQKKLEPAYQV SKGHKIRLTVELADHDAEVKWLKNG QEIQMSGSKYIFESIGAKRTLTISQ CSLADDAAYQCVVGGEKCSTELFVK EPPVLITRPLEDQLVMVGQRVEFEC EVSEEGAQVKWLKDGVELTREETFK YRFKKDGQRHHLIINEAMLEDAGHY ALCTSGGQALAELIVQEKKLEPRQE PPKIHLDCPGRIPDTIVVVAGNKLR LDVPISGDPAPTVIWQKAITQGNKA PARPAPDAPEDTGDSDEWVFDKKLL CETEGRVRVETTKDRSIFTVEGAEK EDEGVYTVTVKNPVGEDQVNLTVKV IDVPDAPAAPKISNVGEDSCTVQWE PPAYDGGQPILGYILERKKKKSYRW MRLNFDLIQELSHEARRMIEGVVYE MRVYAVNAIGMSRPSPASQPFMPIG PPSEPTHLAVEDVSDTTVSLKWRPP ERVGAGGLDGYSVEYCPEGCSEWVA ALQGLTEHTSILVKDLPTGARLLFR VRAHNMAGPGAPVTTTEPVTVQEIL QRPRLQLPRHLRQTIQKKVGEPVNL LIPFQGKPRPQVTWTKEGQPLAGEE VSIRNSPTDTILFIRAARRVHSGTY QVTVRIENMEDKATLVLQVVDKPSP PQDLRVTDAWGLNVALEWKPPQDVG NTELWGYTVQKADKKTMEWFTVLEH YRRTHCVVPELIIGNGYYFRVFSQN MVGFSDRAATTKEPVFIPRPGITYE PPNYKALDFSEAPSFTQPLVNRSVI AGYTAMLCCAVRGSPKPKISWFKNG LDLGEDARFRMFSKQGVLTLEIRKP CPFDGGIYVCRATNLQGEARCECRL EVRVPQ | 106 |

In some embodiments, the disclosure provides a vector comprising a polynucleotide sequence that encodes the potassium voltage gated channel subfamily H member 2 (KCNH2) protein, operatively linked to a modified cardiac TNNT2 promoter. Similarly stated, in some embodiments, the polynucleotide sequence operatively linked to the cardiac-specific promoter (e.g., a modified cardiac TNNT2 promoter) is KCNH2, or a mutant, variant, or fragment thereof (e.g., SEQ ID NO: 107). In humans, the KCNH2 gene encodes the KCNH2 protein (also known as hERG1, e.g., SEQ ID NO: 108), which forms a potassium channel with other KCNH2 proteins to transport potassium out of cells. KCHN2 proteins are abundantly expressed in cardiac muscle, which function to recharge the cardiac tissue after each heartbeat to maintain regular rhythm. In some embodiments, the polynucleotide encoding KCNH2 shares at least 90%, 95%, 99%, or 100% identity to SEQ ID NO: 107. In some embodiments, the KCNH2 protein shares at least 90%, 95%, 99%, or 100% identity to SEQ ID NO: 108.

In some embodiments, the disclosure provides a vector comprising a polynucleotide sequence that encodes the transient receptor potential cation channel subfamily M membrane 4 (TRPM4) protein, operatively linked to a modified cardiac TNNT2 promoter. Similarly stated, in some embodiments, the polynucleotide sequence operatively linked to the cardiac-specific promoter (e.g., a modified cardiac TNNT2 promoter) is TRPM4, or a mutant, variant, or fragment thereof (e.g., SEQ ID NO: 109). In humans, the TRPM4 gene encodes the TRPM4 protein (e.g., SEQ ID NO: 110), which functions as a channel to control the flow of cations into and out of cells. The TRPM4 channel is abundantly expressed in cardiac cells and plays a key role in generating and transmitting electrical signals. In some embodiments, the polynucleotide encoding TRPM4 shares at least 90%, 95%, 99%, or 100% identity to SEQ ID NO: 109. In some embodiments, the TRPM4 protein shares at least 90%, 95%, 99%, or 100% identity to SEQ ID NO: 110.

In some embodiments, the disclosure provides a vector comprising a polynucleotide sequence that encodes the desmoglein 2 (DSG2) protein, operatively linked to a modified cardiac TNNT2 promoter. Similarly stated, in some embodiments, the polynucleotide sequence operatively linked to the cardiac-specific promoter (e.g., a modified cardiac TNNT2 promoter) is DSG2, or a mutant, variant, or fragment thereof (e.g., SEQ ID NO: 111). In humans, the DSG2 gene encodes DSG2 protein (e.g., SEQ ID NO: 112), which is a transmembrane glycoprotein and component of desmosomes. Desmosomes are intercellular junctions that provide strong adhesion between cells giving mechanical strength to tissues. In some embodiments, the polynucleotide encoding DSG2 shares at least 90%, 95%, 99%, or 100% identity to SEQ ID NO: 111. In some embodiments, the DSG2 protein shares at least 90%, 95%, 99%, or 100% identity to SEQ ID NO: 112.

In some embodiments, the disclosure provides a vector comprising a polynucleotide sequence that encodes the ATPase sarcoplasmic/endoplasmic reticulum calcium transporting 2 (ATP2A2) protein, operatively linked to a modified cardiac TNNT2 promoter. Similarly stated, in some embodiments, the polynucleotide sequence operatively linked to the cardiac-specific promoter (e.g., a modified TNNT2 promoter) is ATP2A2, or a mutant, variant, or fragment thereof (e.g., SEQ ID NO: 113). In humans, the ATP2A2 gene encodes sarco(endo)plasmic reticulum calcium-ATPase 2 (SERCA2) protein (e.g., SEQ ID NO: 114), which catalyzes the hydrolysis of ATP coupled with the translocation of calcium from the cytosol into the sarcoplasmic reticulum lumen. The regulation of calcium ions into and out of the sarcoplasmic reticulum assists with muscle contraction and relaxation. In some embodiments, the polynucleotide encoding ATP2A2 shares at least 90%, 95%, 99%, or 100% identity to SEQ ID NO: 113. In some embodiments, the ATP2A2 protein shares at least 90%, 95%, 99%, or 100% identity to SEQ ID NO: 114.

In some embodiments, the disclosure provides a vector comprising a polynucleotide sequence that encodes the calcium voltage-gated channel subunit alpha 1C (CACNA1C) protein, operatively linked to a modified cardiac TNNT2 promoter. Similarly stated, in some embodiments, the polynucleotide sequence operatively linked to the cardiac-specific promoter (e.g., a modified TNNT2 promoter) is CACNA1C, or a mutant, variant, or fragment thereof (e.g., SEQ ID NO: 115). In humans, the CACNA1C gene encodes the alpha 1 subunit of a voltage-dependent calcium channel protein (e.g., SEQ ID NO: 116), which functions to mediate the influx of calcium ions into the cell upon membrane polarization. In some embodiments, the polynucleotide encoding CACNA1C shares at least 90%, 95%, 99%, or 100% identity to SEQ ID NO: 115. In some embodiments, the CACNA1C protein shares at least 90%, 95%, 99%, or 100% identity to SEQ ID NO: 116.

In some embodiments, the disclosure provides a vector comprising a polynucleotide sequence that encodes the dystrophin (DMD) protein, operatively linked to a modified cardiac TNNT2 promoter. Similarly stated, in some embodiments, the polynucleotide sequence operatively linked to the cardiac-specific promoter (e.g., a modified TNNT2 promoter) is DMD, or a mutant, variant, or fragment thereof (e.g., SEQ ID NO: 117). In humans, the DMD gene encodes the DMD protein (e.g., SEQ ID NO: 118), which forms a component of the dystrophin-glycoprotein complex (DGC). The DGC acts as an anchor, connecting the cytoskeleton with the extracellular matrix, thereby strengthening muscle fibers and protecting them from injury as muscles contract and relax. In some embodiments, the polynucleotide encoding DMD shares at least 90%, 95%, 99%, or 100% identity to SEQ ID NO: 117. In some embodiments, the DMD protein shares at least 90%, 95%, 99%, or 100% identity to SEQ ID NO: 118.

In some embodiments, the disclosure provides a vector comprising a polynucleotide sequence that encodes the DM1 protein kinase (DMPK) protein, operatively linked to a modified cardiac TNNT2 promoter. Similarly stated, in some embodiments, the polynucleotide sequence operatively linked to the cardiac-specific promoter (e.g., a modified TNNT2 promoter) is DMPK, or a mutant, variant, or fragment thereof (e.g., SEQ ID NO: 119). In humans, the DMPK gene encodes myotonic dystrophy protein kinase protein (e.g., SEQ ID NO: 120), which plays an important role in brain, muscle and heart development and homeostasis. Myotonic dystrophy protein kinase inhibits myosin phosphatase, which plays a role in muscle tensing and relaxation. In some embodiments, the polynucleotide encoding DMPK shares at least 90%, 95%, 99%, or 100% identity to SEQ ID NO: 119. In some embodiments, the DMPK protein shares at least 90%, 95%, 99%, or 100% identity to SEQ ID NO: 120.

In some embodiments, the disclosure provides a vector comprising a polynucleotide sequence that encodes the ectopic P granules protein 5 homolog (EPG5) protein, operatively linked to a modified cardiac TNNT2 promoter. Similarly stated, in some embodiments, the polynucleotide sequence operatively linked to the cardiac-specific promoter (e.g., a modified TNNT2 promoter) is EPG5, or a mutant, variant, or fragment thereof (e.g., SEQ ID NO: 121). In humans, the EPG5 gene encodes the EPG5 protein (e.g., SEQ ID NO: 122), which functions in autophagy to promote the interaction between autophagosomes and lysosomes. In some embodiments, the polynucleotide encoding EPG5 shares at least 90%, 95%, 99%, or 100% identity to SEQ ID NO: 121. In some embodiments, the EPG5 protein shares at least 90%, 95%, 99%, or 100% identity to SEQ ID NO: 122.

In some embodiments, the disclosure provides a vector comprising a polynucleotide sequence that encodes the EvC ciliary complex subunit 1 (EVC) protein, operatively linked to a modified cardiac TNNT2 promoter. Similarly stated, in some embodiments, the polynucleotide sequence operatively linked to the cardiac-specific promoter (e.g., a modified TNNT2 promoter) is EVC, or a mutant, variant, or fragment thereof (e.g., SEQ ID NO: 123). In humans, the EVC gene encodes the EVC protein (e.g., SEQ ID NO: 124), which is found primarily in cilia, and functions to transmit information between cells. The EVC protein also regulates Sonic Hedgehog, which plays a role in cell growth and differentiation. In some embodiments, the polynucleotide encoding EVC shares at least 90%, 95%, 99%, or 100% identity to SEQ ID NO: 123. In some embodiments, the EVC protein shares at least 90%, 95%, 99%, or 100% identity to SEQ ID NO: 124.

In some embodiments, the disclosure provides a vector comprising a polynucleotide sequence that encodes the limbin protein, operatively linked to a modified cardiac TNNT2 promoter. Similarly stated, in some embodiments, the polynucleotide sequence operatively linked to the cardiac-specific promoter (e.g., a modified TNNT2 promoter) is EVC2, or a mutant, variant, or fragment thereof (e.g., SEQ ID NO: 125). In humans, the EVC2 gene encodes the limbin protein (e.g., SEQ ID NO: 126). While the function of limbin is unknown, it is important for normal growth and development, particularly the development of bones and teeth. In some embodiments, the polynucleotide encoding limbin shares at least 90%, 95%, 99%, or 100% identity to SEQ ID NO: 125. In some embodiments, the limbin protein shares at least 90%, 95%, 99%, or 100% identity to SEQ ID NO: 126.

In some embodiments, the disclosure provides a vector comprising a polynucleotide sequence that encodes the fibrillin-1 protein, operatively linked to a modified cardiac TNNT2 promoter. Similarly stated, in some embodiments, the polynucleotide sequence operatively linked to the cardiac-specific promoter (e.g., a modified TNNT2 promoter) is FBN1, or a mutant, variant, or fragment thereof (e.g., SEQ ID NO: 127). In humans, the FBN1 gene encodes fibrillin-1 and asprosin proteins (e.g., SEQ ID NO: 128). Fibrillin-1 is a glycoprotein that serves as a structural component of calcium-binding microfibrils, which provide force-bearing support in elastic and nonelastic connective tissue throughout the body. Asprosin is a hormone normally secreted by white adipose tissue to regulate glucose homeostasis. In some embodiments, the polynucleotide encoding fibrillin-1 shares at least 90%, 95%, 99%, or 100% identity to SEQ ID NO: 127. In some embodiments, the fibrillin-1 protein shares at least 90%, 95%, 99%, or 100% identity to SEQ ID NO: 128.

In some embodiments, the disclosure provides a vector comprising a polynucleotide sequence that encodes the neurofibromin (NF1) protein, operatively linked to a modified cardiac TNNT2 promoter. Similarly stated, in some embodiments, the polynucleotide sequence operatively linked to the cardiac-specific promoter (e.g., a modified TNNT2 promoter) is NF1, or a mutant, variant, or fragment thereof (e.g., SEQ ID NO: 129). In humans, the NF1 gene encodes the NF1 protein (e.g., SEQ ID NO: 130), which functions as a tumor suppressor and negative regulator of the Ras signaling pathway that stimulates cell growth and division. In some embodiments, the polynucleotide encoding NF1 shares at least 90%, 95%, 99%, or 100% identity to SEQ ID NO: 129. In some embodiments, the NF1 protein shares at least 90%, 95%, 99%, or 100% identity to SEQ ID NO: 130.

In some embodiments, the disclosure provides a vector comprising a polynucleotide sequence that encodes the sodium channel protein type 5 subunit alpha (SCN5A) protein, operatively linked to a modified cardiac TNNT2 promoter. Similarly stated, in some embodiments, the polynucleotide sequence operatively linked to the cardiac-specific promoter (e.g., a modified TNNT2 promoter) is SCN5A, or a mutant, variant, or fragment thereof (e.g., SEQ ID NO: 131). In humans, the SCN5A gene encodes the SCN5A protein (e.g., SEQ ID NO: 132), which is a tetrodotoxin-resistant voltage-gated sodium channel subunit. SCN5A is found primarily in cardiac muscle and is responsible for the initial upstroke of the action potential in an electrocardiogram. In some embodiments, the polynucleotide encoding SCN5A shares at least 90%, 95%, 99%, or 100% identity to SEQ ID NO: 131. In some embodiments, the SCN5A protein shares at least 90%, 95%, 99%, or 100% identity to SEQ ID NO: 132.

In some embodiments, the disclosure provides a vector comprising a polynucleotide sequence that encodes the son of sevenless homolog 1 (SOS1) protein, operatively linked to a modified cardiac TNNT2 promoter. Similarly stated, in some embodiments, the polynucleotide sequence operatively linked to the cardiac-specific promoter (e.g., a modified TNNT2 promoter) is SOS1, or a mutant, variant, or fragment thereof (e.g., SEQ ID NO: 133). In humans, the SOS1 gene encodes the SOS1 protein (e.g., SEQ ID NO: 134), which functions as a component of a trimeric complex that participates in transduction signals from Ras to Rac by promoting Rac-specific guanine nucleotide exchange factor activity. In some embodiments, the polynucleotide encoding SOS1 shares at least 90%, 95%, 99%, or 100% identity to SEQ ID NO: 133. In some embodiments, the SOS1 protein shares at least 90%, 95%, 99%, or 100% identity to SEQ ID NO: 134.

In some embodiments, the disclosure provides a vector comprising a polynucleotide sequence that encodes the natriuretic peptide receptor 1 (NPR1) protein, operatively linked to a modified cardiac TNNT2 promoter. Similarly stated, in some embodiments, the polynucleotide sequence operatively linked to the cardiac-specific promoter (e.g., a modified TNNT2 promoter) is NPR1, or a mutant, variant, or fragment thereof (e.g., SEQ ID NO: 135). The NPR1 gene in humans encodes the NPR1 protein (also referred to as GC-A) (e.g., SEQ ID NO: 136), which is a transmembrane catalytic receptor with intracellular guanylyl cyclase activity. NPR1 serves as a receptor for both atrial and brain natriuretic peptides, which are vasoactive hormones that play a key role in cardiovascular homeostasis. In some embodiments, the polynucleotide encoding NPR1 shares at least 90%, 95%, 99%, or 100% identity to SEQ ID NO: 135. In some embodiments, the NPR1 protein shares at least 90%, 95%, 99%, or 100% identity to SEQ ID NO: 136.

In some embodiments, the disclosure provides a vector comprising a polynucleotide sequence that encodes the receptor tyrosine-protein kinase erbB-4 (ERBB4) protein, operatively linked to a modified cardiac TNNT2 promoter. Similarly stated, in some embodiments, the polynucleotide sequence operatively linked to the cardiac-specific promoter (e.g., a modified TNNT2 promoter) is ERBB4, or a mutant, variant, or fragment thereof (e.g., SEQ ID NO: 137). The ERBB4 gene in humans encodes the ERBB4 protein in humans (e.g., SEQ ID NO: 138), which is a transmembrane receptor in the epidermal growth factor family. Signaling through the ERBB4 receptor induces a variety of cellular responses, including mitogenesis and differentiation. In some embodiments, the polynucleotide encoding ERBB4 shares at least 90%, 95%, 99%, or 100% identity to SEQ ID NO: 137. In some embodiments, the ERBB4 protein shares at least 90%, 95%, 99%, or 100% identity to SEQ ID NO: 138.

In some embodiments, the disclosure provides a vector comprising a polynucleotide sequence that encodes vasoactive intestinal peptide (VIP), operatively linked to a modified TNNT2 promoter. Similarly stated, in some embodiments, the polynucleotide sequence operatively linked to the cardiac-specific promoter (e.g., a modified TNNT2 promoter) is VIP, or a mutant, variant, or fragment thereof (e.g., SEQ ID NO: 139). In humans, the VIP gene encodes the vasoactive intestinal peptide (e.g., SEQ ID NO: 140), which functions as a neuromodulator and neurotransmitter. VIP is a potent vasodilator, regulates smooth muscle activity, epithelial cell secretion and blood flow in the gastrointestinal tract. In some embodiments, the polynucleotide encoding VIP shares at least 90%, 95%, 99%, or 100% identity to SEQ ID NO: 139. In some embodiments, the VIP protein shares at least 90%, 95%, 99%, or 100% identity to SEQ ID NO: 140.

In some embodiments, the disclosure provides a vector comprising a polynucleotide sequence that encodes the beta-myosin heavy chain (MyHC-β), operatively linked to a modified cardiac TNNT2 promoter. Similarly stated, in some embodiments, the polynucleotide sequence operatively linked to the cardiac-specific promoter (e.g., a modified TNNT2 promoter) is MYH7, or a mutant, variant, or fragment thereof (e.g., SEQ ID NO: 141). In humans, the MYH7 gene encodes the MyHC-β protein (e.g., SEQ ID NO: 142), which is a hexameric, asymmetric motor forming the majority of the thick filaments in cardiac muscle. The enzymatic activity of the ATPase in the myosin head hydrolyzes ATP, fueling the process of shortening sarcomeres in order to generate intraventricular pressure and power. In some embodiments, the polynucleotide encoding MyHC-β shares at least 90%, 95%, 99%, or 100% identity to SEQ ID NO: 141. In some embodiments, the MyHC-β protein shares at least 90%, 95%, 99%, or 100% identity to SEQ ID NO: 142.

III. Vectors

In some embodiments, the disclosure provides vectors for the treatment or prevention of heart disease. In particular, the vectors described herein comprise a cardiac-specific promoter operatively linked to a polynucleotide that encodes a therapeutic protein, wherein expression of the therapeutic protein treats a subject in need thereof (e.g., a subject having cardiomyopathy). For example, in some embodiments, the vector is an AAV-based vector comprising the cardiac TNNT2 promoter operatively linked to a polynucleotide that encodes the MYBPC3 protein for the treatment or prevention of cardiomyopathy.

In some embodiments, the vector comprises, in addition to the cardiac-specific promoters (e.g., a modified cardiac troponin T promoter) and therapeutic gene products (e.g., MYBPC3 protein) described herein, a marker gene that facilitates identification or selection of cells that have been transfected, transduced or infected. Examples of marker genes include, but are not limited to, genes encoding fluorescent proteins, e.g., enhanced green fluorescent protein, Ds-Red (DsRed: Discosoma sp. red fluorescent protein (RFP); Bevis et al. (2002) Nat. Biotechnol. 20(11):83-87), yellow fluorescent protein, mCherry, and cyanofluorescent protein; and genes encoding proteins conferring resistance to a selection agent, e.g., a neomycin resistance gene, a puromycin resistance gene, a blasticidin resistance gene, and the like.

In some embodiments, the vector comprises a polynucleotide sequence having a size of at most about 4.0 kilobases, at most about 4.5 kilobases, at most about 5 kilobases, at most about 5.1 kilobases, at most about 5.2 kilobases, at most about 5.3 kilobases, at most about 5.4 kilobases, or at most about 5.5 kilobases. In some embodiments, the vector comprises a polynucleotide sequence having a size of at most about 4.5 kilobases. In some embodiments, the vector comprises a polynucleotide sequence having a size of at most about 5 kilobases. In some embodiments, the vector comprises a polynucleotide sequence having a size of at most about 5.5 kilobases. In some embodiments, the vector comprises a polynucleotide sequence having a size of at most about 6 kilobases.

Methods of introducing polynucleotides into a host cell are known in the art, and any known method can be used to introduce the polynucleotides described herein into a cell. Suitable methods include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery, microfluidics delivery methods, and the like.

A. Non-Viral Vectors

In some embodiments, the polynucleotides described herein are delivered to a cell in a non-viral vector, such as a transposon, a nanoparticle (e.g., a lipid nanoparticle), a liposome, an exosome, an attenuated bacterium, or a virus-like particle. In some embodiments, the non-viral vector is a mammalian virus-like particle. For example, mammalian virus-like particle can be generated (e.g., by purification of the "empty" mammalian virus-like particle followed by ex vivo assembly of the mammalian virus-like particle with the desired cargo). The non-viral vector can also be engineered to incorporate targeting ligands to alter target tissue specificity.

B. Viral Vectors

In some embodiments, the vector is a viral vector. In some embodiments, the viral vector is a retroviral vector, e.g., a lentiviral vector. As used herein, the term "retrovirus" or "retroviral" refers an RNA virus that reverse transcribes its genomic RNA into a linear double-stranded DNA copy and subsequently covalently integrates its genomic DNA into a host genome. Retrovirus vectors are a common tool for gene delivery (Miller, *Nature.* 357:455-460 (2000)). Once the virus is integrated into the host genome, it is referred to as a "provirus." The provirus serves as a template for RNA polymerase II and directs the expression of RNA molecules encoded by the virus. In some embodiments, a retroviral vector is altered so that it does not integrate into the host cell genome.

Illustrative retroviruses (family Retroviridae) include, but are not limited to: (1) genus gammaretrovirus, such as, Moloney murine leukemia virus (M-MuLV), Moloney murine sarcoma virus (MoMSV), murine mammary tumor virus (MuMTV), gibbon ape leukemia virus (GaLV), and feline leukemia virus (FLV), (2) genus spumavirus, such as, simian foamy virus, (3) genus lentivirus, such as, human immunodeficiency virus-1 and simian immunodeficiency virus.

As used herein, the term "lentiviral" or "lentivirus" refers to a group (or genus) of complex retroviruses. Illustrative lentiviruses include, but are not limited to: HIV (human immunodeficiency virus; including HIV type 1, and HIV type 2; visna-maedi virus (VMV) virus; the caprine arthritis-encephalitis virus (CAEV); equine infectious anemia virus (EIAV); feline immunodeficiency virus (Hy); bovine immune deficiency virus (BIV); and simian immunodeficiency virus (SIV).

In some embodiments, the viral vector is an adenoviral vector. The genetic organization of adenovirus includes an approximate 36 kb, linear, double-stranded DNA virus, which allows substitution of large pieces of adenoviral DNA with foreign sequences up to 7 kb (Grunhaus et al., *Seminar in Virology* 200(2):535-546, 1992)).

In some embodiments, the viral vector is an adeno-associated viral (AVV) vector, such as an AAV vector selected from the group consisting of serotype 1, 2, 3, 4, 5, 6, 7, 8, 9, and 10 or chimeric AAV derived thereof.

In some embodiments, the AAV expression vector is pseudotyped to enhance targeting. A pseudotyping strategy can promote gene transfer and sustain expression in a target cell type. For example, the AAV2 genome can be packaged into the capsid of another AAV serotype such as AAV5, AAV7, or AAV8, producing pseudotyped vectors such as AAV2/5, AAV2/7, and AAV2/8 respectively, as described in Balaji et al. *J Surg Res.* September; 184(1): 691-698 (2013). In some embodiments, an AAV9 may be used to target expression in myofibroblast-like lineages, as described in Piras et al. *Gene Therapy* 23:469-478 (2016). In some embodiments, AAV1, AAV6, or AAV9 is used, and in some embodiments, the AAV is engineered, as described in Asokari et al. *Hum Gene Ther.* November; 24(11): 906-913 (2013); Pozsgai et al. Mol Ther. April 5; 25(4): 855-869 (2017); Kotterman, M. A. and D. V. Schaffer Engineering Adeno-Associated Viruses for Clinical Gene Therapy. *Nature Reviews Genetics,* 15:445-451 (2014); and US20160340393A1 to Schaffer et al. In some embodiments, the viral vector is AAV engineered to increase target cell infectivity as described in US20180066285A1.

C. Regulatory Elements

In some embodiments, the disclosure provides a vector comprising one or more regulatory elements operatively linked to a polynucleotide encoding a therapeutic protein or nucleic acid. In some embodiments, the regulatory element is a cardiac-specific promoter (e.g., a modified TNNT2 promoter) that is operatively linked to a therapeutic protein or nucleic acid for the treatment of heart disease.

As used herein, the term "regulatory element" refers those non-translated regions of the vector (e.g., origin of replication, selection cassettes, promoters, enhancers, translation initiation signals (Shine Dalgarno sequence or Kozak sequence) introns, a polyadenylation sequence, 5' and 3' untranslated regions) which interact with host cellular proteins to carry out transcription and translation. Such elements may vary in their strength and specificity. The transcriptional regulatory element may be functional in either a eukaryotic cell (e.g., a mammalian cell) or a prokaryotic cell (e.g., bacterial or archaeal cell). In some embodiments, a polynucleotide sequence encoding the therapeutic gene products (e.g., a therapeutic protein or nucleic acid) described herein is operably linked to multiple control elements that allow expression of the polynucleotide in both prokaryotic and eukaryotic cells.

As used herein, the term "transcription start site" or "TSS" refers to the first base pair transcribed by an RNA polymerase when the RNA polymerase initiates transcription. A TSS is different from the start codon (canonically, ATG), which must be downstream of the TSS in the transcribed region of the polynucleotide. The location of a transcription start site can be determined experimentally or by prediction using any of various prediction algorithms. Annotated TSSs are available from the Eukaryotic Promoter Database and the UCSC Genome Browser. Multiple TSSs for TNNT2 are identified in the UCSC Genome Browser.

As used herein, the TSS for TNNT2 is defined to be the sequence identified by the C at the 5' end of the motif identified by dbTSS: CTCCATC.

The term "modified cardiac TNNT2 promoter" as used herein refers to a promoter that comprises a polynucleotide sequence of at least 200 base pairs that comprises one or more continuous or discontinuous polynucleotide segments each sharing 70%, 80%, 90%, 95%, 96%, 97%, 98%, 99%, or 100% identity to a corresponding segment of the TNNT2p-600 segment provided in Table 1 as SEQ ID NO: 1. As it is a "promoter," a modified cardiac TNNT2 promoter must be capable of promoting initiation of transcription by an RNA polymerase in a host or target cell at or near a TSS within the promoter (i.e. at or near the TTS of TNNT2 as defined herein) or, if the endogenous TSS of TNNT2 is not present in the modified cardiac TNNT2 promoter then at a heterologous TSS at most 100 base pairs downstream (3' on the sense strand) to the downstream (3') end of the modified cardiac TNNT2 promoter. Similarly stated, a modified cardiac TNNT2 promoter may comprise only sequences upstream of the TSS of TNNT2 or more comprise the TSS of TNNT2.

The length of a promoter (e.g., a modified cardiac TNNT2 promoter), a promoter "having" so many base pairs, as used herein, is defined according to the number of base pairs in the polynucleotide sequence of the promoter from its 5' end to its 3' end, inclusive of the endpoints, and inclusive of any intervening sequences that do not align to a reference promoter sequence (e.g., the endogenous cardiac TNNT2 promoter of a human or other organism). The 5' end and the 3' end of the promoter are defined as the last base pair in either direction to match a corresponding sequence in a reference promoter sequence when the sequence are aligned by the BLAST algorithm or the equivalent. Thus, the length of a promoter in a vector can be determined by searching a nucleotide database containing a genome of a reference organism using the polynucleotide sequence of the vector and identifying one or more aligned regions that encompass or are within about 1-5 kb of an endogenous gene, or by aligning the vector to a predetermined reference promoter. If the promoter aligns to the reference genome or reference promoter sequence as a continuous segment, then the length of promoter is the length alignment reported (the 3' end position minus the 5' end position, +1 unless the TSS is included). If the promoter aligns in multiple segments (e.g., 2, 3, 4, or 5 segments), then the length of the promoter can be calculated by the 3' end position of the 3'-most segment of the reference genome or reference promoter sequence, minus the 5' end position of the 5'-most segment of reference genome or reference promoter sequence, plus 1 unless the TSS is included (such that the calculated length includes both end points). For example, the length of a promoter that extends from a base pair 100 bp before the TSS (−100 bp) to 5 bp before the TSS (−5 bp) is −5−(−100)+1=100−5+1=96 bp. The TSS is numbered +1 bp. Therefore, the length of a promoter that extends from a base pair 100 bp before the TSS (−100 bp) to 5 bp after the TSS (+5 bp) is +5−(−100)=100+5=105 bp.

The term "enhancer" refers to a segment of DNA which contains sequences capable of providing enhanced transcription and in some instances can function independent of their orientation relative to another control sequence. An enhancer can function cooperatively or additively with promoters and/or other enhancer elements. An enhancer may overlap with a promoter or be upstream or downstream of the promoter. In some embodiments, the modified cardiac TNNT2 promoter comprises one or more enhancers. In some embodiments, the modified cardiac TNNT2 promoter comprises no enhancer.

In addition to or instead of a modified cardiac TNNT2 promoter, some embodiments employ other eukaryotic promoters, including but not limited to: cytomegalovirus (CMV) immediate early, herpes simplex virus (HSV) thymidine kinase, a viral simian virus 40 (SV40) (e.g., early and late SV40), a spleen focus forming virus (SFFV) promoter, long terminal repeats (LTRs) from retrovirus (e.g., a Moloney murine leukemia virus (MoMLV) LTR promoter or a Rous sarcoma virus (RSV) LTR), a herpes simplex virus (HSV) (thymidine kinase) promoter, H5, P7.5, and P11 promoters from vaccinia virus, an elongation factor 1-alpha (EF1α) promoter, early growth response 1 (EGR1) promoter, a ferritin H (FerH) promoter, a ferritin L (FerL) promoter, a Glyceraldehyde 3-phosphate dehydrogenase (GAPDH) promoter, a eukaryotic translation initiation factor 4A1 (EIF4A1) promoter, a heat shock 70 kDa protein 5 (HSPA5) promoter, a heat shock protein 90 kDa beta, member 1 (HSP90B1) promoter, a heat shock protein 70 kDa (HSP70) promoter, a β-kinesin (β-KIN) promoter, the human ROSA 26 locus (Irions et al., *Nature Biotechnology* 25, 1477-1482 (2007)), a Ubiquitin C (UBC) promoter, a phosphoglycerate kinase-1 (PGK) promoter, a cytomegalovirus enhancer/chicken β-actin (CAG) promoter, a β-actin promoter and a myeloproliferative sarcoma virus enhancer, negative control region deleted, dl587rev primer-binding site substituted (MND) promoter, and mouse metallothionein-1. The vector may also contain a ribosome binding site for translation initiation and a transcription terminator. The vector may also include polynucleotide sequences for amplifying expression. The vector may also include polynucleotide sequences encoding protein tags (e.g., 6xHis tag, hemagglutinin tag, green fluorescent protein, etc.) that are fused to the site-directed modifying polypeptide, thus resulting in a chimeric polypeptide.

In some embodiments, the promoters of the disclosure are tissue-specific. The term "tissue-specific promoter" means a polynucleotide sequence that serves as a promoter, i.e., regulates expression of a selected polynucleotide sequence operably linked to the promoter, and which affects expression of the selected polynucleotide sequence in specific cells of a tissue, such as myocytes or myocardial cells. In some embodiments, the tissue-specific promoter is a cardiac-specific promoter. In some embodiments, the cardiac-specific promoter is TNNT2 or a modified TNNT2 promoter. A tissue-specific promoter causes expression of an operatively linked polynucleotide, or a gene product encoded by that polynucleotide, at 5x, 10x, 20x, 25x or greater levels in the tissue of interest than in a reference tissue.

In some embodiments, the vectors described herein comprise a transcription termination signal. Elements directing the efficient termination and polyadenylation of the heterologous nucleic acid transcripts increases heterologous gene expression. Transcription termination signals are generally found downstream of the polyadenylation signal. In some embodiments, vectors comprise a polyadenylation sequence 3' of a polynucleotide encoding a polypeptide to be expressed. The term "polyA site" or "polyA sequence" as used herein denotes a DNA sequence which directs both the termination and polyadenylation of the nascent RNA transcript by RNA polymerase II. Polyadenylation sequences can promote mRNA stability by addition of a polyA tail to the 3' end of the coding sequence and thus, contribute to increased translational efficiency. Cleavage and polyadenylation is directed by a poly(A) sequence in the RNA. The core poly(A) sequence for mammalian pre-mRNAs has two recognition elements flanking a cleavage-polyadenylation site. Typically, an almost invariant AAUAAA hexamer lies 20-50 nucleotides upstream of a more variable element rich in U or GU residues. Cleavage of the nascent transcript occurs between these two elements and is coupled to the addition of up to 250 adenosines to the 5' cleavage product. In particular embodiments, the core poly(A) sequence is an ideal polyA sequence (e.g., AATAAA, ATTAAA, AGTAAA). In particular embodiments, the poly(A) sequence is an SV40 polyA sequence, a bovine growth hormone polyA sequence (BGHpA), a rabbit β-globin polyA sequence (rβgpA), variants thereof, or another suitable heterologous or endogenous polyA sequence known in the art.

Figure 1B:
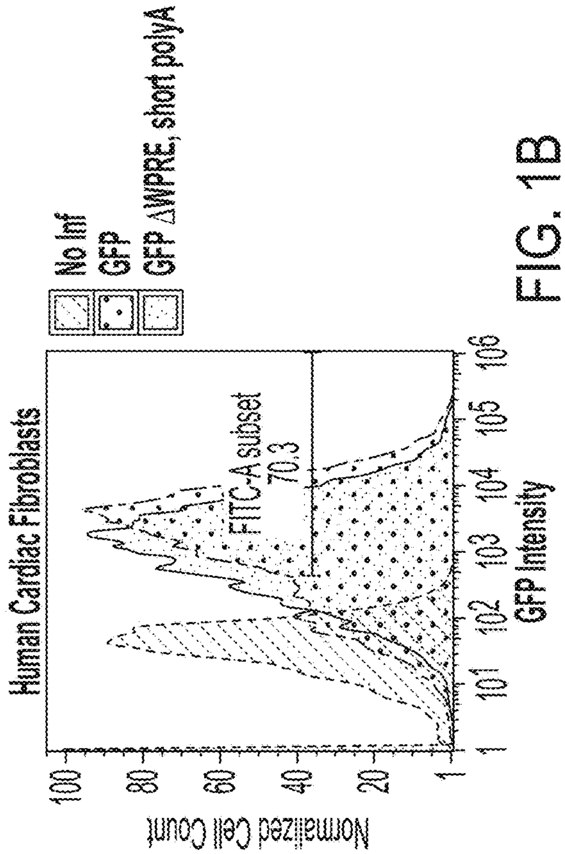
FIG. 1B shows flow cytometry analysis, two days post-infection, of human cardiac fibroblasts (n=2), MOI 160,000 with AAV-packaged constructs.
Figure 1C:
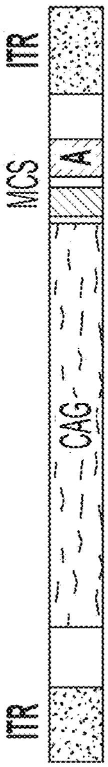
FIG. 1C shows a map of an insert sequence for an AAV vector genome adapted for large cargoes, showing deletion or truncation of two cis-regulatory elements, deletion of the intron, and partial deletion of the sequence 3' to the 5' ITR.
Figure 2A:
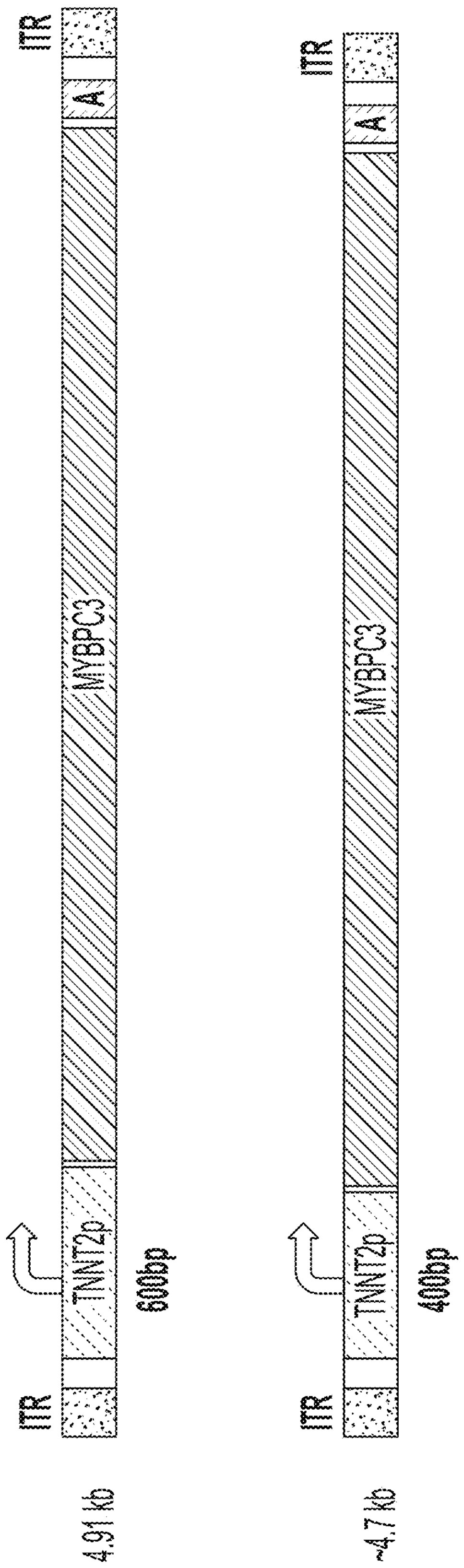
FIG. 2A shows a schematic of the original and altered versions of a viral genome comprising the cardiac-specific troponin (TNNT2) promoter and myosin binding protein C (MYBPC3) transgene.

IV. Recombinant Adeno-Associated Virus (rAAV) Viral Genome, Expression Cassette, and rAAV Virions The disclosure provides an expression cassette comprising a polynucleotide encoding a transgene, e.g. a sequence encoding a MYBPC3 polypeptide, or functional variant thereof. The transgene polynucleotide sequence in an expression cassette can be, for example, an open reading frame encoding a protein. The expression cassette may comprise, optionally, a promoter operatively linked to the transgene, optionally an intron region, optionally a polyadenylation (poly(A)) signal, optionally a woodchuck hepatitis virus post-transcriptional element (WPRE), and optionally a transcription termination signal. The expression cassette may be flanked by one or more inverted terminal repeats (ITRs). An expression cassette flanked by one or more ITRs is herein referred to as a "viral genome." The ITRs in an expression cassette serve as markers used for viral packaging of the expression cassette (Clark et al. *Hum Gene Ther.* 6:1329-41 (1995)). Illustrative and non-limiting embodiments of viral genomes of the disclosure are shown in FIG. 1A, FIG. 1C, and FIG. 2A. The polynucleotide encoding the expression cassette provides the function of expressing the transgene within a host cell. The expression cassette can be integrated into the host cell genome by, for example, infecting the host cell with an rAAV virion comprising capsid protein and a viral genome comprising an expression cassette.

The promoter sequence of the expression cassette, when present, controls expression of the polynucleotide encoding the transgene, e.g. a sequence encoding MYBPC3 or functional variant thereof. Various promoters can be used. The promoter may be cell-type specific. Constitutive promoters are used in expression cassettes and can be, for example, the cytomegalovirus enhancer fused to the chicken β-actin promoter (CAG), simian virus 40 (SV40) promoter, and the herpes simplex virus thymidine kinase (HSV-TK) promoter (Damdindorj et al. *PLoS One.* 9:e106472 (2014)). Other cell-type specific promoters may also be used. Cardiac cell specific promoters can be, for example, the MLC2v promoter (Phillips et al. *Hypertension.* 39:651-5 (2002)) and the cardiac Troponin-T (cTnT) promoter (Konkalmatt et al. *Circ Cardiovasc Imaging.* 6:478-486 (2013)).

In some aspects, the disclosure provides promoters have been optimized for cardiac cell-specific expression and length to accommodate transgenes of specified size. In one embodiment, the promoter of an rAAV vector genome described herein is a polynucleotide having between 300 bp and 500 bp.

Exemplary expression cassette and viral genome sequences of the disclosure can be found in Table 5. In some embodiments, the expression cassette comprises a polynucleotide sequence that shares at least 90%, 95%, 96%, 97%, 98%, 99%, or 100% identity to SEQ ID NO: 95, SEQ ID NO: 99, or SEQ ID NO: 101. In some embodiments, the viral genome comprises a polynucleotide sequence that shares at least 90%, 95%, 96%, 97%, 98%, 99%, or 100% identity to SEQ ID NO: 98, SEQ ID NO: 100, or SEQ ID NO: 102. In another embodiment, an expression cassette can be segmented according to the polynucleotide regions flanking the transgene. The polynucleotide sequence spanning the 5' end of the cassette to the 5' end of the transgene is herein referred to as the 5' segment of the expression cassette. The polynucleotide sequence spanning the 3' end of the transgene to the 3' end of the expression cassette is herein referred to as the 3' segment of the expression cassette. In one embodiment, the 5' segment of the expression cassette comprises a polynucleotide sequence that shares at least 90%, 95%, 96%, 97%, 98%, 99%, or 100% identity to SEQ ID NO: 93. In one embodiment, the 3' segment of the expression cassette comprises a polynucleotide sequence that shares at least 90%, 95%, 96%, 97%, 98%, 99%, or 100% identity to SEQ ID NO: 94.

The ability to express large transgenes delivered by rAAV vectors or rAAV virions is limited. rAAV vector genome sizes have a maximum sequence length of about 5 kb, thus providing a limit for the length of all elements required in an expression cassette including regulatory elements, e.g. promoter, and a transgene, e.g. MYBPC3. rAAV vector genomes exceeding 5 kb result in vector genome truncation during rAAV virion packaging and reduce or ablate transgene expression (Wu et al. *Mol Ther.* 18:80-86 (2010)). In some embodiments, the present disclosure provides rAAV vector genomes that are optimized for carrying large transgenes. Elements of the vector genome have been reduced in length in order to accommodate a larger transgene. In one embodiment, the 5' segment and 3' segment of an expression cassette together comprise at most 0.8 kbp or at most 0.9 kbp. In another embodiment, the 5' ITR, the 5' segment, the 3' segment, and 3' ITR together comprise comprise 1.2 kbp or at most comprise 1.3 kbp. In one embodiment, the 5' segment comprises at most 500 bp or at most 480 bp. In one embodiment, the 3' segment comprises at most 200 bp or at most 150 bp. In another embodiment, the vector genome comprises at most 4.7 kbp. 4.8 kbp, 4.9 kbp, or 5.0 kbp. In some embodiments, the polynucleotide encoding the gene product comprises between 3 kb and 11 kb, between 3 kbp and 5 kbp, between 3.5 kbp and 4.5 kbp, or between 3.7 kbp and 4 kbp. In some embodiments, the polynucleotide encoding the gene product comprises 3.7 kbp to 3.9 kbp. In some embodiments, the polynucleotide encoding the gene product comprises 3.8 kbp.

TABLE 5

Illustrative expression cassette and viral genomes

| Name | DNA Sequence | SEQ ID NO. |
|---|---|---|
| viral genome (600 bp promoter) | Ctgcgcgctcgctcgctcactgagg ccgcccgggcaaagcccgggcgtcg ggcgacctttggtcgcccggcctca gtgagcgagcgagcgcgcagagagg gagtggccaactccatcactagggg ttccttgtagttaatgattaacccg ccatgctacttatctacgtagccat gctctaggaagatcggaattcgccc ttaagtcatggagaagacccacctt gcagatgtcctcactggggctggca gagccggcaacctgcccaaggctgc tcagtccattaggagccagtagcct ggaagatgtctttacccccagcatc agttcaagtggagcagcacataact cttgccctctgccttccaagattct ggtgctgagacttatggagtgtctt ggaggttgccttctgccccccaacc ctgctcccagctggccctcccaggc ctgggttgctggcctctgctttatc aggattctcaagagggacagctggt | 98 |

TABLE 5-continued

Illustrative expression cassette and viral genomes

| Name | DNA Sequence | SEQ ID NO. |
|---|---|---|
| | ttatgttgcatgactgttccctgca<br>tatctgctctggttttaaatagctt<br>atctgagcagctggaggaccacatg<br>ggcttatatggcgtggggtacatgt<br>tcctgtagccttgtccctggcacct<br>gccaaaatagcagccaacacccccc<br>acccccaccgccatccccctgcccc<br>acccgtcccctgtcgcacattcctc<br>cctccgcagggctggctcaccaggc<br>cccagcccacatgcctgcttaaagc<br>cctctccatcctctgcctcacccag<br>tccccgctgagactgagcagacgcc<br>tccagccaccaagcttaataaaaga<br>tctttattttcattagatctgtgtg<br>ttggttttttgtgtgctggggactc<br>gagttaagggcgaattcccgataag<br>gatcttcctagagcatggctacgta<br>gataagtagcatggcgggttaatca<br>ttaactacaaggaacccctagtgat<br>ggagttggccactccctctctgcgc<br>gctcgctcgctcactgaggccgggc<br>gaccaaaggtcgcccgacgcccggg<br>ctttgcccgggcggcctcagtgagc<br>gagcgagcgcgcag | |
| expression cassette (600 bp promoter) | Tgtagttaatgattaacccgccatg<br>ctacttatctacgtagccatgctct<br>aggaagatcggaattcgcccttaag<br>tcatggagaagacccaccttgcaga<br>tgtcctcactggggctggcagagcc<br>ggcaacctgcccaaggctgctcagt<br>ccattaggagccagtagcctggaag<br>atgtctttacccccagcatcagttc<br>aagtggagcagcacataactcttgc<br>cctctgccttccaagattctggtgc<br>tgagacttatggagtgtcttggagg<br>ttgccttctgccccccaaccctgct<br>cccagctggccctcccaggcctggg<br>ttgctggcctctgctttatcaggat<br>tctcaagagggacagctggtttatg<br>ttgcatgactgttccctgcatatct<br>gctctggttttaaatagcttatctg<br>agcagctggaggaccacatgggctt<br>atatggcgtggggtacatgttcctg<br>tagccttgtccctggcacctgccaa<br>aatagcagccaacaccccccacccc<br>caccgccatccccctgccccacccg<br>tcccctgtcgcacattcctccctcc<br>gcagggctggctcaccaggccccag<br>cccacatgcctgcttaaagccctct<br>ccatcctctgcctcacccagtcccc<br>gctgagactgagcagacgcctccag<br>ccaccaagcttaataaaagatcttt<br>attttcattagatctgtgtgttggt<br>tttttgtgtgctggggactcgagtt<br>aagggcgaattcccgataaggatct<br>tcctagagcatggctacgtagataa<br>gtagcatggcgggttaatcattaac<br>tacaa | 99 |
| viral genome (400 bp promoter) | Ctgcgcgctcgctcgctcactgagg<br>ccgcccgggcaaagcccgggcgtcg<br>ggcgacctttggtcgcccggcctca<br>gtgagcgagcgagcgcgcagagagg<br>gagtggccaactccatcactagggg<br>ttccttgtagttaatgattaacccg<br>ccatgctacttatctacgtagccat<br>gctctaggaagatcggaattcgccc<br>ttaagttgccttctgccccccaacc<br>ctgctcccagctggccctcccaggc<br>ctgggttgctggcctctgctttatc<br>aggattctcaagagggacagctggt<br>ttatgttgcatgactgttccctgca | 100 |

TABLE 5-continued

Illustrative expression cassette and viral genomes

| Name | DNA Sequence | SEQ ID NO. |
|---|---|---|
| | tatctgctctggttttaaatagctt<br>atctgagcagctggaggaccacatg<br>ggcttatatggcgtggggtacatgt<br>tcctgtagccttgtccctggcacct<br>gccaaaatagcagccaacacccccc<br>acccccaccgccatccccctgcccc<br>acccgtcccctgtcgcacattcctc<br>cctccgcagggctggctcaccaggc<br>cccagcccacatgcctccaagctta<br>ataaaagatctttattttcattaga<br>tctgtgtgttggttttttgtgtgct<br>ggggactcgagttaagggcgaattc<br>ccgataaggatcttcctagagcatg<br>gctacgtagataagtagcatggcgg<br>gttaatcattaactacaaggaaccc<br>ctagtgatggagttggccactccct<br>ctctgcgcgctcgctcgctcactga<br>ggccgggcgaccaaaggtcgcccga<br>cgcccgggctttgcccgggcggcct<br>cagtgagcgagcgagcgcgcag | |
| expression cassette (400 bp promoter) | Tgtagttaatgattaacccgccatg<br>ctacttatctacgtagccatgctct<br>aggaagatcggaattcgcccttaag<br>ttgccttctgccccccaaccctgct<br>cccagctggccctcccaggcctggg<br>ttgctggcctctgctttatcaggat<br>tctcaagagggacagctggtttatg<br>ttgcatgactgttccctgcatatct<br>gctctggttttaaatagcttatctg<br>agcagctggaggaccacatgggctt<br>atatggcgtggggtacatgttcctg<br>tagccttgtccctggcacctgccaa<br>aatagcagccaacaccccccacccc<br>caccgccatccccctgccccacccg<br>tcccctgtcgcacattcctccctcc<br>gcagggctggctcaccaggccccag<br>cccacatgcctgcttaaagccctct<br>ccatcctctgcctcacccagtcccc<br>gctgagactgagcagacgcctccag<br>ccaccaagcttaataaaagatcttt<br>attttcattagatctgtgtgttggt<br>tttttgtgtgctggggactcgagtt<br>aagggcgaattcccgataaggatct<br>tcctagagcatggctacgtagataa<br>gtagcatggcgggttaatcattaac<br>taca | 101 |
| viral genome + MYBPC3 transgene (400 bp promoter) | ctgcgcgctcgctcgctcactgagg<br>ccgcccgggcaaagcccgggcgtcg<br>ggcgacctttggtcgcccggcctca<br>gtgagcgagcgagcgcgcagagagg<br>gagtggccaactccatcactagggg<br>ttccttgtagttaatgattaacccg<br>ccatgctacttatctacgtagccat<br>gctctaggaagatcggaattcgccc<br>ttaagttgccttctgccccccaacc<br>ctgctcccagctggccctcccaggc<br>ctgggttgctggcctctgctttatc<br>aggattctcaagagggacagctggt<br>ttatgttgcatgactgttccctgca<br>tatctgctctggttttaaatagctt<br>atctgagcagctggaggaccacatg<br>ggcttatatggcgtggggtacatgt<br>tcctgtagccttgtccctggcacct<br>gccaaaatagcagccaacacccccc<br>acccccaccgccatccccctgcccc<br>acccgtcccctgtcgcacattcctc<br>cctccgcagggctggctcaccaggc<br>cccagcccacatgcctgcttaaagc<br>cctctccatcctctgcctcacccag<br>tccccgctgagactgagcagacgcc<br>tccagccaccatgcctgagccgggg | 102 |

TABLE 5-continued

| Illustrative expression cassette and viral genomes | | |
|---|---|---|
| Name | DNA Sequence | SEQ ID NO. |
| | aagaagccagtctcagcttttagca<br>agaagccacggtcagtggaagtggc<br>cgcaggcagccctgccgtgttcgag<br>gccgagacagagcgggcaggagtga<br>aggtgcgctggcagcgcggaggcag<br>tgacatcagcgccagcaacaagtac<br>ggcctggccacagagggcacacggc<br>atacgctgacagtgcgggaagtggg<br>ccctgccgaccagggatcttacgca<br>gtcattgctggctcctccaaggtca<br>agttcgacctcaaggtcatagaggc<br>agagaaggcagagcccatgctggcc<br>cctgcccctgcccctgctgaggcca<br>ctggagcccctggagaagccccggc<br>cccagccgctgagctgggagaaagt<br>gccccaagtcccaaagggtcaagct<br>cagcagctctcaatggtcctacccc<br>tggagcccccgatgaccccattggc<br>ctcttcgtgatgcggccacaggatg<br>gcgaggtgaccgtgggtggcagcat<br>caccttctcagcccgcgtggccggc<br>gccagcctcctgaagccgcctgtgg<br>tcaagtggttcaagggcaaatgggt<br>ggacctgagcagcaaggtgggccag<br>cacctgcagctgcacgacagctacg<br>accgcgccagcaaggtctatctgtt<br>cgagctgcacatcaccgatgcccag<br>cctgccttcactggcagctaccgct<br>gtgaggtgtccaccaaggacaaatt<br>tgactgctccaacttcaatctcact<br>gtccacgaggccatgggcaccggag<br>acctggacctcctatcagccttccg<br>ccgcacgagcctggctggaggtggt<br>cggcggatcagtgatagccatgagg<br>acactgggattctggacttcagctc<br>actgctgaaaaagagagacagtttc<br>cggaccccgagggactcgaagctgg<br>aggcaccagcagaggaggacgtgtg<br>ggagatcctacggcaggcaccccca<br>tctgagtacgagcgcatcgccttcc<br>agtacggcgtcactgacctgcgcgg<br>catgctaaagaggctcaagggcatg<br>aggcgcgatgagaagaagagcacag<br>cctttcagaagaagctggagccggc<br>ctaccaggtgagcaaaggccacaag<br>atccggctgaccgtggaactggctg<br>accatgacgctgaggtcaaatggct<br>caagaatggccaggagatccagatg<br>agcggcagcaagtacatctttgagt<br>ccatcggtgccaagcgtaccctgac<br>catcagccagtgctcattggcggac<br>gacgcagcctaccagtgcgtggtgg<br>gtggcgagaagtgtagcacggagct<br>ctttgtgaaagagccccctgtgctc<br>atcacgcgccccttggaggaccagc<br>tggtgatggtggggcagcgggtgga<br>gtttgagtgtgaagtatcggaggag<br>ggggcgcaagtcaaatggctgaagg<br>acggggtggagctgacccgggagga<br>gaccttcaaataccggttcaagaag<br>gacgggcagagacaccacctgatca<br>tcaacgaggccatgctggaggacgc<br>ggggcactatgcactgtgcactagc<br>gggggccaggcgctggctgagctca<br>ttgtgcaggaaaagaagctggaggt<br>gtaccagagcatcgcagacctgatg<br>gtgggcgcaaaggaccaggcggtgt<br>tcaaatgtgaggtctcagatgagaa<br>tgttcggggtgtgtggctgaagaat<br>gggaaggagctggtgcccgacagcc<br>gcataaaggtgtcccacatcgggcg<br>ggtccacaaactgaccattgacgac<br>gtcacacctgccgacgaggctgact | |

TABLE 5-continued

| Illustrative expression cassette and viral genomes | | |
|---|---|---|
| Name | DNA Sequence | SEQ ID NO. |
| | acagctttgtgcccgagggcttcgc<br>ctgcaacctgtcagccaagctccac<br>ttcatggaggtcaagattgacttcg<br>tacccaggcaggaacctcccaagat<br>ccacctggactgcccaggccgcata<br>ccagacaccattgtggttgtagctg<br>gaaataagctacgtctggacgtccc<br>tatctctggggaccccgctcccact<br>gtgatctggcagaaggctatcacgc<br>aggggaataaggccccagccaggcc<br>agccccagatgccccagaggacaca<br>ggtgacagcgatgagtgggtgtttg<br>acaagaagctgctgtgtgagaccga<br>gggccgggtccgcgtggagaccacc<br>aaggaccgcagcatcttcacggtcg<br>agggggcagagaaggaagatgaggg<br>cgtctacacggtcacagtgaagaac<br>cctgtgggcgaggaccaggtcaacc<br>tcacagtcaaggtcatcgacgtgcc<br>agacgcacctgcggcccccaagatc<br>agcaacgtgggagaggactcctgca<br>cagtacagtgggagccgcctgccta<br>cgatggcgggcagcccatcctgggc<br>tacatcctggagcgcaagaagaaga<br>agagctaccggtggatgcggctgaa<br>cttcgacctgattcaggagctgagt<br>catgaagcgcggcgcatgatcgagg<br>gcgtggtgtacgagatgcgcgtcta<br>cgcggtcaacgccatcggcatgtcc<br>aggcccagccctgcctcccagccct<br>tcatgcctatcggtcccccagcga<br>acccacccacctggcagtagaggac<br>gtctctgacaccacggtctccctca<br>agtggcggcccccagagcgcgtggg<br>agcaggaggcctggatggctacagc<br>gtggagtactgcccagagggctgct<br>cagagtgggtggctgccctgcaggg<br>gctgacagagcacacatcgatactg<br>gtgaaggacctgcccacgggggccc<br>ggctgcttttccgagtgcgggcaca<br>caatatggcagggcctggagcccct<br>gttaccaccacggagccggtgacag<br>tgcaggagatcctgcaacggccacg<br>gcttcagctgcccaggcacctgcgc<br>cagaccattcagaagaaggtcgggg<br>agcctgtgaaccttctcatcccttt<br>ccagggcaagccccggcctcaggtg<br>acctggaccaaagaggggcagcccc<br>tggcaggcgaggaggtgagcatccg<br>caacagccccacagacaccatcctg<br>ttcatccgggccgctcgccgcgtgc<br>attcaggcacttaccaggtgacggt<br>gcgcattgagaacatggaggacaag<br>gccacgctggtgctgcaggttgttg<br>acaagccaagtcctccccaggatct<br>ccgggtgactgacgcctggggtctt<br>aatgtggctctggagtggaagccac<br>cccaggatgtcggcaacacggaact<br>ctgggggtacacagtgcagaaagcc<br>gacaagaagaccatggagtggttca<br>ccgtcttggagcattaccgccgcac<br>ccactgcgtggtgccagagctcatc<br>attggcaatggctactacttccgcg<br>tcttcagccagaatatggttggctt<br>tagtgacagagcggccaccaccaag<br>gagcccgtctttatccccagaccag<br>gcatcacctatgagccacccaacta<br>taaggccctggacttctccgaggcc<br>ccaagcttcacccagcccctggtga<br>accgctcggtcatcgcgggctacac<br>tgctatgctctgctgtgctgtccgg<br>ggtagccccaagcccaagatttcct<br>ggttcaagaatggcctggacctggg | |

TABLE 5-continued

| Illustrative expression cassette and viral genomes | | |
|---|---|---|
| Name | DNA Sequence | SEQ ID NO. |
| | agaagacgcccgcttccgcatgttc | |
| | agcaagcagggagtgttgactctgg | |
| | agattagaaagccctgcccctttga | |
| | cgggggcatctatgtctgcagggcc | |
| | accaacttacagggcgaggcacggt | |
| | gtgagtgccgcctggaggtgcgagt | |
| | gcctcagtaaagcttaataaaagat | |
| | ctttattttcattagatctgtgtgt | |
| | tggtttttttgtgtgctggggactcg | |
| | agttaagggcgaattcccgataagg | |
| | atcttcctagagcatggctacgtag | |
| | ataagtagcatggcgggttaatcat | |
| | taactacaaggaacccctagtgatg | |
| | gagttggccactccctctctgcgcg | |
| | ctcgctcgctcactgaggccgggcg | |
| | accaaaggtcgcccgacgcccgggc | |
| | tttgcccgggcggcctcagtgagcg | |
| | agcgagcgcgcag | |
| expression cassette + MYBPC3 transgene (400 bp promoter) | tgtagttaatgattaacccgccatg | 95 |
| | ctacttatctacgtagccatgctct | |
| | aggaagatcggaattcgcccttaag | |
| | ttgccttctgccccccaaccctgct | |
| | cccagctggccctcccaggcctggg | |
| | ttgctggcctctgctttatcaggat | |
| | tctcaagagggacagctggtttatg | |
| | ttgcatgactgttccctgcatatct | |
| | gctctggttttaaatagcttatctg | |
| | agcagctggaggaccacatgggctt | |
| | atatggcgtggggtacatgttcctg | |
| | tagccttgtccctggcacctgccaa | |
| | aatagcagccaacacccccccacccc | |
| | caccgccatcccccctgccccacccg | |
| | tcccctgtcgcacattcctccctcc | |
| | gcagggctggctcaccaggccccag | |
| | cccacatgcctgcttaaagccctct | |
| | ccatcctctgcctcacccagtcccc | |
| | gctgagactgagcagacgcctccag | |
| | ccaccatgcctgagccggggaagaa | |
| | gccagtctcagcttttagcaagaag | |
| | ccacggtcagtggaagtggccgcag | |
| | gcagccctgccgtgttcgaggccga | |
| | gacagagcgggcaggagtgaaggtg | |
| | cgctggcagcgcggaggcagtgaca | |
| | tcagcgccagcaacaagtacggcct | |
| | ggccacagagggcacacggcatacg | |
| | ctgacagtgcgggaagtgggccctg | |
| | ccgaccagggatcttacgcagtcat | |
| | tgctggctcctccaaggtcaagttc | |
| | gacctcaaggtcatagaggcagaga | |
| | aggcagagcccatgctggcccctgc | |
| | ccctgcccctgctgaggccactgga | |
| | gcccctggagaagccccggccccag | |
| | ccgctgagctgggagaaagtgcccc | |
| | aagtcccaaagggtcaagctcagca | |
| | gctctcaatggtcctacccctggag | |
| | cccccgatgaccccattggcctctt | |
| | cgtgatgcggccacaggatggcgag | |
| | gtgaccgtgggtggcagcatcacct | |
| | tctcagcccgcgtggccggcgccag | |
| | cctcctgaagccgcctgtggtcaag | |
| | tggttcaagggcaaatgggtggacc | |
| | tgagcagcaaggtgggccagcacct | |
| | gcagctgcacgacagctacgaccgc | |
| | gccagcaaggtctatctgttcgagc | |
| | tgcacatcaccgatgcccagcctgc | |
| | cttcactggcagctaccgctgtgag | |
| | gtgtccaccaaggacaaatttgact | |
| | gctccaacttcaatctcactgtcca | |
| | cgaggccatgggcaccggagacctg | |
| | gacctcctatcagccttccgccgca | |
| | cgagcctggctggaggtggtcggcg | |
| | gatcagtgatagccatgaggacact | |

TABLE 5-continued

| Illustrative expression cassette and viral genomes | | |
|---|---|---|
| Name | DNA Sequence | SEQ ID NO. |
| | gggattctggacttcagctcactgc | |
| | tgaaaaagagagacagtttccggac | |
| | cccgagggactcgaagctggaggca | |
| | ccagcagaggaggacgtgtgggaga | |
| | tcctacggcaggcacccccatctga | |
| | gtacgagcgcatcgccttccagtac | |
| | ggcgtcactgacctgcgcggcatgc | |
| | taaagaggctcaagggcatgaggcg | |
| | cgatgagaagaagagcacagccttt | |
| | cagaagaagctggagccggcctacc | |
| | aggtgagcaaaggccacaagatccg | |
| | gctgaccgtggaactggctgaccat | |
| | gacgctgaggtcaaatggctcaaga | |
| | atggccaggagatccagatgagcgg | |
| | cagcaagtacatctttgagtccatc | |
| | ggtgccaagcgtaccctgaccatca | |
| | gccagtgctcattggcggacgacgc | |
| | agcctaccagtgcgtggtgggtggc | |
| | gagaagtgtagcacggagctctttg | |
| | tgaaagagccccctgtgctcatcac | |
| | gcgccccttggaggaccagctggtg | |
| | atggtggggcagcgggtggagtttg | |
| | agtgtgaagtatcggaggaggggc | |
| | gcaagtcaaatggctgaaggacggg | |
| | gtggagctgacccgggaggagacct | |
| | tcaaataccggttcaagaaggacgg | |
| | gcagagacaccacctgatcatcaac | |
| | gaggccatgctggaggacgcggggc | |
| | actatgcactgtgcactagcggggg | |
| | ccaggcgctggctgagctcattgtg | |
| | caggaaaagaagctggaggtgtacc | |
| | agagcatcgcagacctgatggtggg | |
| | cgcaaaggaccaggcggtgttcaaa | |
| | tgtgaggtctcagatgagaatgttc | |
| | ggggtgtgtggctgaagaatgggaa | |
| | ggagctggtgcccgacagccgcata | |
| | aaggtgtcccacatcgggcgggtcc | |
| | acaaactgaccattgacgacgtcac | |
| | acctgccgacgaggctgactacagc | |
| | tttgtgcccgagggcttcgcctgca | |
| | acctgtcagccaagctccacttcat | |
| | ggaggtcaagattgacttcgtaccc | |
| | aggcaggaacctcccaagatccacc | |
| | tggactgcccaggccgcataccaga | |
| | caccattgtggttgtagctggaaat | |
| | aagctacgtctggacgtccctatct | |
| | ctggggaccccgctcccactgtgat | |
| | ctggcagaaggctatcacgcagggg | |
| | aataaggccccagccaggccagccc | |
| | cagatgccccagaggacacaggtga | |
| | cagcgatgagtgggtgtttgacaag | |
| | aagctgctgtgtgagaccgagggcc | |
| | gggtccgcgtggagaccaccaagga | |
| | ccgcagcatcttcacggtcgagggg | |
| | gcagagaaggaagatgagggcgtct | |
| | acacggtcacagtgaagaaccctgt | |
| | gggcgaggaccaggtcaacctcaca | |
| | gtcaaggtcatcgacgtgccagacg | |
| | cacctgcggcccccaagatcagcaa | |
| | cgtgggagaggactcctgcacagta | |
| | cagtgggagccgcctgcctacgatg | |
| | gcgggcagcccatcctgggctacat | |
| | cctggagcgcaagaagaagaagagc | |
| | taccggtggatgcggctgaacttcg | |
| | acctgattcaggagctgagtcatga | |
| | agcgcggcgcatgatcgagggcgtg | |
| | gtgtacgagatgcgcgtctacgcgg | |
| | tcaacgccatcggcatgtccaggcc | |
| | cagccctgcctcccagcccttcatg | |
| | cctatcggtcccccagcgaaccca | |
| | cccacctggcagtagaggacgtctc | |
| | tgacaccacggtctccctcaagtgg | |
| | cggcccccagagcgcgtgggagcag | |

TABLE 5-continued

Illustrative expression cassette and viral genomes

| Name | DNA Sequence | SEQ ID NO. |
|---|---|---|
| | gaggcctggatggctacagcgtgga gtactgcccagagggctgctcagag tgggtggctgccctgcaggggctga cagagcacacatcgatactggtgaa ggacctgcccacgggggcccggctg cttttccgagtgcgggcacacaata tggcagggcctggagcccctgttac caccacggagccggtgacagtgcag gagatcctgcaacggccacggcttc agctgcccaggcacctgcgccagac cattcagaagaaggtcggggagcct gtgaaccttctcatccctttccagg gcaagccccggcctcaggtgacctg gaccaaagaggggcagcccctggca ggcgaggaggtgagcatccgcaaca gccccacagacaccatcctgttcat ccgggccgctcgccgcgtgcattca ggcacttaccaggtgacggtgcgca ttgagaacatggaggacaaggccac gctggtgctgcaggttgttgacaag ccaagtcctccccaggatctccggg tgactgacgcctggggtcttaatgt ggctctggagtggaagccaccccag gatgtcggcaacacggaactctggg ggtacacagtgcagaaagccgacaa gaagaccatggagtggttcaccgtc ttggagcattaccgccgcacccact gcgtggtgccagagctcatcattgg caatggctactacttccgcgtcttc agccagaatatggttggctttagtg acagagcggccaccaccaaggagcc cgtctttatccccagaccaggcatc acctatgagccacccaactataagg ccctggacttctccgaggccccaag cttcacccagcccctggtgaaccgc tcggtcatcgcgggctacactgcta tgctctgctgtgctgtccggggtag ccccaagcccaagatttcctggttc aagaatggcctggacctgggagaag acgcccgcttccgcatgttcagcaa gcagggagtgttgactctggagatt agaaagccctgcccctttgacgggg gcatctatgtctgcagggccaccaa cttacagggcgaggcacggtgtgag tgccgcctggaggtgcgagtgcctc agtaaagcttaataaaagatcttta ttttcattagatctgtgtgttggtt ttttgtgtgctggggactcgagtta agggcgaattcccgataaggatctt cctagagcatggctacgtagataag tagcatggcgggttaatcattaact aca | |
| 5' segment-partial viral genome (400 bp promoter) | tgtagttaatgattaacccgccatg ctacttatctacgtagccatgctct aggaagatcggaattcgcccttaag ttgccttctgcccccaaccctgct cccagctggccctcccaggcctggg ttgctggcctctgctttatcaggat tctcaagagggacagctggtttatg ttgcatgactgttccctgcatatct gctctggttttaaatagcttatctg agcagctggaggaccacatgggctt atatggcgtggggtacatgttcctg tagccttgtccctggcacctgccaa aatagcagccaacacccccaccccc caccgccatcccccctgccccacccg tcccctgtcgcacattcctccctcc gcagggctggctcaccaggccccag cccacatgcctgcttaaagccctct ccatcctctgcctcacccagtcccc gctgagactgagcagacgcctccag ccacc | 93 |
| 3' segment-partial viral genome | agcttaataaaagatctttattttc attagatctgtgtgttggtttttttg tgtgctggggactcgagttaagggc gaattcccgataaggatcttcctag agcatggctacgtagataagtagca tggcgggttaatcattaactaca | 94 |

In some aspects of the disclosure, an rAAV virion is used to deliver the expression cassettes described herein to cardiac cells of a subject, e.g. to treat cardiomyopathy. Accordingly, the disclosure provides an rAAV virion, the rAAV virion comprising an AAV capsid and an expression cassette comprising a polynucleotide encoding a transgene operatively linked to a promoter.

The rAAV virions of the disclosure comprise a capsid protein. Capsid proteins are structural proteins that make up the assembled icosahedral packaging of the rAAV virion that contains the expression cassette. Capsid proteins are classified by the serotype. Wild type capsid serotypes in rAAV virions can be, for example, AAV1, AAV2, AAV3, AAV4, AAV5, AAV6, AAV7, AAV8, AAV9, AAV10, AAV11, or AAV12 (Naso et al. *BioDrugs* 31:317-334 (2017)). Engineered capsid types include chimeric capsids and mosaic capsids (Choi et al. *Curr Gene Ther.* 5:299-310 (2005)). Capsids are selected for rAAV virions based on their ability to transduce specific tissue or cell types (Liu et al. *Curr Pharm Des.* 21:3248-56 (2015)).

Any capsid protein that can facilitate rAAV virion transduction into cardiac cells for delivery of a transgene, as described herein, can be used. Capsid proteins used in rAAV virions for transgene delivery to cardiac cells that result in high expression can be, for example, AAV4, AAV6, AAV7, AAV8, and AAV9 (Zincarelli et al. *Mol. Ther.* 16:P1073-1080 (2008)). Artificial capsids, such as chimeric capsids generated through combinatorial libraries, can also be used for transgene delivery to cardiac cells that results in high expression (see U.S. Ser. No. 63/012,703, the contents of which are herein incorporated by reference). Other capsid proteins with various features can also be used in the rAAV virions of the disclosure. AAV vectors and capsids are provided in U.S. Pat. Pub. Nos. US10011640B2; U.S. Pat. Nos. 7,892,809B2, 8,632,764B2, 8,889,641B2, 9,475,845B2, 10,889,833B2, 10,480,011B2, and 10,894,949B2, the contents of which are herein incorporated by reference; and Intl Pat. Pub. Nos. WO2020198737A1, WO2019028306A2, WO2016054554A1, WO2018152333A1, WO2017106236A1, WO2008124724A1, WO2017212019A1, WO2020117898A1, WO2017192750A1, WO2020191300A1, and WO2017100671A1, the contents of which are herein incorporated by reference.

In some embodiments, the rAAV virions of the disclosure comprise an engineered capsid protein. Engineered capsid proteins can be derived from a parental, e.g. wild type, capsid and include, for example, variant polypeptide sequence with respect to a parental capsid sequence at one or more sites. For example, variant sites of the parental capsid can occur at the VR-IV site, VR-V site, VR-VII site and/or VR-VIII site (see, e.g. Büning and Srivastava. *Mol Ther Methods Clin Dev.* 12:248-265 (2019)).

In some embodiments, the capsid protein is an AAV5/AAV9 chimeric capsid protein. In some embodiments, the chimeric capsid protein comprises at least 1, 2, 3, 4, 5 or more polypeptide segments that are derived from AAV5 capsid protein (SEQ ID NO. 144). In some embodiments, the chimeric capsid protein comprises at least 1, 2, 3, 4, 5 or more polypeptide segments that are derived from AAV9 capsid protein (SEQ ID NO: 143). In some embodiments, at least one polypeptide segment is derived from the AAV5 capsid protein and at least one polypeptide segment is derived from the AAV9 capsid protein.

In some embodiments, the capsid protein is a combinatory capsid proteins. As used herein, "combinatory capsid protein" refers to a AAV5/AAV9 chimeric capsid protein, which further comprises amino acid variations with respect to the chimeric parental sequence at one or more sites. In some embodiments, the one or more sites of the chimeric parental sequence are selected from those equivalent to the VR-IV site, the VR-V site, the VR-VII site and the VR-VIII site of the AAV9 capsid protein.

In some embodiments, the rAAV virions comprise an engineered capsid protein selected from Table 6.

TABLE 6

Engineered Capsid Proteins

| Engineered Capsid | SEQ ID NO: |
|---|---|
| CR9-01 | 145 |
| CR9-07 | 146 |
| CR9-08 | 147 |
| CR9-09 | 148 |
| CR9-10 | 149 |
| CR9-11 | 150 |
| CR9-13 | 151 |
| CR9-14 | 152 |
| CR9-15 | 153 |
| CR9-16 | 154 |
| CR9-17 | 155 |
| CR9-20 | 156 |
| CR9-21 | 157 |
| CR9-22 | 158 |
| ZC23 | 159 |
| ZC24 | 160 |
| ZC25 | 161 |
| ZC26 | 162 |
| ZC27 | 163 |
| ZC28 | 164 |
| ZC29 | 165 |
| ZC30 | 166 |
| ZC31 | 167 |
| ZC32 | 168 |
| ZC33 | 169 |
| ZC34 | 170 |
| ZC35 | 171 |
| ZC40 | 172 |
| ZC41 | 173 |
| ZC42 | 174 |
| ZC43 | 175 |
| ZC44 | 176 |
| ZC45 | 177 |
| ZC46 | 178 |
| ZC47 | 179 |
| ZC48 | 180 |
| ZC49 | 181 |
| ZC50 | 182 |
| TN47-07 | 183 |
| TN47-10 | 184 |
| TN47-13 | 185 |
| TN47-14 | 186 |
| TN47-17 | 187 |
| TN47-22 | 188 |

TABLE 6-continued

Engineered Capsid Proteins

| Engineered Capsid | SEQ ID NO: |
|---|---|
| TN40-07 | 189 |
| TN40-10 | 190 |
| TN40-13 | 191 |
| TN40-14 | 192 |
| TN40-17 | 193 |
| TN40-22 | 194 |
| TN44-07 | 195 |
| TN44-10 | 196 |
| TN44-13 | 197 |
| TN44-14 | 198 |
| TN44-17 | 199 |
| TN44-22 | 200 |

In some embodiments, the rAAV is replication defective, in that the rAAV virion cannot independently further replicate and package its genome. For example, when a cardiac cell is targeted with rAAV virions, the transgene is expressed in the targeted cardiac cell, however, due to the fact that the targeted cardiac cell lacks AAV rep and cap genes and accessory function genes, the rAAV is not able to replicate.

In some embodiments, rAAV virions of the present disclosure encapsulating the expression cassettes as described herein, can be produced using helper-free production. rAAVs are replication-deficient viruses and normally require components from a live helper virus, such as adenovirus, in a host cell for packaging of infectious rAAV virions. rAAV helper-free production systems allow the production of infectious rAAV virions without the use of a live helper virus. In the helper-free system, a host packaging cell line is co-transfected with three plasmids. A first plasmid may contain adenovirus gene products (e.g. E2A, E4, and VA RNA genes) needed for the packaging of rAAV virions. A second plasmid may contain required AAV genes (e.g., REP and CAP genes). A third plasmid contains the polynucleotide sequence encoding the transgene of interest and a promoter flanked by ITRs. A host packaging cell line can be, for example, AAV-293 host cells. Suitable host cells contain additional components required for packaging infectious rAAV virions that are not supplied by the plasmids. In some embodiments, the CAP genes can encode, for example, AAV capsid proteins as described herein.

IV. Methods of Treatment

The present disclosure also provides pharmaceutical compositions comprising the rAAV vector genomes or rAAV virions disclosed herein and one or more pharmaceutically acceptable carriers, diluents or excipients. In particular embodiments, the pharmaceutical composition comprises an rAAV vector genome or rAAV virion as described herein, comprising a polynucleotide sequence that encodes a therapeutic protein or nucleic acid, operatively linked to a cardiac-specific promoter (e.g., a modified TNNT2 promoter). For example, in some embodiments, the pharmaceutical composition is an AAV9 vector comprising the modified cardiac TNNT2 promoter (SEQ ID NO: 3) operatively linked to the MYBPC3 protein (SEQ ID NO: 86). Provided are pharmaceutical compositions, e.g., for use in preventing or treating cardiomyopathy, which comprises a therapeutically effective amount of a vector that comprises a polynucleotide sequence encoding a therapeutic protein or nucleic acid that can restore contractile function in the heart.

The disclosure provides methods for expressing a polynucleotide a cell. The method may comprise, for example, transducing a target cell with the rAAV virions, rAAV vector genomes, or expression cassettes described herein. A target cell can be, for example and without limitation, a cardiac cell, a muscle cell, an induced pluripotent stem cell-derived cardiomyocyte (iPSC-CM), a cardiomyocyte, or a MYBPC3$^{-/-}$ iPSC-CM. In one aspect, a method of expressing a MYBPC3 protein in a cell comprises transducing a target cell or population of target cells with an rAAV virion or rAAV vector genomes described herein. In one embodiment, the cell is a MYBPC3$^{-/-}$ cell. In one embodiment, the cell comprises an inactivating mutation in one or both copies of the endogenous MYBPC3 gene.

The compositions that are described herein can be employed in a method of treating a subject with a cardiac disease or condition. "Treating" or "treatment of a condition or subject in need thereof" refers to (1) taking steps to obtain beneficial or desired results, including clinical results such as the reduction of symptoms; (2) preventing the disease, for example, causing the clinical symptoms of the disease not to develop in a patient that may be predisposed to the disease, but does not yet experience or display symptoms of the disease; (3) inhibiting the disease, for example, arresting or reducing the development of the disease or its clinical symptoms; (4) relieving the disease, for example, causing regression of the disease or its clinical symptoms; or (5) delaying the disease. For purposes of this invention, beneficial or desired clinical results include, but are not limited to, promoting cardiac sarcomere contraction.

Subjects in need of treatment using the compositions and methods of the present disclosure include, but are not limited to, individuals having a congenital heart defect, individuals suffering from a degenerative muscle disease, individuals suffering from a condition that results in ischemic heart tissue (e.g., individuals with coronary artery disease), and the like. In some examples, a method is useful to treat a degenerative muscle disease or condition (e.g., familial cardiomyopathy, dilated cardiomyopathy, hypertrophic cardiomyopathy, restrictive cardiomyopathy, or coronary artery disease with resultant ischemic cardiomyopathy). In some examples, a subject method is useful to treat individuals having a cardiac or cardiovascular disease or disorder, for example, cardiovascular disease, aneurysm, angina, arrhythmia, atherosclerosis, cerebrovascular accident (stroke), cerebrovascular disease, congenital heart disease, congestive heart failure, myocarditis, valve disease coronary, artery disease dilated, diastolic dysfunction, endocarditis, high blood pressure (hypertension), cardiomyopathy, hypertrophic cardiomyopathy, restrictive cardiomyopathy, coronary artery disease with resultant ischemic cardiomyopathy, mitral valve prolapse, myocardial infarction (heart attack), or venous thromboembolism. In some examples, the subject is suffering from or at risk for cardiomyopathy.

In some embodiments, the compositions and methods disclosed herein can be used for the prevention and/or treatment of cardiomyopathies in a subject. In some embodiments, the compositions and methods described herein can be used to treat cardiomyopathies affiliated with mutations in cardiac myosin binding protein C (MYBPC3), such as hypertrophic cardiomyopathy and familial hypertrophic cardiomyopathy. The cardiomyopathy treated by the compositions and methods described herein can also include cardiomyopathies associated with a pulmonary embolus, a venous thrombosis, a myocardial infarction, a transient ischemic attack, a peripheral vascular disorder, atherosclerosis, ischemic cardiac disease and/or other myocardial injury or vascular disease. In certain embodiments, the cardiomyopathies treated by the compositions and methods described herein can include cardiac diseases associated with myocardial tissue hypercontractility, such as heart failure related to left ventricular hypercontractility.

In some embodiments, the compositions and methods described herein can induce detectable expression of a therapeutic protein or nucleic acid (e.g., MYBPC3 protein), or a mutant, variant, or fragment thereof, to modulate contractile function of the myocardial tissue in a subject in need thereof. In some embodiments, the amount, concentration, and volume of the composition that modulates contractile function in myocardial tissue administered to a subject can be controlled and/or optimized to substantially improve the functional parameters of the heart while mitigating adverse side effects.

The amount of the composition that modulates contractile function administered to myocardial tissue can also be an amount required to result in the detectable expression of a therapeutic protein or nucleic acid (e.g., MYBPC3 protein) or a mutant, variant, or fragment thereof in the heart; preserve and/or improve contractile function; delay the emergence of cardiomyopathy or reverse the pathological course of the disease; increase myocyte viability; improve myofilament function; inhibit left ventricular hypertrophy; cardiac hypertrophy regression, normalize systolic and diastolic function in heart; and restore normal cross-bridge behavior at the myofilament level.

In some embodiments, the compositions and methods disclosed herein results in detectable expression of MYBPC3 protein, or a mutant, variant, or fragment thereof, in a cardiac cell of the subject being treated. In some embodiments, administration of an rAAV vector genome or rAAV virion described herein causes specific expression of MYBPC3 protein in the heart of the subject. In some embodiments, administration of rAAV vector genome or rAAV virion described herein causes low or undetectable expression of MYBPC3 in the skeletal tissue, brain, and/or liver of the subject, wherein optionally the subject suffers from or is at risk for cardiomyopathy.

In some embodiments, the compositions and methods disclosed herein results in detectable expression of KCNH2 protein, or a mutant, variant, or fragment thereof, in a cardiac cell of the subject being treated.

In some embodiments, the compositions and methods disclosed herein results in detectable expression of TRPM4 protein, or a mutant, variant, or fragment thereof, in a cardiac cell of the subject being treated.

In some embodiments, the compositions and methods disclosed herein results in detectable expression of DSG2 protein, or a mutant, variant, or fragment thereof, in a cardiac cell of the subject being treated.

In some embodiments, the compositions and methods disclosed herein results in detectable expression of ATP2A2 protein, or a mutant, variant, or fragment thereof, in a cardiac cell of the subject being treated.

In some embodiments, the compositions and methods disclosed herein results in detectable expression of CACNA1C, DMD, DMPK, EPG5, EVC, EVC2, FBN1, NF1, SCN5A, SOS1, NPR1, ERBB4, VIP, or MYH7, or a mutant, variant, or fragment thereof, in a cardiac cell of the subject being treated.

"Detectable expression" typically refers to expression at least 5%, 10%, 15%, 20% or more compared to a control subject or tissue not treated with the vector. In some embodiments, detectable expression means expression at 1.5-fold, 2-fold, 2.5-fold, or 3-fold greater than a no-vector control. Expression can be assess by Western blot, as described in the example that follows, or enzyme-linked immunosorbent assay (ELISA), or other methods known in the art. In some cases, expression is measured quantitatively using a standard curve. Standard curves can be generated using purified protein, e.g. purified MYBPC3 protein, by methods described in the examples or known in the art. Alternatively, expression of the therapeutic gene product can be assessed by quantification of the corresponding mRNA.

In some embodiments, the detectable expression of the therapeutic gene product in heart tissue occurs at doses, in vector genomes (vg) per kilogram weight of subject (kg), of $3\times10^{14}$ vg/kg or less, $2\times10^{14}$ vg/kg or less, $1\times10^{14}$ vg/kg or less, $9\times10^{13}$ vg/kg or less, $8\times10^{13}$ vg/kg or less, $7\times10^{13}$ vg/kg or less, $6\times10^{13}$ vg/kg or less, $5\times10^{13}$ vg/kg or less, $4\times10^{13}$ vg/kg or less, $3\times10^{13}$ vg/kg or less, $2\times10^{13}$ vg/kg or less, or $1\times10^{13}$ vg/kg or less.

In various embodiments, the compositions described herein contain the rAAV virions or vector genomes described herein and one or more pharmaceutically acceptable excipients. Pharmaceutically acceptable excipients can include vehicles (e.g., carriers, diluents and excipients) that are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. Illustrative pharmaceutical forms suitable for injectable use include, e.g., sterile aqueous solutions or dispersions; formulations including sesame oil, peanut oil or aqueous propylene glycol; and sterile powders for the extemporaneous preparation of sterile injectable solutions or dispersions.

In various embodiments, the pharmaceutical compositions of the disclosure comprise about $1\times10^{8}$ genome copies per milliliter (GC/mL), about $5\times10^{8}$ GC/mL, about $1\times10^{9}$ GC/mL, about $5\times10^{9}$ GC/mL, about $1\times10^{10}$ GC/mL, about $5\times10^{10}$ GC/mL, about $1\times10^{11}$ GC/mL, about $5\times10^{11}$ GC/mL, about $1\times10^{12}$ GC/mL, about $5\times10^{12}$ GC/mL, about $5\times10^{13}$ GC/mL, about $1\times10^{14}$ GC/mL, or about $5\times10^{14}$ GC/mL of the viral vector (e.g. rAAV virion).

In various embodiments, the pharmaceutical compositions of the disclosure comprise about $1\times10^{8}$ viral genomes per milliliter (vg/mL), about $5\times10^{8}$ vg/mL, about $1\times10^{9}$ vg/mL, about $5\times10^{9}$ vg/mL, about $1\times10^{10}$ vg/mL, about $5\times10^{10}$ vg/mL, about $1\times10^{11}$ vg/mL, about $5\times10^{11}$ vg/mL, about $1\times10^{12}$ vg/mL, about $5\times10^{12}$ vg/mL, about $5\times10^{13}$ vg/mL, about $1\times10^{14}$ vg/mL, or about $5\times10^{14}$ vg/mL of the viral vector (e.g. rAAV virion).

In some embodiments, the pharmaceutical compositions of the disclosure are administered in a total volume of about 1 mL, 5 mL, 10 mL, about 20 mL, about 25mL, about 30 mL, about 35 mL, about 40 mL, about 45 mL, about 50 mL, about 55 mL, about 60 mL, 65 mL, about 70 mL, about 75 mL, about 80 mL, about 85 mL, about 90 mL, about 95 mL, about 100 mL, about 105 mL, about 110 mL, about 115 mL, about 120 mL, about 125 mL, about 130 mL, about 135 mL, about 140 mL, about 145 mL, about 150 mL, about 155 mL, about 160 mL, about 165 mL, about 170 mL, about 175 mL, about 180 mL, about 185 mL, about 190 mL, about 200 mL, about 205 mL, about 210 mL, about 215 mL, or about 220 mL.

In some embodiments, the methods of the disclosure comprise administering an rAAV virion encoding MYBPC3 at a dose of about $1\times10^{8}$ genome copies per milliliter (GC/mL), about $5\times10^{8}$ GC/mL, about $1\times10^{9}$ GC/mL, about $5\times10^{9}$ GC/mL, about $1\times10^{10}$ GC/mL, about $5\times10^{10}$ GC/mL, about $1\times10^{11}$ GC/mL, about $5\times10^{11}$ GC/mL, about $1\times10^{12}$ GC/mL, about $5\times10^{12}$ GC/mL, about $5\times10^{13}$ GC/mL, about $1\times10^{14}$ GC/mL, or about $5\times10^{14}$ GC/mL of the rAAV virion.

In preferred embodiments, the methods of the disclosure comprise intravenously administering an rAAV virion encoding MYBPC3 at a dose of about $3\times10^{12}$ GC/mL, about $3\times10^{13}$ GC/mL, about $1\times10^{14}$ GC/mL, or about $3\times10^{14}$ GC/mL of the rAAV virion.

In preferred embodiments, the methods of the disclosure comprise administering, by localized delivery to the heart, an rAAV virion encoding MYBPC3 at a dose of about $3\times10^{11}$ GC/mL, about $3\times10^{12}$ GC/mL, about $1\times10^{13}$ GC/mL, or about $3\times10^{13}$ GC/mL of the rAAV virion.

In some embodiments, the methods of the disclosure comprise administering an rAAV virion encoding MYBPC3 at a dose of about $1\times10^{8}$ viral genomes per milliliter (vg/mL), about $5\times10^{8}$ vg/mL, about $1\times10^{9}$ vg/mL, about $5\times10^{9}$ vg/mL, about $1\times10^{10}$ vg/mL, about $5\times10^{10}$ vg/mL, about $1\times10^{11}$ vg/mL, about $5\times10^{11}$ vg/mL, about $1\times10^{12}$ vg/mL, about $5\times10^{12}$ vg/mL, about $5\times10^{13}$ vg/mL, about $1\times10^{14}$ vg/mL, or about $5\times10^{14}$ vg/mL of the rAAV virion.

In preferred embodiments, the methods of the disclosure comprise intravenously administering an rAAV virion encoding MYBPC3 at a dose of about $3\times10^{12}$ vg/mL, about $3\times10^{13}$ vg/mL, about $1\times10^{14}$ vg/mL, or about $3\times10^{14}$ vg/mL of the rAAV virion.

In preferred embodiments, the methods of the disclosure comprise administering, by localized delivery to the heart, an rAAV virion encoding MYBPC3 at a dose of about $3\times10^{11}$ vg/mL, about $3\times10^{12}$ vg/mL, about $1\times10^{13}$ vg/mL, or about $3\times10^{13}$ vg/mL of the rAAV virion.

Genome copies per milliliter can be determined by quantitative polymerase change reaction (qPCR) using a standard curve generated with a reference sample having a known concentration of the polynucleotide genome of the virus. For AAV, the reference sample used is often the transfer plasmid used in generation of the rAAV virion but other reference samples may be used.

Alternatively or in addition, the concentration of a viral vector can be determined by measuring the titer of the vector on a cell line. Viral titer is typically expressed as viral particles (vp) per unit volume (e.g., vp/mL). In various embodiments, the pharmaceutical compositions of the disclosure comprise about $1\times10^{8}$ viral particles per milliliter (vp/mL), about $5\times10^{8}$ vp/mL, about $1\times10^{9}$ vp/mL, about $5\times10^{9}$ vp/mL, about $1\times10^{10}$ vp/mL, about $5\times10^{10}$ vp/mL, about $1\times10^{11}$ vp/mL, about $5\times10^{11}$ vp/mL, about $1\times10^{12}$ vp/mL, about $5\times10^{12}$ vp/mL, about $5\times10^{13}$ vp/mL, or about $1\times10^{14}$ vp/mL, or about $5\times10^{14}$ of the viral vector (e.g., rAAV virion).

In one embodiment, the present disclosure provides a kit comprising a container housing a pharmaceutical composition as described herein.

The rAAV virions or vector genomes of the present disclosure can be administered to a subject in need thereof by systemic application, e.g., by intravenous, intra-arterial or intraperitoneal delivery of a vector in analogy to what has been shown in animal models (Katz et al., 2012, *Gene Ther.* 19:659-669. In some embodiments, the rAAV virions or vector genomes of the present disclosure treat or prevent hypertrophic cardiomyopathy, wherein the vector is administered systemically.

In some embodiments, the rAAV virions or vector genomes of the present disclosure can be delivered by direct administration to the heart tissue, e.g. by intracoronary administration. In some embodiments, the vectors are administered as a single dose by antegrade epicardial coronary artery infusion over a 10-minute period in a cardiac catheterization laboratory after angiography (percutaneous intracoronary delivery without vessel balloon occlusion) with the use of standard 5F or 6F guide or diagnostic catheters (Jaski et al., 2009, *J Card Fail.* 15:171-181).

Subjects who are suitable for treatment using the compositions, compositions and methods of the present disclosure include individuals (e.g., mammalian subjects, such as humans, non-human primates, domestic mammals, experimental non-human mammalian subjects such as mice, rats, etc.) having a cardiac condition.

In some embodiments, the rAAV virions or vector genomes of the present disclosure can be used to treat a subject in need thereof. In some embodiments, the viral vector can be administered to the subject in need to treat a cardiovascular disease. In some embodiments, the rAAV virions or vector genomes are administered to a subject to treat cardiomyopathy. In some embodiments, the viral vector is administered systemically. In other embodiments, the viral vector is delivered by direct administration to the heart tissue.

rAAV virions or vector genomes can be administered by various routes, including without limitation direct injection into the heart or cardiac catheterization. In a preferred embodiment, a pharmaceutical composition comprising an rAAV virion encoding MYBPC3 is administered by intracardiac catheter delivery via retrograde coronary sinus infusion (RCSI). Alternatively, the viral vector can be administered systemically such as by intravenous infusion. When direct injection is used, it may be performed either by open-heart surgery or by minimally invasive surgery. In some cases, the viral vector is delivered to the pericardial space by injection or infusion.

The viral vector administered to the subject can be traced by a variety of methods. For example, recombinant viruses labeled with or expressing a marker (such as green fluorescent protein, or beta-galactosidase) can readily be detected. The recombinant viruses may be engineered to cause the target cell to express a marker protein, such as a surface-expressed protein or a fluorescent protein. Alternatively, the infection of target cells with recombinant viruses can be detected by their expression of a cell marker that is not expressed by the animal employed for testing (for example, a human-specific antigen when injecting cells into an experimental animal). The presence and phenotype of the target cells can be assessed by fluorescence microscopy (e.g., for green fluorescent protein, or beta-galactosidase), by immunohistochemistry (e.g., using an antibody against a human antigen), by ELISA (using an antibody against a human antigen), or by RT-PCR analysis using primers and hybridization conditions that cause amplification to be specific for RNA indicative of a cardiac phenotype.

All patents, patent publications, and other publications referenced and identified in the present specification are individually and expressly incorporated herein by reference in their entirety for all purposes.

EXAMPLES

Example 1: Design of Vector Genome for Large Cargos

The purpose of this study was to evaluate a vector having deletions in non-coding portions of the vector to a parental vector. It demonstrates that, surprisingly, deletion in non-coding regions increases potency of the vector.

With two intact flanking ITR sequences (each ~130 bp), promoter, intron, WPRE and polyadenylation signal, and standard cis-regulatory sequences for optimal transgene expression, typical AAV vector genomes require about 1.8-2.0 kbp of non-coding DNA sequence. Trangenes of about 3.0 kbp or greater, like the 3.8 kbp transgene MYBPC3, cause the vector genome to exceed 5.0 kbp. For example, Mearini et al., *Nat Commun* 5:5515 (2014) reports an AAV vector encoding MYBPC3 having a vector genome size of 5.4 kbp. Without ITR sequences, this is about 5.2 kbp.

A reporter system was generated to test whether an AAV vector would tolerate shortened non-coding regions. A conventional AAV vector having a CAG promoter, intron, WPRE, and standard polyA sequence was modified to remove the WPRE (589 bp) and to shorten the polyA sequence (removing 170 bp) (FIG. 1A). Expression of a GFP reporter cloned into the multiple cloning site (MCS) was maintained but slightly decreased when these vector elements were deleted or shortened (FIG. 1B). The vector was further truncated by deletion of the intron and a portion of the sequence 3' to the 5' ITR (FIG. 1C). The final vector genome was about 1.1 kpb (0.8 kpb without ITRs).

Example 2: MYBPC3 Transgene Expression in Induced Cardiomyocytes in vitro

The purpose of this study was to provide an improved tissue-specific promoter for expression of a therapeutic gene product in induced cardiomyocytes in vitro using an AAV-based vector system. Human induced pluripotent stem cells (iPSCs) were differentiated into cardiomyocytes using mesoderm induction, cardiac specification and metabolic selection as previously described (Tohyama et al. *Cell Stem Cell.* 2013;12(1):127-37; Lian et al. *Proc Natl Acad Sci USA.* 2012;109(27):E1848-57; Burridge P W, Holmstrom A, Wu J C. *Curr Protoc Hum Genet.* 2015;87:21 3 1-15.) iPSC-CM viral transductions were performed with AAV6 at the indicated multiplicities of infection.

The gene expression cassettes depicted in FIG. 2A were constructed for an AAV-based vector system for the treatment of cardiomyopathy. The AAV vector, based on the vector depicted in FIG. 1C, comprised several cis-regulatory elements, including two inverted terminal repeats (ITRs, 260 bp each), a polyadenylation signal (A, 49 bp), and a full-length (SEQ ID NO: 1) or modified cardiac troponin T (TNNT2) promoter (SEQ ID NO: 2-4). No WPRE was included, and the polyA signal and the sequence 3' to the 5' ITR were both shortened. The modified TNNT2 promoters contained 100-200 bp deletions at the 5' (upstream) end of the wild-type TNNT2 promoter. Human myosin binding protein C (MYBPC3, SEQ ID NO: 86) with a polynucleotide sequence length of 3.825 kb was tested as the therapeutic gene product in iPSC-derived cardiomyocytes.

To determine whether wild-type or modified TNNT2 promoters could induce detectable expression of the MYBPC3 protein, MYBPC3$^{-/-}$ iPSC-derived cardiomyocytes were transduced with AAV6 particles at $6\times10^4$ MOI. Cells were analyzed for MYBPC3 protein expression by immunofluorescence or Western blot 5-15 days post-infection.

Figure 2B:
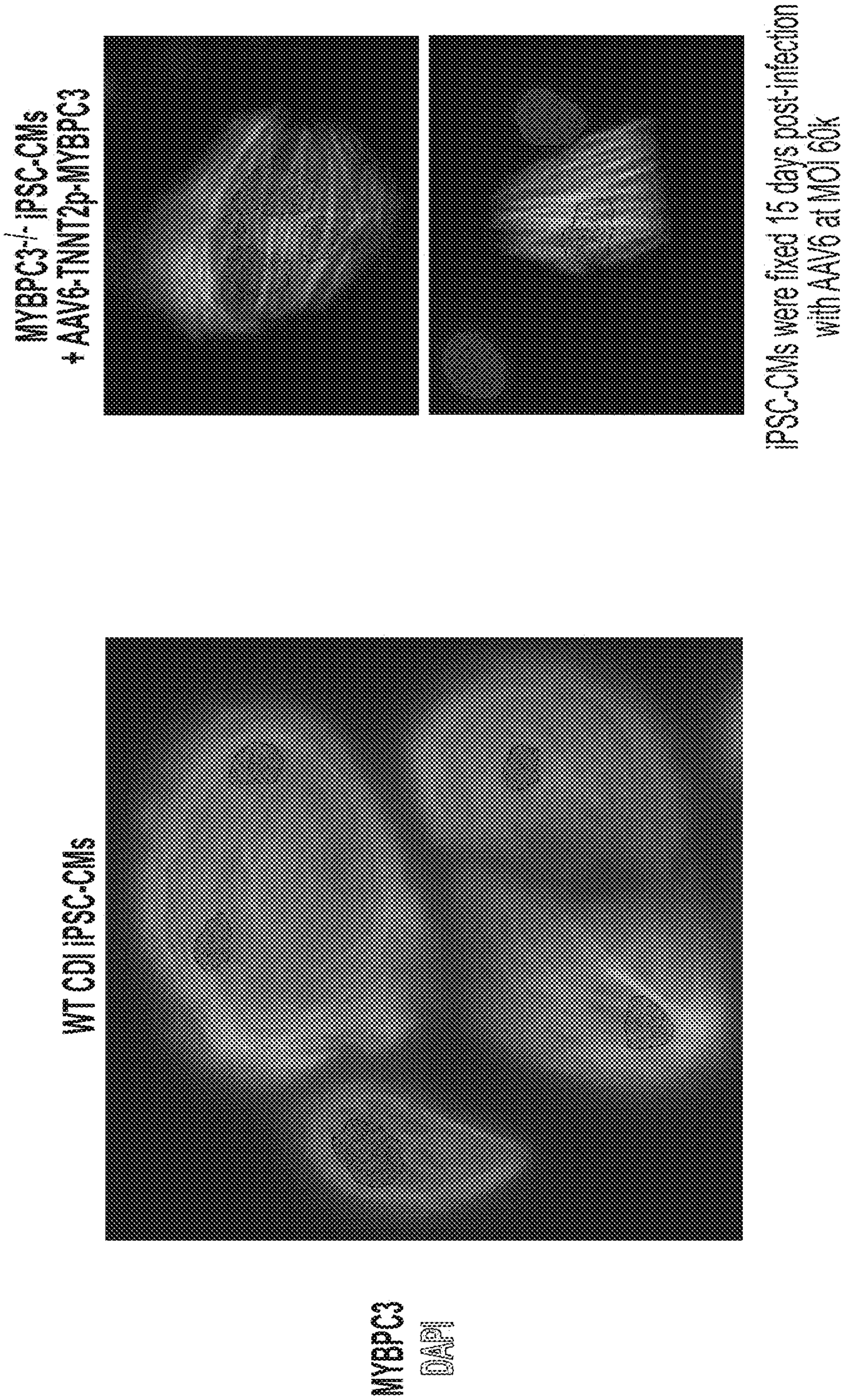
FIG. 2B shows detection of MYBPC3 protein by immunofluorescence in MYBPC3$^{-/-}$ iPSC-derived cardiomyocytes transduced with AAV6-packaged constructs encoding MYBPC3 driven by the cardiac-specific TNNT2 promoter.

FIG. 2B shows that the AAV vector comprising the wild-type TNNT2 promoter (SEQ ID NO: 1) drives expression of MYBPC3 protein in the sarcomeres of MYBPC3$^{-/-}$ iPSC-derived cardiomyocytes.

Figure 3A:
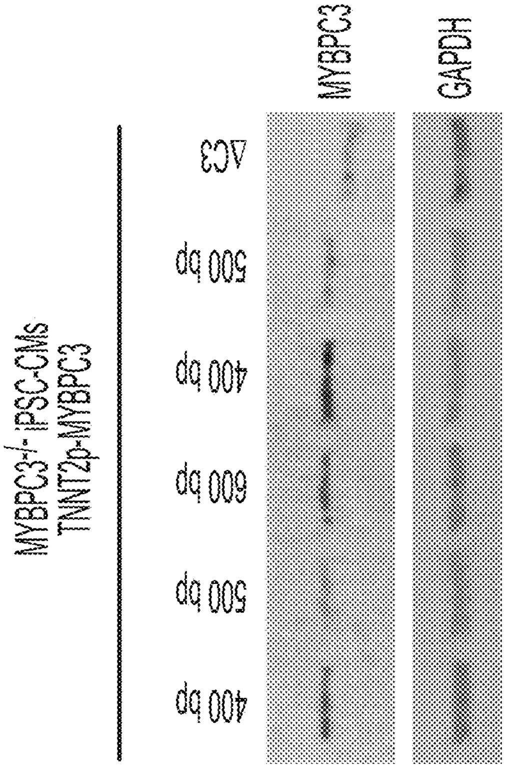
FIG. 3A shows detection of MYBPC3 protein by Western blot in MYBPC3$^{-/-}$ iPSC-derived cardiomyocytes transduced with AAV6-packaged constructs encoding human MYBPC3 driven by various sizes (400-600 bp) of the cardiac-specific TNNT2 promoter. GAPDH was used as a loading control.
Figure 3B:
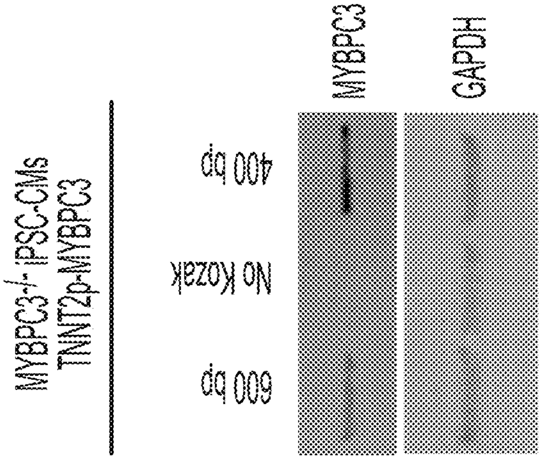
FIG. 3B shows detection of MYBPC3 protein by Western blot in MYBPC3$^{-/-}$ iPSC-derived cardiomyocytes transduced with AAV6-packaged constructs encoding human MYBPC3 driven by various sizes (400 or 600 bp) of the human cardiac TNNT2 promoter. No Kozak sequence was used as a negative control and GAPDH was used as a loading control.
Figure 3C:
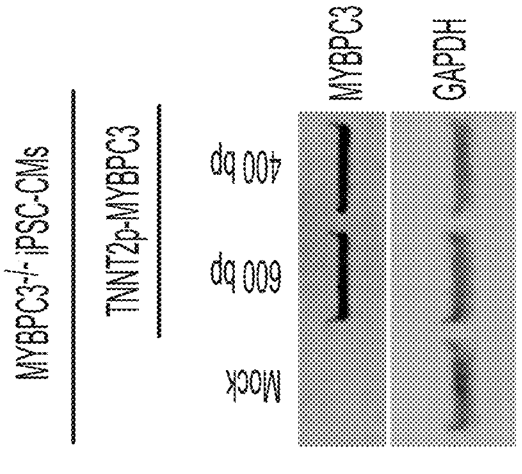
FIG. 3C shows detection of MYBPC3 protein by Western blot in MYBPC3$^{-/-}$ iPSC-derived cardiomyocytes transfected with AAV6 plasmids encoding human MYBPC3 driven by various sizes (400 or 600 bp) of the human cardiac TNNT2 promoter. GAPDH was used as a loading control.

FIG. 3A-FIG. 3C show that the AAV vector comprising the 400 bp modified TNNT2 promoter (SEQ ID NO: 3) drives higher MYBPC3 protein expression than either the 600 bp wild-type TNNT2 (SEQ ID NO: 1) or 500 bp modified TNNT2 (SEQ ID NO: 2) promoters in transduced MYBPC3$^{-/-}$ iPSC-derived cardiomyocytes. In contrast, MYBPC3$^{-/-}$ iPSC-derived cardiomyocytes transfected with a plasmid (rather than transduced with virus) encoding MYBPC3 under the control of either the 600 bp wild-type TNNT2 (SEQ ID NO:1) or 400 bp modified TNNT2 promoter (SEQ ID NO: 3) showed similar MYBPC3 protein expression.

Example 3: Mybpc3$^{-/-}$ Mice Model Hypertrophic Severe Cardiomyopathy

Figure 4A:
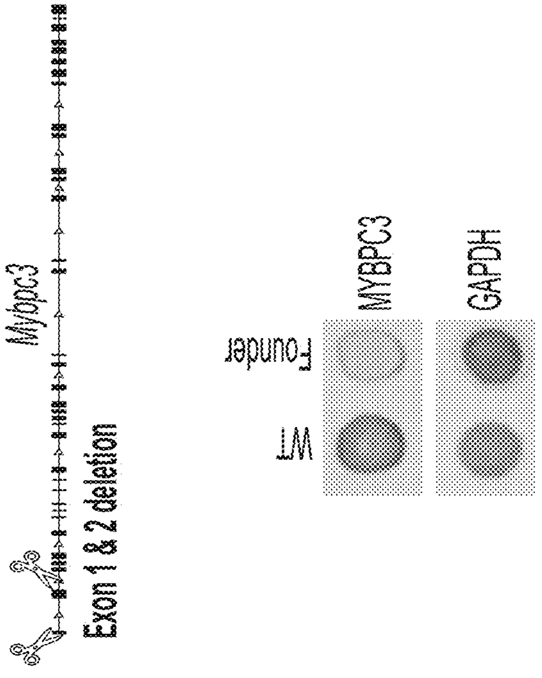
FIG. 4A shows a map of the introns of the Mybpc3 gene and a dot blot of MYBPC3 protein expression in the founder mouse of the KO line.
Figure 4B:
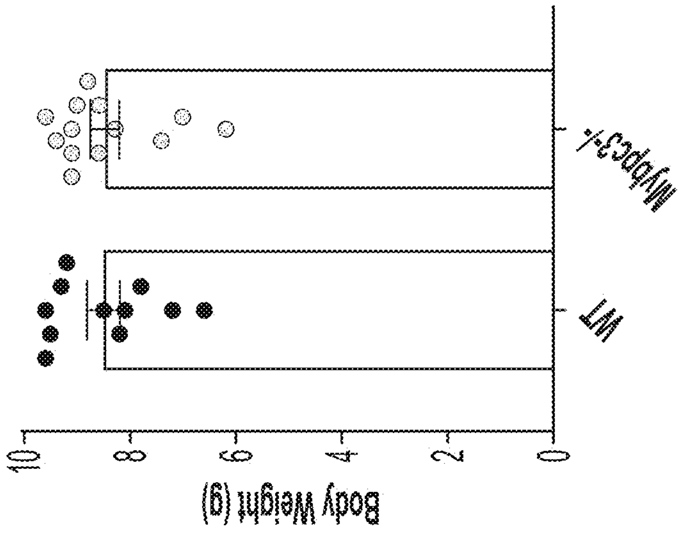
FIG. 4B shows a bar graph of body weight of wild-type (WT) or KO mice (Mybpc3$^{-/-}$) littermates at two weeks of age. WT (n=11), Mybpc3$^{-/-}$ (n=7) and Mybpc3$^{-/-}$ (n=13).
Figure 4D:
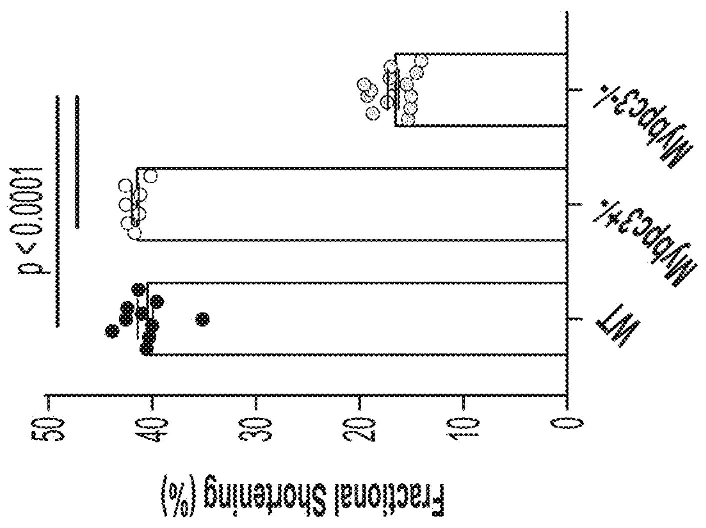
FIG. 4D shows a bar graph of fractional shortening measured by echocardiography in wild-type (WT), heterozygous KO mice (Mybpc3$^{-/-}$), or homozygous KO mice (Mybpc3$^{-/-}$) at two weeks of age.
Figure 4C:
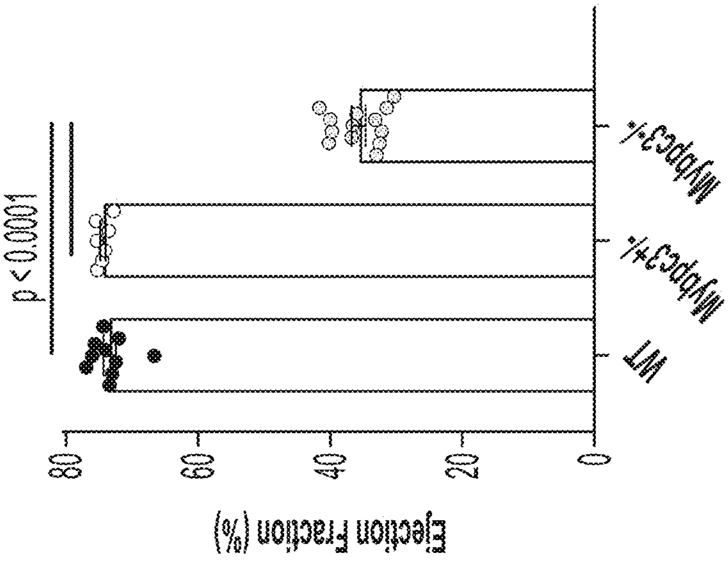
FIG. 4C shows a bar graph of ejection fraction (%) measured by echocardiography in wild-type (WT), heterozygous KO mice (Mybpc3$^{-/-}$), or homozygous KO mice (Mybpc3$^{-/-}$) at two weeks of age.
Figure 4E:
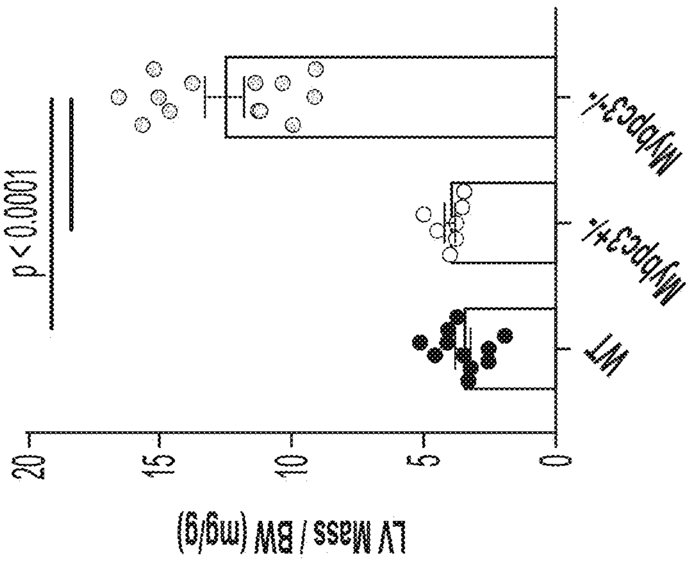
FIG. 4E shows a bar graph of left ventricular (LV) mass normalized by body weight (BW) in wild-type (WT), heterozygous KO mice (Mybpc3$^{-/-}$), or homozygous KO mice (Mybpc3$^{-/-}$) at two weeks of age.
Figure 4F:
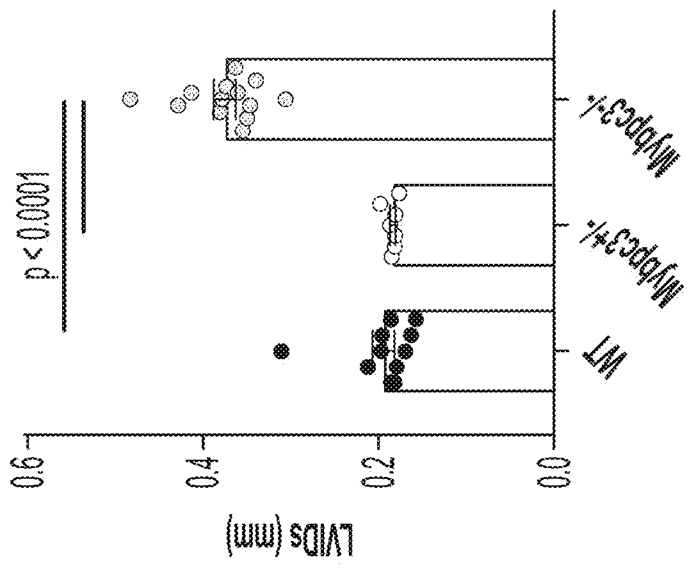
FIG. 4F shows a bar graph of Left ventricular internal diameter during systole (LVIDs) normalized by body weight in wild-type (WT), heterozygous KO mice (Mybpc3$^{-/-}$), or homozygous KO mice (Mybpc3$^{-/-}$) at two weeks of age.
Figure 4G:
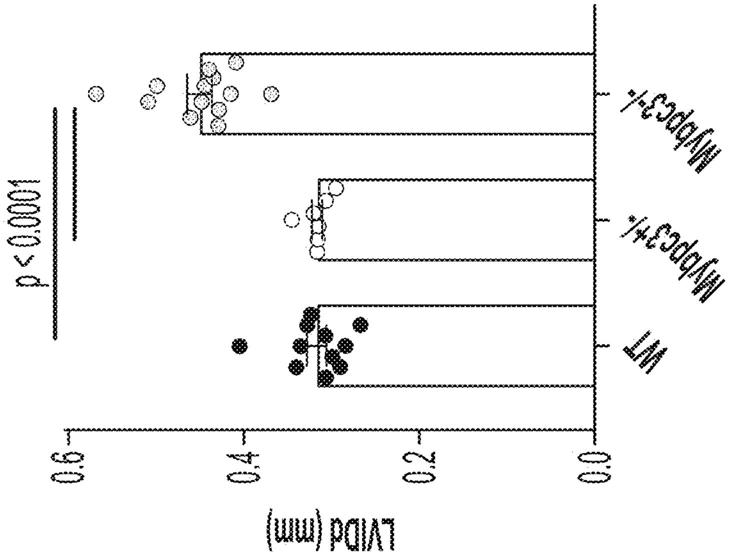
FIG. 4G shows a bar graph of Left ventricular internal diameter during diastole (LVIDd) normalized by body weight in wild-type (WT), heterozygous KO mice (Mybpc3$^{-/-}$), or homozygous KO mice (Mybpc3$^{-/-}$) at two weeks of age.

Homozygous Mybpc3 knockout mice (KO) were generated on a C57Bl/6 background by a CRISPR-Cas9 paired gRNA deletion of exons one and two (FIG. 4A). KO mice exhibited severe deficits in cardiac function (FIG. 4C and FIG. 4D) and pronounced cardiac hypertrophy (FIGS. 4E-4G) at two weeks of age, despite normal Mendelian ratios and comparable body weight to wild-type littermates (FIG. 4B). This model has more severe cardiac hypertrophy than other models (Schlossarek et al. *Basic Res. Cardiol.* 107:1-13 (2012)). Our KO mice exhibit severe, early-onset HCM in juveniles (two-week-old mice) that models pediatric onset of HCM in humans, as well as late-stage HCM in adults. See Lekanne Deprez et al., *J Med Genet* 43:829-832 (2006); Xin et al., *Am J Med Genet Part A* 143A:2662-2667 (2007); Zahka et al., *Heart* 94:1326-1330 (2008); Marziliano et al., *Neonatology* 102:254-258 (2012); Wessels et al., *Eur J Hum Genet* 23:922-928 (2015).

Example 4: MYBPC3 Transgene Expression in Heart Tissue in vivo

The purpose of this study was to examine therapeutic protein expression in vivo using an AAV-based vector system comprising a modified cardiac-specific promoter.

Adult mice were retro-orbitally injected with AAV9 recombinant virus comprising either the 600 bp wild-type TNNT2 (SEQ ID NO: 1) or 400 bp modified TNNT2 (SEQ ID NO: 3) promoter operatively linked to a polynucleotide that encodes MYBPC3. Tissue samples from heart, skeletal muscle (tibialis anterior), liver and whole brain were harvested 2 weeks post-infection. RNA was extracted from all tissues, synthesized to cDNA and analyzed by qRT-PCR using primers specific to human MYBPC3.

Figure 5:
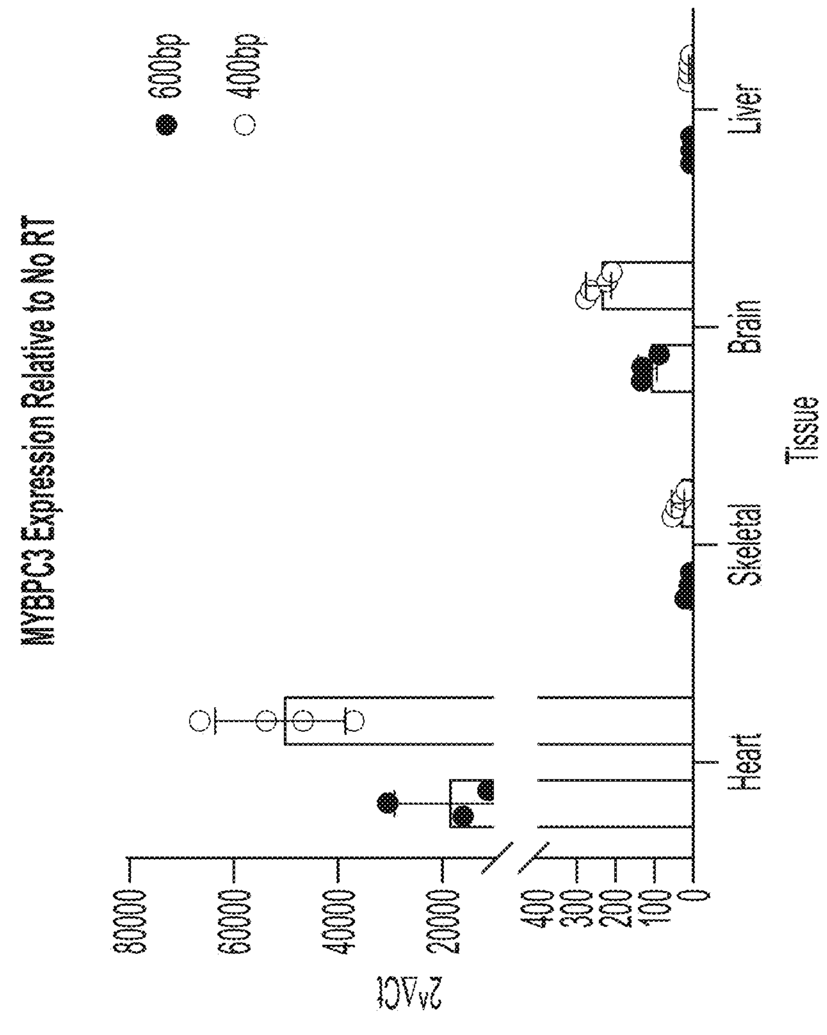
FIG. 5 shows detection of MYBPC3 mRNA by qRT-PCR in heart, skeletal, brain and liver tissue harvested from mice retro-orbitally injected with E12 GC AAV9-packaged constructs encoding human MYBPC3 driven by various sizes (400 or 600 bp) of the human cardiac TNNT2 promoter.

As shown in FIG. 5, mice injected with the AAV9-based vector comprising either the wild-type or modified TNNT2 promoter showed high levels of MYBPC3 mRNA in heart tissue compared to skeletal, brain or liver tissue. The 400 bp modified TNNT2 promoter showed increased expression ofMYBPC3 mRNA in heart tissue compared to the 600 bp wild-type TNNT2 promoter.

Figure 6A:
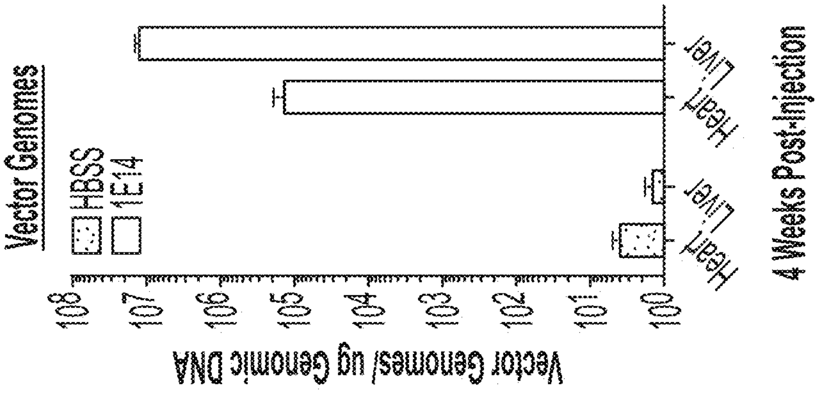
FIG. 6A shows a bar graph showing absolute quantification of vector genomes per microgram of genomic DNA in the heart and liver of adult mice 4 weeks after intravenous administration with an AAV9 vector containing the 400 bp modified TNNT2 promoter cassette.
Figure 6B:
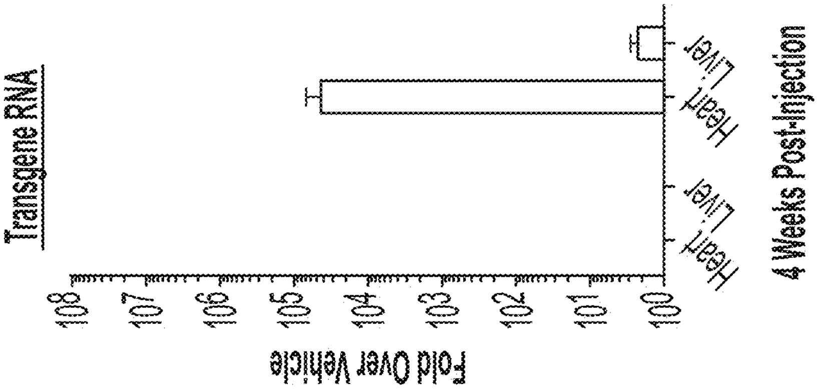
FIG. 6B shows a bar graph showing fold increase over vehicle of transgene RNA in the heart and liver of adult mice 4 weeks after intravenous administration with an AAV9 vector containing the 400 bp modified TNNT2 promoter cassette.

As shown in FIGS. 6A-6B, adult mice were intravenously dosed via tail vein injection with an AAV9 vector with the 400 bp modified TNNT2 promoter cassette. Tissue samples from heart and liver were harvested 4 weeks post-injection. Absolute quantification of viral genomes per microgram of genomic DNA was assessed by qPCR using linearized standards. RNA was extracted from all tissues, synthesized to cDNA and analyzed by qRT-PCR using primers specific to human MYBPC3. Surprisingly, the 400 bp TNNT2 promoter retains high selectivity for the heart: despite the 100-fold greater vector genomes detected in the liver than the heart 4 weeks post-injection in the adult-dosed animals (FIG. 6A, logarithmic scale), liver expression of the transgene was less than 1/10,000th of cardiac expression (FIG. 6B, logarithmic scale).

Collectively, these results indicate that a 200 bp deletion from the wild-type TNNT2 promoter, i.e., the 400 bp modified TNNT2 promoter (SEQ ID NO: 3), effectively drives expression of MYBPC3 protein in cardiomyocytes with high selectivity despite deletion of a substantial portion of the promoter sequence.

Example 5: Rescue of Cardiac Function in Mybpc3 Null Mice

This example demonstrates functional rescue of loss of function in the Mybpc3 in mice, using the vector designed for large cargoes described in Example 1 and the 400 bp modified hTNNT2 promoter described in Examples 2 and 3.

The 400 bp hTNNT2 promoter and murine Mybpc3 gene were cloned into the vector shown in FIG. 1C. This vector was packaged using an AAV9 capsid to generate the test vector.

Figure 7:
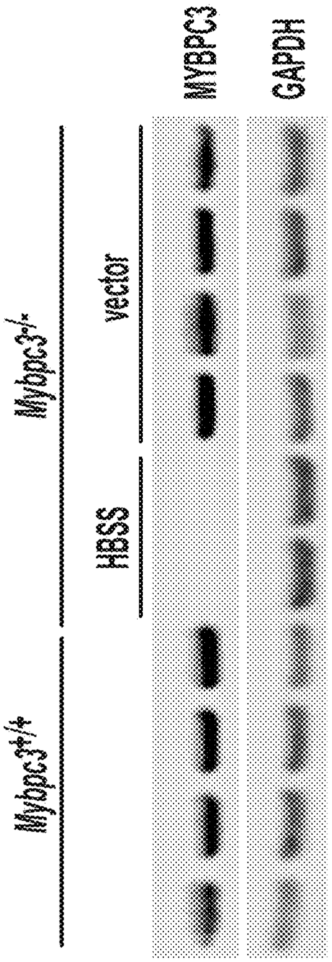
FIG. 7 shows a western blot of MYBPC3 protein expression in homozygous Mybpc3$^{-/-}$ mice injected retro-orbitally at two weeks of age with 1E14 vg·kg$^{-1}$ test vector encoding Mybpc3 or vehicle, HBSS.
Figure 8:
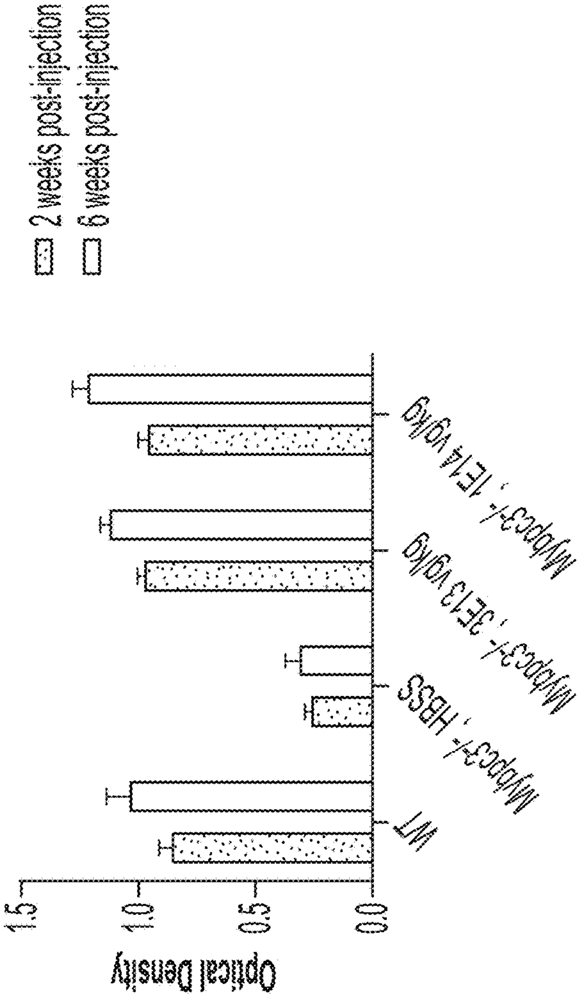
FIG. 8 shows a bar graph showing MYBPC3 expression in homozygous Mybpc3$^{-/-}$ mice injected retro-orbitally at two weeks of age 3E13 vg·kg$^{-1}$ and 1E14 vg·kg$^{-1}$ test vector encoding Mybpc3 or vehicle, HBSS.

In a first experiment, homozygous Mybpc3$^{-/-}$ mice were injected retro-orbitally at two weeks of age with 1E14 vg·kg$^{-1}$test vector encoding Mybpc3 or vehicle, HB SS. Cardiac tissue was harvested two weeks later (at four weeks), along with that of wild-type littermates. The experimental vector achieved wild-type levels of MYBPC3 protein expression in Mybpc3$^{-/-}$ mice at two weeks post-injection (FIG. 7). We conclude the test vector was capable of expressing MYBPC3 at physiological levels in juvenile animals at a dose as low as 1E14 vg·kg$^{-1}$ In a second experiment, the first experiment was repeated at a lower dose, 3E13 vg·kg$^{-1}$. Homozygous Mybpc3$^{-/-}$ mice were injected retro-orbitally at two weeks of age with 3E13 vg·kg$^{-1}$ and 1E14 vg·kg$^{-1}$ test vector encoding Mybpc3 or vehicle, HBSS. Wild-type levels of cardiac MYBPC3 protein expression were detected by ELISA in Mybpc3$^{-/-}$ mice at two and six weeks post-injection (FIG. 8) We conclude the test vector was capable of expressing MYBPC3 at physiological levels in juvenile animals at a dose as low as 3E13 vg·kg$^{-1}$ In a third experiment, cardiac function was assessed using assays relevant to hypertrophic cardiomyopathy. Hypertrophic cardiomyopathy presents physiologically as (1) an increase in heart size, measured as reported as the ratio of left ventricular mass/total body mass (LVM/BW) in mg·g$^{-1}$; and (2) as fractional shortening (FAS), measured by echocardiography.

Figure 9A:
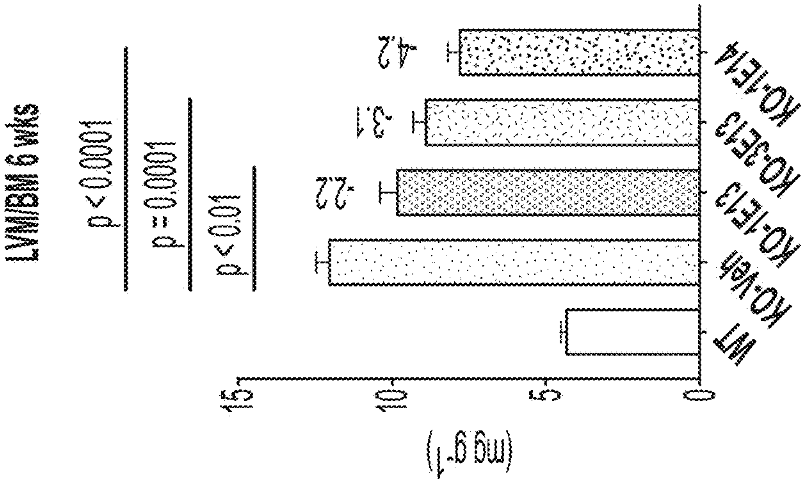
FIG. 9A shows a bar graph showing left ventricular mass normalized to body weight (LVM/BM) in homozygous Mybpc3$^{-/-}$ mice 6 weeks after they were injected retro-orbitally at two weeks of age with 1E13 vg·kg−1, 3E13 vg·kg$^{-1}$, and 1E14 vg·kg$^{-1}$ of test vector encoding Mybpc3 or vehicle, HBSS.
Figure 9B:
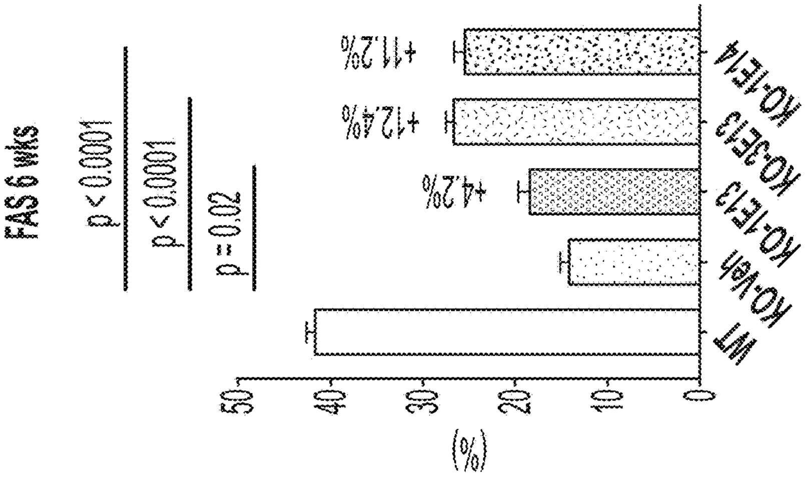
FIG. 9B shows a bar graph showing FAS expressed as % percentage change in LV internal dimensions between systole and diastole in homozygous Mybpc3$^{-/-}$ mice 6 weeks after they were injected retro-orbitally at two weeks of age with 1E13 vg·kg$^{-1}$, 3E13 vg·kg$^{-1}$, and 1E14 vg·kg−1 of test vector encoding Mybpc3 or vehicle, HBSS.
Figure 9C:
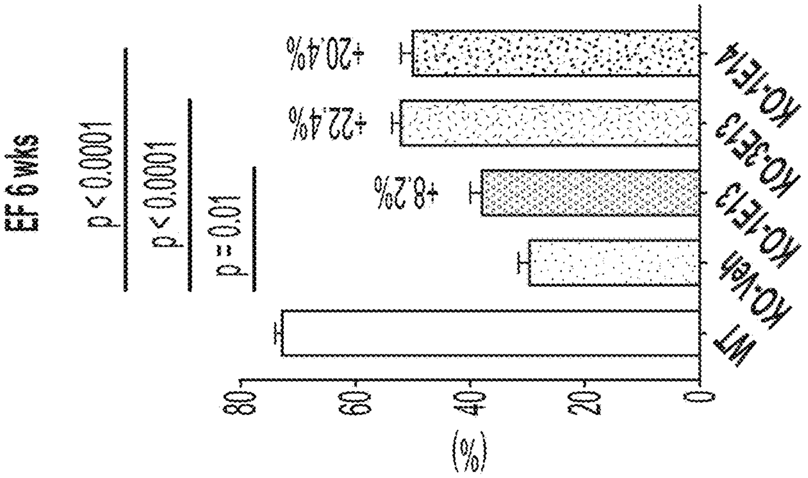
FIG. 9C shows a bar graph showing ejection fraction in homozygous Mybpc3$^{-/-}$ mice 6 weeks after they were injected retro-orbitally at two weeks of age with 1E13 vg·kg$^{-1}$, 3E13 vg·kg$^{-1}$ and 1E14 vg·kg−1 of test vector encoding Mybpc3 or vehicle, HBSS.
Figure 9F:
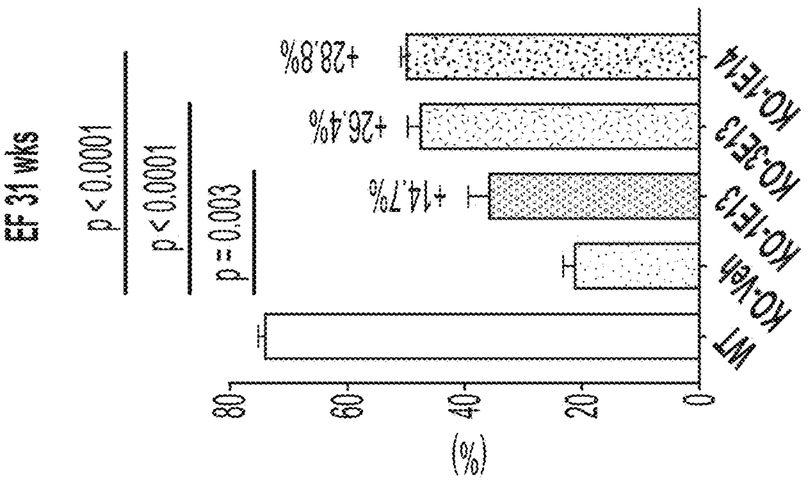
FIG. 9F shows a bar graph showing ejection fraction in homozygous Mybpc3$^{-/-}$ mice 31 weeks after they were injected retro-orbitally at two weeks of age with 1E13 vg·kg$^{-1}$, 3E13 vg·kg$^{-1}$, and 1E14 vg·kg$^{-1}$ of test vector encoding Mybpc3 or vehicle, HBSS.
Figure 9E:
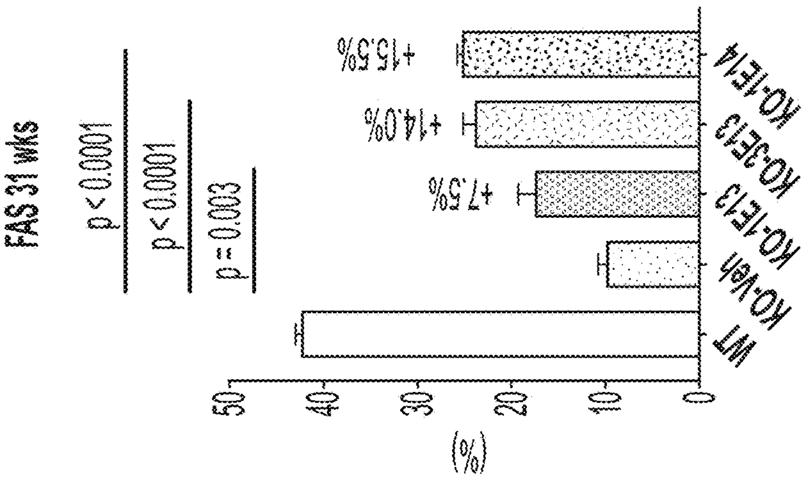
FIG. 9E shows a bar graph showing FAS expressed as % percentage change in LV internal dimensions between systole and diastole in homozygous Mybpc3$^{-/-}$ mice 31 weeks after they were injected retro-orbitally at two weeks of age with 1E13 vg·kg$^{-1}$, 3E13 vg·kg$^{-1}$, and 1E14 vg·kg$^{-1}$ of test vector encoding Mybpc3 or vehicle, HBSS.
Figure 9D:
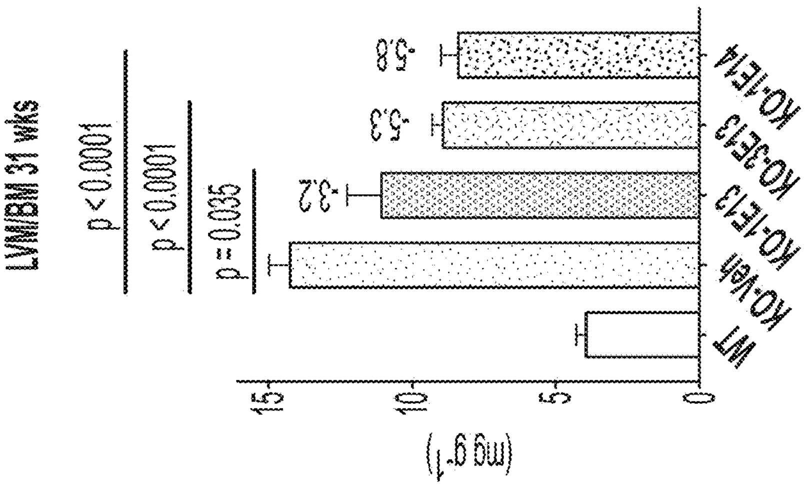
FIG. 9D shows a bar graph showing left ventricular mass normalized to body weight (LVM/BM) in homozygous Mybpc3$^{-/-}$ mice 31 weeks after they were injected retro-orbitally at two weeks of age with 1E13 vg·kg−1, 3E13 vg·kg$^{-1}$, and 1E14 vg·kg$^{-1}$ of test vector encoding Mybpc3 or vehicle, HBSS.

Homozygous Mybpc3$^{-/-}$ mice were injected retro-orbitally at two weeks of age with 1E13 vg·kg$^{-1}$, 3E13 vg·kg$^{-1}$, and 1E14 vg·kg$^{-1}$ of test vector encoding Mybpc3 or vehicle, HBSS. Dose-dependent rescue of cardiac function was observed at all tested doses (1E13 vg·kg$^{-1}$, 3E13 vg·kg$^{-1}$, and 1E14 vg·kg$^{-1}$). LVM/BM was decreased from vehicle control at all tested doses six weeks post-injection (FIG. 9A). FAS (expressed as % percentage change in LV internal dimensions between systole and diastole, FIG. 9B) and ejection fraction (FIG. 9C) were increased from vehicle control at all tested doses six weeks post-injection. Even greater improvements in LVM/BM (FIG. 9D), FAS (FIG. 9E), and EF (FIG. 9F) were observed 31 weeks following injection. Consistent with equal levels of MYBPC3 protein expression observed at 3E13 vg·kg$^{-1}$ and 1E14 vg·kg$^{-1}$ doses (see FIG. 8), animals treated with 3E13 vg·kg$^{-1}$ or 1E14 vg·kg$^{-1}$ exhibit similar improvements in hypertrophy, FAS or EF improvements. Even at only 1E13 vg·kg$^{-1}$ dose, hypertrophy, FAS and EF are all improved compared to vehicle control.

We conclude the test vector was capable of rescue of cardiac function in juvenile animals at a dose as low as 1E13 vg·kg$^{-1}$.

Rescue of function in symptomatic juvenile mice is, in the case of hypertrophic cardiomyopathy, more challenging than prevention of decline in function in infants, because hypertrophic cardiomyopathy is a progressive disorder. Older animals exhibit more severe disease than younger animals. To our knowledge, rescue of MYBPC3 loss of function in symptomatic juvenile animals has never been demonstrated before with AAV. Our model is also a complete loss of function caused by deletion of the Mybpc3 gene, not a partial loss of function due to mutation.

We compared our results to those reported in Mearini et al., *Nat. Commun.* 5:5515 (2014), which used a 5.4 kb expression cassette encoding Mybpc3 in mice having a single nucleotide polymorphism in the endogenous Mybpc3 gene. Mearni et al. report prevention of high LVM/BW at two-weeks of age in mice injected as neonates (not symptomatic juveniles) with very high doses (1E12 vg and 3E12 vg, which corresponds to 7E14 vg·kg$^{-1}$ and 2E15 vg·kg$^{-1}$, based on an average neonate mass of 1.5 g) of an AAV9 vector encoding the same Mybpc3 gene. Mearni et al. used a 550 bp hTNNT2 promoter, rather than the present 400 bp modified hTNNT2 promoter. The vector Mearini et al. does not significantly prevent FAS decline, even at 2E15 vg·kg$^{-1}$. By contrast, the present vector demonstrates improvement in physiological parameters in juveniles animals (not only neonates) at doses at least as low as 1E13 vg·kg$^{-1}$ to 1E14 vg·kg$^{-1}$.

The vector and promoter modifications dramatically and surprisingly increase potency of the vector.

Example 6: Direct Comparison of 5.4 kbp Cassette to 4.7 kbp Cassette

This example directly compares a 5.4 kbp cassette encoding the Mybpc3 gene to a 4.7 kbp cassette encoding the Mybpc3 gene in mature (2.5 months of age) homozygous mice with advanced disease.

Figures 10A, 10B, 10C, 10D:
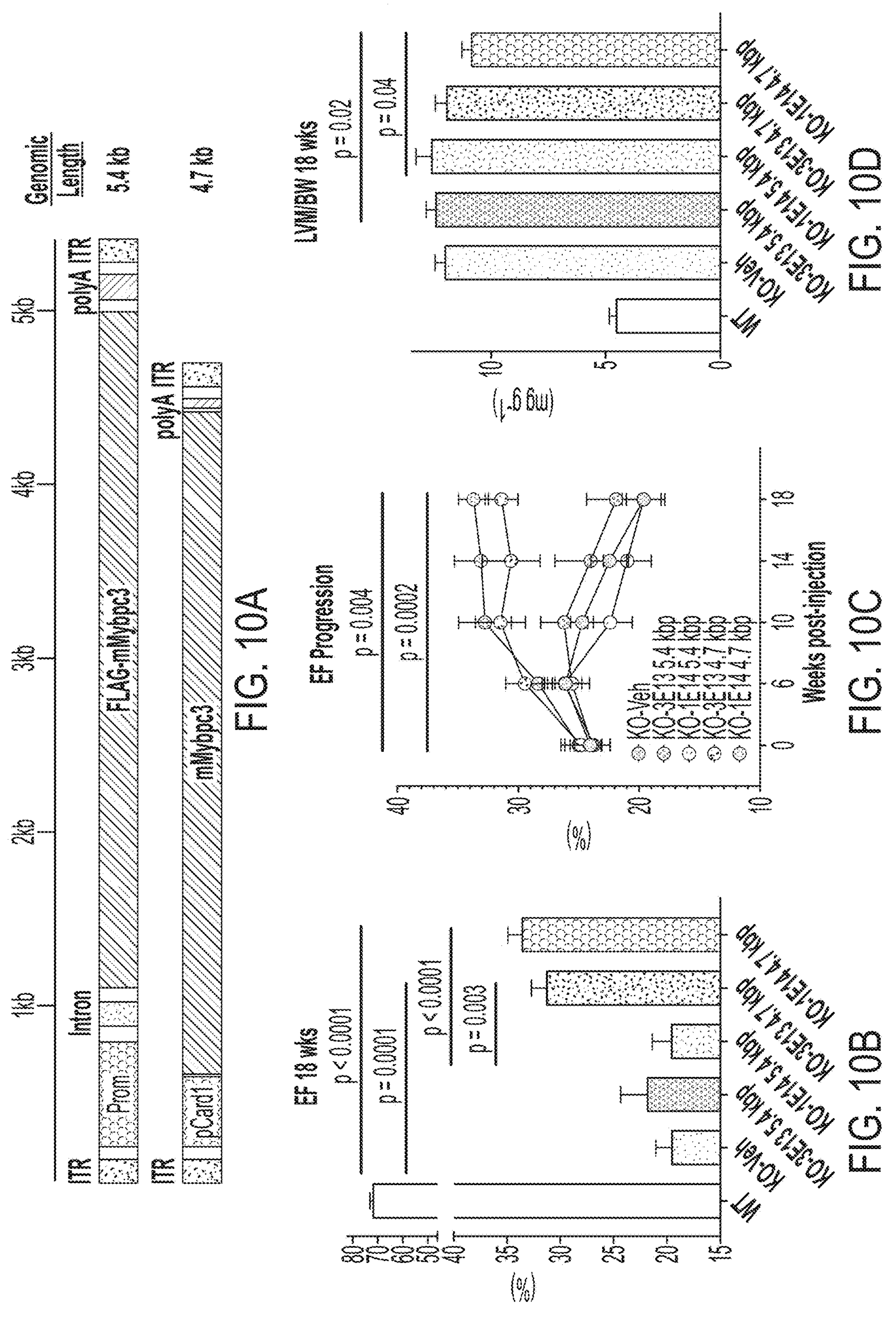
FIG. 10A is an illustration of an AAV9 vector encoding Mybpc3 in the context of the 5.4 kbp or 4.7 kbp expression cassettes.
FIG. 10B is a bar graph showing ejection fraction in homozygous Mybpc3$^{-/-}$ mice 18 weeks after they were injected retro-orbitally at three months of age with 3E13 vg·kg$^{-1}$ or 1E14 vg·kg$^{-1}$ of AAV9 vector encoding Mybpc3 in the context of the 5.4 kbp or 4.7 kbp cassettes, or injected with vehicle control, HBSS.
FIG. 10C is a plot showing ejection fraction progression in homozygous Mybpc3$^{-/-}$ mice after they were injected retro-orbitally at three months of age with 3E13 vg·kg$^{-1}$ or 1E14 vg·kg$^{-1}$ of AAV9 vector encoding Mybpc3 in the context of the 5.4 kbp or 4.7 kbp cassettes, or injected with vehicle control, HBSS.
FIG. 10D is a bar graph showing left ventricular mass normalized to body weight (LVM/BM) in homozygous Mybpc3$^{-/-}$ mice 18 weeks after they were injected retro-orbitally at three months of age with 3E13 vg·kg$^{-1}$ or 1E14 vg·kg$^{-1}$ of AAV9 vector encoding Mybpc3 in the context of the 5.4 kbp or 4.7 kbp cassettes, or injected with vehicle control, HBSS.

Homozygous Mybpc3$^{-/-}$ mice were injected retro-orbitally with 3E13 vg·kg$^{-1}$ or 1E14 vg·kg$^{-1}$ of AAV9 vector encoding Mybpc3 in the context of the 5.4 kbp or 4.7 kbp cassettes (FIG. 10A), or injected with vehicle control, HBSS. Even when dosed at this advanced stage of cardiac decline, the 4.7 kbp cassette significantly improved cardiac function based on ejection fraction (EF) (FIG. 10B), with clear restoration of function above pre-dose baseline (FIG. 10C), unlike animals treated with vehicle (Veh) or the 5.4 kbp cassette. Further, compared to the 5.4 kbp cassette, the 4.7 kbp cassette was also able to significantly decrease hypertrophy, as indicated by LVM/BM, eighteen weeks post-injection (FIG. 10D).

This example demonstrates functional rescue of loss of function in the Mybpc3 in mice, using the vector backbone and promoter modifications described in Examples 1-3.

This example also demonstrates that, in a challenging model of disease—adult, homozygous Mybpc3$^{-/-}$ mice—a 5.4 kbp vector (SEQ ID NO: 201) at low dose fails to generate any physiological improvement; whereas a 4.7 kbp vector according to the present disclosure causes statistically significant improvement in physiological parameters related to cardiomyopathy at doses as low as 3E13 vg·kg$^{-1}$.

Example 7: Greater Efficacy with an Improved AAV Capsid encoding MYBPC3

This example demonstrates how the improved potency of the large cargo vector (Example 1) and modified promoter (Examples 2 and 3) based on rescue of Mybpc3$^{-/-}$ mice (Example 5) can be further improved by use of an engineered AAV capsid.

Figure 11C:
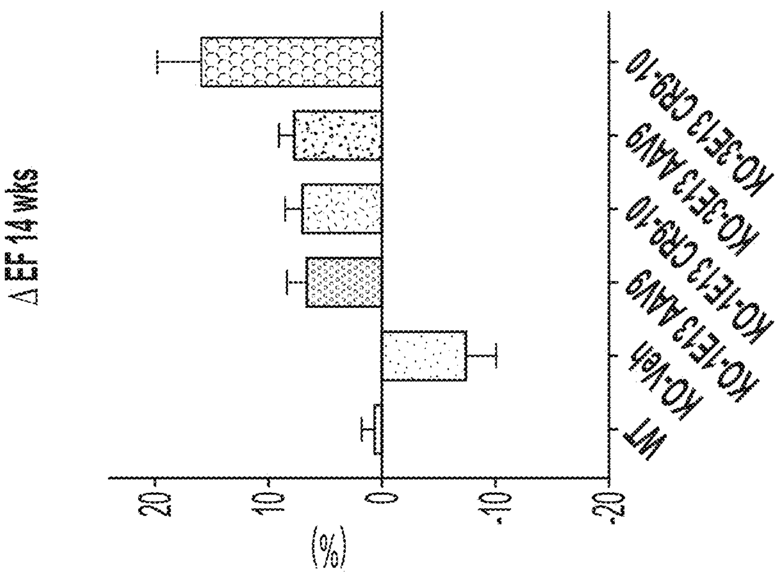
FIG. 11C is a bar graph showing ejection fraction compared to pre-dose baseline (ΔEF) in Mybpc3$^{-/-}$ mice injected retro-orbitally at two weeks of age with 1E13 vg·kg−1 and 3E13 vg·kg−1 of AAV9 vector encoding an expression cassette Mybpc3 gene, CR9-10 vector encoding an expression cassette Mybpc3 gene, or vehicle control HBSS.
Figure 11B:
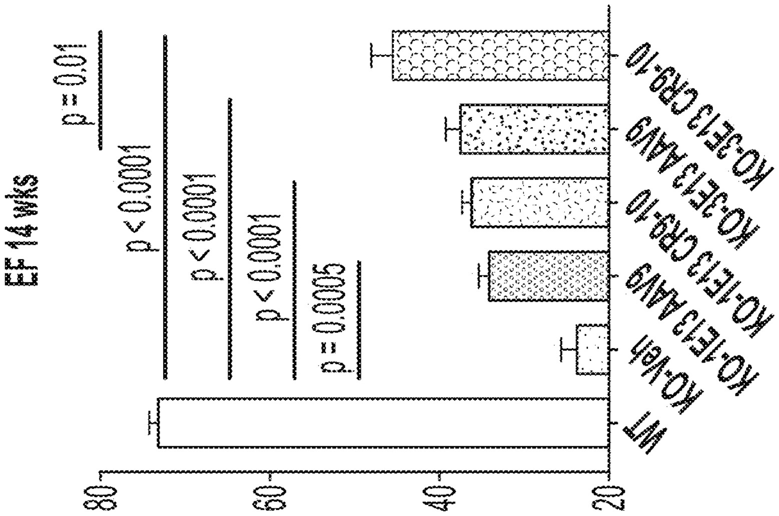
FIG. 11B is a bar graph showing ejection fraction in Mybpc3$^{-/-}$ mice injected retro-orbitally at two weeks of age with 1E13 vg·kg−1 and 3E13 vg·kg−1 of AAV9 vector encoding Mybpc3, CR9-10 vector encoding Mybpc3, or vehicle control HBSS.
Figure 11A:
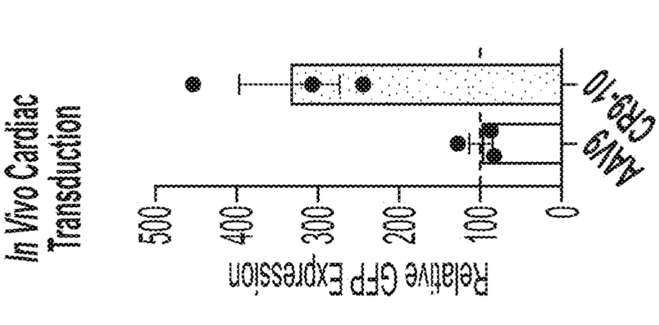
FIG. 11A is a bar graph showing GFP expression in cardiac tissue following systemic delivery of an AAV9 capsid variant, CR9-10, with a GFP-encoding cassette or AAV9 with a GFP-encoding cassette in adult mice ($p<0.05$, One-way ANOVA; Dunnett's multiple comparison test).

An AAV9 capsid variant, CR9-10 exhibited significantly higher cardiac transduction upon systemic delivery in adult mice than AAV9 with a GFP-encoding cassette as determined by ELISA ($p<0.05$, One-way ANOVA; Dunnett's multiple comparison test) (FIG. 11A).

In a second experiment, the expression cassette encoding the murine Mybpc3 gene was packaged into either AAV9 or CR9-10 and the potency of cardiac rescue in Mybpc3$^{-/-}$ mice compared. Homozygous Mybpc3$^{-/-}$ mice were injected retro-orbitally at two weeks of age with 1E13 vg·kg$^{-1}$ and 3E13 vg·kg$^{-1}$ of AAV9 vector, CR9-10 vector, or vehicle control HBSS. All test articles significantly improved cardiac function based on ejection fraction (EF) (FIG. 11B), with clear restoration of function above pre-dose baseline (ΔEF) (FIG. 11C). Consistent with improved cardiac transduction, CR9-10 resulted in greater EF improvement than AAV9.

Example 8: Non-Human Primate Study of Engineered AAV Capsid Variants

Biodistribution of AAV vectors having engineered capsids (described in U.S. Provisional Patent Appl. No. 63/012,703, which is incorporated herein in its entirety), were assessed in male cynomolgus macaques (Macaca fascicularis) following intravenous delivery.

Figure 12A:
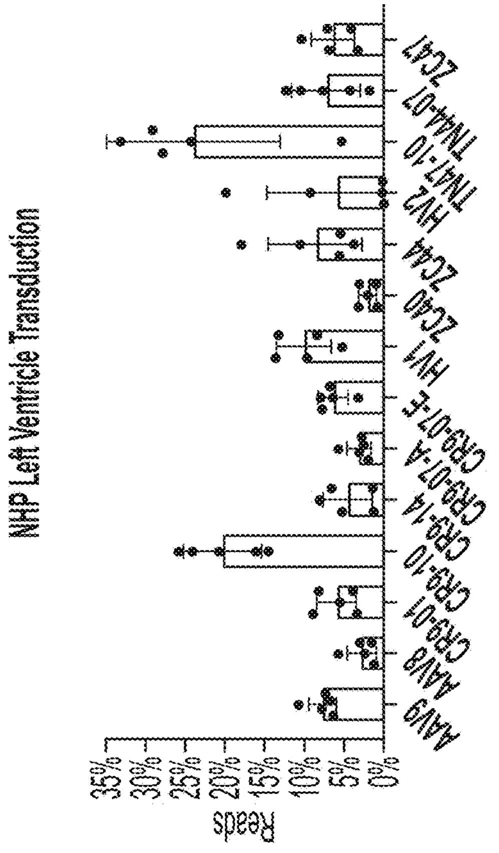
FIG. 12A is a bar graph showing GFP expression in the left ventricle of non-human primates one month after intravenous delivery of 1E13 vg·kg−1 dose of AAV vector encoding GFP packaged in one of fourteen different capsid proteins.
Figure 12B:
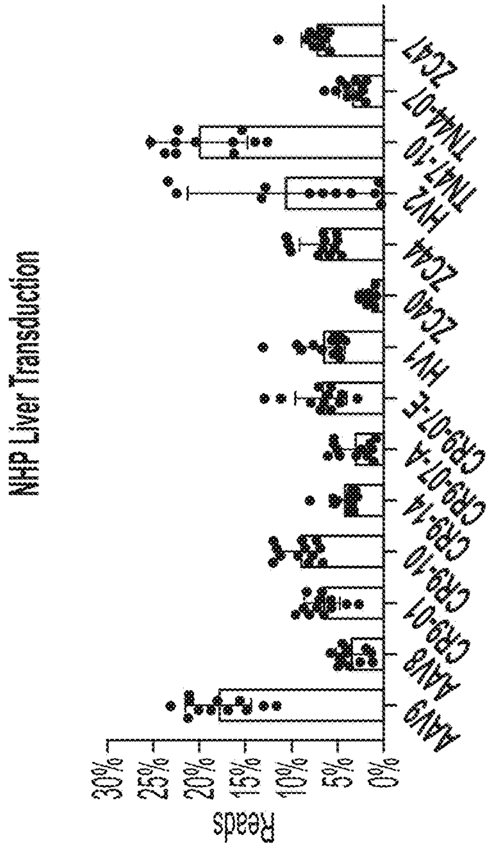
FIG. 12B is a bar graph showing GFP expression in the liver of non-human primates one month after intravenous delivery of 1E13 vg·kg−1 dose of AAV vector encoding GFP packaged in one of fourteen different capsid proteins.
Figure 12C:
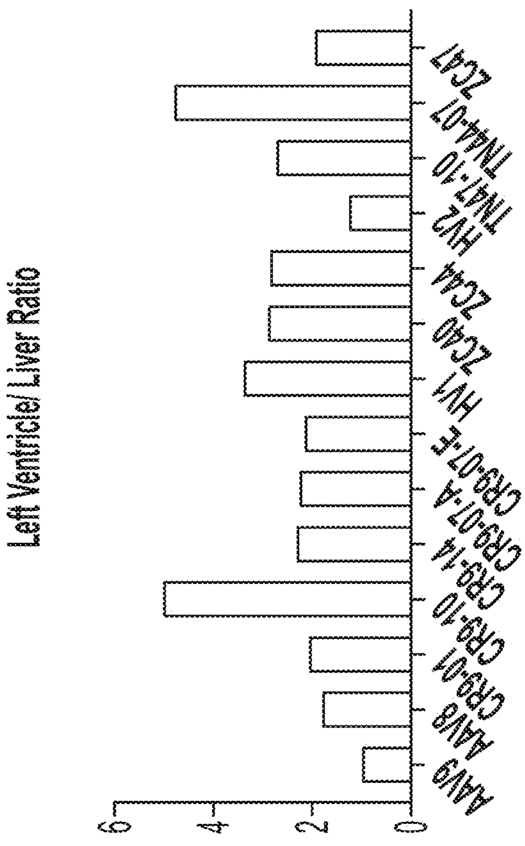
FIG. 12C is a bar graph showing the ratio of GFP expression in the left ventricle:liver of non-human primates one month after intravenous delivery of 1E13 vg·kg$^{-1}$ dose of AAV vector encoding GFP packaged in one of fourteen different capsid proteins.

AAV vector generated with fourteen different capsids, including AAV9, were pooled and injected into NHPs at a 1E13 vg·kg−1 dose (n=3). Viral DNA was extracted from left ventricle and liver one month after systemic delivery. Consistent with the murine results, CR9-10 exhibited increased cardiac transduction compared to AAV9 (FIG. 12A). Additionally, many variants decreased liver viral burden relative to AAV9 (FIG. 12B), improving the ratio of left ventricle transduction to liver infection (FIG. 12C).

Example 10: Rescue of Cardiac Function with the Human MYBPC3 Gene in Mybpc3 Null Mice This example demonstrates the ability of human MYBPC3 gene to rescue Mybpc3$^{-/-}$ mice.

Figure 13A:
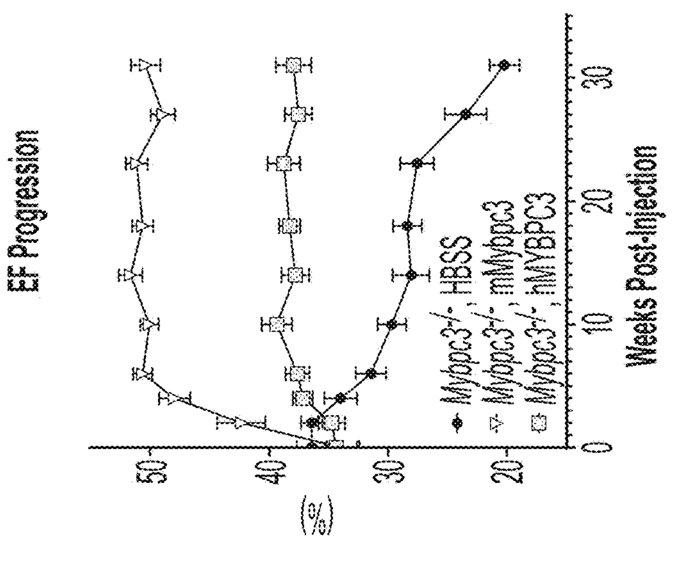
FIG. 13A is a plot showing ejection fraction progression in homozygous Mybpc3$^{-/-}$ mice that were injected retro-orbitally at two weeks of age with AAV9 encoding the mouse Mybpc3 gene (mMybpc3) (at 1E14 vg·kg$^{-1}$), AAV9 encoding the human MYBPC3 gene (hMYBPC3) (at 1E14 vg·kg$^{-1}$), or vehicle, HBSS.
Figure 13B:
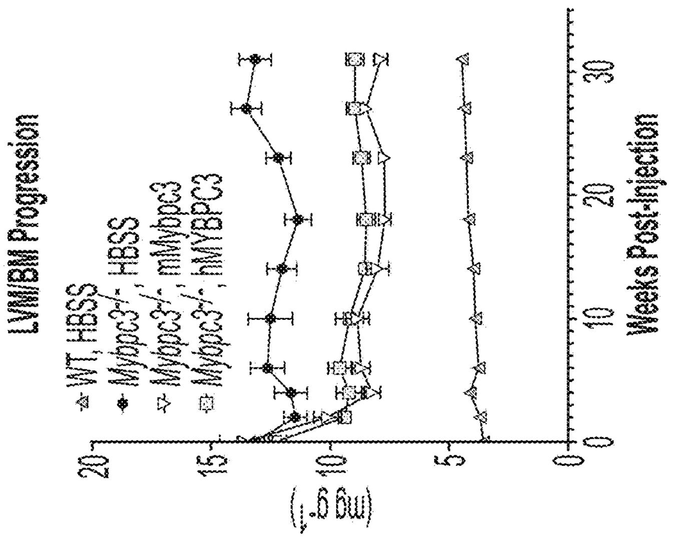
FIG. 13B is a plot showing left ventricular mass normalized to body weight (LVM/BW) progression in homozygous Mybpc3$^{-/-}$ mice that were injected retro-orbitally at two weeks of age with AAV9 encoding the mouse Mybpc3 gene (mMybpc3) (at 1E14 vg·kg$^{-1}$), AAV9 encoding the human MYBPC3 gene (hMYBPC3) (at 1E14 vg·kg$^{-1}$), or vehicle, HBSS.
Figure 13C:
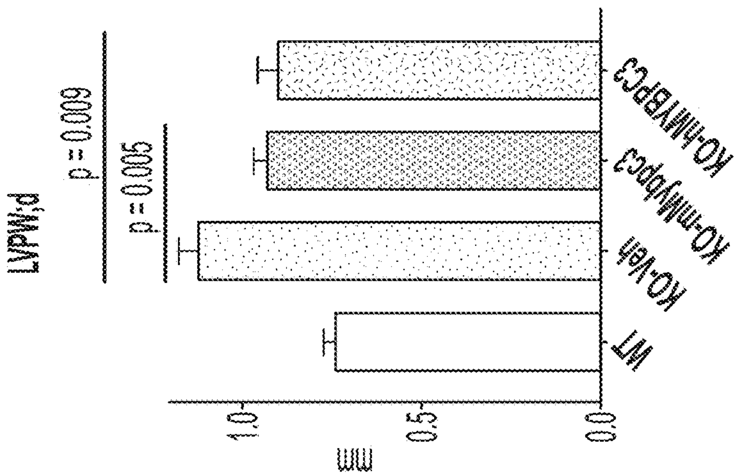
FIG. 13C is a bar graph left ventricular posterior wall thickness during diastole (LVPW;d) in homozygous Mybpc3$^{-/-}$ mice that were injected retro-orbitally at two weeks of age with AAV9 encoding the mouse Mybpc3 gene (mMybpc3) (at 1E14 vg·kg$^{-1}$), AAV9 encoding the human MYBPC3 gene (hMYBPC3) (at 1E14 vg·kg$^{-1}$), or vehicle, HBSS.

Homozygous Mybpc3$^{-/-}$ mice were injected retro-orbitally at two weeks of age with AAV9 encoding the mouse Mybpc3 gene (mMybpc3) (at 1E14 vg·kg−1), AAV9 encoding the human MYBPC3 gene (hMYBPC3) (at 1E14 vg·kg−1), or vehicle, HBSS. Cardiac size and function were monitored by echocardiography up to eight months post-injection. The results indicate that AAV9-mediated cardiac MYBPC3 replacement of either mMybpc3 and hMYBPC3 in Mybpc3$^{-/-}$ mice resulted in recovery of cardiac size and function. Ejection fraction (EF) was significantly improved by both the human and mouse orthologs of MYBPC3, with mMybpc3 yielding greater improvement in EF compared to hMYBPC3 (FIG. 13A). Importantly, hMYBPC3 was just as potent as mMybpc3 at reducing cardiac hypertrophy over time, as evidenced by left ventricular mass normalized to body weight (LVM/BW) (FIG. 13B). This was further validated by comparable decreases in left ventricular posterior wall thickness during diastole (LVPW;d) (FIG. 13C). Critically, all improvements exhibited robust stability out to 8 months post-injection.

Figure 14C:
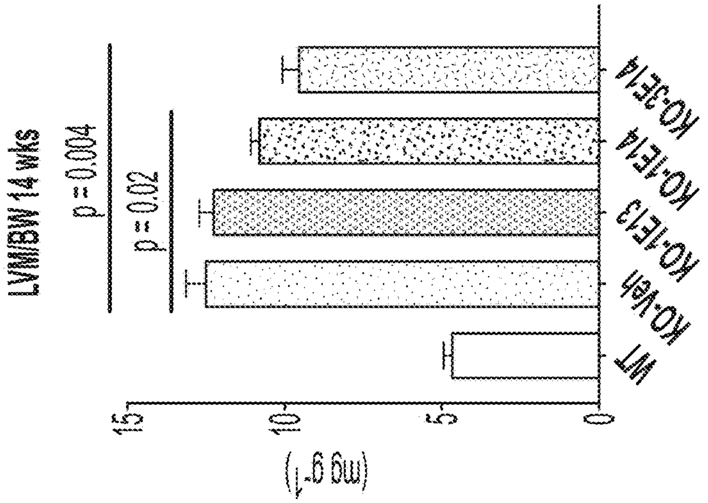
FIG. 14C is a bar graph showing left ventricular mass normalized to body weight (LVM/BW) in homozygous Mybpc3$^{-/-}$ mice that were injected retro-orbitally at two weeks of age with 1E13 vg·kg$^{-1}$, 1E14 vg·kg$^{-1}$, and 3E14 vg·kg$^{-1}$ of test vector encoding the human MYBPC3 gene or vehicle, HBSS.
Figure 14B:
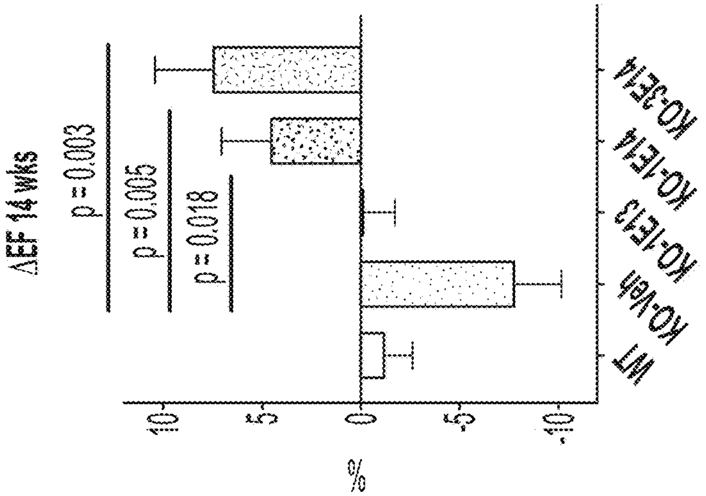
FIG. 14B is a bar graph showing ejection fraction compared to pre-dose baseline (ΔEF) in homozygous Mybpc3$^{-/-}$ mice that were injected retro-orbitally at two weeks of age with 1E13 vg·kg$^{-1}$, 1E14 vg·kg$^{-1}$, and 3E14 vg·kg$^{-1}$ of test vector encoding the human MYBPC3 gene or vehicle, HBSS.
Figure 14A:
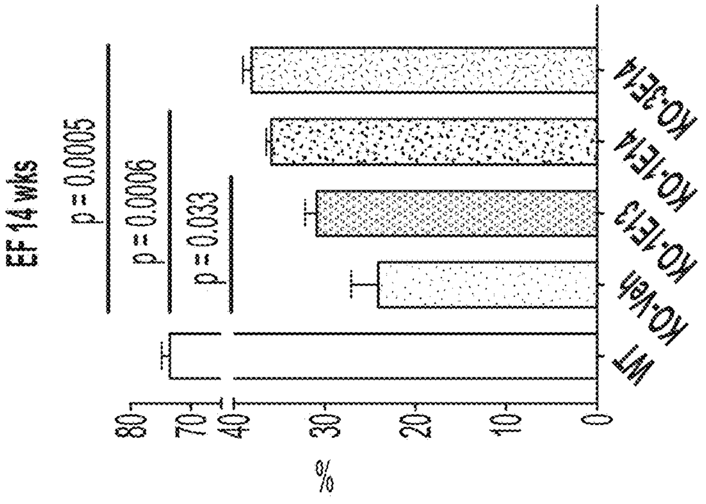
FIG. 14A is a bar graph showing ejection fraction in homozygous Mybpc3$^{-/-}$ mice that were injected retro-orbitally at two weeks of age with 1E13 vg·kg$^{-1}$, 1E14 vg·kg$^{-1}$, and 3E14 vg·kg$^{-1}$ of test vector encoding the human MYBPC3 gene or vehicle, HBSS.

In a second study, the efficacy of hMYBPC3 was assessed over a range of viral doses. Homozygous Mybpc3$^{-/-}$ mice were injected retro-orbitally at two weeks of age with 1E13 vg·kg−1, 1E14 vg·kg−1, and 3E14 vg·kg−1 of test vector encoding the human MYBPC3 gene or vehicle, HBSS. Dose-dependent improvement of cardiac function was observed for all tested doses (1E13 vg·kg−1, 1E14 vg·kg−1, and 3E14 vg·kg−1) fourteen weeks post-injection, as indicated by EF (FIG. 14A), with significant improvement above pre-dose baseline for 1E14 vg·kg−1 and 3E14 vg·kg−1 treatments (FIG. 14B). Significant reduction in cardiac hypertrophy was also observed for 1E14 vg·kg−1 and 3E14 vg·kg−1 treatments, based on LVM/BW (FIG. 14C). Thus, we conclude the hMYBPC3 test vector was capable of preserving cardiac function in adult animals at a dose as low as 1E13 vg·kg−1.

Example 11: Treatment of Hypertrophic Cardiomyopathy (HCM)

Cardiomyopathy is the number-one cause of sudden cardiac arrest in children under 18. Hypertrophic cardiomyopathy (HCM) affects 0.5 million Americans, potentially resulting in heart failure or sudden death. Loss-of-function mutations in Myosin Binding Protein C3, MYBPC3, are the most common genetic cause of HCM. The majority of MYBPC3 mutations causative for HCM result in truncations, via nonsense, frameshift or splice-site mutations. The sarcomeric pathophysiology of the majority of HCM patients with MYBPC3 mutations appears to be due to haploinsufficiency, as the total amount of MYBPC3 protein incorporated into sarcomeres falls significantly below normal. Decreased sarcomeric levels of MYBPC3 result in decreased myosin inhibition with more myosin heads engaged on the actin filament, resulting in hypercontractility.

The clearest path to the treatment of haploinsufficiency is the restoration of the insufficient gene product; in this case wild-type MYBPC3. Thus, we have successfully engineered an AAV vector (TN-201) with superior properties for selective restoration of MYBPC3 to cardiomyocytes upon systemic delivery. Critically, we have demonstrated for the first time with AAV the ability of both a mouse surrogate and TN-201 to reverse cardiac dysfunction and hypertrophy in a symptomatic murine model of disease.

Dose-ranging efficacy studies exhibited restoration of wild-type MYBPC3 protein levels and saturation of cardiac improvement at the clinically relevant dose of 3E13 vg/kg. Further, pilot safety studies in adult and infant mice injected with >10X an efficacious dose exhibited no clinical observations, no alterations in cardiac function, and no histopathological findings. Importantly, we have determined that TN-201 produced utilizing the highly scalable Sf9 platform results in similarly potent efficacy in a Mybpc3$^{-/-}$ model of disease. Finally, we have established that our observed efficacy is sufficiently meaningful for stable benefit up to 8 months post-injection, as well as reversal of cardiac dysfunction even in late-stage homozygote disease.

Example 12: Clinical Studies

A pharmaceutical composition comprising rAAV virions encoding MYBPC3, as described herein, is administered by intravenously or by retrograde coronary sinus (RCSI). Functional efficacy is determined by cardiac functional status assessments (e.g., New York Heart Association Functional Classification, NYHA; Cardiopulmonary exercise test, CPET), quality of life questionnaires (e.g., Kansas City Cardiomyopathy Questionnaire Clinical Quality Score, KCCQ-CSS), cardiac imaging (e.g., echocardiography), cardiac biomarkers (e.g. troponin and NT-proBNP), cardiac rhythm and immunologic assessments, cardiac functional status assessments (e.g., Pediatric Interagency Registry for Mechanically Assisted Circulatory Support, PEDIMACS; Ross classifications), and/or Major Adverse Cardiac Events (MACE) (total death, cardiac transplantation, initiation of inotropes, initiation of ventilatory, or mechanical circulatory support). Clinical studies may include monitoring safety and continued efficacy (e.g., adverse events, severe adverse events, electrocardiogram, cardiac enzymes, biomarkers, functional status, left ventricular (LV) function/mass, quality of life, serum chemistries, liver function tests) on an annual basis for up to 10 years.

The invention claimed is:

1. A recombinant vector comprising a modified human cardiac troponin T promoter, wherein the modified human cardiac troponin T promoter consists of a polynucleotide having between 400 bp to 425 bp of SEQ ID NO: 1 and comprising the sequence of SEQ ID NO: 3, and wherein the modified human cardiac troponin T promoter expresses a gene product at least 10%, at least 20%, or at least 30% more than a native human cardiac troponin T promoter or a promoter having the sequence of SEQ ID NO: 1.

2. The vector of claim 1, wherein the polynucleotide consists of 400 bp and has the sequence of SEQ ID NO: 3.

3. The vector of claim 1, wherein the modified human cardiac troponin T promoter is operatively linked to a polynucleotide encoding a gene product.

4. The vector of claim 3, wherein the gene product is selected from the group consisting of myosin binding protein C (MYBPC3), potassium voltage-gated channel subfamily H member 2 (KCNH2), transient receptor potential cation channel subfamily M member 4 (TRPM4), desmoglein 2 (DSG2), ATPase sarcoplasmic/endoplasmic reticulum Ca2+ transporting 2 (ATP2A2), calcium voltage-gated channel subunit alphal C (CACNAIC), dystrophin (DMD), DM1 protein kinase (DMPK), ectopic P-granules 5 autophagy tethering factor (EPG5), EvC ciliary complex subunit 1 (EVC), EvC ciliary complex subunit 2 (EVC2), fibrillin 1 (FBN1), neurofibromin 1 (NF1), sodium voltage-gated channel alpha subunit 5 (SCN5A), SOS Ras/Rac guanine nucleotide exchange factor 1 (SOS1), natriuretic peptide receptor 1 (NPR1), erb-b2 receptor tyrosine kinase 4 (ERBB4), vasoactive intestinal peptide (VIP), myosin heavy chain 7 (MYH7), and CRISPR-associated protein 9 (Cas9).

5. The vector of claim 4, wherein the Cas9 is selected from the group consisting of *Streptococcus pyrogenes* Cas9 (SpCas9), *Streptococcus thermophilus* Cas9 (St1Cas9), and *Staphylococcus aureus* Cas9 (SaCas9).

6. The vector of claim 3, wherein the gene product is human MYBPC3 or a functional variant thereof.

7. The vector of claim 6, wherein the polynucleotide encoding MYBPC3 shares at least 80%, at least 90%, at least 95%, or 100% sequence identity to SEQ ID NO: 86, and/or wherein the human MYBPC3 shares at least 90% or 95% sequence identity to SEQ ID NO: 103.

8. The vector of claim 6, wherein the gene product is full-length human MYBPC3 and/or comprises the amino acid sequence of SEQ ID NO: 103.

9. The vector of claim 1, wherein the vector is a viral vector.

10. The vector of claim 9, wherein the vector has a packaging limit of at most about 5.5 kb.

11. The vector of claim 9, wherein the viral vector is an adeno-associated virus (AAV) vector.

12. A recombinant adeno-associated virus (rAAV) virion, comprising the vector of claim 1 and an AAV capsid protein.

13. The rAAV virion of claim 12, wherein the AAV capsid protein is an AAV9 capsid protein or a variant thereof.

14. A recombinant adeno-associated virus (rAAV) virion comprising a vector genome and an AAV capsid protein or a variant thereof, wherein the vector genome comprises an expression cassette comprising a polynucleotide encoding MYBPC3 operatively linked to a modified human cardiac troponin T promoter, wherein the expression cassette is flanked by a 5' inverted terminal repeat (ITR) and a 3' ITR, wherein the modified human cardiac troponin T promoter has no more than 425 bp and comprises the sequence of SEQ ID NO: 3, wherein the MYBPC3 is human MYBPC3 or a functional variant thereof, and wherein the polynucleotide encoding MYBPC3 comprises at least 3.5 kb.

15. The rAAV virion of claim 14, wherein the modified human cardiac troponin T promoter has 400 bp and has the sequence of SEQ ID NO: 3.

16. The rAAV virion of claim 15, wherein the polynucleotide encoding MYBPC3 shares at least 80%, at least 90%, at least 95%, or 100% sequence identity to SEQ ID NO: 86, and/or wherein the human MYBPC3 shares at least 90% or 95% sequence identity to SEQ ID NO: 103.

17. The rAAV virion of claim 14, wherein the human MYBPC3 is full-length human MYBPC3 and/or comprises the amino acid sequence of SEQ ID NO: 103.

18. The rAAV virion of claim 15, wherein the human MYBPC3 is full-length human MYBPC3 and/or comprises the amino acid sequence of SEQ ID NO: 103.

19. The rAAV virion of claim 14, wherein the 5' ITR comprises a sequence that shares at least 95% or 100% sequence identity to SEQ ID NO: 96, and the 3' ITR comprises a sequence that shares at least 95% or 100% sequence identity to SEQ ID NO: 97.

20. The rAAV virion of claim 14, wherein the AAV is AAV9.

21. The rAAV virion of claim 18, wherein the AAV is AAV9.

22. A pharmaceutical composition comprising the rAAV virion of claim 14 and a pharmaceutically acceptable excipient.

23. An isolated cell comprising the rAAV virion of claim 14, wherein the isolated cell is an induced pluripotent stem cell, a cardiac cell, or a cardiomyocyte.

24. An in vitro or ex vivo method of expressing a MYBPC3 protein in a cell, comprising transducing the cell with the rAAV virion of claim 14, wherein the cell is an induced pluripotent stem cell, a cardiac cell, or a cardiomyocyte.

* * * * *